US012746240B2

(12) United States Patent
Kahatt et al.

(10) Patent No.: US 12,746,240 B2
(45) Date of Patent: *Sep. 29, 2026

(54) METHOD OF TREATING SCLC AND MANAGING NEUTROPENIA

(71) Applicant: PHARMA MAR, S.A., Madrid (ES)

(72) Inventors: Carmen Kahatt, Madrid (ES); José María Fernandez, Madrid (ES); Salvador Fudio, Madrid (ES); Arturo Soto, Madrid (ES); Pilar Lardelli, Madrid (ES); Cristian Fernandez, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 19/336,341

(22) Filed: Sep. 22, 2025

(65) Prior Publication Data

US 2026/0014148 A1 Jan. 15, 2026

Related U.S. Application Data

(63) Continuation of application No. 18/448,124, filed on Aug. 10, 2023, now Pat. No. 12,433,890, which is a continuation of application No. 17/777,982, filed as application No. PCT/EP2020/065093 on May 29, 2020.

(30) Foreign Application Priority Data

| | | |
|---|---|---|
| Nov. 21, 2019 | (EP) | 19383025 |
| May 14, 2020 | (EP) | 20382409 |
| May 15, 2020 | (WO) | PCT/EP2020/063734 |

(51) Int. Cl.

| | |
|---|---|
| ***A61K 31/4995*** | (2006.01) |
| ***A61K 9/00*** | (2006.01) |
| ***A61K 31/4738*** | (2006.01) |
| ***A61K 31/4745*** | (2006.01) |
| ***A61K 31/573*** | (2006.01) |
| ***A61K 38/19*** | (2006.01) |
| ***A61P 11/00*** | (2006.01) |
| ***A61P 35/00*** | (2006.01) |
| ***C07D 519/00*** | (2006.01) |

(52) U.S. Cl.

CPC ........ *A61K 31/4995* (2013.01); *A61K 9/0019* (2013.01); *A61K 31/4738* (2013.01); *A61K 31/4745* (2013.01); *A61K 31/573* (2013.01); *A61K 38/193* (2013.01); *A61P 11/00* (2018.01); *A61P 35/00* (2018.01); *C07D 519/00* (2013.01); *C07B 2200/13* (2013.01)

(58) Field of Classification Search

CPC ............ A61K 31/4378; A61K 31/4995; A61P 35/00

See application file for complete search history.

(56) References Cited

U.S. PATENT DOCUMENTS

| | | | |
|---|---|---|---|
| 5,089,273 A | 2/1992 | Rinehart et al. | |
| 5,149,804 A | 9/1992 | Rinehart et al. | |
| 5,256,663 A | 10/1993 | Rinehart et al. | |
| 5,478,932 A | 12/1995 | Rinehart et al. | |
| 5,654,426 A | 8/1997 | Rinehart et al. | |
| 5,721,362 A | 2/1998 | Corey | |
| 5,929,059 A | 7/1999 | Sanger et al. | |
| 5,985,876 A | 11/1999 | Rinehart et al. | |
| 6,069,150 A | 5/2000 | Spinelli et al. | |
| 6,124,292 A | 9/2000 | Corey | |
| 6,124,293 A | 9/2000 | Rinehart et al. | |
| 6,316,214 B1 | 11/2001 | Rinehart et al. | |
| 6,348,467 B1 | 2/2002 | Corey | |
| 6,569,859 B1 | 5/2003 | Corey | |
| 6,686,470 B2 | 2/2004 | Danishefsky | |
| 6,815,544 B2 | 11/2004 | Corey | |
| 6,867,334 B2 | 3/2005 | Rinehart et al. | |
| 6,936,714 B2 | 8/2005 | Danishefsky et al. | |
| 7,041,634 B2 | 5/2006 | Weber et al. | |
| 7,097,836 B1 | 8/2006 | Seon | |
| 7,763,615 B2 * | 7/2010 | Gallego | A61P 35/00 514/249 |
| RE41,614 E | 8/2010 | Corey | |
| 7,795,260 B2 | 9/2010 | Barrasa et al. | |

(Continued)

FOREIGN PATENT DOCUMENTS

| | | |
|---|---|---|
| CN | 1823794 A | 10/2005 |
| CN | 106974902 A | 7/2017 |

(Continued)

OTHER PUBLICATIONS

Paz-Ares (Abstract #8506 J. Clin. Oncology vol. 35 published online May 26, 2019) (Year: 2019).*
Paz-Ares (Abstract #8506 J. Clin. Oncology vol. 35 #15 published online May 26, 2019) (Year: 2019).*
Singh (Clinical Cancer Research vol. 27 pp. 2378-2382. Published 2021) (Year: 2021).*
Jones, R.L., Efficacy and Safety of Trabectedin in an Elderly Patient Subgroup (>65 years) with Advanced LMS or LPS for the EAP, CTOS 22nd Annual Meeting, 2017, Abs No. 223.
Borgoni, S., Depletion of tumor-associated macrophages switches the epigenetic profile of pancreatic cancer infiltrating T cells and restores anti-tumor phenotype, OncoImmunology, 2017, vol. 7(2) pp. e 1393596.

(Continued)

*Primary Examiner* — George W Kosturko
(74) *Attorney, Agent, or Firm* — Ballard Spahr LLP

(57) ABSTRACT

Provided are methods for the treatment of SCLC patients by administering therapeutic amounts of lurbinectedin by intravenous infusion. Also provided are methods of treating cancer by administering lurbinectedin in combination with other anticancer drugs, in particular topoisomerase inhibitors. The invention further relates to the administration of lurbinectedin in combination with anti-emetic agents for effective control of symptoms related to nausea and vomiting, reduced lurbinectedin dosages to achieve a safer administration and an increase in the number of treatment cycles. Stable lyophilized formulations of lurbinectedin are also provided.

30 Claims, 8 Drawing Sheets

(56) References Cited

U.S. PATENT DOCUMENTS

| | | | | |
|---|---|---|---|---|
| 8,975,248 | B2 | 3/2015 | Zakneon et al. | |
| 11,883,402 | B2 | 1/2024 | Baek et al. | |
| 12,324,806 | B2 * | 6/2025 | Kahatt | A61K 31/4738 |
| 12,433,890 | B2 * | 10/2025 | Kahatt | A61K 9/0019 |
| 12,440,490 | B2 * | 10/2025 | Kahatt | A61K 31/4995 |
| 12,443,890 | B2 * | 10/2025 | Singhal | G06N 3/098 |
| 2003/0216397 | A1 | 11/2003 | Flores et al. | |
| 2004/0019056 | A1 | 1/2004 | Manzanares et al. | |
| 2004/0059112 | A1 | 3/2004 | Rinehart et al. | |
| 2004/0108086 | A1 | 6/2004 | Takahashi et al. | |
| 2005/0267140 | A1 | 12/2005 | Miller et al. | |
| 2006/0030571 | A1 | 2/2006 | Rinehart et al. | |
| 2007/0082856 | A1 | 4/2007 | Gianni et al. | |
| 2007/0093658 | A1 | 4/2007 | Martinez | |
| 2007/0197517 | A1 | 8/2007 | Jani et al. | |
| 2008/0234279 | A1 | 9/2008 | Rinehart et al. | |
| 2008/0255132 | A1 | 10/2008 | Rowinsky et al. | |
| 2009/0247533 | A1 | 10/2009 | Rinehart et al. | |
| 2009/0253685 | A1 | 10/2009 | Provost et al. | |
| 2013/0266666 | A1 | 10/2013 | Ocana et al. | |
| 2018/0008602 | A1 | 1/2018 | Moneo Ocaña et al. | |

FOREIGN PATENT DOCUMENTS

| | | | | |
|---|---|---|---|---|
| CN | 111298122 | A | 6/2020 | |
| CN | 116284054 | | 6/2023 | |
| CN | 116332932 | | 6/2023 | |
| EP | 0 309 477 | | 6/1987 | |
| EP | 1806349 | A1 | 7/2007 | |
| JP | 59-225189 | | 12/1984 | |
| JP | 60-84288 | | 5/1985 | |
| TW | 202027750 | A | 8/2020 | |
| WO | WO 87/07610 | | 12/1987 | |
| WO | WO 92/09607 | | 6/1992 | |
| WO | WO 98/12198 | | 3/1998 | |
| WO | WO 98/46080 | | 10/1998 | |
| WO | WO 99/51238 | | 10/1999 | |
| WO | 1999058125 | A1 | 11/1999 | |
| WO | WO 99/58125 | | 11/1999 | |
| WO | WO 00/18233 | | 4/2000 | |
| WO | WO 00/69862 | | 11/2000 | |
| WO | WO 01/77115 | | 10/2001 | |
| WO | 200187895 | A1 | 11/2001 | |
| WO | WO0187894 | | 11/2001 | |
| WO | 03014127 | A1 | 2/2002 | |
| WO | 2003008423 | A1 | 1/2003 | |
| WO | 2003066638 | A2 | 8/2003 | |
| WO | 2004017964 | A1 | 3/2004 | |
| WO | WO2004035613 | | 4/2004 | |
| WO | 2005000852 | A2 | 1/2005 | |
| WO | WO 2005/049031 | | 6/2005 | |
| WO | 2005077341 | A1 | 8/2005 | |
| WO | 2006046079 | A1 | 5/2006 | |
| WO | 2006065780 | A2 | 6/2006 | |
| WO | WO 2009/140675 | | 11/2009 | |
| WO | WO2011017145 | A1 | 2/2011 | |
| WO | WO2011147828 | | 12/2011 | |
| WO | WO-2012062920 | A1 * | 5/2012 | A61P 43/00 |
| WO | WO2013082660 | A1 | 6/2013 | |
| WO | 2016137985 | A1 | 9/2016 | |
| WO | 2016192680 | A1 | 12/2016 | |
| WO | WO2021098992 | | 5/2020 | |
| WO | WO2020254471 | A1 | 6/2020 | |
| WO | WO2021043949 | | 3/2021 | |
| WO | WO2021104442 | A1 | 6/2021 | |
| WO | WO2021228414 | | 11/2021 | |
| WO | WO2023116861 | | 12/2022 | |

OTHER PUBLICATIONS

Sugiyama, M., A Case of Malignant Melanoma-like Spindle Sarcoma Treated with Nivolumab and Trabectedin, 59th Annual Meeting of the JSHP, 2017, vol. 64(Supl 4) pp. S41 Abs. N 08-1-5.

McGovern, Y., Systemic Therapy in Metastatic or Unresectable Well-Differentiated/Dedifferentiated Liposarcoma, Front oncol, 2017, vol. 7 arn 292.

Mantovani, A., Tumour-associated macrophages as treatment targets in oncology, Nat Rev Clin Oncol, 2017, vol. 14(7) pp. 399-416.

Petty, A.J., Tumor-associated macrophages: implications in cancer immunotherapy., Immunotherapy, 2017, vol. 9(3) pp. 289-302.

Lee, A.T., Phase III Soft Tissue Sarcoma Trials: Success or Failure?, Curr Treat Opt Oncol, 2017, vol. 18(3) pp. arn 19.

Jones, R.L., Efficacy and safety of trabectedin in an elderly patient subgroup (65 years) with advanced LMS or LPS from the EAP, 42nd ESMO European Cancer Congress, 2017, vol. 28 (Supl 5) pp. 529 Abs No. 1498P.

Magriotis, P. A., Synthetic Approaches to the Stereochemically Complex Antitumor Drug Ecteinascidin-743: A marine natural product named Yondelis . . . , ACS Symosium Series, 2017, vol. 1258(Cap 5) pp. 61-78.

Sinder, B., The Chemotherapeutic Trabectedin Negatively Impacts Osteal Macrophages, Bone Formation and Bone Healing., 2017 Annual Meeting of the ASBMR, 2017, vol. 32 (Supl 1) pp. S 387 Abs N MO0687.

Simetić L., The treatment of locally advanced or metastatic soft tissue sarcomas in the era of innovative therapies . . . historical review in Croatia, 1st Regional Congress of Medicinal Oncology, 2017, vol. 45 (Supl 1) p. 72 Abs No. P27.

Schlenk, R., Randomized Phase 2 Study of Trabectedin/Olaparib Compared to Physician's Choice in subjects with solid tumors . . . DNA Repair Deficiencies, 33 Deutscher Krebskongress, 2018, vol. 41(Supl 1) pp. 120-121 Abs N 236.

Camorani, S., Trabectedin modulates the senescence-associated secretory phenotype and promotes cell death in senescent tumor cells . . . , Oncotarget, 2018, vol. 9(28) pp. 19929-19944.

Pham, L.V., The Role of Macrophage/B-Cell Interactions in the Pathophysiology of B-Cell Lymphomas, Front Oncol, 2018, vol. 8 arn 147.

Gordon, E.M., Phase 1/2 study of safety/efficacy using trabectedin, ipilimumab and nivolumab triple therapy as first line treatment of advanced STS., ASCO 54th Annual Meeting, 2018, vol. 36 (Supl) Abs. N TPS11591 (poster).

Gordon, E.M., Phase 1/2 study of safety/efficacy using trabectedin, ipilimumab and nivolumab triple therapy as first line treatment of advanced STS., ASCO 54th Annual Meeting, 2018, vol. 36 (Supl) Abs. N TPS11591 (abstract).

Chawla, S.P., Clinical experience with combination chemo-/immunotherapy using trabectedin and nivolumab for advanced soft tissue sarcoma, ASCO 54th Annual Meeting, 2018, vol. 36 (Supl) Abs. N e23568.

Chawla, S.P., Clinical Experience with Combination Chemo-/Immunotherapy using Trabectedin and Nivolumab for Advanced Soft Tissue Sarcoma, J Sarcoma Res, 2018, vol. 2(1) pp. 1009.

Gadducci, A., A phase II randomised (calibrated design) study on the activity of the single-agent trabectedin in metastatic/relapsed uterine LMS, Br J Cancer, 2018, vol. 119(5)pp. 565-571.

Jones, R.L., Efficacy and tolerability of trabectedin in elderly sarcoma patients: subgroup analysis from a phase 3 study of trabectedin or dacarbazine . . . , Ann Oncol, 2018, vol. 29(9) pp. 1995-2002.

Kuroshima, M., Multimodality therapy for the patients with advanced or recurrent uterine leiomyosarcoma., 70th Annual Congress JSOG, 2018, vol. 44(8) pp. 1610 Abs.N ISP-38-7.

Nelson, J., Budget Impact Analysis of Trabectedin for Second-Line Treatment of pts with unresectable or metastatic LPS or LMS, AMCP Managed Care Annual Meeting, 2018, vol. 24 (Supl 4-A) pp. S91 Abs N M24.

Navarria, F., Radiotherapy (RT) combined with Trabectedine for locally advanced or metastatic STS: update of a single institution experience, CTOS 23nd Annual Meeting, 2018, Abs 084.

Italiano, A., Targeting Microenvironment and Cellular Immunity in sarcomas with weekly Trabectedin combined with Metronomic Cyclophosphamide (TARMIC), CTOS 23nd Annual Meeting, 2018, Abs 086 (poster).

(56) References Cited

OTHER PUBLICATIONS

Italiano, A., Targeting Microenvironment and Cellular Immunity in sarcomas with weekly Trabectedin combined with Metronomic Cyclophosphamide (TARMIC), CTOS 23nd Annual Meeting, 2018, Abs 086 (abstract).
Gordon, E.M., The Saint: Initial Results of a Phase 1/2 study of Safety/Efficacy using Ipilimumab, Nivolumab and Trabectedin in 1st line advanced STS, CTOS 23nd Annual Meeting, 2018, Abs 237.
Casagrande, N., Trabectedin Inhibits Classic Hodgkin Lymphoma Growth, Monocytes Immunosuppressive Polarization and Synergizes with CCR5-Antagonist Maraviroc, 11th Int. Symposium on HL, 2018, vol. 2(Supl 3) Abs No. T005(007).
Denton, N.L., Myelolytic Treatments Enhance Oncolytic Herpes Virotherapy in Models of Ewing Sarcoma by Modulating the Immune Microenvironment., Mol Ther Oncolytics, 2018, vol. 11 pp. 62-74.
Sebio, A., The current landscape of early durg development for patients with sarcoma in immunotherapy era, Future Oncol, 2018, vol. 14(12) pp. 1197-1211.
Gordon, E.M., Cancer immunotherapy using trabectedin and nivolumab in advanced soft tissue sarcoma: A retrospective analysis., ASCO-SITC Clinical Symposium 2018, 2018, vol. 36(5 Supl) Abs N 40 (poster).
Gordon, E.M., Cancer immunotherapy using trabectedin and nivolumab in advanced soft tissue sarcoma: A retrospective analysis., ASCO-SITC Clinical Symposium 2018, 2018, vol. 36(5 Supl) Abs N 40 (abstract).
Jones, J.D., Trabectedin Reduces Skeletal Prostate Cancer Tumor Size in Association with Effects on M2 Macrophages and Efferocytosis, Neoplasia, 2019, vol. 21(2) pp. 172-184.
Gronchi, A., Trabectedin and Radiotherapy in STS (TRASTS): Results of a Phase I Study in Myxoid Liposarcoma from Spanish, Italian, French Groups, EClinicalMedicine, 2019, vol. 9 pp. 35-43.
Peraza, D.A., Re-Education of Tumor Associated Macrophages by Trabectedin, 63rd Annual Meeting Biophysical-Society, 2019, vol. 116 (3 Supl 1) pp. 539-540 Abs N 2675-Pos.
Peraza, D.A., Trabectedin Re-Educates Resting Peritoneal Macrophages into M1 Subtype, 63rd Annual Meeting Biophysical-Society, 2017, vol. 116 (3 Supl 1) pp. 405 Abs N 1995-Poster.
Larionova, I., Interaction of tumor-associated macrophages and cancer chemotherapy, Oncolmmunology, 2019, vol. 8 (7) arn 1596004.
Preusser, M., Trabectedin for recurrent WHO grade II or III meningioma: Randomized phase II study of the EORTC Brain Tumor Group, ASCO 55th Annual Meeting, 2019, vol. 37 (Supl 15) Abs N 2007 (poster).
Preusser, M., Trabectedin for recurrent WHO grade II or III meningioma: Randomized phase II study of the EORTC Brain Tumor Group, ASCO 55th Annual Meeting, 2019, vol. 37 (Supl 15) Abs N 2007 (abstract).
Gordon, E.M., Saint: Results of a phase 1/2 study using safe amounts of ipilimumab, nivolumab, and trabectedin in advanced STS., ASCO 55th Annual Meeting, 2019, vol. 37(Supl 15) Abs N 11016 (poster).
Gordon, E.M., Saint: Results of a phase 1/2 study using safe amounts of ipilimumab, nivolumab, and trabectedin in advanced STS., ASCO 55th Annual Meeting, 2019, vol. 37(Supl 15) Abs N 11016 (abstract).
Patel, S., Overall Survival and Histology-Specific Subgroup Analyses From a Phase 3 study of Trabectedin or Dacarbazine in Advanced LPS or LMS, Cancer, 2019, vol. 125(15) pp. 2610-2620.
Monk, B.J., randomized study comparing trabectedin and PLD with PLD alone for advanced-relapsed epithelial ovarian, primary peritoneal, or fallopian tube cancer, 50th Annual Meeting SGO, 2019, vol. 154(Supl 1) pp. 12-13 Abs N 20 (poster).
Monk, B.J., randomized study comparing trabectedin and PLD with PLD alone for advanced-relapsed epithelial ovarian, primary peritoneal, or fallopian tube cancer, 50th Annual Meeting SGO, 2019, vol. 154(Supl 1) pp. 12-13 Abs N 20 (abstract).
Prenen, H., Tumor-associated macrophages: a short compendium, Cell Mol Life Sci, 2019, vol. 76(8) pp. 1447-1458.
Blay, J.Y., Treatment of advanced soft tissue sarcoma by histological subtype: wish, prediction or reality?, Future Oncol, 2019, vol. 15(26 Supl) pp. 5-10.
Banerjee, P., Trabectedin reveals a strategy of immunomodulation in chronic lymphocytic leukemia, Cancer Immunol Res, 2019, vol. 7(12) pp. 2036-2051.
Colombo, N., Multicenter, randomised trial on bevacizumab and trabectedin with or without carboplatin in platinum-sensitive ROC., Br J Cancer, 2019, vol. 121(9) pp. 744-750.
Martín-Broto, J., Trabectedin with concurrent low-dose radiation therapy for metastatic STS: A phase II trial of Spanish, French and Italian groups, ESMO Congress, Barcelona, 2019, vol. 30 (Supl 5) pp. v686-v687 Abs No. 1674PD (poster).
Martín-Broto, J., Trabectedin with concurrent low-dose radiation therapy for metastatic STS: A phase II trial of Spanish, French and Italian groups, ESMO Congress, Barcelona, 2019, vol. 30 (Supl 5) pp. v686-v687 Abs No. 1674PD (abstract)—2019.
Heilig, Ch.E., TOP-ART / PMO-1603: Randomized Phase 2 Study of Trabectedin/Olaparib in subjects with DNA Repair Deficiencies, ESMO Congress, Barcelona, 2019, vol. 30 (Supl 5) pp. v795-v796 Abs N 1979TiP (poster).
History of Changes for Study:NCT06088290—Oct. 16, 2023.
Pharma Mar clinical study report—PM1183-C-004-14 2014-005251-39—May 31, 2019.
EU Clinical Trials Register 2015-00206-18—Nov. 27, 2019.
REEC 2019-001553-12—Dec. 13, 2019.
REEC 2019-002261-35—Jul. 9, 2020.
REEC 2021-001930-20—Feb. 22, 2022.
REEC 2021-004471-13—Jun. 6, 2022.
REEC 2022-502975-45-00—Dec. 11, 2023.
EU Clinical Trials Register 2015-000206-18—Nov. 27, 2019.
AEMPS 2015-001141-80—Pivotal Clinical Study Report Synopsis phase I—Apr. 7, 2016.
AEMPS 2015-001141-80—Pivotal Clinical Study Report Synopsis phase II—Jan. 14, 2019.
AEMPS 2015-001641-89—Pharma Mar clinical study report PM1183-C-003-14—Feb. 10, 2021.
EU Clinical Trials Register 2015-003602-16—Mar. 3, 2023.
EU Clinical Trials Register 2017-001016-11—Jan. 13, 2021.
EU Clinical Trials Register 2019-001553-12—Sep. 4, 2019.
EU Clinical Trials Register 2019-002261-35—Feb. 28, 2020.
EU Clinical Trials Register 2021-001930-20—Dec. 28, 2021.
EU Clinical Trials Register 2021-004471-13—Jun. 7, 2022.
EU Clinical Trials Register 2022-001114-19—Apr. 3, 2023.
History of Changes for Study: NCT04253145—Jan. 31, 2020.
Record History: NCT04253145—Jan. 31, 2020.
History of Changes for Study:NCT04291937—Jun. 17, 2020.
History of Changes for Study:NCT04607954—Oct. 27, 2020.
History of Changes for Study:NCT04610658—Oct. 26, 2020.
History of Changes for Study:NCT04638491—Nov. 16, 2020.
History of Changes for Study:NCT04802174—Mar. 16, 2021.
History of Changes for Study:NCT04894591—May 20, 2021.
History of Changes for Study:NCT05042934—Sep. 8, 2021.
History of Changes for Study:NCT05063318—Sep. 27, 2021.
History of Changes for Study:NCT05072106—Sep. 27, 2021.
History of Changes for Study:NCT06021483—Aug. 16, 2023.
History of Changes for Study:NCT05099666—Oct. 18, 2021.
History of Changes for Study: NCT05101265—Oct. 19, 2021.
History of Changes for Study: NCT05126433—Nov. 8, 2021.
History of Changes for Study: NCT05153239—Nov. 29, 2021.
History of Changes for Study: NCT05229588—Feb. 4, 2022.
History of Changes for Study:NCT05244239—Feb. 8, 2022.
History of Changes for Study:NCT05285033—Mar. 16, 2022.
History of Changes for Study:NCT05572476—Oct. 5, 2022.
History of Changes for Study:NCT05574504—Oct. 7, 2022.
History of Changes for Study:NCT05578326—Oct. 12, 2022.
History of Changes for Study:NCT05636111—Nov. 23, 2022.
History of Changes for Study:NCT05734066—Feb. 15, 2023.
History of Changes for Study:NCT05740566—Feb. 21, 2023.
History of Changes for Study:NCT05800587—Mar. 24, 2023.
History of Changes for Study:NCT05876715—May 17, 2023.
History of Changes for Study:NCT05918640—Jun. 15, 2023.

(56) References Cited

OTHER PUBLICATIONS

Le Cesne, A., Assessing the clinical impact of trabectedin in patients with Lsarcomas progressing despite prior conventional chemotherapy . . . , ECCO 14 Barcelona, 2007, vol. 5(4) pp. 405 (Abs. No. P7512) (poster).
Chawla, S., Clinical tolerability of Trabectedin administered by two different schedules (weekly for 3 of 4 weeks vs. q3 weeks) in L-sarcomas . . . , ECCO 14 Barcelona, 2007, vol. 5(4) pp. 407 (Abs. No. P7517) (abstract).
Chawla, S., Clinical tolerability of Trabectedin administered by two different schedules (weekly for 3 of 4 weeks vs. q3 weeks) in L-sarcomas . . . , ECCO 14 Barcelona, 2007, vol. 5(4) pp. 407 (Abs. No. P7517) (poster).
Sica, A., Targeting tumour-associated macrophages, Expert Opin Ther Targets, 2007, vol. 11(9) pp. 1219-1229.
Porta, C., Tumor promotion by tumor-associated macrophages., Adv Exp Med Biol, 2007, vol. 604 pp. 67-86.
Sleijfer, S., Trial Methodology in Soft Tissue Sarcomas; the "One Plus One is Three or Zero" Phenomenon, Onkologie, 2008, vol. 31(1-2) p. 6-8.
Tercero, J.C., Predicting sarcoma-patients response to Trabectedin treatment with molecular markers detected by immunohistochemistry, AACR International Conference, 2008, Abs. No. B8 (abstract).
Tercero, J.C., Predicting sarcoma-patients response to Trabectedin treatment with molecular markers detected by immunohistochemistry, AACR International Conference, 2008, Abs. No. B8 (poster).
Germano, G., Anti-inflammatory properties of the novel anti-tumor agent trabectedin: Reduction of ccl2, il-6 and pentraxin-3 . . . , AACR Annual Meeting, 2008, Abs. N 1197.
Barthomeuf, C., Marine metabolites overcoming or circumventing multidrug resistance mediated by ATP-dependent transporters . . . , Anticancer Agents Med Chem, 2008, vol. 8(8) pp. 886-903.
Forouzesh, B., Phase I and Pharmacokinetic Study of Trabectedin as a 1- or 3-hour Infusion Weekly in Patients with Advanced Solid Malignancies, Clin Cancer Res, 2009, vol. 15(10) pp. 3591-3599.
Delaloge, S., Preliminary safety and activity results of trabectedin in a phase II trial dedicated to triple-negative, HER2+++, or BRCA1/2 germ-line-mutated MBC pts., ASCO 45th Annual Meeting, 2009, vol. 27(15 Supl) p. 43 Abs. N 1010 (poster).
Delaloge, S., Preliminary safety and activity results of trabectedin in a phase II trial dedicated to triple-negative, HER2+++, or BRCA1/2 germ-line-mutated MBC pts., ASCO 45th Annual Meeting, 2009, vol. 27(15 Supl) p. 43 Abs. N 1010 (abstract).
Demetri, G.D., Long-term results of a randomized phase II study of trabectedin by two regimens in pts with advanced LPS or LMS after failure of prior chemotherapy, ASCO 45th Annual Meeting, 2009, vol. 27(15 Supl) p. 538 Abs. N 10509 (poster).
Demetri, G.D., Long-term results of a randomized phase II study of trabectedin by two regimens in pts with advanced LPS or LMS after failure of prior chemotherapy, ASCO 45th Annual Meeting, 2009, vol. 27(15 Supl) p. 538 Abs. N 10509 (abstract).
McMeekin, D.S., Single-agent trabectedin as second-line therapy of persistent or recurrent endometrial cancer: Results of a multicenter phase II study, Gynecol Oncol, 2009, vol. 114(2) pp. 288-292.
Del Campo, J.M., Phase II randomized study of trabectedin given as two different every 3 weeks dose schedules to patients with relapsed, platinum-sensitive ovarian cancer, Ann Oncol, 2009, vol. 20(11) pp. 1794-1802.
Demetri, G.D., Efficacy and Safety of Trabectedin in Patients With Advanced or Metastatic LPS or LMS After Failure of Prior Anthracyclines and Ifosfamide . . . , J Clin Oncol, 2009, vol. 27(25) pp. 4188-4196.
Pecorelli, S., Phase II of oral gimatecan in patients with recurrent epithelial ovarian, fallopian tube or peritoneal cancer . . . , Ann Oncol, 2009, vol. 21(4) pp. 759-765.
Petrelli, F., Current data of targeted therapies for the treatment of triple-negative advanced breast cancer: empiricism or evidence-based?, Expert Opin Invest Drugs, 2009, vol. 18(10) pp. 1467-1477.
Zhang, C.H., Can hepatocellular carcinoma be treated by Yondelis through targeting both tumor cells and tumor-associated macrophages?, Hepatogastroenterology, 2010, vol. 57(97) pp. 114-116.
Kim, H, Experience of the use of trabectedin (ET-743) in patients with advanced soft tissue sarcoma failing doxorubicin and/or ifosfamide in Korea, ASCO 46th Annual Meeting, 2010, Abs N e20518—2010.
Monk, B.J., Activity of docetaxel plus trabectedin in recurrent or persistent ovarian and primary peritoneal cancer: Phase II study of the GOG., ASCO 46th Annual Meeting, 2010, vol. 28(15 Supl) p. 401 Abs No. 5046 (poster).
Monk, B.J., Activity of docetaxel plus trabectedin in recurrent or persistent ovarian and primary peritoneal cancer: Phase II study of the GOG., ASCO 46th Annual Meeting, 2010, vol. 28(15 Supl) p. 401 Abs No. 5046 (abstract).
Monk, B.J., Docetaxel plus trabectedin appears active in recurrent or persistent ovarian and primary peritoneal cancer after up to three prior regimens . . . , Gynecol Oncol, 2011, vol. 120(3) pp. 459-463.
Martinez-Serra, J., Yondelis (ET-743, Trabectedin) sensitizes cancer cell lines to CD95-mediated cell death: New molecular insight into the mechanism of action, Eur J Pharmacol, 2011, vol. 658(2-3) pp. 57-64.
Mabuchi, S., The activity of trabectedin as a single agent or in combination with everolimus for clear cell carcinoma of the ovary, Clin Cancer Res, 2011, vol. 17(13)pp. 4462-4473.
Markman, M., Docetaxel plus trabectedin appears active in recurrent or persistent ovarian and primary peritoneal cancer after up to three prior regimes . . . , Gynecol Oncol, 2011, vol. 122(2)pp. 462.
Chahine, G.Y., Experience of the use of trabectedin in pretreated unresectable, advanced, or metastatic soft tissue sarcoma in nine centers in Lebanon . . . , ASCO 47th Annual Meeting, 2011, vol. 29(15 Supl) Abs N e20533.
Sill, M.W., Comments on: "Docetaxel plus trabectedin appears active in recurrent or persistent ovarian and primary peritoneal cancer . . . ", Gynecol Oncol, 2011, vol. 122(2) pp. 462-463.
Germano, G., Targeting of the innate immunity/inflammation as complementary anti-tumor therapies, Ann Med, 2011, vol. 43(8) pp. 581-593.
Morgan, S.S., Systematic Therapy for Unresectable or Metastatic Soft-Tissue Sarcomas: Past, Present, and Future, Curr Oncol Rep, 2011, vol. 13(4) pp. 331-349.
Mabuchi, S., The Activity of Trabectedin as a Single Agent or in Combination with Everolimus for clear Cell Carcinoma of the Ovary, 17th International Meeting of the ESGO, 2011, vol. 21(Supl 3) (poster).
Mabuchi, S., The Activity of Trabectedin as a Single Agent or in Combination with Everolimus for clear Cell Carcinoma of the Ovary, 17th International Meeting of the ESGO, 2011, vol. 21(Supl 3) (abstract).
Liguori, M., Tumor-Associated Macrophages as Incessant Builders and Destroyers of the Cancer Stroma, Cancers, 2011, vol. 3(4) pp. 3740-3761.
Paz-Ares, L., Trabectedin in pre-treated patients with advanced or metastatic soft tissue sarcoma: a phase II study evaluating co-treatment with dexamethasone, Invest New Drugs, 2012, vol. 30(2) pp. 729-740.
Monk, B.J., A phase II evaluation of trabectedin in the treatment of advanced, persistent, or recurrent uterine leiomyosarcoma: A GOG study, Gynecol Oncol, 2012, vol. 124(1)pp. 48-52.
Massuti, B., Trabectedin in patients with advanced NSCLC with XPG and/or ERCC1 overexpression and BRCA1 underexpression pretreated with platinum, Lung Cancer, 2012, vol. 76(3)pp. 354-361.
Adam, K., Efficacy and Safety of Trabectedin versus Gemcitabine/Docetaxel in Patients with Sarcoma after failure of Anthracycline and/or Ifosfamide, AOS Asian Oncology Summit, 2012, vol. 48(Supl 4) pp. 7-8 Abs No. AOS12 (poster).
Adam, K., Efficacy and Safety of Trabectedin versus Gemcitabine/Docetaxel in Patients with Sarcoma after failure of Anthracycline and/or Ifosfamide, AOS Asian Oncology Summit, 2012, vol. 48(Supl 4) pp. 7-8 Abs No. AOS12 (abstract).
Pink, D., Efficacy of Trabectedin in Patients with Advanced or Metastatic Alveolar Soft-Part Sarcoma, Onkologie, 2012, vol. 35(5) pp. 249-252.

(56) References Cited

OTHER PUBLICATIONS

Palomo Colli, M.A., Trabectedin in pretreated pediatric patients with relapsed or progressive advanced sarcomas: Toxicity and efficacy., ASCO 48th Annual Meeting, 2012, Abs. N e20005.
Saada, E., Rechallenge with trabectedin in patients with locally advanced or metastatic STS following drug holiday: experience of the FSG., ASCO 48th Annual Meeting, 2012, vol. 30 (Supl 1) Abs. N 10062 (poster).
Saada, E., Rechallenge with trabectedin in patients with locally advanced or metastatic STS following drug holiday: experience of the FSG., ASCO 48th Annual Meeting, 2012, vol. 30 (Supl 1) Abs. N 10062 (abstract).
Verweij, J., Alveolar Soft Part Sarcoma: Should We Be Targeting the Tumor or Targeting the Vasculature?, Onkologie, 2012, vol. 35(5) pp. 237-238.
Chuk, M.K., A phase I trial and pharmacokinetic study of a 24-hour infusion of trabectedin in children and adolescents with solid tumors., Pediatr Blood Cancer, 2012, vol. 59(5) pp. 865-869.
Martin Broto, J., Randomized clinical trial of doxorubicin vs. trabectedin plus Doxo in 1st-line treatment of advanced non-operable/ metastatic STS: GEIS-20, 37th ESMO Congress, 2012, vol. 23(Supl 9) p. 490 Abs. N 1517TiP (poster).
Martin Broto, J., Randomized clinical trial of doxorubicin vs. trabectedin plus Doxo in 1st-line treatment of advanced non-operable/ metastatic STS: GEIS-20, 37th ESMO Congress, 2012, vol. 23(Supl 9) p. 490 Abs. N 1517TiP (abstract).
Yue, Z-q., Tumor-associated macrophages: a novel potential target for cancer treatment, Chinese Med J, 2012, vol. 125(18) pp. 3305-3311.
Benedetti Panici, P., Phase II trial of weekly trabectedin plus weekly pegylated liposomal doxorubicin for recurrent ovarian carcinoma, IGCS 14th Biennial Meeting, 2012, vol. 22(8 Supl3) p. 271 (poster).
Grant, "Single-Agent Chemotherapy Trials in Small-Cell Lung Cancer, 1970- to 1990: The Case for Studies in Previously Treated Patients," 10(3) J. Clin. Oncology 484, 485-86 (1992).
Planting, "Phase II Study of ACNU as Second-Line Treatment in Small-Cell Lung Cancer," 29 Cancer Chemotherapy & Pharmacology 409, 409 (1992).
Giaccone, "4'-Deoxydoxorubicin, an Inactive Drug in Small Cell Lung Cancer," 23(9) Eur. J. Cancer Clin. Oncology 1407, 1408 (1987).
Viallet, "Tallimustine Is Inactive in Patients with Previously Treated Small Cell Lung Cancer. A Phase II Trial of the National Cancer Institute of Canada Clinical Trials Group," 15 Lung Cancer 367, 372 (1996)6.
Fiebig, "Phase II Clinical Trial of Lobaplatin (D-19466) in Pretreated Patients with Small-Cell Lung Cancer," 19 Onkologie 328, 330 (1996).
Dy, "A Phase II Trial of Imatinib (ST1571) in Patients with C-Kit Expressing Relapsed Small-Cell Lung Cancer: a CALGB and NCCTG Study," 16 Annals of Oncology 1811, 1811 (2005).
Baggstrom, "A Phase II Study of AT-101 (Gossypol) in Chemotherapy-Sensitive Recurrent Extensive Stage Small Cell Lung Cancer (ES-SCLC)," 6(10) J. Thoracic Oncology 1757, Oct. 2011.
Rudin, "Phase II Study of Single-Agent Navitoclax (ABT-263) and Biomarker Correlates in Patients with Relapsed Small Cell Lung Cancer," 18(11) Clinical Cancer Research 3163, 3163, Jun. 1, 2012.
Otterson, "Phase II Study of the HDAC Inhibitor Romidepsin in Relapsed Small Cell Lung Cancer (CALGB 30304)," 5 (1) J. Thoracic Oncology 1644, 1644, Oct. 2010.
Bleehen, "Controlled Trial of Twelve Versus Six Courses of Chemotherapy in the Treatment of Small-Cell Lung Cancer," 59 Brit. J. Cancer 584, 584, 589-90 (1989).
Schiller, "Topotecan Versus Observation After Cisplatin Plus Etoposide in Extensive-Stage Small-Cell Lung Cancer: E7593-A Phase III Trial of the Eastern Cooperative Oncology Group," 19(8) J. Clin. Oncology 2114, 2114 (2001).
Shepherd, "Prospective, Randomized, Double-Blind, Placebo-Controlled Trial of Marimastat After Response to First-Line Chemotherapy in Patients With Small-Cell Lung Cancer: A Trial of the National Cancer Institute of Canada—Clinical Trials Group and the European Organization for Research and Treatment of Cancer," 20(22) J. Clin. Oncology 4434, 4434 (2002).
Arnold, "Phase II Study of Vandetanib or Placebo in Small-Cell Lung Cancer Patients After Complete or Partial Response to Induction Chemotherapy With or Without Radiation Therapy: National Cancer Institute of Canada Clinical Trials Group Study BR.20," 25 J. Clin. Oncology 4278, 4282 (2007).
Lee, "Anti-Angiogenic Therapy Using Thalidomide Combined With Chemotherapy in Small Cell Lung Cancer: A Randomized, Double-Blind, Placebo-Controlled Trial," 101(15) J. National Cancer Institute 1049, 1049 (2009).
Highleyman, FDA Approves Zepzelca for Metastatic Small-Cell Lung Cancer, Cancer Health (Jun. 16, 2020), https://www.cancerhealth.com/article/fda-zepzelca-sclc (last visited Jul. 17, 2025).
Subbiah, Data on FDA Approved Therapy for Relapsed/Refractory SCLC, Onclive (Aug. 20, 2020), https://www.onclive.com/view/data-onfda-approved-therapy-for-relapsed-refractory-sclc (last visited Jul. 17, 2025).
Zepzelca New Therapy Approved for Metastatic Small-Cell Lung Cancer, 10(7) Oncology Practice Management (Jul. 20, 2020), https://oncpracticemanagement.com/articles/1638:zepzelca-new-therapy-approved-formetastatic-small-cell-lung-cancer (last visited Jul. 17, 2025).
Pollock, "Appropriate Prescribing of Medications: An Eight-Step Approach," 75(2) Am. Family Physician 231, 231-33 (2007).
https://www.zepzelca.com/what-zepzelca-does/—Mar. 4, 2026.
https://www.zepzelcapro.com/mechanism-of action/—Mar. 4, 2026.
Jazz Pharmaceuticals, Jazz 239 Pharmaceuticals Announces U.S. FDA Accelerated Approval of Zepzelca™ (lurbinectedin) for the Treatment of Metastatic Small Cell Lung Cancer, https://investor.jazzpharma.com/news-releases/news-release-details/jazz-pharmaceuticalsannounces-us-fda-accelerated-approval (last accessed Jul. 31, 2025)—Jun. 15, 2020.
clinicaltrial.gov Search Results for Lurbinectedin trials sponsored by PharmaMar (25 results), https://clinicaltrials.gov/search?intr=lurbinectedin&spons=PharmaMar), Mar. 4, 2026.
Caves, "Patent Expiration, Entry, and Competition in the U.S. Pharmaceutical Industry," Brookings Papers on Econ. Activity: Microeconomics 44-45 (1991).
Reiffen "Generic Drug Industry Dynamics," 87(1) Rev. Econ. & Stats. 37-38 (2005).
Jazz Pharmaceuticals, PharmaMar and Jazz Pharmaceuticals Sign Exclusive License Agreement for Lurbinectedin in the U.S. (Dec. 19, 2019), https://investor.jazzpharma.com/news-releases/news-release-details/pharmamar-and-jazz[1]pharmaceuticals-sign-exclusive-license (last accessed Jul. 31, 2025)—Dec. 19, 2019.
Seaman, Comparative NMR and Modeling Study of Et 743, Et 736, and Et 729 Adducts of DNA Duplexes Containing Either the Favored or Less-Favored Target Sequences, PROC. 1999 AACR-NCI-EORTC INT'L CONF., Molecular Targets and Cancer Therapeutics: Discovery, Development and Clinical Validation, vol. 5 (Nov. Suppl.), 3851s, Abstract No. 604 (1999).
Simon, Lungenkarzinom: Kombination mit Lurbinectedin schlagt Antikorper-Monotherapie [Lung Cancer: Combination with lurbinectedin beats antibody monotherapy] Tumor Diagnosis and Therapy 2025: 46 16 202S. (Original)—Nov. 25, 2025.
Simon, Lungenkarzinom: Kombination mit Lurbinectedin schlagt Antikorper-Monotherapie [Lung Cancer: Combination with lurbinectedin beats antibody monotherapy] Tumor Diagnosis and Therapy 2025: 46 16 202S. (English)—Nov. 25, 2025.
Shields et al. ISL1: A Novel Neuroendocrine Subtype in Small Cell Lung Cancer Predicts Durable Response to Lurbinectedin. Mol Cancer Ther—Jan. 26, 2026.
Goodman & Gilman, The Pharmacological Basis of Therapeutics, p. 36 (1975).
Riccardi et al., "Effective Combinations ofET-743 and Doxorubicin for Tumor Growth Inhibitions Against Murine and Human Sarcomas in Athymic Mice," from the Proceedings of the AACR, vol. 42, Abstract 1132 (Mar. 2001).

(56) References Cited

OTHER PUBLICATIONS

Takahashi et al., "Ecteinascidin 743 (ET-743) and doxorubicin produce synergistic cytotoxic effects in soft tissue sarcoma lines HT-1080 and HS-IS," Clinical Cancer Research, vol. 6, Abstract 208 (Nov. 2000).
Erba et al., "Synergistic cytotoxic effect ofET-743 and cisplatin," Clinical Cancer Research, vol. 6, Abstract 209 (Nov. 2000).
Faircloth et al., "In Vivo Combinations of Chemotherapeutic Agents with Ecteinascidin 743 (ET743) Against Solid Tumors," from the Proceedings ofthe AACR NCI-EORTC Conference ofNov. 2001, Abstract 387—Nov. 1, 2001.
Riccardi et al., "Preclinical Activity and Biodistribution ofEcteinascidin 743 (ET-743) and Doxorubicin (DOX) Combinationsin Human Rhabdomyosarcorna," from the AACR-NCI-EORTC Conference on Molecular Targets and Cancer Therapeutics of, Oct. 29-Nov. 2, 2001, Abstract 405.
Erba et al., "ET-743 and Cisplatin (DDP) Show in Vitro and in Vivo Synergy Against Human Sarcoma and Ovarian Carcinoma Cell Lines," from the AACR NCI-EORTC Conference on Molecular Targets and Cancer Therapeutics Oct. 29-Nov. 2, 2001, Abstract 406.
Donald et al., "Complete Protection by High-Dose Dexamethasone against the Hepatotoxicity ofthe Novel Antitumor Drug Yondelis (ET-743) in the Rat," Cancer Research 63: 5902-5908, Sep. 15, 2003.
D'Incalci et al., "The Combination ofET-743 and Cisplatin (DDP): From a Molecular Pharmacology Study to a Phase I Clinical Trial," from the AACR Annual Meeting of Apr. 6-10, 2002, Abstract 404.—Apr. 6, 2002.
D'Incalci et al., "The combination of yondelis and cisplatin is synergistic against human tumor xenografts," European Journal of Cancer 39: 1920-1926 (2003).—Sep. 1, 2003.
Erba et al., "Combination ofyondelis (ET-743) and oxaliplatin in experimental ovarian cancer," from the AACR-NCI-EORTC International Conference on Molecular Targets and Cancer Therapeutics of Nov. 17-21, 2003, Abstract C247.
Meco et al., "The combination ofET-743 and Irinotecan is active in preclincal models in rhabomyosarcoma," presented at the 16th EORTC-NCI-AARC Symposium on Molecular Targets and Cancer Therapeutics held in Geneva on Sep. 28-Oct. 1, 2004.
FDA approved label for Pharmacist and Upjohn's Doxorubicin Hydrochloride for Injection (May 8, 2003).
Kesteren et al., "Yondelis® (trabectedin, ET-743): the development of an anticancer agent of marine origin," Anti-Cancer drugs, 14:487-502 (2003).
McLeod, "Clinically relevant drug-drug interactions in oncology," Br. J. Clin. Pharmacol., 45:539-544 (1998).
Dick et al., "Building on bortezomib: second-generation proteasome inhibitors as anti-cancer therapy", Drug Discovery Today, Elsevier, Rahway, NJ, US, vol. 15, No. 5-6, pp. 243-249, Mar. 2010.
G J Peters et al., "Basis for effective combination cancer chemotherapy with antimetabolites", Pharmacology & Therapeutics, pp. 227-253, 2000.
Robert et al., "Pharmacokinetics of Doxorubicin in Sarcoma Patients," European Journal of Clinical Pharmacology, 31: 695-699, 1987.
Cvitkovic et al., "Final Results of a Phase I Study of Ecteinascidin-743 (ET-743) 24 Hour (h) Continuous Infusion (CI) in Advanced Solid Tumors (AST) Patients (PTS) (Meeting Abstract)," 1999 ASCO Annual Meeting, Abstract No. 690, 1999.
Tannock, I.F. and Hill, R.P., The Basic Science of Oncology, New York, McGraw-Hill, 1992.
Villalona-Calero et al., "Final Results of a Phase I and Pharmacokinetic (PK) Study of the Marine Minor Groove Binder ET-743 on a Daily X 5 Schedule. (Meeting abstract)," 1999 ASCO Annual Meeting, Abstract No. 691, 1999.
Takuro Mizukami, et al. Immunotherapy for gastric cancer. Medical History, 2018, vol. 266 No. 9, pp. 711-716.
Tomita Y., A New era of Immune Checkpoint Inhibitor Cancer Drug Therapy Current Status of Immune Checkpoint Inhibitors in Each Tumor Urological Cancer (Renal Cell Carcinoma, Urothelial Carcinoma). Yakuji (The Pharmaceuticals Monthly). 2017; 59(12): 2413-2419 (37-43).
Rotte. Combination of CTLA-4 and PD-1 blockers for treatment of cancer. J Exp Clin Cancer Res. Jun. 13, 2019;38 (1):255.
"Lurbinectedin Approved in the U.S. for Advanced Small Cell Lung Cancer" URL https://medical.nikkeibp.co.jp/leaf/all/cancernavi/news/202006/566098.html, Jun. 18, 2020.
Zepzelca label, Feb. 2026.
Cheuvart et al. Doxorubicin paclitaxel in pretreated advanced small-cell lung cancer: a large real-life retrospective study. TLCR vol. 14, No. 10, Oct. 2025.
Beibei Liu et al. Biomimetic 3D-Bioprinted organoids of thymic epithelial tumors for translational drug screening and biomarker identification. Materials Today Bio vol. 37, 102878, Apr. 2026.
Kurshid et al. Multidisciplinary assessment of patients with extensive stage small cell lung cancer: A geriatric tumor board. CA: A Cancer Journal for Clinicians, vol. 75, Issue 6 pp. 475-484, Jun. 24, 2025.
Yang et al. Synthetic strategies and therapeutic insights into FDA-approved indole-containing drugs. Journal of Enzyme Inhibition and Medicinal Chemistry vol. 41, Issue 1, 2026.
Ponce. Combination of Lurbinectedin plus Irinotecan: Preclinical and Early Clinical Results in Relapsed Small Cell Lung Cancer Patients. Journal of Thoracic Oncology. Articles in Press103654, Mar. 3, 2026.
Polymorphism in Pharmaceutical Solids, edited by Harry G. Brittain; Drugs and the Pharmaceutical Sciences, vol. 95; Publisher Marcel Dekker, Inc., Mar. 18, 1999.
Barber, N.A., et al., "Hematologic toxicities of small molecule tyrosine kinase inhibitors," Targ Oncol, 6, 203-215, Nov. 30, 2011.
Izak, M., et al., "Management of thrombocytopenia," F1000Prime Reports, 6/45, 1-10, Jun. 2, 2014.
Curt, K., et al., "Brief Report: Real-World Outcomes of Lurbinectedin in Veterans With Small Cell Lung Cancer," Clinical lung cancer. vol. 27, Issue 3 p. 17-21, Apr. 1, 2026.
Quan & Palackdharry, Part III Immunotherapy for Cancer: Harnessing the Host Immune-Defenses-Biologic Mechanisms and Results in Melanoma and Renal Cell Carcinoma, 43(11) Disease-A-Month 755, 758 (1997).
Bodey, Genetically Engineered Monoclonal Antibodies for Direct Anti-Neoplastic Treatment and Cancer Cell Specific Delivery of Chemotherapeutic Agents, 6 Current Pharmaceutical Design 261 (2000).
Carter, Improving the Efficacy of Antibody-Based Cancer Therapies, 1 Nature Reviews 118, 118 (2001).
Johnston, Farnesyl Transferase Inhibitors: a Novel Targeted Therapy for Cancer, 2 Lancet Oncology 18, (2001).
Gasparini, The Rationale and Future Potential of Angiogenesis Inhibitors in Neoplasia, 58(1) Drugs 17, 18 (1999).
Oehler & Bicknell, The Promise of Anti-Angiogenic Cancer Therapy, 82(4) Br. J. Cancer 749, 749 (2000).
Gourley & Williamson, Angiogenesis: New Targets for Development of Anticancer Chemotherapies, 6 Current Pharm. Design 417, 419 (2000).
Druker & Lydon, Lessons Learned from the Development of an Abl Tyrosine Kinase Inhibitor for Chronic Myelogenous Leukemia, 105(1) J. Clin. Investigation 3, 3 (2000).
Gleevec Is Approved for Chronic Myelogenous Leukeia, 10(6) Oncology News International, https://www.cancernetwork.com/view/gleevec-approved-chronic-myelogenous-leukemia—Jun. 1, 2001.
Blume-Jensen & Hunter, Oncogenic Kinase Signaling, 411 Nature 355 (May 2001).
Mendelsohn & Baselga, The EGF Receptor Family as Targets for Cancer Therapy, 19 Oncogene 6550, 6550 (2000).
Dorai, Development of a Hammerhead Ribozyme Against BCL-2. II. Ribozyme Treatment Sensitizes Hormone-Resistant Prostate Cancer Cells to Apoptotic Agents, 17(5A) Anticancer Research 3307 (1997).
Waters, Phase I Clinical and Pharmacokinetic Study of Bcl-2 Antisense Oligonucleotide Therapy in Patients with Non-Hodgkin's Lymphoma, 18(9) J. Clin. Oncology 1812 (2000).

(56) References Cited

OTHER PUBLICATIONS

Jansen, Chemosensitisation of Malignant Melanoma by BCL2 Antisense Therapy, 356 (9243) Lancet P1728, Nov. 18, 2000.
Gautam, Inhibition of Experimental Lung Metastasis by Aerosol Delivery of PEI-p53 Complexes, 2(4) Molecular Therapy 318 (2000)—Oct. 2000.
Roth, Gene Therapy for Non-Small Cell Lung Cancer: a Preliminary Report of a Phase I trial of Adenoviral P53 Gene Replacement, 25 (3 Suppl. 8) SEMIN. ONCOL. 33 (1998).
Brown & Strathdee, Epigenomics and Epigenetic Therapy of Cancer, 8(4 Suppl.) Trends in Molecular Medicine S43, S43 (2002).
Geffen & Man, New Drugs for the Treatment of Cancer, 1990-2001, 4(12) Israeli Medical Association Journal 1124-1131, vol. 4, Dec. 2002.
Altmann, Microtubule-Stabilizing Agents: a Growing Class of Important Anticancer Drugs, 5 Current Opinion in Chemical Biology 424 (Aug. 1, 2001).
Abrams, New Chemotherapeutic Agents for Breast Cancer, 74(3) Cancer Supp. 1164, 1167, Aug. 1, 1994.
Georg, Taxane Anticancer Agents: Basic Science and Current Status, ACS Symposium Series 583, ix (1994).
Taxol® Label, 2000.
Taxotere® Label—Dec. 23, 1999.
Ojima, New Taxanes as Highly Efficient Reversal Agents for Multi-Drug Resistance in Cancer Cells, 8 Bioorganic & Medicinal Chemistry Letters 189 (1998).
Navelbine® Label, 2000.
Gmeiner, Antimetabolite Incorporation into DNA: Structural and Thermodynamic Basis for Anticancer Activity, 65 Biopolymers (Nucleic Acid 20 Sciences) 180, 180 (2002).
Kaye, New Antimetabolites in Cancer Chemotherapy and Their Clinical Impact, 78 (Suppl. 3) British J. Cancer 1 (1998).
Gemzar® Label, 1998.
Camptostar® Label, 2000.
Hycamtin® Label, 1998.
Arbuck & Takimoto, An Overview of Topoisomerase I-Targeting Agents, 35(3) (Suppl 4) Seminars in Hematology 3, 3, 5, 8, Jul. 1998.
Hande, Clinical Applications of Anticancer Drugs Targeted to Topoisomerase II, 1400 Biochimica Et Biophysica Acta 173, 173, 178-79, 183 (1998).
Simoni, Heterocycle-Containing Retinoids. Discovery of a Novel Isoxazole Arotinoid Possessing Potent Apoptotic Activity in Multidrug and Drug-Induced Apoptosis-Resistant Cells, 44(14) J. Med. Chem. 2308 (2001).
Rocha, Natural Products in Anticancer Therapy, 1 Current Opinion in 25 Pharmacology 364, 366 (Aug. 1, 2001).
Yang & Wang, Structural Studies of Atom-Specific Anticancer Drugs Acting on DNA, 83 Pharmacology & Therapeutics 181, 183 (1999).
Hurley, DNA and Associated Targets for Drug Design, 32(9) J. Med.Chem. 2027, 2029, 2031 (1989).
Gerson, Chapter 1: Alkylating and Platinating Agents, in Current Cancer Therapeutics (eds. Kirkwood et al., 4th edition 2001) 29—2001.
Balfour & Goa, Adis New Drug Profile: Bendamustine 61(5) Drugs 631 (2001).
Raymond, Oxaliplatin: A Review of Preclinical and Clinical Studies, 9 Annals of Oncology 1053, 1053-54, 1064 (1998).
Jimeno, Progress in the Acquisition of New Marine-Derived Anticancer Compounds: Development of Ecteinascidin-743 (ET-743), 21(11) Drugs of the Future 1155, 1158 (1996).
Rinehart, Prospects for Pharmaceuticals from Marine Organisms, Medicinal Chemistry: Today and Tomorrow, Procs. of the Afmcint'L Med. Chem. Symp. (Sep. 3-8, 1995) (pub. Int'l Union of Pure and Appl. Chem., ed. Yamazaki, 1997), Jul. 14, 1995.
Nuijen, Pharmaceutical Development of Anticancer Agents Derived from Marine Sources, 11 Anti-Cancer Drugs, 793-811 (2000).
Urban, Bioactive Marine Alkaloids, 4 Curr. Org. Chem. 7, 765-807 (2000).
Record History Tab NCT00002904—Jun. 23, 2005.
Record History Tab NCT00006463—Jun. 23, 2005.
Record History Tab NCT00003939—Jun. 23, 2005.
Record History Tab NCT00005625—Jun. 23, 2005.
van Kesteren, Pharmacokinetics and Pharmacodynamics of the Novel Marine-Derived Anticancer Agent Ecteinascidin 743 in a Phase I Dose-Finding Study, 6 Clin. Cancer Rsch. 4725-32, Dec. 2000.
Erba, Isolation and Characterization of an IGROV-1 Human Ovarian Cancer Cell Line Made Resistant to Ecteinascidin-743 (ET-743), 82 BR. J. Cancer 10, 1732-39 (2000).
Takebayashi, Poisoning of Human DNA Topoisomerase I by Ecteinascidin 743, an Anticancer Drug that Selectively Alkylates DNA in the Minor Groove, 96 Proc. Nat'L Acad. Sci. USA 7196-201, Jun. 1999.
Reichardt et al. Efficacy and safety of nivolumab and trabectedin in pretreated patients with advanced soft tissue sarcomas (STS): Results of a phase II trial of the German Interdisciplinary Sarcoma Group (GISG-15, NitraSarc) ASCO American Society of Clinical Oncology, 59th Annual Meeting, Jun. 2-6, 2023. Chicago, Illinois. J Clin Oncol. vol. 41 (Supl 16) Abs No. 11500 (Abstract).
Reichardt et al. Efficacy and safety of nivolumab and trabectedin in pretreated patients with advanced soft tissue sarcomas (STS): Results of a phase II trial of the German Interdisciplinary Sarcoma Group (GISG-15, NitraSarc) ASCO American Society of Clinical Oncology, 59th Annual Meeting, Jun. 2-6, 2023. Chicago, Illinois. J Clin Oncol. vol. 41 (Supl 16) Abs No. 11500 (Poster).
Jang et al. Therapeutic Targeting of Macrophage Plasticity Remodels the Tumor-Immune Microenvironment. Cancer Res. vol. 82(14) pp. 2593-2609, 2022.
Guo et al. Leukemic progenitor cells enable immunosuppression and post-chemotherapy relapse via IL-36-inflammatory monocyte axis. Sci Adv. vol. 7(41) pp. abg4167, Oct. 2021.
Belgiovine et al. Inhibition of Tumor-Associated Macrophages by trabectedin improves the anti-tumor adaptive immunity in response to anti-PD-1 therapy. Eur J Immunol. vol. 51(11) pp. 2677-2686, Nov. 2021.
Corbellari et al. The immunocytokine L19-TNF eradicates sarcomas in combination with chemotherapy agents or with immune check-point inhibitors . Anticancer Drugs. vol. 31(8) pp. 799-805, Sep. 2020.
Gordon et al. The Saint: Results of a Phase 1/2 study of safety/efficacy using safe amounts of ipilimumab, nivolumab and trabectedin as first line treatment of advanced soft tissue sarcoma (NCT 03138161). CTOS Connective Tissue Oncology Society, 24th Annual Meeting, Nov. 13-16, 2019, Tokyo, Japan. Abs No. 3255343, 2019.
Gordon et al Cancer immunotherapy using trabectedin and nivolumab in advanced soft tissue sarcoma: A retrospective analysis. ASCO-SITC Clinical Immuno-Oncology Symposium 2018. J Clin Oncol. vol. 36(5 Supl) Abs No. 40 (abstract).
Gordon et al Cancer immunotherapy using trabectedin and nivolumab in advanced soft tissue sarcoma: A retrospective analysis. ASCO-SITC Clinical Immuno-Oncology Symposium 2018. J Clin Oncol. vol. 36(5 Supl) Abs No. 40 (poster).
Gordon et al. The Saint: Initial Results of a Phase 1/2 study of Safety/Efficacy using safe amounts of Ipilimumab, Nivolumab and Trabectedin as first line treatment of Advanced Soft Tissue Sarcoma. CTOS Connective Tissue Oncology Society, 23nd Annual Meeting, Nov. 14-17, 2018, Rome, Italy. Abs 237.
Liu et al. Advances of systemic treatment for adult soft-tissue sarcoma. Chinese Clin Oncol. vol. 7(4) pp. 42, 2018.
Chawla et al. Clinical Experience with Combination Chemo-/Immunotherapy using Trabectedin and Nivolumab for Advanced Soft Tissue Sarcoma. J Sarcoma Res. vol. 2(1) pp. 1009, May 16, 2018.
Chawla et al. Clinical experience with combination chemo-/immunotherapy using trabectedin and nivolumab for advanced soft tissue sarcoma. ASCO American Society of Clinical Oncology, 54th Annual Meeting, Jun. 1-5, 2018. Chicago, Illinois. J Clin Oncol. vol. 36 (Supl) Abs. No. e23568.
Sugiyama et al. A Case of Malignant Melanoma-like Spindle Sarcoma Treated with Nivolumab and Trabectedin. 59th Annual Meeting of the Japanese Society of Pediatric Hematology and

(56) References Cited

OTHER PUBLICATIONS

Oncology. Matsuyama City, Japan Nov. 9-11, 2017. Pediatr Blood Cancer. vol. 64(Supl 4) pp. S41 Abs. No. 08-1-5.
Chawla et al. Cancer Immunotherapy using Trabectedin and Nivolumab in Advanced Soft Tissue Sarcoma: A retrospective Analysis. CTOS Connective Tissue Oncology Society, 22nd Annual Meeting, Nov. 8-11, 2017, Grand Wailea Resort, Maui, Hawaii. Abs No. 020.
Gordon et al. Cancer immunotherapy with sequential administration of trabectedin and nivolumab in advanced soft tissue sarcoma. 4th Immuno Therapy of Cancer Conference. Prague, Czech Republic. Mar. 20, 2017-Mar. 22, 2017 J Immunother Cancer. vol. 5(Supl 1) pp. 17 Abs. No. A42.
Ratti et al. Trabectedin Overrides Osteosarcoma Differentiative Block and Reprograms the Tumor Immune Environment Enabling Effective Combination with Immune Checkpoint Inhibitors. Clin Cancer Res. vol. 23(17) pp. 5149-5161, 2017.
Turano et al. Trabectedin for Treatment of Soft-Tissue Sarcomas in Patients Failing Anthracycline Treatment. CTOS Connective Tissue Oncology Society, 17th Annual Meeting, Nov. 14-17, 2012, Prague, Czech Republic, 2012.
Mispelaere et al. Natural course and clinical features of myxoid and round cell liposarcoma (MRCL)—a retrospective single center analysis.J Clin Oncol. ASCO American Society of Clinical Oncology, 43rd Annual Meeting, Jun. 1-5, 2007. Chicago, Illinois. vol. 25(18S) Part I Abs. No. 10066.
Di Fonte et al. Cervical cancer benefits from trabectedin combination with the blocker propranolol: in vitro and ex vivo evaluations in patient-derived organoids. Front Dev Biol. vol. 11 pp. 1178316, 2023.
Muller et al. A non-randomized, open-label phase II trial evaluating efficacy and feasibility of combined treatment with trabectedin and nivolumab in patients with metastatic or inoperable soft tissue sarcomas (STS) after failure of an anthracycline-containing regimen. ESMO Virtual Congress 2020. Sep. 19-21, 2020. Ann Oncol. vol. 31(Suppl 4) pp. S991 Abs No. 1669TiP (abstract).
Muller et al. A non-randomized, open-label phase II trial evaluating efficacy and feasibility of combined treatment with trabectedin and nivolumab in patients with metastatic or inoperable soft tissue sarcomas (STS) after failure of an anthracycline-containing regimen. ESMO Virtual Congress 2020. Sep. 19-21, 2020. Ann Oncol. vol. 31(Suppl 4) pp. S991 Abs N 1669TiP (poster).
Borgoni et al. Depletion of tumor-associated macrophages switches the epigenetic profile of pancreatic cancer infiltrating T cells and restores their anti-tumor phenotype. Oncolmmunology. vol. 7(2) pp. e 1393596, 2017.
Povo-Retana et al. Trabectedin and Lurbinectedin Modulate the Interplay between Cells in the Tumour Microenvironment—Progresses in Their Use in Combined Cancer Therapy. Molecules 2024, 29, 331. (2024).
Sasi and Rastogi Current stand on systemic therapy in localized soft tissue sarcomas: a clinician's perspective. 19 (31):2135-2145 (2023).
Sun et al. Impact of metronomic trabectedin combined with low-dose cyclophosphamide on sarcoma microenvironment and correlation with clinical outcome: results from the Tarmic. Molecular Cancer (2024) 23:37 study.
Nishio and Nakayama. Biology and Management of High-Grade Myxofibrosarcoma: State of the Art and Future Perspectives Diagnostics 2023, 13, 3022.
Kournoutas et al. Objective Responses in Metastatic Pleomorphic Rhabdomyosarcoma Treated with Combination of Doxorubicin and Pembrolizumab: A Case Series Case Rep Oncol 2024; 17:344-351.
Dalisay et al. Marine-Derived Anticancer Agents Targeting Apoptotic Pathways: Exploring the Depths for Novel Cancer Therapies . Mar. Drugs 2024.
Kyriazoglou et al. Well-differentiated liposarcomas and dedifferentiated liposarcomas: Systemic treatment options for two sibling neoplasms. Cancer Treatment Reviews 125 (2024) 102716.
Toru Imai, Yuki Kojima et al. Predicting Trabectedin Efficacy in Soft Tissue Sarcoma: Inflammatory Biomarker Analysis. Anticancer Research 44: 2125-2132 (2024).
Yalan Zhou, Siqi Peng et al. Review of Personalized Medicine and Pharmacogenomics of Anti-Cancer Compounds and Natural Products. Genes 2024, 15, 468. (2024).
Andrea Franza et al. New targeted therapies in liposarcoma: state of art and future perspectives. Curr Opin Oncol 2024, 36:000-000 (2024).
Yang et al. Comprehensive Review of Uterine Leiomyosarcoma: Pathogenesis, Diagnosis, Prognosis, and Targeted Therapy, Cells 2024, 13, 1106, 2024.
Siddhi N. Paudel etal. Myelomodulatory treatments augment the therapeutic benefit of oncolytic viroimmunotherapy in murine models of malignant peripheral nerve sheath tumors. Front. Immunol. 15:1384623—Jun. 25, 2024.
Siddhi N. Paudel etal. Corrigendum Myelomodulatory treatments augment the therapeutic benefit of oncolytic viroimmunotherapy in murine models of malignant peripheral nerve sheath tumors. Front. Immunol. 15:1384623—Jul. 9, 2024.
Federica Recine et al. Clinical and translational implications of immunotherapy in sarcomas. Front. Immunol. 15:1378398—Jun. 25, 2024.
Tejas and Anusha. Uterine Sarcoma, Review of Advances in Management in the Last Decade. Indian Journal of Gynecologic Oncology (2024) 22:89—Jul. 26, 2024.
Radaelli et al. Progress in histology specific treatments in soft tissue sarcoma. Expert Review of Anticancer Therapy, 24(9), 845-868—Aug. 5, 2024.
Yu et al. The therapeutic potential and application of marine alkaloids in treating breast cancer. Front. Mar. Sci. 11:1440928.—Jul. 15, 2024.
Zhou et al. Molecular characteristics and systemic treatment options of liposarcoma: A systematic review. Biomedicine & Pharmacotherapy 178 (2024) 117204.
Boulouta et al. Pathologic complete response in patients with localized soft tissue sarcoma treated with neoadjuvant therapy and its correlation with clinical outcomes: A systematic review. vol. 130102820—Aug. 24, 2024.
Arfan et al. Molecular Heterogeneity in Leiomyosarcoma and Implications for Personalised Medicine. Curr Treat Options Oncol . May 2024;25(5):644-658—Apr. 24, 2024.
Anju et al. An overview on liposarcoma subtypes: Genetic alterations and recent advances in therapeutic strategies. Journal of Molecular Histology (2024) 55:227-240—May 2, 2024.
Toledo et al. Deciphering the performance of macrophages in tumour microenvironment: a call for precision immunotherapy. Journal of Hematology & Oncology vol. 17, Article No. 44 (2024).
Haddox et al. Diagnosis and management of dedifferentiated liposarcoma: A multidisciplinary position statement. vol. 131102846, Dec. 2024.
Gupta et al. Consensus recommendations for systemic therapies in the management of relapsed Ewing sarcoma: A report from the National Ewing. Sarcoma Tumor Board. vol. 130, Issue 23 pp. 4028-4039, 2024.
Van Houdt et al. Sarcoma: Last Year's Practice Changing Papers. Ann Surg Oncol 32, 1497-1503 (2025).
Lee, T. Y., & von Mehren, M. (2024). Novel pharmacotherapies for the treatment of liposarcoma: a comprehensive update. Expert Opinion on Pharmacotherapy, 25(17), 2293-2306.
Schwartz et al. Trabectedin enhances the antitumor effects of IL-12 in triple-negative breast cancer. Cancer Immunol Res. 2025.
Yu-Jung Kim, et al: "A phase II study of pembrolizumab and paclitaxel in patients with relapsed or refractory small-cell lung cancer". Lung Cancer. 136 (2019) 122-128.
Shields et al. Top advances of the year: Small cell lung cancer. Cancer. 2025; e35770. 841.
Youlong Du et al. FDA-approved drugs featuring macrocycles or medium-sized rings. Arch. Pharm. 2025;358:e2400890.(2025).
Yeong Uk Lim et al. Current and future perspectives in extensive-stage small-cell lung cancer. Ther Adv Med Oncol. vol. 17: 1-25 (2025).
Simon et al. A phase II study of lurbinectedin with or without avelumab in small cell carcinoma of the bladder (laser)—design and rationale. Future Oncology, Mar. 21, 2025.

(56) References Cited

OTHER PUBLICATIONS

Lubromirov et al. CYP3A Genotype Is Associated With Variability in the Exposure and Clearance of the Novel Oncogenic Transcription Inhibitor Lurbinectedin. Clinical and Translational Science, 2025; 18:e70173.
Paz-Ares et al. Unmet Needs in Maintenance Therapy for Extensive Stage Small Cell Lung Cancer. Clinical Lung Cancer, 2025.
So Yeon Kim et al. Small Cell Lung Cancer: JAMA Review, Mar. 31, 2025.
Chakraborty et al. Protocol to co-culture SCLC cells with human CD8+ T cells to measure tumor cell killing and T cell activation, STAR Protocols 6, 103767, Jun. 20, 2025.
Schöche et al. Current and future pharmacological therapies for extensive-stage small-cell lung cancer. memo 18, 116-124, Apr. 28, 2025.
Singh et al. Combination of Lurbinectedin and Osimertinib for Treatment of EGFR-Mutated Transformed SCLC: A Brief Report. JTO Clinical and Research Reports vol. 6 No. 6: 100807, Feb. 13, 2025.
Apar Kishor Ganti et al. Real-world use, effectiveness, and safety of second-line lurbinectedin monotherapy in small cell lung cancer. Future Oncology, 21(13), 1675-1685, May 26, 2025.
Paz-Ares et al. Efficacy and safety of first-line maintenance therapy with lurbinectedin plus atezolizumab in extensive-stage small-cell lung cancer (IMforte): a randomised, multicentre, open-label, phase 3 trial. The Lancet vol. 405, Issue 10495 p. 2129-2143, Jun. 14, 2025.
Shi et al. Lurbinectedin-induced Pneumonitis and DAH in Recurrent Stage IV SCLC: Possible Pulmonary Toxicity From a Novel Alkylating Agent. A80-1 Pulmonary Toxicities and Treatment-Related Complications in Thoracic Oncology / Thematic Poster Session / Sunday, May 18, 2025.
Giannis Mountzios et al. Tarlatamab in Small-Cell Lung Cancer after Platinum-Based Chemotherapy. New England Journal of Medicine, Jun. 2, 2025.
Krayim et al. Lurbinectedin for extensive stage—small cell lung cancer (ES-SCLC): real world response patterns and survival outcomes. Lung Cancer 205, Jun. 2, 2025.
Romero, Diana. Adding lurbinectedin to maintenance therapy improves outcomes in ES-SCLC. Nature reviews. Clinical oncology, 2025.
Choudhury and Harassino Lurbinectedin with atezolizumab maintenance therapy in extensive-stage small-cell lung cancer. The Lancet vol. 405 Jun. 14, 2025.
Povo-Retana et al. Trabectedin and Lurbinectedin Modulate the Interplay between Cells in the Tumour Microenvironment-Progresses in Their Use in Combined Cancer Therapy. Molecules, 29, 331, Jan. 9, 2024.
Povo-retana. Immunometabolic actions of trabectedin and lurbinectedin on human macrophages: relevance for their anti-tumor activity. Front. Immunology, Aug. 22, 2023.
Jiminez et al. Enriching cancer pharmacology with drugs of marine origin. British Journal of Pharmacologyvol. 177, Issue 1 pp. 3-27, Feb. 26, 2019.
Small-cell tumors: improvements in the second-line setting. ASCO : memo-inOncology Special Issue, Congress Report ASCO 2019, pp. 18-20 (Feb. 2019).
Joss et al. Ondansetron plus dexamethasone is superior to ondansetron alone in the prevention of emesis in chemotherapy-naive and previously treated patients. Annals of Oncology 5: 253-258, 1994.
Highlights of Prescribing Information—Zepzelca (lurbinectedin) for injection, for intravenous use. Jazz Pharmaceuticals, Inc. FDA Official Website—Drug Approvals and Databases—FDA-Approved Drugs, Apr. 2025.
Yubin Ji et al., The extraction, separation and purification of alkaloids in the natural medicine. Journal of Chemical and Pharmaceutical Research 1-338 (2014): 338-45.
Paz-Ares et a. Lurbinectedin (lurbi) + atezolizumab (atezo) as first-line (1L) maintenance treatment (tx) in patients (pts) with extensive-stage small cell lung cancer (ES-SCLC): Primary results of the phase 3 IMforte trial. ASCO presentation (Poster), May 30, 2025.
Paz-Ares et a. Lurbinectedin (lurbi) + atezolizumab (atezo) as first-line (1L) maintenance treatment (tx) in patients (pts) with extensive-stage small cell lung cancer (ES-SCLC): Primary results of the phase 3 IMforte trial. ASCO presentation (Abstract), May 30, 2025.
Peranzoni et al. Macrophages impede CD8 T cells from reaching tumor cells and limit the efficacy of anti-PD-1 treatment. Proc. Natl. Acad. Sci. U.S.A. 115 (17) E4041-E4050, Apr. 9, 2018.
Virtudes Céspedes et al. Lurbinectedin induces depletion of tumor-associated macrophages, an essential component of its in vivo synergism with gemcitabine, in pancreatic adenocarcinoma mouse models Disease Models & Mechanisms (2016) 9, 1461-1471, Oct. 10, 2016.
Xu et al. Targeting immune checkpoints on tumor-associated macrophages in tumor immunotherapy. Front. Immunol. 14:1199631, May 29, 2023.
Cerrato et al. AI-based classification of anticancer drugs reveals nucleolar condensation as a predictor of immunogenicity. Molecular Cancer (2024) 23:275.
Singh et al. Immune checkpoint inhibitors: a promising anticancer therapy. Drug Discovery Today vol. 25, Issue 1, Jan. 2020, pp. 223-229.
Jotte et al. Atezolizumab in Combination With Carboplatin and Nab-Paclitaxel in Advanced Squamous NSCLC (IMpower131): Results From a Randomized Phase III Trial. J Thorac Oncol . Aug. 2020;15(8):1351-1360.
Laroche-Clary et al. Synergistic Effects of ATR Inhibition and Lurbinectedin in Soft-Tissue Sarcomas: The Predictive Role of SLFN11 Expression. Clin Cancer Res OF1-OF9, Jul. 29, 2025.
Sacattolin et al. Outcome and safety of lurbinectedin as compassionate use in extensive stage small cell lung cancer: A multicentric international cohort. European Journal of Cancer 226 (2025) 115595.
U.S. Department of Health and Human Services, National Institutes of Health, & National Cancer Institute. Common Terminology Criteria for Adverse Events (CTCAE) Version 5.0 (p. 3) [Report], Nov. 27, 2017.
Kuter, David J. "General Aspects of Thrombocytopenia, Platelet Transfusions, and Thrombopoietic Growth Factors." Elsevier eBooks, 2019, pp. 108-126, Sep. 10, 2018.
Calles Blanco et al. 1989MO Lurbinectedin (LUR) in combination with pembrolizumab (PBL) in relapsed small cell lung cancer (SCLC): The phase I/II Luper study Abstract ESMO Congress, Madrid, Spain, Ann Oncol., vol. 34, Supplement 2S1060-S1061, Oct. 2023.
Tummala et al. Preclinical synergistic combination therapy of lurbinectedin with irinotecan and 5-fluorouracil in pancreatic cancer. Absrtact Mol Cancer Ther (2023) 22 (12_Supplement): B026.
Garcia-Carbonero et al. Lurbinectedin plus irinotecan in pre-treated gastroenteropancreatic neuroendocrine carcinomas(GEP-NECs). Abstract ESMO Open vol. 9—Issue S2, 2024.
Cote et al. Efficacy and safety of lurbinectedin (LUR) with irinotecan (IRI) in a phase 2 expansion cohort of patients (Pts) with synovial sarcoma (SS). Abstract ASCO American Society of Clinical Oncology, 60th Annual Meeting, May 31-Jun. 4, 2024. Chicago, Illinois. J Clin Oncol.vol. 42 (Supl 16) Abs No. 8094 (Abstract), May 29, 2024.
Cote et al. Efficacy and safety of lurbinectedin (LUR) with irinotecan (IRI) in a phase 2 expansion cohort of patients (Pts) with synovial sarcoma (SS). Poster ASCO American Society of Clinical Oncology, 60th Annual Meeting, May 31-Jun. 4, 2024. Chicago, Illinois. J Clin Oncol.vol. 42 (Supl 16) Abs No. 8094 (Poster), May 29, 2024.
Paz-Ares et al. Efficacy and safety of lurbinectedin (LUR) with irinotecan (IRI) in patients (Pts) with relapsed small cell lung cancer (SCLC): Results from a phase 2 expansion cohort. Poster Journal of Clinical Oncology vol. 42, No. 16_suppl, May 29, 2024.
Paz-Ares et al. Efficacy and safety of lurbinectedin (LUR) with irinotecan (IRI) in patients (Pts) with relapsed small cell lung cancer (SCLC): Results from a phase 2 expansion cohort. May 29, 2024.

(56) References Cited

OTHER PUBLICATIONS

Zugazagoitia et al. Phase II data of lurbinectedin (LUR) and irinotecan (IRI) in relapsed small cell lung cancer (SCLC) patients (pts) with chemotherapy-free interval (CTFI)>30 days (d). Poster ESMO Congress, Barcelona, Spain Sep. 13-17, 2024. Ann Oncol.
Ruiz Torres et al. Abstract 5986: Lurbinectedin/Irinotecan as a new therapeutic combination for small cell lung cancer. Abstract Cancer Res., 85 (8_Supplement_1): 5986 (Abstract), 2025.
Ruiz Torres et al. Abstract 5986: Lurbinectedin/Irinotecan as a new therapeutic combination for small cell lung cancer. Poster Cancer Res., 85 (8_Supplement_1): 5986 (Poster), 2025.
Sanchez-Becerra et al. Abstract 5996: New therapeutic approaches in NUT carcinoma: An unmet need. Abstract Cancer Res., 85 (8_Supplement_1): 5996 (Abstract), 2025.
Sanchez-Becerra et al. Abstract 5996: New therapeutic approaches in NUT carcinoma: An unmet need. Abstract Cancer Res., 85 (8_Supplement_1): 5996, (Poster), 2025.
Calles Blanco et al. 1989MO Lurbinectedin (LUR) in combination with pembrolizumab (PBL) in relapsed small cell lung cancer (SCLC): The phase I/II Luper study Poster ESMO Congress, Madrid, Spain Oct. 20-24, 2023. Ann Oncol. vol. 34, Supplement 2S1060-S1061, Oct. 2023.
Zepzelca label, Jun. 15, 2020.
Zepzelca approval letter, Jun. 15, 2020.
Zepzelca Product Quality Review, May 21, 2020.
Zepzelca Proprietary Name Review, May 20, 2020.
Zepzelca Officer/Employee List, Jun. 10, 2020.
Zepzelca Other Review, Jun. 10, 2020.
Zepzelca Risk Assessment and Risk Mitigation Review, Jun. 9, 2020.
Zepzelca Administrative and Correspondence Documents, Aug. 2019.
Zepzelca Efficacy—New Indication label, Oct. 2, 2025.
Zepzelca Efficacy—New Indication approval letter, Oct. 2, 2025.
Zepzelca Labeling—Medication Guide label, Apr. 30, 2025.
Zepzelca Labeling—Medication Guide approval letter, Apr. 30, 2025.
Zepzelca Labeling—Package Insert label, Jul. 28, 2023.
Zepzelca Labeling—Package Insert approval letter, Jul. 28, 2023.
Zepzelca Labeling—Container/Carton Labels, Labeling—Package Insert label, Apr. 1, 2022.
Desai et al. Systematic review and network meta-analysis: evaluation of systemic therapies for platinum refractory or resistant small cell lung cancer. Lung Cancer, vol. 210, 108812, Nov. 3, 2025.
Wang et al. Efficacy outcomes between tarlatamab and real-world physicians' choice of therapies for previously treated extensive stage small cell lung cancer, The Oncologist, vol. 30, Issue 9,Sep. 1, 2025.
Vejzovic et al. Drug screening reveals differential drug response in primary and metastatic clear cell sarcoma, Cancer Letters, accepted Nov. 9, 2025.
Kepp and Kroemer FDA approves lurbinectedin in combination with atezolizumab for extensive-stage small cell lung cancer. Oncolmmunology, 14:1, Nov. 18, 2025.
Sankar, K., Unni, S., Eberl, M. et al. Real-World Treatment Patterns and Clinical Outcomes in Patients With Extensive—Stage Small Cell Lung Cancer Treated With First-Line Platinum-Based Chemotherapy and ≥ 2 Subsequent Lines of Therapy in the United States. Adv Therapy, Nov. 12, 2025.
Cigrang et al. Ecteinascidins: When marine pharmacology targets the transcriptional dependency of cancer, Oct. 2025.
Reck et al. MA11.04 Safety of Lurbinectedin + Atezolizumab as 1L Maintenance Treatment in ES-SCLC: Results From the Phase 3 IMforte Study. Journal of Thoracic Oncology vol. 20, Issue 10, Supplement 1, Slides, Sep. 9, 2025.
Reck et al. MA11.04 Safety of Lurbinectedin + Atezolizumab as 1L Maintenance Treatment in ES-SCLC: Results From the Phase 3 IMforte Study. Journal of Thoracic Oncology vol. 20, Issue 10, Supplement 1, Abstract, Sep. 9, 2025.
Halmos et al. P3.13.31 Real-World Effectiveness and Safety of Lurbinectedin for Small Cell Lung Cancer (SCLC): Updates From Jazz EMERGE 402 Journal of Thoracic Oncology vol. 20, Issue 10, Supplement 1, pp. S518-S519, Sep. 9, 2025.
Zhou and Zhou P3.18.78 A Prospective Study of Lurbinectedin Plusivonescimab Assecond-Line Treatment for Extensive-Stage Small Cell Lung Cancer. Journal of Thoracic Oncology, vol. 20, Issue 10, Supplement 1S579, Sep. 9, 2025.
Scattolin EP.13.15 Outcome and Safety of Lurbinectedin as Compassionate Use in SCLC: A Retrospective Nulticentric International Study Journal of Thoracic Oncology, vol. 20, Issue 10, Supplement 1, Oct. 2025, p. S832.
Otegui EP.13.27 Co-Targeting SFKs and DNA Damaging Chemotherapy Drugs as a Novel Therapeutic Strategy in SCLC. Journal of Thoracic Oncology vol. 20, Issue 10, Supplement 1, Oct. 2025, pp. S838-S839.
Calip EP.17.35 Treatment-Associated Interstitial Lung Disease in Extensive-Stage Small Cell Lung Cancer. Journal of Thoracic Oncology, vol. 20, Issue 10, Supplement 1S893-S894, Oct. 2025.
Banerjee et al. Molecular Landscape and Therapeutic Strategies of Lung Cancer Lineage Plasticity. Journal of Thoracic Oncology, vol. 20, Issue 11, p. 1582-1593, Nov. 2025.
Kotha et al. A Novel LC—MS/MS Technique for the Quantitation of Lurbinectedin in Human Plasma: Application of Stability Studies. International Journal of Applied Pharmaceutics Home / Archives / vol. 17, Issue 6 (Nov.-Dec.), 2025.
Abraxane label, Aug. 1, 2018.
Pediatric Subcommittee Oncology Drug Advisory Committee Meeting. Advisory Committee Briefing Material: Available for Public Release, May 19, 2017.
Hycamtin label, Oct. 1, 2019.
Ixempra label, Oct. 18, 2011.
Bethesda LiverTox: Clinical and Research Information on Drug-Induced Liver Injury. Severity grading in drug induced liver injury. May 4, 2019.
Taxol label, Apr. 1, 2011.
Yondelis label, Dec. 1, 2018.
FDA Briefing Document Pediatric Oncology Subcommittee of the Oncologic Drugs Advisory Committee (ODAC), Jun. 21, 2017.
Zepzelca Labeling—Container/Carton Labels, Labeling—Package Insert approval letter, Apr. 1, 2022.
Russo-Cabrera et al. 1050P Sensitization to immunotherapy through manipulation of tumor transcription by lurbinectedin. Abstract. ESMO Congress, Madrid, Spain Oct. 20-24, 2023. Ann Onco. vol. 34, Supplement 2S636 Oct. 2023.
Russo-Cabrera et al. 1050P Sensitization to immunotherapy through manipulation of tumor transcription by lurbinectedin. Poster. ESMO Congress, Madrid, Spain Oct. 20-24, 2023. Ann Onco. vol. 34, Supplement 2S636 Oct. 2023.
Sen 167P Lurbinectedin: A DNA minor groove inhibitor launches a multimodal immune response through activation of the cytosolic DNA-sensing cGAS-STING pathway. Abstract ESMO Immuno-Oncology Congress, Dec. 6-8, 2023, Geneva, Switzerland. Immuno Oncol Technol. vol. 20, Supplement 100626, Dec. 2023.
Sen 207P Lurbinectedin induces multimodal immune activation and augments the anti-tumor immune response in small cell lung cancer. Abstract European Lung Cancer Congress (ELCC). Prague, Czech Republic Mar. 20-23, 2024 ESMO Open. vol. 9, Supplement 3102780, Mar. 2024.
Gordon et al. Abstract CT287: Linnovate: A Phase 1/2 study of safety/efficacy using lurbinectedin, combined with ipilimumab, and nivolumab for advanced soft tissue sarcomas (NCT05876715) Cancer Res (2024) 84 (7_Supplement): CT287.
Chakraborty et al. Abstract 6554: Lurbinectedin induces multimodal immune activation and augments the anti-tumor immune response in small-cell lung cancer. Cancer Res (2024) 84 (6_Supplement): 6554.
Tummala et al. Abstract 4550: Synergistic combinations of lurbinectedin with ONC212 in pancreatic cancer. Cancer Res (2024) 84 (6_Supplement): 4550.
Simon et al. A phase II study of lurbinectedin with or without avelumab in small cell carcinoma of the bladder (Laser). ASCO

(56) References Cited

OTHER PUBLICATIONS

American Society of Clinical Oncology, 60th Annual Meeting, May 31-Jun. 4, 2024. Chicago, Illinois. J Clin Oncol. vol 42 (Supl 16) Abs N TPS4629.
Simon et al. A phase II study of lurbinectedin with or without avelumab in small cell carcinoma of the bladder (Laser). ASCO American Society of Clinical Oncology, 60th Annual Meeting, May 31-Jun. 4, 2024. Chicago, Illinois. J Clin Oncol. vol. 42 (Supl 16), (Poster).
Gordon et al. 1739P Linnovate: A phase I/II study of safety/efficacy using lurbinectedin combined with ipilimumab and nivolumab for advanced soft tissue sarcoma (NCT05876715)—Interim analysis of phase I part. Sarcoma, vol. 35, Supplement 2S1040, (Abstract) Sep. 2024.
Gordon et al. 1739P Linnovate: A phase I/II study of safety/efficacy using lurbinectedin combined with ipilimumab and nivolumab for advanced soft tissue sarcoma (NCT05876715)—Interim analysis of phase I part. Sarcoma, vol. 35, Supplement 2S1040,(Poster) Sep. 2024.
Russo-Cabrera et al.2261-WS21.6 Lurbinectedin-induced transcriptional reprogramming: a pathway to sensitise SCLC to immunotherapy. Eur. J. Immunol. 2024. 54(Suppl. 1): 1-1746, Sep. 2024.
Russo-Cabrera et al. Abstract 5837: Lurbinectedin-induced transcriptional reprogramming: A pathway to sensitise SCLC to immunotherapy. y [abstract]. In: Proceedings of the American Association for Cancer Research Annual Meeting 2025; Part 1 (Regular Abstracts); Apr. 25-30, 2025; Chicago, IL. Philadelphia (PA): AACR; Cancer Res 2025;85 (8_Suppl_1): Abstract nr 5837. (Abstract).
Russo-Cabrera et al. Abstract 5837: Lurbinectedin-induced transcriptional reprogramming: A pathway to sensitise SCLC to immunotherapy. y [abstract]. In: Proceedings of the American Association for Cancer Research Annual Meeting 2025; Part 1 (Regular Abstracts); Apr. 25-30, 2025; Chicago, IL. Philadelphia (PA): AACR; Cancer Res 2025;85 (8_Suppl_1):Abstract nr 5837. (Poster).
"Tummala et al. Abstract 7212 Preclinical analysis of ONC206 and ONC212 with lurbinectedin in pancreatic cancer. r [abstract]. In: Proceedings of the American Association for Cancer Research Annual Meeting 2025; Part 1 (Regular Abstracts); Apr. 25-30, 2025; Chicago, IL. Philadelphia (PA): AACR; Cancer Res 2025;85(8_Suppl_1):Abstract nr 7212.".
Paz-Ares et al. 8006 Lurbinectedin (lurbi) + atezolizumab (atezo) as first-line (1L) maintenance treatment (tx) in patients (pts) with extensive-stage small cell lung cancer (ES-SCLC): Primary results of the phase 3 IMforte trial. Journal of Clinical Oncology vol. 43, No. 16_sup (Abstract), May 2025.
Paz-Ares et al. 8006 Lurbinectedin (lurbi) + atezolizumab (atezo) as first-line (1L) maintenance treatment (tx) in patients (pts) with extensive-stage small cell lung cancer (ES-SCLC): Primary results of the phase 3 IMforte trial. Journal of Clinical Oncology vol. 43, No. 16_sup (Poster), May 2025.
Ponce Aix et al. 8013 Safety and efficacy of lurbinectedin plus atezolizumab as second-line treatment for advanced small-cell lung cancer: Results of the 2SMALL phase 1/2 study (NCT04253145). Journal of Clinical Oncology vol. 43, No. 16_suppl, (Poster) May 2025.
Ponce Aix et al. 8013 Safety and efficacy of lurbinectedin plus atezolizumab as second-line treatment for advanced small-cell lung cancer: Results of the 2SMALL phase 1/2 study (NCT04253145). Journal of Clinical Oncology vol. 43, No. 16_suppl, (Abstract) May 2025.
Basharat et al. e20100 Lurbinectedin with immunotherapy in extensive-stage small cell lung cancer: Current insights and future prospects A systematic review. Journal of Clinical Oncology vol. 43, No. 16_suppl, May 2025.
Bustos Moran et al. e14614 Evaluation of the combination of lurbinectedin and atezolizumab in a humanized mouse model. Journal of Clinical Oncology vol. 43, No. 16_supp, May 2025.
Chakraborty et al. Increasing the Efficacy of ICB by Lurbinectedin Mediated Re-Activation of Tumor Microenvironment in SCLC. vol. 20, Issue 8, Supplement 2S, Aug. 28, 2025.
Chen et al. E-1026 Combination Therapy of Lurbinectedin and AZD6738 for Effective Elimination of ALT Cancer Cells, Sep. 21, 2023.
Navarro et al. Efficacy of Platinum after Lurbinectedin + DOX or Topotecan/CAV in Sensitive Relapsed SCLC Patients in the Atlantis Trial. IASLC 2023 World Conference on Lung Cancer (WCLC 2023). Sep. 9-12, Singapore. 2023. J Thorac Oncol. vol. 18 (11 Supl) pp. S380-S381 Abs No. P2.17-06 (abstract).
Navarro et al. Efficacy of Platinum after Lurbinectedin + DOX or Topotecan/CAV in Sensitive Relapsed SCLC Patients in the Atlantis Trial. IASLC 2023 World Conference on Lung Cancer (WCLC 2023). Sep. 9-12, Singapore. 2023. J Thorac Oncol. vol. 18 (11 Supl) pp. S380-S381 Abs No. P2.17-06 Poster).
Cote et al. TPS11590 Randomized controlled, open-label, phase IIb/III study of lurbinectedin in combination with doxorubicin versus doxorubicin alone as first-line treatment in patients with metastatic leiomyosarcoma.ASCO American Society of Clinical Oncology, 60th Annual Meeting, May 31-Jun. 4, 2024. Chicago, Illinois. J Clin Oncol. vol. 42 (Supl 16) Abs N TPS11590 (Abstract).
Cote et al. TPS11590 Randomized controlled, open-label, phase IIb/III study of lurbinectedin in combination with doxorubicin versus doxorubicin alone as first-line treatment in patients with metastatic leiomyosarcoma.ASCO American Society of Clinical Oncology, 60th Annual Meeting, May 31-Jun. 4, 2024. Chicago, Illinois. J Clin Oncol. vol. 42 (Supl 16) Abs N TPS11590, (Poster).
Moreno et al. 679P Lurbinectedin (LRB) pharmacokinetics (PK) and safety when co-administered with itraconazole (ITZ) in patients with advanced solid tumor. ESMO Congress, Madrid, Spain Oct. 20-24, 2023. Ann Oncol (Abstract).
Moreno et al. 679P Lurbinectedin (LRB) pharmacokinetics (PK) and safety when co-administered with itraconazole (ITZ) in patients with advanced solid tumor. ESMO Congress, Madrid, Spain Oct. 20-24, 2023. Ann Oncol (Poster).
Curt et al. EP13.07-01 Understanding Real-Life Response to Lurbinectedin as Second Line Therapy in Patients with Extensive Stage Small-Cell Lung Cancer. IASLC 2023 World Conference on Lung Cancer (WCLC 2023). Sep. 9-12, Singapore. 2023. J Thorac Oncol. vol. 18 (11 Supl) pp. S705-S706 Abs No. EP13.07-01.
Trigo et al. EP13.07-06 Efficacy of Platinum Given after Lurbinectedin in Sensitive Relapsed SCLC Patients. IASLC 2023 World Conference on Lung Cancer (WCLC 2023). Sep. 9-12, Singapore. 2023. J Thorac Oncol. vol. 18 (11 Supl) pp. S705-S706 Abs No. EP13.07-06 (Abstract).
Trigo et al. EP13.07-06 Efficacy of Platinum Given after Lurbinectedin in Sensitive Relapsed SCLC Patients. IASLC 2023 World Conference on Lung Cancer (WCLC 2023). Sep. 9-12, Singapore. 2023. J Thorac Oncol. vol. 18 (11 Supl) pp. S705-S706 Abs No. EP13.07-06 (Poster).
Polani et al. EP13.07-07 Exploring Outcomes in Second-line Therapy for Small Cell Lung Cancer with Brain Metastases: Lurbinectedin vs Others. IASLC 2023 World Conference on Lung Cancer (WCLC 2023). Sep. 9-12, Singapore. 2023. J Thorac Oncol. vol. 18 (11 Supl) pp. S709 Abs No. EP13.07-07.
Ganti et al. Effectiveness and Safety Profile of Lurbinectedin in Second-Line Small Cell Lung Cancer: A Real-World Study. IASLC 2023 World Conference on Lung Cancer (WCLC 2023). Sep. 9-12, Singapore. 2023. J Thorac Oncol. vol. 18 (11 Supl) pp. S378-S379 Abs No. P2.17-02 (Abstract).
Ganti et al. Effectiveness and Safety Profile of Lurbinectedin in Second-Line Small Cell Lung Cancer: A Real-World Study. IASLC 2023 World Conference on Lung Cancer (WCLC 2023). Sep. 9-12, Singapore. 2023. J Thorac Oncol. vol. 18 (11 Supl) pp. S378-S379 Abs No. P2.17-02 (Poster).
Halmos et al. P2.17-07 Real-world Safety and Dosing of Lurbinectedin-Treated Patients with Small Cell Lung Cancer: Jazz Emerge 402 Preliminary Analysis. IASLC 2023 World Conference on Lung Cancer (WCLC 2023). Sep. 9-12, Singapore. 2023. J Thorac Oncol. vol. 18 (11 Supl) pp. S381 Abs No. P2.17-07 (Abstract).
Halmos et al. Real-world Safety and Dosing of Lurbinectedin-Treated Patients with Small Cell Lung Cancer: Jazz Emerge 402

(56) References Cited

OTHER PUBLICATIONS

Preliminary Analysis. IASLC 2023 World Conference on Lung Cancer (WCLC 2023). Sep. 9-12, Singapore. 2023. J Thorac Oncol. vol. 18 (11 Supl) pp. S381 Abs No. P2.17-07 (Poster).
Domine et al. 2024p Supportive measures to control myelosuppression and costs for patients with SCLC with lurbinectedin, CAV or topotecan with or without trilaciclib: A review on the basis of clinical trials. ESMO Congress, Madrid, Spain Oct. 20-24, 2023. Ann Oncol. vol. 34 (Supl 2) pages++, (Abstract).
Domine et al. Supportive measures to control myelosuppression and costs for patients with SCLC with lurbinectedin, CAV or topotecan with or without trilaciclib: A review on the basis of clinical trials. ESMO Congress, Madrid, Spain Oct. 20-24, 2023. Ann Oncol. vol. 34 (Supl 2) (Poster).
Meyer et al. Lurbinectedin in prostatic small cell and neuroendocrine carcinoma. ASCO American Society of Clinical Oncology Genitourinary Cancers Symposium. Jan. 25-27, 2024. San Francisco, CA. J Clin Oncol. vol. 42 (Suppl 4) Abs No. 164.
Moussa et al. Clinical efficacy of lurbinectedin in metastatic neuroendocrine carcinomas of the genitourinary tract: Multi-institutional real-world experience. ASCO American Society of Clinical Oncology Genitourinary Cancers Symposium. Jan. 25-27, 2024. San Francisco, CA. J Clin Oncol. vol. 42 (Suppl 4) Abs No. 601 (abstract).
Moussa et al. Clinical efficacy of lurbinectedin in metastatic neuroendocrine carcinomas of the genitourinary tract: Multi-institutional real-world experience. ASCO American Society of Clinical Oncology Genitourinary Cancers Symposium. Jan. 25-27, 2024. San Francisco, CA. J Clin Oncol. vol. 42 (Suppl 4) (Poster).
Veluvolu et al. Abstract 1082 Exploiting lurbinectedin-driven nucleolar relocalization of EWS-FLI1 to develop novel combination therapies for Ewing sarcoma. AACR American Association for Cancer Research. Annual Meeting. Apr. 5-10, 2024. San Diego. CA. Philadelphia (PA) Cancer Res. vol. 84 (6 Supl) Abs No. 1082.
Fathima and Chakradhar. Marine Derived Drug Lurbinectidin: A Potential Anticancer Agent. 5th IUPHAR World Conference on the Pharmacology of Natural Medicine, WCP-NP-2019 and 51st Annual Conference of Indian Pharmacologica society, IPSCON-2019. Hyderabad, India. Indian J Pharmacol. vol. 53(7 Supl 1) pp. S105-S106, Dec. 2021.
Libre et al. Lurbinectedin versus platinum rechallenge in relapsed extensive stage small cell lung cancer: A retrospective cohort study. ASCO American Society of Clinical Oncology, 60th Annual Meeting, May 31-Jun. 4, 2024. Chicago, Illinois. J Clin Oncol. vol. 42 (Supl 16) Abs No. e20110.
Badin et al. Real-world safety and healthcare resource utilization (HCRU) of lurbinectedin (lurbi) in patients (pts) with small cell lung cancer (SCLC): Jazz Emerge 402 updated analysis. ASCO American Society of Clinical Oncology, 60th Annual Meeting, May 31-Jun. 4, 2024. Chicago, Illinois. J Clin Oncol. vol. 42 (Supl 16) Abs No. e23266.
Ganti et al. PP01.117 Real-World Effectiveness and Safety Profile of Lurbinectedin and Other Second-Line Treatments in Small Cell Lung Cancer. IASLC 2023 North America Conference on Lung Cancer (NACLC). Chicago, Illinois, United States. Dec. 1-3, 2023. J Thorac Oncol. vol. 19 (7 Supl) pp. e50-e51 Abs No. PP01.117.
Halmos et al. PP01.119 Real-World Use of Lurbinectedin in Patients with Small Cell Lung Cancer: Jazz Emerge 402 Updated Analysis. IASLC 2023 North America Conference on Lung Cancer (NACLC). Chicago, Illinois, United States. Dec. 1-3, 2023. J Thorac Oncol. vol. 19 (7 Supl) pp. e52 Abs No. PP01.119.
Pons-Tostivint at al. Second-line treatment outcomes following first-line chemotherapy plus immunotherapy in patients with extensive-stage small cell lung cancer (ES-SCLC): A multicenter study. ASCO American Society of Clinical Oncology, 60th Annual Meeting, May 31-Jun. 4, 2024. Chicago, Illinois. J Clin Oncol. vol. 42 (Supl 16) Abs No. e20122, 2024.
Halmos et al. Efficacy and Safety of Lurbinectedin for Small Cell Lung Cancer in a Real-World Setting: Jazz Emerge 402 Study. IASLC 2024 World Conference on Lung Cancer (WCLC 2024). Sep. 7-10, 2024, San Diego. 2024. J Thorac Oncol. vol. 19(10 Supl) pp. S210-S211 Abs No. P1.13A.10.
Benedetti Panici, P., Phase II trial of weekly trabectedin plus weekly pegylated liposomal doxorubicin for recurrent ovarian carcinoma, IGCS 14th Biennial Meeting, 2012, vol. 22(8 Supl 3) p. 271 (abstract).
Benedetti Panici, P., Trabectedin Plus cisplatin in recurrent or metastatic cervical cancer: A phase I-II dose-finding study, IGCS 14th Biennial Meeting, 2012, vol. 22(8 Supl 3) p. 561 (poster).
Benedetti Panici, P., Trabectedin Plus cisplatin in recurrent or metastatic cervical cancer: A phase I-II dose-finding study, IGCS 14th Biennial Meeting, 2012, vol. 22(8 Supl 3) p. 561 (abstract).
Gupta, A.A., Systematic Chemotherapy for Inoperable, Locally Advanced, Recurrent, or Metastatic Uterine Leiomyosarcoma: A Systematic Review, Clin Oncol, 2013, vol. 25(6) pp. 346-355.
Germano, G., Role of Macrophage Targeting in the Antitumor Activity of Trabectedin, Cancer Cell, 2013, vol. 23(2) pp. 249-262.
Martin-Liberal, J., Systemic Chemotherapy for Inoperable, Locally Advanced, Recurrent or Metastatic Uterine Leiomyosarcoma, Clin Oncol, 2013, vol. 25(6)pp. 343-345.
Nuzzo, C., Tumor response assessment in locally unresectable or metastatic soft tissue sarcoma (aSTS) patients: IRE experience . . . , ASCO 49th Annual Meeting, 2013, vol. 31(15 Supl) Abs. N e21517.
Sharma, S., Efficacy and safety of pharmacological interventions in second- or later-line treatment of patients with advanced STS: a systematic review, BMC Cancer, 2013, vol. 13(1) 385.
Allavena, P., Trabectedin: A drug from the sea that strikes tumor-associated macrophages, Oncoimmunology, 2013, vol. 2(6) e24614.
Richards, D.M, Monocytes and Macrophages in Cancer: Development and Functions, Cancer Microenviron, 2013, vol. 6(2) pp. 179-191.
Redini, F., Drugs targeting the bone microenvironment: new therapeutic tools in Ewing's sarcoma?, Expert Opin Emerg Drugs, 2013, vol. 18(3) pp. 339-352.
Chawla, S.P., Results of a multivariate analysis for potential factors affecting outcome in translocation related sarcomas (TRS) treated with trabectedin . . . , 17th ECCO European Cancer Congress, 2013, vol. 49(Supl 2) pp. 885 Abs No. 3829 (poster).
Chawla, S.P., Results of a multivariate analysis for potential factors affecting outcome in translocation related sarcomas (TRS) treated with trabectedin . . . , 17th ECCO European Cancer Congress, 2013, vol. 49(Supl 2) pp. 885 Abs No. 3829 (abstract).
Martí Broto, J., Randomized phase II trial of doxorubicin vs. trabectedin plus doxorubicin in first line treatment of patients with advanced non-resectable or metastatic STS . . . , 17th ECCO European Cancer Congress, 2013, vol. 49 (Supl 2) pp. 875 Abs. No. 3800 (poster).
Martí Broto, J., Randomized phase II trial of doxorubicin vs. trabectedin plus doxorubicin in first line treatment of patients with advanced non-resectable or metastatic STS . . . , 17th ECCO European Cancer Congress, 2013, vol. 49 (Supl 2) pp. 875 Abs. No. 3800 (abstract).
Pautier, P., LMS-02: Phase II study of doxorubicin in combination with trabectedin as a 1st line treatment of metastatic uterine or STS leiomyosarcoma . . . , 17th ECCO European Cancer Congress, 2013, vol. 49(Supl 2) pp. 887 Abs. No. 3834 (poster).
Pautier, P., LMS-02: Phase II study of doxorubicin in combination with trabectedin as a 1st line treatment of metastatic uterine or STS leiomyosarcoma . . . , 17th ECCO European Cancer Congress, 2013, vol. 49(Supl 2) pp. 887 Abs. No. 3834 (abstract).
Diken, M., Advancing targeted therapies—report on the 11th Annual Meeting of the Association for Cancer Immunotherapy, 2013, Mainz, Germany, Hum Vaccin Immunother, 2013, vol. 9(9) pp. 2025-2032.
Benedetti Panici, P., Phase II trial of weekly trabectedin plus weekly pegylated liposomal doxorubicin for treatment of advanced ovarian carcinoma, 18th International Meeting of the ESGO, 2013, vol. 23 (8 Supl 1) pp. 573 (poster).
Benedetti Panici, P., Phase II trial of weekly trabectedin plus weekly pegylated liposomal doxorubicin for treatment of advanced ovarian carcinoma, 18th International Meeting of the ESGO, 2013, vol. 23 (8 Supl 1) pp. 573 (abstract).

(56) References Cited

OTHER PUBLICATIONS

Gupta, A.A., Chemotherapy (gemcitabine, docetaxel plus gemcitabine, doxorubicin, or trabectedin) in inoperable, locally advanced uterine leiomyosarcoma . . . , Curr Oncol, 2013, vol. 20(5) pp. 448-454.

Duffaud, F., LMS-02: A phase II study of trabectedin in combination with doxorubicin as first line treatment of metastatic leiomyosarcoma . . . , CTOS 18th Annual Meeting, 2013, Abs No. 012.

Nuzzo, C., Retrospective tumor response assessment in locally unresectable or metastatic soft tissue sarcoma (ASTS) pts: Irene experience . . . , CTOS 18th Annual Meeting, 2013, Abs No. PO 322—2013.

Cook, J., Tumour-associated macrophages and cancer, Curr Opin Pharmacol, 2013, vol. 13(4) pp. 595-601.

Blay, J.Y., Efficacy and safety of trabectedin as an early treatment for advanced or metastatic liposarcoma and leiomyosarcoma, Future Oncol, 2014, vol. 10(1) pp. 59-68.

Gettys, S.C., New and emerging therapies for advanced or metastatic soft tissue sarcoma, J Oncol Pharm Pract, 2014, vol. 20(4)pp. 288-297.

Galmarini, C.M., Trabectedin and Plitidepsin: Drugs form the Sea that Strike the Tumor Microenvironment, Mar Drugs, 2014, vol. 12(2) pp. 719-733.

D'Incalci, M., Trabectedin, a drug acting on both cancer cells and the tumour microenvironment, Br J Cancer, 2014, vol. 111(4) pp. 646-650.

Kawano, M., Combination Treatment With Trabectedin and Irinotecan or Topotecan Has Synergistic Effects Against Ovarian Clear Cell Carcinoma Cells, Int J Gynecol Cancer, 2014, vol. 24(5) pp. 829-837.

Coleman, R.L., A phase 3 study of trabectedin plus pegylated liposomal doxorubicin (PLD) versus PLD for treatment of advanced-relapsed epithelial ovarian cancer . . . , ASCO 50th Annual Meeting, 2014, Abs No. TPS5612 (poster).

Coleman, R.L., A phase 3 study of trabectedin plus pegylated liposomal doxorubicin (PLD) versus PLD for treatment of advanced-relapsed epithelial ovarian cancer . . . , ASCO 50th Annual Meeting, 2014, Abs No. TPS5612 (abstract).

Machiels, J-P., Effects of cytochrome P450 inducer and inhibitor coadministration on the pharmacokinetics of trabectedin in pts with advanced solid tumors., ASCO 50th Annual Meeting, 2014, Abs. No. e13520.

Antoun, S., Low skeletal muscle density as predictive for febrile neutropenia in patients treated by doxorubicin/trabectedin/pegfilgrastim . . . , ASCO 50th Annual Meeting, 2014, Abs. N e20640.

Libertini, M., Activity of chemotherapy in a series of patients with locally advanced or metastatic pleomorphic rhabdomyosarcoma: retrospective analysis., ASCO 50th Annual Meeting, 2014, Abs. N 10592 (poster).

Libertini, M., Activity of chemotherapy in a series of patients with locally advanced or metastatic pleomorphic rhabdomyosarcoma: retrospective analysis., ASCO 50th Annual Meeting, 2014, Abs. N 10592 (abstract).

Castelli, C., Modulation of the myeloid compartment of the immune system by angiogenic and kinase inhibitor targeted anticancer therapies, Cancer Immunol Immunother, 2014, vol. 64(1) pp. 83-89.

Mantovani, A., Pharmacological modulation of monocytes and macrophages, Curr Opin Pharmacol, 2014, vol. 17(1) pp. 38-44.

Antoun, S., Low skeletal muscle density is predictive for febrile neutropenia in patients treated by doxorubicin/trabectedin/pegfilgrastim . . . , 39th ESMO Congress, 2014, vol. 25(Supl 4) pp. 494 Abs N 1445P (poster).

Antoun, S., Low skeletal muscle density is predictive for febrile neutropenia in patients treated by doxorubicin/trabectedin/pegfilgrastim . . . , 39th ESMO Congress, 2014, vol. 25(Supl4) pp. 494 Abs N 1445P (abstract).

Antoun, S., Low skeletal muscle density is predictive for febrile neutropenia in patients treated by doxorubicin/trabectedin combination . . . , CTOS 19th Annual Meeting, 2014, pp. 189-190 Abs N 97 (poster).

Antoun, S., Low skeletal muscle density is predictive for febrile neutropenia in patients treated by doxorubicin/trabectedin combination . . . , CTOS 19th Annual Meeting, 2014, pp. 189-190 Abs N 97 (abstract).

Angarita, F.A., Trabectedin for inoperable or recurrent soft tissue sarcoma in adult patients, CTOS 19th Annual Meeting, 2014, pp. 197 Abs N 110 (poster).

Angarita, F.A., Trabectedin for inoperable or recurrent soft tissue sarcoma in adult patients, CTOS 19th Annual Meeting, 2014, pp. 197 Abs N 110 (abstract).

Menjon S., Clinical experience with trabectedin in monotherapy or with doxorrubicine hidroclorure in patients with metastatic cancer., IGCS 15th Biennial Meeting, 2014, vol. 24(9 Supl 4) pp. 1031 Abs N IGCSM-0369.

Gerardi, C., An open-label, randomized phase II study on trabectedin and bevacizumab with or without carboplatin in PPS ovarian cancer, IGCS 15th Biennial Meeting, 2014, vol. 24(9 Supl 4) pp. 455-456 Abs N IGCSM-1249 (poster).

Gerardi, C., An open-label, randomized phase II study on trabectedin and bevacizumab with or without carboplatin in PPS ovarian cancer, IGCS 15th Biennial Meeting, 2014, vol. 24(9 Supl 4) pp. 455-456 Abs N IGCSM-1249 (abstract).

Benedetti Panici, P., Phase II trial of weekly trabectedin plus weekly peylated liposomal doxorubicin for treatment of advanced ovarian carcinoma, IGCS 15th Biennial Meeting, 2014, vol. 24(9 Supl 4) pp. 123 Abs N IGCSM-0383.

Guo Z. Combined Trabectadin and anti-PD1 antibody produces a synergistic antitumor effect in a murine model of ovarian cancer. J Transl Med (2015) 13:247.

Edwards, S.J., Topotecan, PLD, paclitaxel, trabectedin and gemcitabine for advanced recurrent ovarian cancer: systematic review . . . , Health Technol Assess, 2015, vol. 19(7) pp. 1-480.

Pautier, P., Trabectedin in combination with doxorubicin for first-line treatment of advanced uterine or soft-tissue leiomyosarcoma (LMS-02) . . . , Lancet Oncol, 2015, vol. 16(4) pp. 457-464.

Chawla, N., TNT: Talimogene Laherparepvec, Nivolumab and Trabectedin for Advanced Leiomyosarcoma: A Phase 2 Study, 26th Annual Meeting ASGCT, 2023, vol. 31, No. 4S1, Abstract No. No. 54.

Tansir, G., A phase II study of gemcitabine and docetaxel combination in relapsed metastatic or unresectable synovial sarcoma, BMC Cancer, 2023, vol. 23(1) 639.

Liu, Y., Host obesity alters the ovarian tumor immune microenvironment and impacts response to standard of care chemotherapy, J Exp Clin Cancer Res, 2023, vol. 42(1) pp. 165.

Wang, X., Dose-related immunomodulatory effects of recombinant Trail in the tumor immune microenvironment, J Exp Clin Cancer Res, 2023, vol. 42(1) 216.

Povo-Retana, A., Immunometabolic actions of trabectedin and lurbinectedin on human macrophages: relevance for anti-tumor activity., Front Immunol, 2023, vol. In press pp. 1-20.

Assi, T., Trabectedin and radiotherapy in soft tissue sarcomas: friends or foes?, Future Oncol, 2023, vol. 19(28) pp. 1893-1896.

Cope, B.M., Targeting the Molecular and Immunologic Features of Leiomyosarcoma, Cancers, (2023), vol. 15(7), 2099.

Sun, C-M., Targeting microenvironment and cellular immunity in sarcomas with trabectedin combined with metronomic cyclophosphamide: TARMIC study, ESMO Congress, Madrid, 2023, vol. 34 (Supl 2) pp. S1035 Abs No. 1924P.

D'Ambrosio, L., TOMAS2: A randomized phase II study of trabectedin plus olaparib (T+O) or trabectedin (T) in advanced STS . . . , ESMO Congress, Madrid, 2023, vol. 34 (Supl 2) pp. S1332 Abs N LBA91.

Pautier, P., randomised multicenter phase-III study comparing doxorubicin alone vs dox with trabectedin in metastatic LMS: LMS-04, ESMO Congress, Madrid, 2023, vol. 34 (Supl 2) pp. S103 Abs No. 1913 (poster).

Pautier, P., randomised multicenter phase-III study comparing doxorubicin alone vs dox with trabectedin in metastatic LMS: LMS-04, ESMO Congress, Madrid, 2023, vol. 34 (Supl 2) pp. S103 Abs No. 1913 (abstract).

Shang, L., Subverted macrophages in the triple-negative breast cancer ecosystem, Biomed Pharmacother, 2023, vol. 166 pp. 115414.

(56) References Cited

OTHER PUBLICATIONS

Enea, D., Tumour-infiltrating immune cells as a predictive factor in advanced/metastatic leiomyosarcomas: uterine vs non-uterine, 35th European Congress of Pathology, 2023, vol. 483 (Supl 1) p. S257 Abs N E-PS-10-021.
Zweifler, L.E., Parathyroid hormone and trabectedin have differing effects on macrophages and stress fracture repair, Bone, 2023, vol. 179 pp. 116983.
Casagrande, N., In Doxorubicin-Adapted Hodgkin Lymphoma Cells, Acquiring Multidrug Resistance and improved immunosuppression . . . , Cells, 2023, vol. 12(23) pp. 2732.
Pasquali, S., A comparative assessment of selinexor with trabectedin or lurbinectedin in PDX of dedifferentiated liposarcoma (DDLPS), AACR-NCI-EORTC International Conference, 2023, vol. 22(12 Supl) Abs No. B096.
Jain, N., The portrayal of macrophages as tools and targets: A paradigm shift in cancer management, Life Sci, 2023, vol. 316 pp. 121399.
Jumaniyazova, E., Immune Cells in the Tumor Microenvironment of Soft Tissue Sarcomas, Cancers, 2023, vol. 15(24) arn 5760.
Povo-Retana, A., Trabectedin and Lurbinectedin Modulate the Interplay between Cells in the Tumour Microenvironment . . . , Molecules, 2024, vol. 29(2)pp. 331.
Lorusso, D., Single-Agent Trabectedin Versus Physician's Choice Chemotherapy in Recurrent Ovarian Cancer with BRCAness: Phase III Trial, J Clin Oncol, 2024, vol. 42(13) pp. 1488-1498.
C.M., Impact of metronomic trabectedin combined with low-dose cyclophosphamide on sarcoma microenvironment: Tarmic study, Mol Cancer, 2024, vol. 23(1) pp. 37.
Casagrande, N., In ovarian cancer maraviroc potentiates the antitumoral activity and further inhibits tumor-promoting microenvironment . . . , Biomed Pharmacother, 2024, vol. 172 pp. 116296.
Kournoutas, I., Objective Responses in Metastatic Pleomorphic Rhabdomyosarcoma Treated with Doxorubicin and Pembrolizumab: Case Series, Case Rep Oncol, 2024, vol. 17(1) pp. 344-351.
Ringwalt, E.M., Trabectedin Enhances Oncolytic Virotherapy by Reducing Barriers to Virus Spread in Preclinical Bone Sarcoma, bioRxiv, 2024, vol. In press pp. 1-44.
Ringwalt, E., Synergistic mechanisms against pediatric bone sarcoma models: Trabectedin enhances oncolytic virotherapy spread . . . , AACR Annual Meeting 2024, 2024, vol. 84 (6 Supl) Abs N 1087.
Gordon, E.M., Seven year update on SOC-1702: Phase 2 study of trabectedin with ipilimumab and nivolumab in untreated advanced STS., ASCO 60th Annual Meeting, 2024, vol. 42 (Supl 16) Abs No. 11577 (poster).
Gordon, E.M., Seven year update on SOC-1702: Phase 2 study of trabectedin with ipilimumab and nivolumab in untreated advanced STS., ASCO 60th Annual Meeting, 2024, vol. 42 (Supl 16) Abs No. 11577 (abstract).
Chawla, S.P., An update on SOC-1882: A phase 2 study using talimogene laherparepvec, nivolumab, and trabectedin for advanced leiomyosarcoma., ASCO 60th Annual Meeting, 2024, vol. 42 (Supl 16) Abs No. e23570.
Genestie, C., Tumour-infiltrating immune cells as a predictive factor in advanced or metastatic leiomyosarcomas: uterine vs non-uterine, ESMO Sarcoma & Rare Cancers, 2024, vol. 9(Supl 2) pp. 16 Abs N 92P.
Recine, F., Clinical and translational implications of immunotherapy in sarcomas, Front Immunol, 2024, vol. 15 pp. 1378398.
Agarwal, A.D., Update on Saint: A phase II study using trabectedin (T) in combination with ipilimumab (I) and nivolumab (N) in treated STS, ESMO Congress, Barcelona, 2024, vol. 35 (Supl 2) pp. S1036 Abs No. 1729P.
Chawla, S.P., Results of Tnt: A phase II study using talimogene laherparepvec, nivolumab and trabectedin for advanced LMS and LPS, ESMO Congress, Barcelona, 2024, vol. 35 (Supl 2) pp. S1035-S1036 Abs No. 1728P.
Schlenk, R.F., Randomized phase II study of trabectedin/olaparib compared to physician's choice in solid tumors with DNA repair deficiencies, ESMO Congress, Barcelona, 2024, vol. 35 (Supl 2) pp. S294 Abs N 196P.
Reghu, G., Harnessing the innate immune system by revolutionizing macrophage-mediated cancer immunotherapy, J Biosci, 2024, vol. 49 pp. 68 63.
Toledo, B., Deciphering the performance of macrophages in tumour microenvironment: a call for precision immunotherapy, J Hematol Oncol, 2024, vol. 17(1) arn 44.
Luo, W., Circumventing resistance within the Ewing sarcoma microenvironment by combinatorial innate immunotherapy, J Immunother Cancer, 2024, vol. 12(9) arn e009726.
Ringwalt, E.M., Trabectedin promotes oncolytic virus antitumor efficacy, viral gene expression, and effector function in bone sarcoma, Mol Ther Oncol, 2024, vol. 32(4) arn 200886.
Schlenk, R.F., Randomized phase II study of trabectedin/olaparib compared to physician's choice in solid tumors with DNA repair deficiencies, Oncol Res Treat, 2024, vol. 47(Suppl 2) Abs No. 894.
Waldschmidt, J.M., Trabectedin priming and subsequent PD-1 inhibition for long-term disease control in a patient with DDLPS, Jahrestagung der DGHO, 2024, vol. 47(Supl 2) pp. 296-297 Abs N P1055.
Almeida, J.S., Peripheral immune profiling of soft tissue sarcoma: perspectives for disease monitoring, Front Immunol, 2024, vol. 15 pp. 1391840.
Nazzaro, M., Trabectedin modulates the glioma innate and adaptive immune microenvironment in vivo, J Immunol, 2024, vol. 212 (1 Supl) pp. 1461_5482.
Nazzaro, M., Trabectedin demonstrates immunomodulatory properties that improve efficacy of anti-PD1 and delay glioma progression, SITC 2024, 2024, vol. 12(Supl 2) pp. A811 Abs N 709.
Malik, S., Tumor-associated macrophages: A sentinel of innate immune system in tumor microenvironment gone haywire, Cell Biol Int., 2024, vol. 48(10) pp. 1406-1449.
Bergamini, A., Treatment of ovarian cancer cells with olaparib and trabectedin modulates immune molecules and killing ability of TCR-edited T cells, 25th Int. Meeting ESGO, 2024, vol. 34 (Supl 1) pp. A504 Abs No. 780.
Mai, S., Inhibition of Telomerase and the Alternative Lengthening Telomere Pathway Induces Cell Death in Multiple Myeloma, 21st Annual Meeting Int. Myeloma Society, 2024, vol. 24 (Supl 2) pp. S193-S194 Abs No. P-273.
Waldschmidt, J.M., Long-term disease control in dedifferentiated liposarcoma: case report on trabectedin priming followed by PD-1 inhibition, Front Oncol, 2025, vol. 14 pp. 1518775.
Sobczuk, P., Systemic inflammation index is a predictive and prognostic factor in pts with LPS or LMS treated with trabectedin, Sci Rep, 2025, vol. 15(1) pp. 5247.
Rodrigues-Santos, P., Immune monitoring of trabectedin therapy in refractory soft tissue sarcoma patients—the Immunyon study, Front Immunol, 2025, vol. 16 pp. 1516793.
Lai, G., origin and polarization of Macrophages and their role in the formation of the Pre-Metastatic niche in osteosarcoma, Int Immunopharmacol, 2025, vol. 150 pp. 114260.
Aobo, Z., Combination of ICIs and anthracyclines as potential first-line regimen for DDLPS: systematic review and meta-analysis, Cancer Immunol Immunother, 2025, vol. 74(6) pp. 179.
PharmaMar presents at ASCO that the Zepzelca® (lurbinectedin) and atezolizumab (Tecentriq®) combination significantly improves survival as first-line maintenance therapy for extensive-stage small cell lung cancer, May 21, 2025.
FDA Grants Priority Review for Zepzelca® (lurbinectedin) and atezolizumab (Tecentriq®) combination in Extensive Stage Small Cell Lung Cancer, Jun. 10, 2025.
PharmaMar Group Announces Financial Results for First Half 2025, Jun. 30, 2025.
FDA approves PharmaMar's Zepzelca® (lurbinectedin) and Atezolizumab (Tecentriq®) Combination as First-line Maintenance Therapy for Extensive-stage Small Cell Lung Cancer, Oct. 3, 2025.
PharmaMar receives US$50 million milestone payment from Jazz Pharmaceuticals for the FDA's approval of Zepzelca® (lurbinectedin), Oct. 15, 2025.

(56) References Cited

OTHER PUBLICATIONS

Shunyakov et al. Place in therapy of key treatments for platinum-sensitive, relapsed, extensive-stage small cell lung cancer with a focus on lurbinectedin: a narrative review with case studies. Drugs Context. 2025; 14:2025-7-9.
Mavroeidis et al. Novel Therapeutics in Soft Tissue Sarcoma. Cancers 2025, 17, 10.
Waldschmidt et al. Long-term disease control in dedifferentiated liposarcoma: a case report on trabectedin priming followed by PD-1 inhibition. Front. Oncol. , Jan. 16, 2025.
Woo Yen Hwang et al. Clinical practice guidelines for uterine corpus cancer: an update to the Korean Society of Gynecologic Oncology guidelines. J Gynecol Oncol. Jan. 2025;36(1):e71.
Assi &Axel Le Cesne. Doxorubicin and trabectedin in leiomyosarcoma: pioneering a new era of smart combinations in soft tissue sarcomas Future Oncology vol. 21, Issue 8, 2025.
Jozwiak-Hagymasy et al. Economic evaluations and health economic models of soft tissue sarcomas: Systematic literature review from a European and North American perspective. Critical Reviews in Oncology / Hematology 209 (2025) 104661.
Torrado et al. Advancing Understanding and Therapeutic Strategies for NUT Sarcomas: Comprehensive Review of the Literature and Two Cases. J Immunother Precis Oncol. 2025; 8:113-120.
Lai et al. The origin and polarization of Macrophages and their role in the formation of the Pre-Metastatic niche in osteosarcoma. International Immunopharmacology 150 (2025) 114260.
Rao et al. Retrospective Analysis of BRCA-Altered Uterine Sarcoma Treated With Poly(ADP-ribose) Polymerase Inhibitors. Precicision oncology—Mar. 21, 2025.
Zhuang Aobo et al. Combination of immune checkpoint inhibitors and anthracyclines as a potential first-line regimen for dedifferentiated liposarcoma: systematic review and meta-analysis. Cancer Immunology, Immunotherapy (2025) 74:179.
Legallois et al. Identification of Anticancer Drugs Associated to Cancer Therapy-Related Cardiac Dysfunction: A VigiBase® Disproportionality Analysis. uropean Heart Journal—Cardiovascular Pharmacotherapy, pvaf027, 2025.
Hofer et al. Conference on challenges in sarcoma (CCS) 2024: Expert opinions on non-evidence-based management aspects. European Journal of Cancer 220 (2025) 115368.
Hakim et al. Multimodal treatment with cisplatin for metastatic disease in malignant peripheral nerve sheath tumors: a case report and review. Anticancer Drugs. May 1, 2025.
Morand et al. Clinical characterization and therapeutic targeting of fusion genes in oncology. Future Oncology 2025, vol. 21, No. 10, 1249-1260—Mar. 24, 2025.
Serrano et al. SEOM-GEIS Spanish clinical guidelines for the management of soft-tissue sarcomas (2024). Clinical and Translational Oncology (2025) 27:1460-1471, 2025.
Gupta et al. Targeting ovarian cancer: The promise of liposome-based therapies. International Journal of Pharmaceutics 677 (2025) 125647—Apr. 27, 2025.
Underdown et al. Ewing Sarcoma, Desmoplastic Small Round Cell Tumor, and Other Round Cell Sarcomas. Hematology/Oncology Clinics of North America vol. 39, Issue 4, pp. 709-726, Aug. 2025.
Jonczak et al. Liposarcoma: Novel Approaches to Systemic Therapy and Multidisciplinary Care. Hematology/Oncology Clinics of North America vol. 39, Issue 4, Aug. 2025, pp. 805-824, 2025.
Haddox et al. Leiomyosarcoma Therapeutic Approaches and Future Directions. Hematology/Oncology Clinics of North America vol. 39, Issue 4, Aug. 2025, pp. 785-804, 2025.
Penel et al. Maintenance after first-line treatment for advanced soft tissue sarcoma. Critical Reviews in Oncology/Hematology vol. 216, Dec. 2025, 104959, 2025.
Daley et al. New Approaches to Investigate Novel Agents in Ewing Sarcoma: A Report From the Children's Oncology Group Bone Tumor Committee. Pediatric Blood & Cancer, 2025; 72:e31917, 2025.
Mayasin et al. Targeting TAMs & CAFs in melanoma: New approaches to tumor microenvironment therapy. Oncology Research 2025, 33(9), 2221-2242.
VanderWerf B A, Immunosuppressive effect of Ecteinascidia turbinata in mice, Surgical Forum, 1973, vol. 24, pp. 326-328.
Ghaffar, A., et al., Immunomodulation by Extract of Ecteinascidia-Turbinata., Res: J Reticuloendothel Soc, 1977, vol. 22 (AbsSup), pp. 62A—1977.
McCumber, L.J., Modulation of the Eel Anguilla-Rostrata Immune System by Ecteinascidia-Turbinata Extract., 19th National Meeting Reticuloendothelial Society, 1982, vol. 32 (1), pp. 674-679, 1982.
Sigel, M. Michael, A substance from the marine tunicate Ecteinascidia turbinata with selective action on macrophages., Immunol Ser 26 (Mononucl Phagocyte Biol ), 1984, vol. 26, pp. 451-471.
Sigel M M, Immunostimulatory activity of Ecteinascidia turbinata (Ete) extract on a variety of animal species., Prog Clin Biol Res, 1984, vol. 161, pp. 543-554.
Goodbody, The ascidian fauna or two contrasting lagoons in the netherlands antilles . . . study curaçao 202, Uitgaben Natuurwet Stud Suriname Ned Antillen, 1987, vol. 0 (114), pp. 21-61—1987.
Rinehart, Kenneth L., Antitumor, antiviral, and immunosuppressive compounds from marine tunicates, Bioact Compd Mar Org Indo-U S Symp, 1989, pp. 301-307.
Stanley, A., Use of the immunomodulator ecteinascidia-turbinata extract ete in association with Edward Siella-Ictaluri infections, 92nd General Meeting of the ASM, 1992, vol. 92 (0), p. 81.
Stanley, L. A., Effects of the immunomodulator Ecteinascidia turbinata extract on Edwardsiella ictaluri infection of channel catfish., J Aquatic Animal Health, 1995, vol. 7 (2), pp. 141-146.
Uma, A., Immunomodulators in aquaculture., Seafood Export J, 1996, vol. 27 (6), pp. 23-26.
Seaman, F.C., Comparative NMR and modeling study Et743, Et736, and Et729 adducts of DNA duplexes . . . , AACR- NCI-EORTC Conference, 1999, pp. 123(abs.604).
De Angelo, D.J., Phase II Study of Irinotecan (CPT-11) in Relapsed or Refractory Soft Tissue Sarcoma (STS)., ASCO Annual Meeting, 2000, Abs N 2186.
Takahashi N, Sequence-dependent enhancement of cytotoxicity produced by ET-743 with doxorubicin or paclitaxel in STS cells., Clin Cancer Res, 2001, vol. 7 (10), pp. 3251-3257.
Casanova, M, Phase II study of 3-hour infusion ET-743 in pretreated adult and pediatric patients with advanced or recurrent sarcomas . . . , 24th Annual Meeting SIOP, 2002, abs.514.
D'Incalci, In human tumor xenografts the resistance to ET-743 or to cisplatin can be overcome by giving the two drugs in combination, 14th EORTC-NCI-AACR Symposium, 2002, vol. 38 suppl 7, pp. 34 Abs. N 97—2002.
Twelves, C, Phase I and pharmacokinetic study of Yondelis TM administered as an infusion over 1 h or 3 h every 21 days in patients with solid tumours, Eur J Cancer, 2003, vol. 39(13), pp. 1842-1851—2003.
Habeck, M., To approve or not to approve?, Lancet Oncol, 2003, vol. 4(11) pp. 646-2003.
Koeppel, F., Acquired irofulven resistance is accompanied by decreased tumorigenicity without changes in sensitivity . . . , Proc Annu Meet Am Assoc Cancer Res, 2003, vol. 44 pp. 480 (Abs. N 2450).
McMeekin, S, A phase II study of trabectedin (ET-743) as a second line therapy in patients with persistent or recurrent endometrial carcinoma, ASCO 40th Annual Meeting, 2004, vol. 22(14), pp. 5086 (abstract).
McMeekin, S, A phase II study of trabectedin (ET-743) as a second line therapy in patients with persistent or recurrent endometrial carcinoma, ASCO 40th Annual Meeting, 2004, vol. 22(14), pp. 5086 (poster).
Chu, Q S-C, Phase I and pharmacokinetic study of sequential paclitaxel followed by Trabectedin in 24-hr every 2 weeks . . . , ESMO 29th Congress, 2004, vol. 15(Supl 3) pp. iii107 Abs. N 398P (poster).
Chu, Q S-C, Phase I and pharmacokinetic study of sequential paclitaxel followed by Trabectedin in 24-hr every 2 weeks . . . , ESMO 29th Congress, 2004, vol. 15(Supl 3) pp. iii107 Abs. N 398P (abstract).

(56) References Cited

OTHER PUBLICATIONS

Samuels, BL, Randomized phase II study of trabectedin given by two different dosing schedules in LMS or LPS pts . . . , ASCO 40th Annual Meeting, 2004, vol. 22(14s), pp. 818s (poster).
Samuels, BL, Randomized phase II study of trabectedin given by two different dosing schedules in LMS or LPS pts . . . , ASCO 40th Annual Meeting, 2004, vol. 22(14s), pp. 818s (abstract).
Verweij, J., Ecteinascidin-743 (ET-743): Early Test or Effective Treatment in Soft Tissue Sarcomas?, J Clin Oncol, 2005, vol. 23(24), pp. 5420-5423—2005.
Allavena, P., Anti-inflammatory Properties of the Novel Antitumor Agent Yondelis: Inhibition of Macrophage Differentiation and Cytokine Production, Cancer Res, 2005, vol. 65(7), pp. 2964-2971.
Sica, A., Tumour-associated macrophages are a distinct M2 polarised population promoting tumour progression . . . , Eur J Cancer, 2006, vol. 42(6) pp. 717-727.
Demetri, G.D., Impact of independent review on efficacy outcomes in a randomised trial of trabectedin given by two regimens in Lsarcomas, ECCO 14 Barcelona, 2007, vol. 5(4) pp. 402 (Abs. No. O7500).
Le Cesne, A., Assessing the clinical impact of trabectedin in patients with Lsarcomas progressing despite prior conventional chemotherapy . . . , ECCO 14 Barcelona, 2007, vol. 5(4) pp. 405 (Abs. No. P7512) (abstract).
A Phase II Multi-Strata Study of PM01183 as a Single Agent or in Combination with Conventional Chemotherpay in Metastatic and/or Unresectable Sarcomas, NCT02448537, Protocol 15-083, version date Feb. 5, 2016, 63 pages.
PM01183, Advisory Committee Briefing Material: Available for Public Release, Briefing Package, Pediatric Subcommittee Oncology Drug Advisory Committee Meeting held Jun. 21, 2017, 30 pages.
54th ASCO Annual Meeting, Jun. 1-5, 2018, Chicago, IL, Abstract No. 8570, published in J. Clin. Oncol. 36, 2018 (suppl).
Paz-Ares, Luis G; ASCO 2019; Abstract; Efficacy and safety profile of lurbinectedin in second-line SCLC patients: Results from a phase II single-agent trial. ASCO American Society of Clinical Oncology, 55th Annual Meeting, May 31-Jun. 4, 2019. Chicago, Illinois. J Clin Oncol.
Paz-Ares, Luis G; ASCO 2019; Poster; Efficacy and safety profile of lurbinectedin in second-line SCLC patients: Results from a phase II single-agent trial. ASCO American Society of Clinical Oncology, 55th Annual Meeting, May 31-Jun. 4, 2019. Chicago, Illinois. J Clin Oncol. vol. 37 (Supl 15) Abs N 8506.
Trigo Perez, J.M., ASCO 2019 Conference (IASLC), Antitumor activity of single agent Lurbinectedin in patients with relapsed SCLC occurring ≥30 days after last platinum dose. Abstract n. 1710, Poster P1.12-03.
S. Ponce et al. Lurbinectedin combined with Paclitaxel or irinotecan in relapsed SCLC. Results from two phase lb trials. IASLC 20th World Conference on Lung Cancer. Sep. 7-10, 2019. Barcelona, Spain. J Thorac Oncol. vol. 14(Supl) pp. 854 Abs N P2.12-13 (Poster).
S. Ponce et al. Lurbinectedin combined with Paclitaxel or irinotecan in relapsed SCLC. Results from two phase lb trials. IASLC 20th World Conference on Lung Cancer. Sep. 7-10, 2019. Barcelona, Spain. J Thorac Oncol. vol. 14(Supl) pp. 854 Abs N P2.12-13 (Abstract).
S. Ponce ESMO 2019 , Abstract Lurbinectedin (LUR) in combination with irinotecan (IRI) in patients(pts) with advanced solid tumours. ESMO Congress, Barcelona, Spain Sep. 27-Oct. 1, 2019. Ann Oncol. vol. 30 (Supl 5) pp. v178 Abs N 471P.
S. Ponce ESMO 2019, Poster Lurbinectedin in combination with Irinotecan in patients with advanced solid tumors. ESMO Congress, Barcelona, Spain Sep. 27-Oct. 1, 2019. Ann Oncol. vol. 30 (Supl 5) pp. v178 Abs N 471P.
Lum and Alamgeer, Article Technological and Therapeutic Advances in Advanced Small Cell Lung Cancer. Cancers. vol. 11(10) arn 1570.
Laura Mannarino et al. Lurbinectedin down-regulates ASCL1 transcription factor in Small Cell Lung Cancer (SCLC). AACR-NCI-EORTC International Conference on Molecular Targets and Cancer Therapeutics; Oct. 26-30, 2019 Boston, Massachusetts. Mol Cancer Ther. vol. 18(12 Supl) Abs N LB-B13. (Poster).
Laura Mannarino et al. Lurbinectedin down-regulates ASCL1 transcription factor in Small Cell Lung Cancer (SCLC). AACR-NCI-EORTC International Conference on Molecular Targets and Cancer Therapeutics; Oct. 26-30, 2019 Boston, Massachusetts. Mol Cancer Ther. vol. 18(12 Supl) Abs N LB-B13. (Abstract).
Garcia San, Cost comparison of adverse events and treatment administration of lurbinectedin versus intravenous topotecan for relapsed small cell lung cancer in Spain and the United Kingdom. ISPOR Internation Society for Pharmacoeconomics and Outcomes Research ; Nov. 2-6, 2019 Copenhagen, Denmark. Value Health. vol. 22 (Supl 3) Abs N PCN 137. (Poster).
Garcia San, Cost comparison of adverse events and treatment administration of lurbinectedin versus intravenous topotecan for relapsed small cell lung cancer in Spain and the United Kingdom. ISPOR Internation Society for Pharmacoeconomics and Outcomes Research ; Nov. 2-6, 2019 Copenhagen, Denmark. Value Health. vol. 22 (Supl 3) Abs N PCN 137. (Abstract).
Noemi Reguart et al. Article in search of the long-desired 'Copernican Therapeutic revolution in Small Cell Lung Cancer. Drugs. vol. 80(3) pp. 241-262, Jan. 8, 2020.
M. Dómine T. Moran, Article SEOM clinical guidelines for the treatment of small-cell lung cancer (SCLC) (2019) Clinical and Translational Oncology (2020) 22:245-255.
Clinical trial information "Study Escalating Doses of PM01183 in Combination With Fixed Doxorubicin in Patients With Specific Advanced Unresectable Solid Tumors" ClinicalTrials.gov Identifier: NCT01970540.
Diego Kauffmann-Guerrero , Article Orphan drugs in development for the treatment of small-cell lung cancer: Emerging Data on Lurbinectedin. Lung Cancer Targets Ther. vol. 11 pp. 27-31, (2020).
Clinical trial information "Clinical Trial of Lurbinectedin (PM01183) in Selected Advanced Solid Tumors" ClinicalTrials.gov Identifier: NCT02454972.
Trigo J, Article Lurbinectedin as a second-line treatment for patients with small-cell lung cancer; a single-arm, open label, phase 2 basket trial. Lancet Oncol. vol. 21(5) pp. 645-654.
Oscar Arrieta, Article New opportunities in a challenging disease: lurbinectedin for relapsed small-cell lung cancer. Lancet Oncol. vol. 21(5) pp. 605-607.
Poirier, Article New Approaches to SCLC Therapy: From the Laboratory to the Clinic. Journal of Thoracic Oncology vol. 15 No. 4: 520-540.
Santiago Ponce, ASCO 2020 Abstract Lurbinectedin (LUR) in combination with Irinotecan (IRI) in patients (pts) with advanced solid tumors: Updated results from a phase Ib-II trial.
Clinical trial information "Pharmacokinetic Study of PM01183 in Combination With Irinotecan in Patients With Selected Solid Tumors".
Matt L. Harlow et al, "Lurbinectedin Inactivates the Ewing Sarcoma Oncoprotein EWS-FLI1 by Redistributing It within the Nucleus" Cancer Res. vol. 76(22) pp. 6657-6668.
Ryoko Takahashi et al, "Preclinical Investigations of PM01183 (Lurbinectedin) as a Single Agent or in Combination with Other Anticancer Agents for Clear Cell Carcinoma of the Ovary" Plos One. vol. 11 (3) pp. e0151050.
Anna F Farago et al, "Atlantis: a Phase III study of lurbinectedin/doxorubicin versus topotecan or cyclophosphamide/doxorubicin/vincristine in patients with small-cell lung cancer who have failed one prior platinum-containing line" Future Oncol. vol. 15(3) pp. 231-239.
Weiming He et al, "A Scalable Total Synthesis of the Antitumor Agents Et-743 and Lurbinectedin" Angewandte Chemie International Edition vol. 58, Issue12 pp. 3972-3975.
Jimeno Antonio et al, Phase I study of lurbinectedin, a synthetic tetrahydroisoquinoline that inhibits activated transcription, induces DNA single- and double-strand breaks, on a weekly x 2 every-3-week schedule. Invest New Drugs. vol. 35(4) pp. 471-477.

(56) References Cited

OTHER PUBLICATIONS

Kauffmann-Guerrero et al., Orphan Drugs in Development for the Treatment of Small-Cell Lung Cancer: Emerging Data on Lurbinectedin. Lung Cancer (Auckl) Mar. 2, 2020;11:27-31.
Cote Gregory M et al, A phase II multi-strata study of lurbinectedin as a single agent or in combination with conventional chemotherapy in metastatic and/or unresectable sarcomas Eur, J. Cancer 126 (2020) p. 21-32.
M. E. Elez et al, "First-In-Human Phase I Study of Lurbinectedin (PM01183) in Patients with Advanced Solid Tumors" Clin. Cancer Res. 2014, 20(8), 2205-2212.
Paz-Ares Luis et al Phase I clinical and pharmacokinetic study of PM01183 (a tetrahydroisoquinoline, Lurbinectedin) in combination with gemcitabine in patients with advanced solid tumors. Annals of Oncology., Nov. 21, 2016 (Nov. 21, 2016), vol. 35, No. 2, p. 198-206, vol. 37 (Supl 15) Abs N 8506.
José Trigo et al, "Lurbinectedin as second-line treatment for patients with small-cell lung cancer: a single-arm, open-label, phase 2 basket trial"Lancet Oncol. vol. 21(5) pp. 645-654.
Eugenia Olmedo Garcia et al, "Activity of lurbinectedin as single agent and in combination in patients with advanced small cell lung cancer (SCLC) Trials design and schedule Acknowledgements" Annals of Oncology 28 (Supplement 5): v539-v542, 2017.
Y. Metaxas et al, "SAKK 17/16—Lurbinectedin monotherapy in patients with progressive malignant pleural mesothelioma: A multicenter, single-arm phase II trial"Annals of Oncology, vol. 29, Supplement 8, VIII644.
Metaxas Yannis et al, "Combination of cisplatin and lurbinectedin as palliative chemotherapy in progressive malignant pleural mesothelioma: Report of two cases"(Lung Cancer 2016, 12, vol. 102 136-138).
Cortinovis Diego et al, "Novel Cytotoxic Chemotherapies in Small Cell Lung Carcinoma" Cancers (Basel). Mar. 8, 2021;13(5):1152.
Anonymous, "History of Changes for Study: NCT04358237; Lurbinectedin (PM01183) Combined With Pembrolizumab in Small Cell Lung Cancer. (LUPER)".
Ponce Aix Santiago et al, "Lurbinectedin (LUR) in combination with Irinotecan (IRI) in patients (pts) with advanced solid tumors: Updated results from a phase Ib-II trial" Journal of Clinical Oncology. vol. 38. Issue 15 Suppl.
Ponce Aix S et al, "Lurbinectedin (LUR) in combination with irinotecan (IRI) in patients (pts) with advanced solid tumours" Annals of Oncology. vol. 30, Suppl 5.
Anonymous, "Pharmacokinetic Study of Lurbinectedin in Combination With Irinotecan in Patients With Selected Solid Tumors".
Anonymous, "NCT05091567: A Phase III, Open-Label Study of Maintenance Lurbinectedin in Combination With Atezolizumab Compared With Atezolizumab in Participants With Extensive-Stage Small-Cell Lung Cancer (IMforte)".
Anonymous, "Study to Assess Safety, Tolerability, Efficacy of PM01183 and Atezolizumab in Patients w/ Advanced Small Cell Lung Cancer (NCT04253145)".
Metaxas (J. Thor. Oncol. Nov. 2018; 13(11): 1784-1791) Pembrolizumab as Palliative Immunotherapy in Malignant Pleural Mesothelioma.
Leal; JFM et. al. Br. J. Pharmacol. 2010, 161, 1099-110 PM01183, a new DNA minor groove covalent binder with potent in vitro and in vivo anti-tumour activity.
Belgiovine, C et. al. Br. J. Cancer, 2017; 117(5): 628-638 Lurbinectedin reduces tumour-associated macrophages and the inflammatory tumour microenvironment in preclinical models. Br J Cancer. vol. 117(5)pp. 628-638.
Elez, me. et al. Clin. Cancer Res. 2014, 20(8), 2205-2212 First-In-Human Phase I Study of Lurbinectedin (PM01183) in Patients with Advanced Solid Tumors.
"Design and Applications of Prodrugs" (H. Bundgaard et., 1985, Harwood Academic Publisher). Remington Pharmaceutical Sciences by E.W. Martin.
Casares N, Caspase-dependent immunogenicity of doxorubicin-induced tumor cell death. J Exp Med Dec. 19, 2005;202(12):1691-701.
Mattarollo SR, Loi S, Duret H, Ma Y, Zitvogel L, Smyth MJ. Pivotal role of innate and adaptive immunity in anthracycline chemotherapy of established tumors. Cancer Res (2011) 71 (14): 4809-4820.
Ray-Coquard I. Lymphopenia as a prognostic factor for overall survival in advanced carcinomas, sarcomas, and lymphomas. Cancer Res. 2009;69(13):5383-5391 . doi:10.1158/0008-5472.CAN-08-3845.
Fucikova J, Kralikova P, Fialova A, et al. Human tumor cells killed by anthracyclines induce a tumor-specific immune response. Cancer Res. . Jul. 15, 2011;71(14):4821-33.
Ma Y, Adjemian S, Mattarollo SR, et al. Anticancer chemotherapy-induced intratumoral recruitment and differentiation of antigen-presenting cells. Immunity. 2013;38(4):729-741.
Santamaria Nunez G, Robles CM, Giraudon C, et al. Lurbinectedin specifically triggers the degradation of phosphorylated RNA polymerase II and the formation of DNA breaks in cancer cells. Mol Cancer Ther. 2016 ; 15(10):2399-2412. doi : 10.1 158/1535-7163. MCT-16-0172.
Peltonen K, Colis L, Liu H, et al. A targeting modality for destruction of RNA polymerase I that possesses anticancer activity. Cancer Cell. 2014;25(1 ):77-90. doi : 10.1016/j.ccr.2013.12.009.
Xie et al., Lurbinectedin synergizes with immune checkpoint blockade to generate anticancer immunity Oncoimmunology, 2019, vol. 8, No. 11 , e1656502 (9 pages).
Study GO28915—MPDL3280A or Docetaxel in Patients with NSCLA.
Study GO28753—Anit-PDL1 in NSCLA.
Drug Metabolism, the importance of cytochrome P450 3A4, Medsafe NZ, Mar. 2014) 35(1): 4-6.
Drug development and drug interactions, table of substrates, inhibitors and inducers, FDA website, dated on Aug. 24, 2022).
Clinical Drug Interaction Studies—Cytochrome P450 Enzyme- and Transporter-Mediated Drug Interactions Guidance for Industry U.S. Department of Health and Human Services Food and Drug Administration Center for Drug Evaluation and Research (CDER) dated Jan. 2020.
Beroukhim R, Mermel CH, Porter D, et al. The landscape of somatic copy-number alteration across human cancers. Nature. 2010;463(7283):899-905.
Xiang W, Yang CY, Bai L. MCL-1 inhibition in cancer treatment. Onco Targets Ther. Oct. 23, 2018;11:7301-7314. doi: 10.2147/OTT. S146228.
Cancers (Basel) Mar. 2021; 13(6):1292 Targeting BCL-2 in Cancer: Advances, Challenges, and Perspectives.
Hoda et al. Mol. Cancer Ther. 15(10), 1-13 Trabectedin is active agaisnt malignant pleural mesothelioma cell and xenograft models and synergizes with chemotherapy and BCL-2 inhibition in vitro.
Yecies et al. Blood. 2010, 115: 3304-3313, Acquired resistance to ABT-737 in lymphoma cells that up-regulate MCL-1 and BFL-1.
Haolan Wang et al, Hematol. Oncol., 2021;14:67 Targeting MCL-1 in cancer: current status and perspectives.
Tan et al., Clin. Cancer Res.; 17(6), 2011, Navitoclax enhances the efficacy of taxanes in Non-small cell lung cancer models.
Mukherjee et al, Cancers 2020, 12, 2182; Simultaneously Inhibiting BCL2 and MCL1 Is a Therapeutic Option for Patients with Advanced Melanoma.
Yasuda et al., Cell Death and Disease (2020) 11:177, MCL1 inhibition is effective against a subset of small-cell lung cancer with high MCL1 and low BCL-XL expression.
Bolomsky et al., J Hematol Oncol (2020) 13:173, MCL-1 inhibitors, fast-lane development of a new class of anti-cancer agents.
Yan et al., 2022, Cell Reports 40, 111304. Sep. 13, 2022 BET inhibition induces vulnerability to MCL1 targeting through upregulation of fatty acid synthesis pathway in breast cancer. Cell Rep. Sep. 13, 2022;40(11):111304. doi: 10.1016/j.celrep.2022.111304.
Vogler, Targeting BCL2-Proteins for the Treatment of Solid Tumours Adv Med. 2014;2014:943648, Mol Cancer Jul. 2, 2015;14:126.
Lochmann et al. BCL-2 inhibition is a promising therapeutic strategy for small cell lung cancerOncoscience Aug. 14, 2018;5(7-8):218-219.
Metaxas et al., Abstract "SAKK 17/16—Lurbinectedin as second or third line palliative chemotherapy in malignant pleural mesothelioma (MPM): A multi-center, single-arm phase II trial", 43rd ESMO

(56) References Cited

OTHER PUBLICATIONS

European Cancer Congress, Munich, Germany Oct. 19-23, 2018. Ann Oncol, 2019, vol. 30, Supplement 5, V748.
Metaxas et al., Presentation ESMO 2019—Proffered paper (abstract and slides)—Metaxas et al., "1316—SAKK 17/16: Lurbinectedin as second or third line palliative chemotherapy in malignant pleural mesothelioma (MPM): A multi-center, single-arm Phase II trial.".
Metaxas et al., Abstract ESMO 2019—Proffered paper (abstract and slides)—Metaxas et al., "1316—SAKK 17/16: Lurbinectedin as second or third line palliative chemotherapy in malignant pleural mesothelioma (MPM): A multi-center, single-arm Phase II trial.".
Metaxas et al., "Lurbinectedin as second- or third-line palliative therapy in malignant pleural mesothelioma: an international, multicentre, single-arm, phase II trial (SAKK 17/16)", Annals of Oncology, 2020, 31(4), 495-500.
Kepp et al., Oncoimmunology 2020, vol. 9, No. 1, 1-3 Lurbinectedin: an FDA-approved inducer of immunogenic cell death for the treatment of small-cell lung cancer.
Galluzzi et al, Nature reviews. Clinical oncology, (20201200) vol. 17, No. 12, pp. 725-741. Journal code: 101500077. E-ISSN: 1759-4782. L-ISSN: 1759-4774. Electronic Publication Date: Aug. 5, 2020.
Humeau et al., An unexpected link between immunogenic cell death and inhibition of gene transcription, OncoImmunology, 9:1, 1792039, DOI: 10.1080/2162402X.2020.1792039.
Vanmeerbeek et al, Trial watch: chemotherapy-induced immunogenic cell death in immuno-oncology, OncoImmunology, 9:1, 1703449, DOI: 10.1080/2162402X.2019.1703449.
Galluzzi et al, Consensus guidelines for the definition, detection and interpretation of immunogenic cell death. Journal for Immuno Therapy of Cancer, 2020;8:e000337 doi: 10.1136/jitc-2019-000337.
Peng et al, Crizotinib-induced immunogenic cell death in non-small cell lung cancer, Nature Communications, (Dec. 1, 2019) vol. 10, No. 1. arn. 1486. https://doi.org/10.1038/s41467-019-09415-3.
Levesque et al, A synergistic triad of chemotherapy, immune checkpoint inhibitors, and caloric restriction mimetics eradicates tumors in mice, OncoImmunology, 8:11, e1657375, DOI: 10.1080/2162402X.2019.1657375 https://doi.org/10.1080/2162402X.2019.1657375.
Humeau et al, Inhibition of transcription by dactinomycin reveals a new characteristic of immunogenic cell stress, EMBO molecular medicine, vol. 12, No. 5, pp. e11622 DOI 10.15252/emmm.201911622.
Priyanka et al, Trabectedin Reveals a Strategy of Immunomodulation in Chronic Lymphocytic Leukemia, Cancer immunology research, (20191200) vol. 7, No. 12, pp. 2036-2051.
Li et al. Molecular Cancer (2019) 18:177 https://doi.org/10.1186/s12943-019-1102-3 Harnessing tumor-associated macrophages as aids for cancer immunotherapy.
Vernadou et al, International Journal of Gynecological Cancer, (Nov. 2019) vol. 29, Supp. Supplement 4, pp. A375. Abstract No. EP648.
Roberts et al, Provocative Questions in Osteosarcoma Basic and Translational Biology: A Report From the Children's Oncology Group; Cancer 2019;125:3514-3525.DOI: 10.1002/cncr.32351.
Moura Immune-checkpoint genes as predictive biomarkers of trabectedin in advanced soft-tissue sarcoma (STS): A Spanish Group for Research on Sarcomas (GEIS) translational study. Journal of Clin Onc. vol. 38, Issue 15_suppl >.
Chawla the TNT protocol: A phase II study using talimogene laherparepvec (TVEC), nivolumab (N) and trabectedin (T) as first, second/third line therapy for advanced sarcoma, including desmoid tumor and chordoma. Journal of Clin Onc. vol. 38, Issue 15_suppl.
NCT03886311—Talimogene Laherparepvec, Nivolumab and Trabectedin for Sarcoma (TNT).
Gordon et al Saint: Results of an expanded phase II study using safe amounts of ipilimumab (I), nivolumab (N), and trabectedin (T) as first-line treatment of advanced soft tissue sarcoma [NCT03138161]. Journal of Clin Onc. vol. 38, Issue 15_suppl.
Gu et al, Combined Trabectedin and anti-PD1 antibody produces a synergistic antitumor effect in a murine model of ovarian cancer, Journal of Translational Medicine vol. 13, Article No. 247 (2015).
Christian et al, Combined cytotoxic chemotherapy and immunotherapy of cancer: modern times, NAR cancer, (Mar. 2020) vol. 2, No. 1, pp. zcaa002. Electronic.
Jimenez et al, Enriching cancer pharmacology with drugs of marine origin, British Journal of Pharmacology (2020), 177(1), 3-27.
NCT03138161 Saint: Trabectedin, Ipilimumab and Nivolumab as First Line Treatment for Advanced Soft Tissue Sarcoma—Full Text View—ClinicalTrials.gov.
Ayodele et al, Immunotherapy in soft-tissue sarcoma, Current Oncology, (2020) vol. 27, Supp. Supplement 1, pp. 17-23.
Guo et al, Advances and challenges in immunotherapy of small cell lung cancer, Chinese journal of cancer research = Chung-kuo yen cheng yen chiu, (Feb. 2020) vol. 32, No. 1, pp. 115-128.
Domine et al, SEOM clinical guidelines for the treatment of small-cell lung cancer (SCLC), Clinical and Translational Oncology, (Feb. 1, 2020) vol. 22, No. 2, pp. 245-255. Refs: 40 ISSN: 1699-048X; E-ISSN: 1699-3055.
Poirier et al, New Approaches to SCLC Therapy: From the Laboratory to the Clinic, Journal of Thoracic Oncology vol. 15 No. 4: 520-540, https://doi.org/10.1016/j.itho. Jan. 16, 2020.
Arrieta et al, Carboplatin plus etoposide or topotecan for small-cell lung cancer, Lancet Oncology (2020), 21(9), 1132-1134.
Blay et al, The current reality of soft tissue sarcomas: advances, controversies, areas for improvement, and promising new treatments, Expert Review of Anticancer Therapy, (Apr. 30, 2020) vol. 20, No. sup1, pp. 29-39. https://doi.org/10.1080/14737140.2020.1753511.
Saltos et al, Breaking the Impasse: Advances in Treatment of Small Cell Lung Cancer, Clinics in Chest Medicine, (Jun. 2020) vol. 41, No. 2, pp. 269-280.
Pharma Mar Press Release (Dec. 17, 2018—Phase II trial of Lurbinectidin).
Pharma Mar Press Release (Sep. 23, 2019 Phase II stiudy results of Lurbinectedin).
Pharma Mar press release (Jan. 10, 2019 Lurbinectedin data in Prog).
Povo-Retana, et al Cancers (2020), 12(10), 3060 Coden: CANCCT; ISSN: 2072-6694 URL: http://mdpi.com/journal/cancers Publisher: MDPI AG L34 17/156 HCAPLUS Specific effects of trabectedin and lurbinectedin on human macrophage function and fate-novel insights Accession No. 2020:2650246 HCAPLUS | Full-text Document Type: Journal; (online computer file).
Pacheco Jose M L34 14/156 Medline Journal of thoracic disease, (Oct. 2020) vol. 12, No. 10, pp. 6264-6274. Journal code: 101533916. ISSN: 2072-1439. L-ISSN: 2072-1439. Report No. PMC-PMC7656348. Systemic therapy options following first-line chemoimmunotherapy in small-cell lung cancer. Accession No. 2023267104 Medline.
Muller, D.W. L34 23/156 Embase, A non-randomized, open-label phase II trial evaluating efficacy and feasibility of combined treatment with trabectedin and nivolumab in patients with metastatic or inoperable soft tissue sarcomas (STS) after failure of an anthracycline-containing regimen. Annals of Oncology, (Sep. 2020) vol. 31, Supp. Supplement 4, pp. S991. Meeting Info: ESMO Virtual Congress 2020. Virtual, Online. Oct. 16, 2020-Oct. 18, 2020 ISSN: 0923-7534; E-ISSN: 1569-8041 Publisher: Elsevier Ltd.
Toulmonde, M.; L34 21/156 Embase Tramune, a phase Ib study combining trabectedin and durvalumab, results of the expansion cohort in patients with advanced pretreated soft tissue sarcomas. Accession No. 0053907745 EMBASE | Full-text Annals of Oncology, (Sep. 2020) vol. 31, Supp. Supplement 4, pp. S1199. Meeting Info: ESMO Virtual Congress 2020. Virtual, Online. Oct. 16, 2020-Oct 18, 2020 ISSN: 0923-7534; E-ISSN: 1569-8041 Publisher: Elsevier Ltd.
Burger 'Medicinal Chemistry and Drug Discovery' 6th ed. (Donald J. Abraham ed. 2001, Wiley).
Benton Christopher B. et al., "Safety and tolerability of lurbinectedin (PM01183) in patients with acute myeloid leukemia and myelodysplastic syndrome" Hematol Oncol. vol. 37(1) pp. 96-102.
Buikhuisen et al. (Lung cancer, 2015, 89, 223-231) Second line therapy in malignant pleural mesothelioma: A systematic review.

(56) References Cited

OTHER PUBLICATIONS

Scherpereel et al. Lancet Oncol in press, 2018) Novel therapies for malignant pleural mesothelioma.
Disselhorst et al. Immuno-Oncology in malignant pleural mesothelioma (Lancet Respir Med in press, 2018) vol. 6, Issue 6, p. 408-410.
Aviles et al 100th AACR Annual Meeting, Apr. 18-22, 2009, Denver CO, Abstract Nr. 2679.
Aviles et al 100th AACR Annual Meeting, Apr. 18-22, 2009, Denver CO, Abstract Nr. 2679 (Poster).
Moneo et al 100th AACR Annual Meeting, Apr. 18-22, 2009, Denver CO, Abstract Nr. 4525.
Moneo et al 100th AACR Annual Meeting, Apr. 18-22, 2009, Denver CO, Abstract Nr. 4525 (Poster).
50th asco annual meeting, May 30-Jun. 3, 2014, chicago, il, abstract 5505.
26th eortc-nti-aacr symposium on molecular targets and cancer therapeutics; Nov. 18-21, 2014, barcelona, spain, published in Eur. J. Cancer 2014, 50 (Suppl. 6), pp. 13-14, Abs. No. 23.
51st asco annual meeting, May 29-Jun. 2, 2015, chicago, IL, abstract No. TPS2604 and Anstract Nr 7509 published in J. Clin. Oncol. 33, 2015 (suppl).
54th asco annual meeting, Jun. 1-5, 2018, chicago, IL, Abstract No. 11519 Published in J. Clin. Oncol. 36, 2018 (suppl).
Cruz et al. Multicenter Phase II Study of Lurbinectedin in BRCA Mutated and Unselected Metastatic Advanced Breast Cancer and Biomarker Assessment SubstudyClin. Oncol. 2018; in press 1-21.
Saur et al. Lurbinectedin (PM01183) On Days (D) 1 & 8 In Combination With Capecitabine (XEL) in Patients (PTS) With Metastatic Breast (MBC), Colorectal (CRC) or Pancreatic (PAC) Cancer 39th ESMO Congress, Sep. 26-30, 2014, Madrid, Spain, published in Ann. Oncol,2014, 25(Suppl. 4), p. 146 Abs No. 482P.
EU Pharmacopoeia 7.2, 1.2 (2011).
Fridman WH, Zitvogel L, Sautes-Fridman C, Kroemer G. The immune contexture in cancer prognosis and treatment. Nat Rev Clin Oncol. 14(12):717-734.
Lesterhuis WJ, Haanen JB, Punt CJ. Cancer immunotherapy-revisited. Nat Rev Drug Discovery. 2011 ; 10(8) :591-600. doi:10.1038/nrd3500.
Zitvogel L, Kepp O, Kroemer G. Immune parameters affecting the efficacy of chemotherapeutic regimens. Nat Rev Clin Oncol. 2011 ;8(3):151-160.
Ghiringhelli F, Apetoh L, Tesniere A, et al. Activation of the NLRP3 inflammasome in dendritic cells induces IL-1 beta-dependent adaptive immunity against tumors. Nat Med. 2009; 15(10):1170-1178. doi:10.1038/nm.2028.
Michaud M, Martins I, Sukkurwala AQ, et al. Autophagy-dependent anticancer immune responses induced by chemotherapeutic agents in mice. Science.2011 ;334(6062) : 1573-1577. doi : 10.1126/science.1208347.
Apetoh L, Ghiringhelli F, Tesniere A, et al. The interaction between HMGB1 and TLR4 dictates the outcome of anticancer chemotherapy and radiotherapy. Immunol Rev. 2007;220:47-59. doi:10.1 11 1/j.1600-065X.2007.00573.x.
Sistigu A, Yamazaki T, Vacchelli E, et al. Cancer cell-autonomous contribution of type I interferon signaling to the efficacy of chemotherapy. Nat Med. 2014;20(1 1 ):1301-1309. doi:10.1038/nm.3708.
Apetoh L, Ghiringhelli F, Tesniere A, et al. Toll-like receptor 4-dependent contribution of the immune system to anticancer chemotherapy and radiotherapy. Nat Med. 2007; 13(9) :1050-1059. doi:10.1038/nm1622.
Vacchelli E, Ma Y, Baracco EE, et al. Chemotherapy-induced antitumor immunity requires formyl peptide receptor 1. Science. 2015;350(6263):972-978. doi : 10.1126/science.aad0779.
Glisson 2003 Reccurent Small Cell Lung Cancer Update Seminars in Oncology. Seminars in Oncology, vol. 30, No. 1. pp. 72-78.
Davies et al. Treatment of recurrent small cell lung cancer 2004. Hematol Oncol Clin North Am . Apr. 2004; 18(2):387-416.
Sundstrom et al. Second line chemotherapy in recurrent small cell lung cancer May 2005;48(2):251-61.
Jackman and Johnson. Small-cell lung cancer. Lancet 2005; 366: 1385-96.
Huisman et al. Second-line chemotherapy and its evaluation in small cell lung cancer. Cancer Treatment Reviews 1999; 25 (4):199-206. Ar ticle No. ctr v. 1999.0125.
Clark and Ihde 1998 Smal cell lung caner: treatment progress and prospects. Clark 1998 Smal cell lung caner: treatment progress and prospects.
Martins I, Kepp O, Schlemmer F, et al. Restoration of the immunogenicity of cisplatin-induced cancer cell death by endoplasmic reticulum stress. Oncogene. 2011 ;30( 10):1 147-1158.
Wertz IE, Kusam S, Lam C, et al. Sensitivity to antitubulin chemotherapeutics is regulated by MCL1 and FBW7. Nature. 2011;471(7336):110-114.
Leverson et al. Science translational medicine, vol. 7, 279, Exploiting selective BCL-2 family inhibitors to dissect cell survival dependencies and define improved strategies for cancer therapy.
Chou T.C., Pharmacol. Rev., (2006), vol. 58, pp. 621-681 Theoretical basis, experimental design, and computerized simulation of synergism and antagonism in drug combination studies.
Fisher et al., Annu Rev Public Health, (19990000), vol. 20, pp. 145-157 Time-dependent covariates in the Cox proportional-hazards regression model.
Poveda et al., Lurbinectedin (PM01183), an active compound in platinum-resistant/refractory ovarian cancer (PRROC) patients: Results of a two-stage, controlled phase II study. ASCO American Society of Clinical Oncology, 50th Annual Meeting, May 30-Jun. 3, 2014. Chicago, Illinois. J Clin Oncol. vol. 32(Supl 15) Abs N 5505 (Poster).
Poveda et al., Lurbinectedin (PM01183), an active compound in platinum-resistant/refractory ovarian cancer (PRROC) patients: Results of a two-stage, controlled phase II study. ASCO American Society of Clinical Oncology, 50th Annual Meeting, May 30-Jun. 3, 2014. Chicago, Illinois. J Clin Oncol. vol. 32(Supl 15) Abs N 5505 (Abstract).
Grazziotin-Soares et al The Marine Products Yondelis and Tryptamicidin (PM01183) Show Activity Toward Platinum-Resistant Cells and Attenuates Nucleotide Excision Repair (Presentation). 31st EORTC-PAMM (Pharmacology and Molecular Mechanisms) Group Annual Winter Meeting, Jan. 27-30, 2010. Toulouse, France.
Grazziotin-Soares et al The Marine Products Yondelis and Tryptamicidin (PM01183) Show Activity Toward Platinum-Resistant Cells and Attenuates Nucleotide Excision Repair (Abstract). 31st EORTC-PAMM (Pharmacology and Molecular Mechanisms) Group Annual Winter Meeting, Jan. 27-30, 2010. Toulouse, France.
Grazziotin-Soares et al The Marine Products Yondelis and Tryptamicidin (PM01183) Show Activity Toward Platinum-Resistant Cells and Attenuates Nucleotide Excision Repair (Poster). 22nd EORTC-NCI-AACR Symposium on Molecular Targets and Cancer Therapeutics; Nov. 16-19, 2010. Berlin, Germany. Eur J Cancer vol. 8(7) pp. 166-167 Abs. No. 522.
Grazziotin-Soares et al.The Marine Products Yondelis and Tryptamicidin (PM01183) Show Activity Toward Platinum-Resistant Cells and Attenuates Nucleotide Excision Repair (Abstract). 22nd EORTC-NCI-AACR Symposium on Molecular Targets and Cancer Therapeutics; Nov. 16-19, 2010. Berlin, Germany. Eur J Cancer vol. 8(7) pp. 166-167 Abs. No. 522.
Ratain et al PM01183 clinical and pharmacokinetic (PK) preliminary results of the first first-in in-man phase I study following an accelerated titration design. 22nd EORTC-NCI-AACR Symposium on Molecular Targets and Cancer Therapeutics; Nov. 16-19, 2010. Berlin, Germany. Eur J Cancer. vol. 8(7) pp. 137-138 Abs. No. 434 (Poster).
Ratain et al PM01183 clinical and pharmacokinetic (PK) preliminary results of the first first-in in-man phase I study following an accelerated titration design. 22nd EORTC-NCI-AACR Symposium on Molecular Targets and Cancer Therapeutics; Nov. 16-19, 2010. Berlin, Germany. Eur J Cancer. vol. 8(7) pp. 137-138 Abs. N 434 (Abstract).
Guillen et al. In vivo combination studies of PM01183 with alkylating, antimetabolites, DNA-topoisomerase inhibitors and tubulin

(56) References Cited

OTHER PUBLICATIONS binding agents. AACR American Association for Cancer Research; 102nd Annual Meeting; Apr. 2-6, 2011. Orlando, Florida. Abs. No. 3538 (Poster).

Guillen et al. In vivo combination studies of PM01183 with alkylating, antimetabolites, DNA-topoisomerase inhibitors and tubulin binding agents. AACR American Association for Cancer Research; 102nd Annual Meeting; Apr. 2-6, 2011. Orlando, Florida. Abs. No. 3538 (Abstract).

Grazziotin-Soares et al The Marine Products Yondelis and Tryptamicidin (PM01183) Show Activity Toward Platinum-Resistant Cells and Attenuates Nucleotide Excision Repair (Poster). AACR American Association for Cancer Research; 102nd Annual Meeting; Apr. 2-6, 2011. Orlando, Florida. Abs. N5431.

"Grazziotin-Soares et al The Marine Products Yondelis and Tryptamicidin (PM01183) Show Activity Toward Platinum-Resistant Cells and Attenuates Nucleotide Excision Repair (Abstract). AACR American Association for Cancer Research; 102nd Annual Meeting; Apr. 2-6, 2011. Orlando, Florida. Abs. N5431".

Calabuig Modelado Molecular de la Interacción de Fármacos Antitumorales y Nucleasas con el and. Alcalá de Henares, 2011 Departamento de Farmacología Universidad de Alcalá (with English translation).

Bishop et al. Antitumor effect and tumor distribution of PM01183 in human pancreatic and breast xenograft mouse models. AACR American Association for Cancer Research; Annual Meeting; Mar. 31-Apr. 4, 2012. Chicago, IL. Abs. N 1779 (Poster).

Bishop et al. Antitumor effect and tumor distribution of PM01183 in human pancreatic and breast xenograft mouse models. AACR American Association for Cancer Research; Annual Meeting; Mar. 31-Apr. 4, 2012. Chicago, IL. Abs. N 1779 (Abstract).

Villanueva et al Antitumor effect of PM01183 in a patient-derived Cisplatin-sensitive and -resistant serous epithelial ovarian orthotopic tumor model. AACR American Association for Cancer Research; Annual Meeting; Mar. 31-Apr. 4, 2012. Chicago, IL Abs N 1778 (Poster).

Villanueva et al Antitumor effect of PM01183 in a patient-derived Cisplatin-sensitive and -resistant serous epithelial ovarian orthotopic tumor model. AACR American Association for Cancer Research; Annual Meeting; Mar. 31-Apr. 4, 2012. Chicago, IL Abs N 1778 (Abstract).

Cespedes et al. Antitumor effect of PM01183 in a human pancreatic adenocarcinoma orthotopic model. AACR American Association for Cancer Research; Annual Meeting; Mar. 31-Apr. 4, 2012. Chicago, IL. Abs N 1777 (Poster).

Cespedes et al. Antitumor effect of PM01183 in a human pancreatic adenocarcinoma orthotopic model. AACR American Association for Cancer Research; Annual Meeting; Mar. 31-Apr. 4, 2012. Chicago, IL. Abs N 1777 (Abstract).

Vidal et al. Lurbinectedin (PM01183), a New DNA Minor Groove Binder, Inhibits Growth of Orthotopic Primary Graft of Cisplatin-Resistant Epithelial Ovarian Cancer. Clin Cancer Res. vol. 18(19)pp. 5399-5411.

Berton-Rigaud et al. Lurbinectedin (PM01183) activity in platinum-resistant/refractory ovarian cancer patients. Preliminary results of an ongoing two-stage Phase II study. 37th ESMO Congress, Vienna, Austria Sep. 28-Oct. 2, 2012. Ann Oncol. vol. 23(Supl 9) p. 3 Abs. No. 968O (Presentation).

Berton-Rigaud et al. Lurbinectedin (PM01183) activity in platinum-resistant/refractory ovarian cancer patients. Preliminary results of an ongoing two-stage Phase II study. 37th ESMO Congress, Vienna, Austria Sep. 28-Oct. 2, 2012. Ann Oncol. vol. 23(Supl 9) p. 3 Abs. No. 968O (Abstract).

Calvo et al Lurbinectedin (PM01183) in combination with gemcitabine (GEM). Preliminary results of an ongoing phase Ib study. 37th ESMO Congress, Vienna, Austria Sep. 28-Oct. 2, 2012. Ann Oncol. vol. 23(Supl 9) p. 66-67 Abs. N 484P (Poster).

Calvo et al Lurbinectedin (PM01183) in combination with gemcitabine (GEM). Preliminary results of an ongoing phase Ib study. 37th ESMO Congress, Vienna, Austria Sep. 28-Oct. 2, 2012. Ann Oncol. vol. 23(Supl 9) p. 66-67 Abs. N 484P (Abstract).

Santamaria et al TC-NER Dependent Degradation of RNA Pol II in Response to Lurbinectedin (PM01183). 24th EORTC-NCI-AACR Symposium on Molecular Targets and Cancer Therapeutics; Nov. 6-9, 2012. Dublin, Ireland. Eur J Cancer. vol. 48(Supl 6) pp. 66 Abs. N 218 (poster).

Santamaria et al TC-NER Dependent Degradation of RNA Pol II in Response to Lurbinectedin (PM01183). 24th EORTC-NCI-AACR Symposium on Molecular Targets and Cancer Therapeutics; Nov. 6-9, 2012. Dublin, Ireland. Eur J Cancer. vol. 48(Supl 6) pp. 66 Abs. N 218 (Abstract).

Frapolli et al Lurbinectedin (PM01183): Antineoplastic Activity in Murine and Human Experimental Models. 24th EORTC-NCI-AACR Symposium on Molecular Targets and Cancer Therapeutics; Nov. 6-9, 2012. Dublin, Ireland. Eur J Cancer. vol. 48(Supl 6) pp. 66-67 Abs. N 220 (Poster).

Frapolli et al Lurbinectedin (PM01183): Antineoplastic Activity in Murine and Human Experimental Models. 24th EORTC-NCI-AACR Symposium on Molecular Targets and Cancer Therapeutics; Nov. 6-9, 2012. Dublin, Ireland. Eur J Cancer. vol. 48(Supl 6) pp. 66-67 Abs. N 220 (Abstract).

Lopez-Casas et al Lurbinectedin (PM01183) in Combination with Gemcitabine in Patient-Derived, Pancreatic Ductal Adenocarcinoma (PDA) Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67 Abs. N 221 (Poster).

Lopez-Casas et al Lurbinectedin (PM01183) in Combination with Gemcitabine in Patient-Derived, Pancreatic Ductal Adenocarcinoma (PDA) Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67 Abs. N 221 (Abstract).

Aviles et al. Lurbinectedin (PM01183): Pharmacokinetics/Pharmacodynamic (PK/PD) Properties in Pancreas, Ovarian and NSCLC Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67 Abs. N 222 (Poster).

Aviles et al. Lurbinectedin (PM01183): Pharmacokinetics/Pharmacodynamic (PK/PD) Properties in Pancreas, Ovarian and NSCLC Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67 Abs. N 222 (Abstract).

Mangues et al Lurbinectedin (PM01183) Synergizes with Gemcitabine in NSCLC, Ovarian and Pancreas Tumor Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67-68 Abs. N 223 (poster).

Mangues et al Lurbinectedin (PM01183) Synergizes with Gemcitabine in NSCLC, Ovarian and Pancreas Tumor Xenografts. 24th EORTC-NCI-AACR Symposium on Molecular Targets and Cancer Therapeutics; Nov. 6-9, 2012. Dublin, Ireland. Eur J Cancer. vol. 48(Supl 6) pp. 67-68 Abs. N 223 (Abstract).

Guillén et al Lurbinectedin (PM01183) in vivo synergizes the antitumor activity of taxanes. AACR American Association for Cancer Research; Annual Meeting; Apr. 6-10, 2013. Washington, DC. Cancer Res. vol. 73(8 Supl 1) Abs N 5495 (Poster).

Guillén et al Lurbinectedin (PM01183) in vivo synergizes the antitumor activity of taxanes. AACR American Association for Cancer Research; Annual Meeting; Apr. 6-10, 2013. Washington, DC. Cancer Res. vol. 73(8 Supl 1) Abs N 5495 (Abstract).

Aviles et al. Synergism of Lurbinectedin (PM01183) combined with 5-fluorouracil (5-FUU): in vitro and in vivo studies. AACR American Association for Cancer Research; Annual Meeting; Apr. 6-10, 2013. Washington, DC. Cancer Res. vol. 73(8 Supl 1) Abs N 5498 (Poster).

Aviles et al Synergism of Lurbinectedin (PM01183) combined with 5-fluorouracil (5-FUU): in vitro and in vivo studies. AACR American Association for Cancer Research; Annual Meeting; Apr. 6-10, 2013. Washington, DC. Cancer Res. vol. 73(8 Supl 1) Abs N 5498 (Abstract).

Galmarini et al Lurbinectedin (PM01183) synergizes with topoisomerase I inhibitors in vitro and in vivo. AACR American Association for

(56) References Cited

OTHER PUBLICATIONS

Cancer Research; Annual Meeting; Apr. 6-10, 2013. Washington, DC. Cancer Res. vol. 73(8 Supl 1) Abs N 5499 (Poster).
Galmarini et al Lurbinectedin (PM01183) synergizes with topoisomerase I inhibitors in vitro and in vivo. AACR American Association for Cancer Research; Annual Meeting; Apr. 6-10, 2013. Washington, DC. Cancer Res. vol. 73(8 Supl 1) Abs N 5499 (Abstract).
Santamaria et al . Lurbinectedin (PM01183) specifically targets RNA Pol II for degradation via the proteasome pathway in a TC-NER-dependent fashion. AACR American Association for Cancer Research; Annual Meeting; Apr. 6-10, 2013. Washington, DC. Cancer Res. vol. 73(8 Supl 1) Abs N 5558 (Poster).
Santamaria et al . Lurbinectedin (PM01183) specifically targets RNA Pol II for degradation via the proteasome pathway in a TC-NER-dependent fashion. AACR American Association for Cancer Research; Annual Meeting; Apr. 6-10, 2013. Washington, DC. Cancer Res. vol. 73(8 Supl 1) Abs N 5558 (Abstract).
Romano et al. Comparison of in vitro and in vivo biological effects of trabectedin, lurbinectedin (PM01183) and Zalypsis® (PM00104). Int J Cancer. vol. 133(9)pp. 2024-2033.
Mallarkey and Coombes. Targeted therapies in medical oncology: successes, failures and next steps. Ther Adv Med Oncol. vol. 5(1) pp. 5-16.
Calvo et al. Lurbinectedin (PM01183) in combination with doxorubicin (DOX): Preliminary results of a phase Ib study. 17th ECCO—38th ESMO—32nd ESTRO European Cancer Congress, Amsterdam, Sep. 27-Oct. 1, 2013. Eur J Cancer. vol. 49(Supl 2) pp. 178-179 Abs. No. 860 (Poster).
Poveda et al. Lurbinectedin (PM01183) activity in platinum-resistant/refractory ovarian cancer patients: Updated results of an ongoing two stage Phase II study. 17th ECCO—38th ESMO—32nd ESTRO European Cancer Congress, Amsterdam, Sep. 27-Oct. 1, 2013. Eur J Cancer. vol. 49(Supl 2) pp. 732 Abs. N 3065. (Poster).
Poveda et al. Lurbinectedin (PM01183) activity in platinum-resistant/refractory ovarian cancer patients: Updated results of an ongoing two stage Phase II study. 17th ECCO—38th ESMO—32nd ESTRO European Cancer Congress, Amsterdam, Sep. 27-Oct. 1, 2013. Eur J Cancer. vol. 49(Supl 2) pp. 732 Abs. N 3065. (Abstract).
Cruz et al. Analysis of secondary mutations in BRCA1/2 genes as a mechanism of resistance to PM01183 in BRCA-mutation carriers. AACR-NCI-EORTC International Conference on Molecular Targets and Cancer Therapeutics; Oct. 19-23, 2013. Boston, MA. Abs N B117 (Poster).
Cruz et al. Analysis of secondary mutations in BRCA1/2 genes as a mechanism of resistance to PM01183 in BRCA-mutation carriers. AACR-NCI-EORTC International Conference on Molecular Targets and Cancer Therapeutics; Oct. 19-23, 2013. Boston, MA. Abs N B117 (Abstract).
Paz-Ares et al. Clinical activity of lurbinectedin (PM01183) in combination with gemcitabine (GEM) in non-small cell lung cancer (NSCLC) patients (pts): preliminary subgroup analysis of a phase Ib study. IASLC 15th World Conference on Lung Cancer. Oct. 27-31, 2013. Sydney, Australia. J Thorac Oncol. vol. 8 (Suppl 2) Abs No. 955 (Poster).
Paz-Ares et al. Clinical activity of lurbinectedin (PM01183) in combination with gemcitabine (GEM) in non-small cell lung cancer (NSCLC) patients (pts): preliminary subgroup analysis of a phase Ib study. IASLC 15th World Conference on Lung Cancer. Oct. 27-31, 2013. Sydney, Australia. J Thorac Oncol. vol. 8 (Suppl 2) Abs No. 955 (Abstract).
Forster et al. Clinical activity of lurbinectedin (PM01183) in combination with doxorubicin (DOX) in small-cell lung cancer (SCLC) patients (pts): Preliminary results of a phase Ib study subpopulation analysis. IASLC 15th World Conference on Lung Cancer. Oct. 27-31, 2013. Sydney, Australia. J Thorac Oncol. vol. 8(Supl 2) Abs No. 954 (Poster).
Forster et al. Clinical activity of lurbinectedin (PM01183) in combination with doxorubicin (DOX) in small-cell lung cancer (SCLC) patients (pts): Preliminary results of a phase Ib study subpopulation analysis. IASLC 15th World Conference on Lung Cancer. Oct. 27-31, 2013. Sydney, Australia. J Thorac Oncol. vol. 8(Supl 2) Abs No. 954 (Abstract).
Isakoff et al. Multicenter phase II trial of the novel compound PM01183 (lurbinectedin) in BRCA1/2-associated or unselected metastatic breast cancer. San Antonio Breast Cancer Symposium (SABCS). Dec. 10-14, 2013. San Antonio, Texas, USA. Camcer Res. vol. 73 (24 Supl) Abs No. OT1-4-01. (Poster).
Isakoff et al. Multicenter phase II trial of the novel compound PM01183 (lurbinectedin) in BRCA1/2-associated or unselected metastatic breast cancer. San Antonio Breast Cancer Symposium (SABCS). Dec. 10-14, 2013. San Antonio, Texas, USA. Camcer Res. vol. 73 (24 Supl) Abs No. OT1-4-01. (Abstract).
Harlow et al. PM01183 shows an improved therapeutic index relative to trabectedin and suppresses EWS/FLI1 activity at clinically achievable concentrations. AACR American Association for Cancer Research; 105th Annual Meeting; Apr. 5-9, 2014. San Diego, California. Abs N 3962 (Poster).
Harlow et al. PM01183 shows an improved therapeutic index relative to trabectedin and suppresses EWS/FLI1 activity at clinically achievable concentrations. AACR American Association for Cancer Research; 105th Annual Meeting; Apr. 5-9, 2014. San Diego, California. Abs N 3962 (Abstract).
Sauri et al. Lurbinectedin (PM01183) on days (D) 1 & 8 in combination with capecitabine (XEL) in patients (PTS) with metastatic breast (MBC), colorectal (CRC) or pancreatic (PAC) cancer. 39th ESMO Congress, Madrid, España Sep. 26-30, 2014. Ann Oncol. vol. 25(Supl 4) pp. 146 Abs No. 482P. (poster).
Sauri et al. Lurbinectedin (PM01183) on days (D) 1 & 8 in combination with capecitabine (XEL) in patients (PTS) with metastatic breast (MBC), colorectal (CRC) or pancreatic (PAC) cancer. 39th ESMO Congress, Madrid, España Sep. 26-30, 2014. Ann Oncol. vol. 25(Supl 4) pp. 146 Abs No. 482P. (Abstract).
Santamaria et al. Lurbinectedin (PM01183) specifically targets RNA Pol II for degradation via the proteasome pathway in a transcription and TC-NER dependent fashion. 26th EORTC-NCI-AACR Symposium on Molecular Targets and Cancer Therapeutics; Nov. 18-21, 2014. Barcelona, Spain. Eur J Cancer. vol. 50(Supl 6) pp. 20-21 Abs N 47. (Poster).
Santamaria et al. Lurbinectedin (PM01183) specifically targets RNA Pol II for degradation via the proteasome pathway in a transcription and TC-NER dependent fashion. 26th EORTC-NCI-AACR Symposium on Molecular Targets and Cancer Therapeutics; Nov. 18-21, 2014. Barcelona, Spain. Eur J Cancer. vol. 50(Supl 6) pp. 20-21 Abs N 47. (Abstract).
Ratain et al. Phase I study of lurbinectedin (PM01183) administered on days (D) 1 & 8 every 3 weeks (q3wk) in patients (pts) with solid tumors. 26th EORTC-NCI-AACR Symposium on Molecular Targets and Cancer Therapeutics; Nov. 18-21, 2014. Barcelona, Spain. Eur J Cancer. vol. 50(Supl 6) pp. 13-14 Abs N 23. (Poster).
Ratain et al. Phase I study of lurbinectedin (PM01183) administered on days (D) 1 & 8 every 3 weeks (q3wk) in patients (pts) with solid tumors. 26th EORTC-NCI-AACR Symposium on Molecular Targets and Cancer Therapeutics; Nov. 18-21, 2014. Barcelona, Spain. Eur J Cancer. vol. 50(Supl 6) pp. 13-14 Abs N 23. (Abstract).
Fernandez et al. Pharmacokinetic and Pharmacodynamic modeling of neutropenia for Lurbinectedin. XXVII Congress of the Spanish Society for Clinical Pharmacology, Oct. 2-4, 2014. Sevilla, Spain. Basic Clin Pharmacol Toxicol. vol. 115(Supl 3) pp. 20 Abs. N 53.
Balmana et al. Lurbinectedin (PM01183) activity in BRCA 1/2-associated or unselected metastatic breast cancer: interim results of an ongoing phase II trial. 37th San Antonio Breast Cancer Symposium (SABCS). Dec. 9-13, 2014. San Antonio, Texas, USA. Abs N P3-13-01 (Poster).
Balmana et al. Lurbinectedin (PM01183) activity in BRCA 1/2-associated or unselected metastatic breast cancer: interim results of an ongoing phase II trial. 37th San Antonio Breast Cancer Symposium (SABCS). Dec. 9-13, 2014. San Antonio, Texas, USA. Abs N P3-13-01 (Abstract).
Guillen et al. Lurbinectedin (PM01183) synergizes in vivo the antitumor activity of doxorubicin in SCLC tumor xenografts. AACR American Association for Cancer Research; 106th Annual Meeting;

(56) References Cited

OTHER PUBLICATIONS

Apr. 18-22, 2015. Philadelphia, Pennsylvania. Cancer Res. vol. 75(15 Supl)Abs N 2542. (Poster).
Guillen et al. Lurbinectedin (PM01183) synergizes in vivo the antitumor activity of doxorubicin in SCLC tumor xenografts. AACR American Association for Cancer Research; 106th Annual Meeting; Apr. 18-22, 2015. Philadelphia, Pennsylvania. Cancer Res. vol. 75(15 Supl)Abs N 2542. (Abstract).
Santamaria et al. Synergistic combination of lurbinectedin and PARP inhibitors in breast cancer tumor cell lines. AACR American Association for Cancer Research; 106th Annual Meeting; Apr. 18-22, 2015. Philadelphia, Pennsylvania. Cancer Res. vol. 75(15 Supl) Abs No. 2520. (Poster).
Santamaria et al. Synergistic combination of lurbinectedin and PARP inhibitors in breast cancer tumor cell lines. AACR American Association for Cancer Research; 106th Annual Meeting; Apr. 18-22, 2015. Philadelphia, Pennsylvania. Cancer Res. vol. 75(15 Supl) Abs No. 2520. (Abstract).
Takashi et al. Antitumor activity of lurbinectedin toward ovarian clear cell carcinoma. AACR American Association for Cancer Research; 106th Annual Meeting; Apr. 18-22, 2015. Philadelphia, Pennsylvania. Cancer Res. vol. 75(15 Supl) Abs N 1642. (Poster).
Takashi et al. Antitumor activity of lurbinectedin toward ovarian clear cell carcinoma. AACR American Association for Cancer Research; 106th Annual Meeting; Apr. 18-22, 2015. Philadelphia, Pennsylvania. Cancer Res. vol. 75(15 Supl) Abs N 1642. (Abstract).
Forster et al. Lurbinectedin (PM01183) with doxorubicin (DOX), an active treatment as second-line therapy in small cell lung cancer (SCLC). ASCO American Society of Clinical Oncology, 51th Annual Meeting, May 29-Jun. 2, 2015. Chicago, Illinois. Abs No. 7509 (Presentation).
Forster et al. Lurbinectedin (PM01183) with doxorubicin (DOX), an active treatment as second-line therapy in small cell lung cancer (SCLC). ASCO American Society of Clinical Oncology, 51th Annual Meeting, May 29-Jun. 2, 2015. Chicago, Illinois. Abs No. 7509 (Poster).
Forster et al. Lurbinectedin (PM01183) with doxorubicin (DOX), an active treatment as second-line therapy in small cell lung cancer (SCLC). ASCO American Society of Clinical Oncology, 51th Annual Meeting, May 29-Jun. 2, 2015. Chicago, Illinois. Abs No. 7509 (Abstract).
Provencio Pulla et al. A multicenter phase II basket clinical trial of lurbinectedin (PM01183) in selected advanced solid tumors. ASCO American Society of Clinical Oncology, 51th Annual Meeting, May 29-Jun. 2, 2015. Chicago, Illinois. Abs N TPS2604. (Poster).
Provencio Pulla et al. A multicenter phase II basket clinical trial of lurbinectedin (PM01183) in selected advanced solid tumors. ASCO American Society of Clinical Oncology, 51th Annual Meeting, May 29-Jun. 2, 2015. Chicago, Illinois. Abs N TPS2604. (Abstract).
Marchetti et al. An overview of early investigational therapies for chemoresistant ovarian cancer. Expert Opin Invest Drugs. vol. 24(9) pp. 1163-1183.
Forster et al. Phase I study of lurbinectedin (PM01183) in combination with cisplatin (C) with or without aprepitant(Ap) in patients (pts) with advanced solid tumors. 18th ECCO—40th ESMO European Cancer Congress, Vienna, Austria, Sep. 25-29, 2015. Eur J Cancer. vol. 51(Supl 3) pp. 60 Abs. N 316. (Poster).
Forster et al. Phase I study of lurbinectedin (PM01183) in combination with cisplatin (C) with or without aprepitant(Ap) in patients (pts) with advanced solid tumors. 18th ECCO—40th ESMO European Cancer Congress, Vienna, Austria, Sep. 25-29, 2015. Eur J Cancer. vol. 51(Supl 3) pp. 60 Abs. N 316. (Abstract).
Garralda et al. Lurbinectedin (PM01183) in combination with paclitaxel (P) in patients (pts) with advanced solid tumors. 18th ECCO—40th ESMO European Cancer Congress, Vienna, Amsterdam, Sep. 25-29, 2015. Eur J Cancer. vol. 51 (Supl 3) pp. 66 Abs. No. 335 (Poster).
Garralda et al. Lurbinectedin (PM01183) in combination with paclitaxel (P) in patients (pts) with advanced solid tumors. 18th ECCO—40th ESMO European Cancer Congress, Vienna, Amsterdam, Sep. 25-29, 2015. Eur J Cancer. vol. 51(Supl 3) pp. 66 Abs. No. 335 (Abstract).
Fernandez et al. Lurbinectedin (PM01183) efficacy in Platinum-Resistant/refractroy Ovarian Cancer (PRROC) Patients Correlates with Drug Exposure using Pharmacokinetic/Pharmacodynamic (PK/PD) Modelling. 19th International Meeting of the European Society of Gynaecological (ESGO), Oct. 24-27, 2015. Nice, France. Int J Gynecol Cancer. vol. 25(Supl 1 9) pp. 433 Abs N ESGO-0843 (Poster).
Fernandez et al. Lurbinectedin (PM01183) efficacy in Platinum-Resistant/refractroy Ovarian Cancer (PRROC) Patients Correlates with Drug Exposure using Pharmacokinetic/Pharmacodynamic (PK/PD) Modelling. 19th International Meeting of the European Society of Gynaecological (ESGO), Oct. 24-27, 2015. Nice, France. Int J Gynecol Cancer. vol. 25(Supl 1 9) pp. 433 Abs N ESGO-0843 (Abstract).
Pernice et al. Development of a liquid chromatography/tandem mass spectrometry assay for the quantification of PM01183 (lurbinectedin), a novel antineoplastic agent, in mouse, rat, dog, Cynomolgus monkey and mini-pig plasma. J Pharm Biomed Anal. vol. 123 pp. 37-41.
Santamaria et al. Lurbinectedin specifically targets transcription in cancer cells, triggering DNA breaks and degradation of phosphorylated Pol II. AACR American Association for Cancer Research; 107th Annual Meeting; Apr. 16-20, 2016. New Orleans, Louisiana. Abs. N 3039 (Poster).
Santamaria et al. Lurbinectedin specifically targets transcription in cancer cells, triggering DNA breaks and degradation of phosphorylated Pol II. AACR American Association for Cancer Research; 107th Annual Meeting; Apr. 16-20, 2016. New Orleans, Louisiana. Abs. N 3039 (Abstract).
Allavena et al. Lurbinectedin reduces tumor-associated macrophages and the production of inflammatory cytokines, chemokines, and angiogenic factors in preclinical models. AACR American Association for Cancer Research; 107th Annual Meeting; Apr. 16-20, 2016. New Orleans, Louisiana. Abs N 1284 (Poster).
Allavena et al. Lurbinectedin reduces tumor-associated macrophages and the production of inflammatory cytokines, chemokines, and angiogenic factors in preclinical models. AACR American Association for Cancer Research; 107th Annual Meeting; Apr. 16-20, 2016. New Orleans, Louisiana. Abs N 1284 (Abstract).
Harlow et al. PM01183 inactivates the EWS/FLI1 transcription factor by redistributing the protein within the nucleus. AACR American Association for Cancer Research; 107th Annual Meeting; Apr. 16-20, 2016. New Orleans, Louisiana. Abs. N LB-177 (Poster).
Harlow et al. PM01183 inactivates the EWS/FLI1 transcription factor by redistributing the protein within the nucleus. AACR American Association for Cancer Research; 107th Annual Meeting; Apr. 16-20, 2016. New Orleans, Louisiana. Abs. N LB-177 (Abstract).
Gaillard et al. Corail trial: Randomized phase III study of lurbinectedin (PM01183) versus pegylated liposomal doxorubicin (PLD) or topotecan (T) in patients with platinum-resistant ovarian cancer. ASCO American Society of Clinical Oncology, 52th Annual Meeting, Jun. 3-7, 2016. Chicago, Illinois. Abs No. TPS5597 (Poster).
Gaillard et al. Corail trial: Randomized phase III study of lurbinectedin (PM01183) versus pegylated liposomal doxorubicin (PLD) or topotecan (T) in patients with platinum-resistant ovarian cancer. ASCO American Society of Clinical Oncology, 52th Annual Meeting, Jun. 3-7, 2016. Chicago, Illinois. Abs No. TPS5597 (Abstract).
Drilon et al. Lurbinectedin (PM01183) plus paclitaxel (P), recommended dose (RD) expansion results with or withut the addition of bevacizumab (Bev) in patients (pts) with selected solid tumors. 41st ESMO European Cancer Congress, Copenhagen, Denmark Oct. 7-11, 2016. Ann Oncol. vol. 27 (Supl 6) p. 127 Abs N 391P (Poster).
Drilon et al. Lurbinectedin (PM01183) plus paclitaxel (P), recommended dose (RD) expansion results with or withut the addition of bevacizumab (Bev) in patients (pts) with selected solid tumors. 41st ESMO European Cancer Congress, Copenhagen, Denmark Oct. 7-11, 2016. Ann Oncol. vol. 27(Supl 6) p. 127 Abs N 391P (Abstract).
Sauri et al. Lurbinectedin (PM01183) administered once (D1) every 3 weeks (q3w) in combiantion with capecitabine (XEL) in patients

(56) References Cited

OTHER PUBLICATIONS (pts) with metastatic breast (MBC), colorectal (CRC) or pancreatic (PaC) cancer. 41st ESMO European Cancer Congress, Copenhagen, Denmark Oct. 7-11, 2016. Ann Oncol. vol. 27(Supl 6) p. 127 Abs N 392P. (Poster).

Sauri et al. Lurbinectedin (PM01183) administered once (D1) every 3 weeks (q3w) in combiantion with capecitabine (XEL) in patients (pts) with metastatic breast (MBC), colorectal (CRC) or pancreatic (PaC) cancer. 41st ESMO European Cancer Congress, Copenhagen, Denmark Oct. 7-11, 2016. Ann Oncol. vol. 27(Supl 6) p. 127 Abs N 392P. (Abstract).

Poveda et al. Phase Ib/II study to evaluate the efficacy and tolerability of PM01183 (lurbinectedin) in combiantion with olaparib in patients with advanced solid tumors. 41st ESMO European Cancer Congress, Copenhagen, Denmark Oct. 7-11, 2016. Ann Oncol. vol. 27(Supl 6) p. 127 Abs N 901TiP. (Poster).

Poveda et al. Phase Ib/II study to evaluate the efficacy and tolerability of PM01183 (lurbinectedin) in combiantion with olaparib in patients with advanced solid tumors. 41st ESMO European Cancer Congress, Copenhagen, Denmark Oct. 7-11, 2016. Ann Oncol. vol. 27(Supl 6) p. 127 Abs N 901TiP. (Abstract).

Balmana et al. Anti-tumor activity of PM01183 (lurbinectedin) in BRCA1/2-associated metastatic breast cancer patietns: resutls of a single-agent phase II trial. 41st ESMO European Cancer Congress, Copenhagen, Denmark Oct. 7-11, 2016. Ann Oncol. vol. 27(Supl 6) Abs No. 223O (Presentation).

Balmana et al. Anti-tumor activity of PM01183 (lurbinectedin) in BRCA1/2-associated metastatic breast cancer patietns: resutls of a single-agent phase II trial. 41st ESMO European Cancer Congress, Copenhagen, Denmark Oct. 7-11, 2016. Ann Oncol. vol. 27(Supl 6) Abs No. 223O (Abstract).

Cruz et al. Lurbinectedin (PM01183) exhibits antitumor activity in PARP-inhibitor resistant germline BRCA PDX and lacks cross-resistance with cisplatin. 41st ESMO European Cancer Congress, Copenhagen, Denmark Oct. 7-11, 2016. Ann Oncol. vol. 27(Supl 6) Abs. N 1520O (Presentation).

Cruz et al. Lurbinectedin (PM01183) exhibits antitumor activity in PARP-inhibitor resistant germline BRCA PDX and lacks cross-resistance with cisplatin. 41st ESMO European Cancer Congress, Copenhagen, Denmark Oct. 7-11, 2016. Ann Oncol. vol. 27(Supl 6) Abs. N 1520O (Abstract).

Cespedes et al. Lurbinectedin induces depletion of tumor-associated macrophages, an essential component of its in vivo synergism with gemcitabine, in pancreatic adenocarcinoma mouse models. Dis Model Mech. vol. 9(12) pp. 1461-1471.

Cote et al. Phase II study of PM01183 as a single agent or in combination with conventional chemotherapy in metastatic and/or unresectable soft tissue sarcomas. CTOS Connective Tissue Oncology Society, 21st Annual Meeting, Nov. 9-12, 2016, Lisbon, Portugal. pp. 351 Abs. N 097.

Santamaria et al. Lurbinectedin inhibits active transcription affecting tumor cell burden and its inflammatory microenvironment. 15th International Congress on Targeted Anticancer Therapies (TAT), Mar. 6-8, 2017. Paris, France. Abs N 010.4.

Poveda et al. Phase II randomized study of PM01183 versus topotecan in patients with platinum resistant/refractory advanced ovarian cancer. Ann Oncol. vol. 28(6) pp. 1280-1287.

Santamaria et al. Lurbinectedin reverses platinum dependent IRF1 overexpression and nuclear localization, partially responsible for resistance to platinum drugs in ovarian cancer. AACR American Association for Cancer Research; 108th Annual Meeting; Apr. 1-5, 2017. Washington, DC. vol. 58 pp. 311 Abs N 1211. (Poster).

Santamaria et al. Lurbinectedin reverses platinum dependent IRF1 overexpression and nuclear localization, partially responsible for resistance to platinum drugs in ovarian cancer. AACR American Association for Cancer Research; 108th Annual Meeting; Apr. 1-5, 2017. Washington, DC. vol. 58 pp. 311 Abs N 1211. (Abstract).

Benton et al. Phase I study of lurbinectedin (PM11083) in patients with advanced AML and MDS. ASCO American Society of Clinical Oncology, 53rd Annual Meeting, Jun. 2-6, 2017. Chicago, Illinois. J Clin Oncol. vol. 35 (Supl) Abs. N e18521.

Forster et al. Activity of lurbinectedin (PM01183) as single agent and in combination in patients with endometrial cancer. ASCO American Society of Clinical Oncology, 53rd Annual Meeting, Jun. 2-6, 2017. Chicago, Illinois. J Clin Oncol. vol. 35 (Supl) Abs. N 5586 (Poster).

Forster et al. Activity of lurbinectedin (PM01183) as single agent and in combination in patients with endometrial cancer. ASCO American Society of Clinical Oncology, 53rd Annual Meeting, Jun. 2-6, 2017. Chicago, Illinois. J Clin Oncol. vol. 35 (Supl) Abs. N 5586 (Abstract).

Poveda et al. Phase I study to evaluate the tolerability, pharmacokinetics (PK) and pharmacodynamic(PD) of PM01183 (Lurbinectedin) in combination with olaparib in patients with advanced solid tumors. ASCO American Society of Clinical Oncology, 53rd Annual Meeting, Jun. 2-6, 2017. Chicago, Illinois. J Clin Oncol. vol. 35 (Supl) Abs. No. 5573 (Poster).

Poveda et al. Phase I study to evaluate the tolerability, pharmacokinetics (PK) and pharmacodynamic(PD) of PM01183 (Lurbinectedin) in combination with olaparib in patients with advanced solid tumors. ASCO American Society of Clinical Oncology, 53rd Annual Meeting, Jun. 2-6, 2017. Chicago, Illinois. J Clin Oncol. vol. 35 (Supl) Abs. No. 5573 (Abstract).

Calvo et al. Antitumor Activity of Lurbinectedin (Pm01183) and Doxorubicin in Relapsed Small Cell Lung Cancer: Results from a Phase I Study. Ann Oncol. vol. 28(10) pp. 2559-2566.

Olmedo Garcia et al. Activity of lurbinectedin as single agent and in combination in patients with advanced small cell lung cancer (SCLC ). 42nd ESMO European Cancer Congress, Madrid, Spain Sep. 8-12, 2017. Ann Oncol. vol. 28 (Supl 5) pp. 539-540 Abs N 1529PD. (Poster).

Fernandez et al. Drug-exposure response models for safety and efficacy in the use of doxorubicin plus lurbinectedin. ICPAD Workshop 2017 end International Workshop on Clinical Pharmacology of Anticancer Drugs, Madrid, Spain Sep. 13-14, 2017.

Sanz-Garcia et al. Efficacy and Safety of Lurbinectedin (PM1183) in Ewing Sarcoma: Results from a Phase 2 Study. CTOS Connective Tissue Oncology Society, 22nd Annual Meeting, Nov. 8-11, 2017, Grand Wailea Resort, Maui, Hawaii. Abs N 048. (Presentation).

Sanz-Garcia et al. Efficacy and Safety of Lurbinectedin (PM1183) in Ewing Sarcoma: Results from a Phase 2 Study. CTOS Connective Tissue Oncology Society, 22nd Annual Meeting, Nov. 8-11, 2017, Grand Wailea Resort, Maui, Hawaii. Abs N 048. (Abstract).

Pujade-Lauraine. New treatments in ovarian cancer. Ann Oncol. vol. 28(Supl 8) pp. 57-60.

Forster et al. Phase I study of lurbinectedin (PM01183) in combination with cisplatin (CDDP) with or without aprepitant in patients (pts) with advanced solid tumors. ECCO 2017 European Cancer Congress, Amsterdam, The Netherlands, Jan. 27-30, 2017. Eur J Cancer. vol. 72(Supl 1) pp. 134 Abs. N1324.

McLellan Z. Zepsyre: Product Analysis. pp. 2-12.

Calvo et al. Activity and Safety of the Combination of PM01183 and Doxorubicin in Relapsed SCLC. Final Results of a Phase Ib Trial. IASLC 18th World Conference on Lung Cancer. Oct. 15-18, 2017. Yokohama, Japan. J Thorac Oncol. vol. 12(Supl 2) pp. S1800 Abs N MA 01.05.

Foy et al. Targeting DNA damage in SCLC. Lung Cancer. vol. 114 pp. 12-22.

Farago et al. Atlantis: Phase III Study of PM01183 with Doxorubicin vs. CAV or Topotecan in Small-Cell Lung Cancer After Platinum Therapy. IASLC 18th World Conference on Lung Cancer. Oct. 15-18, 2017. Yokohama, Japan. J Thorac Oncol. vol. 12(Supl 2) pp. S2400-S2401 Abs N P2.04-008.

Kuroda et al. PM01183 inhibits myeloid-derived suppressor cells in vitro and in vivo. Immunotherapy. vol. 9(10) pp. 805-817.

Soria, J-Ch. Novel Cytotoxic Drugs in Lung Cancer. IASLC 17th World Conference on Lung Cancer. Dec. 4-6, 2016. Vienna, Austria. J Thorac Oncol. vol. 12 (1 Supl1) pp. S85-S86 Abs N SC05.02.

Parkes et al. Systemic Treatment Strategies for Patients with Hereditary Breast Cancer Syndromes. Oncologist. vol. 22(6) pp. 655-666.

Ferrara et al. Progress in the Management of Advanced Thoracic Malignancies in 2017. J Thorac Oncol. vol. 13(3) pp. 301-322.

(56) References Cited

OTHER PUBLICATIONS

Van Andel et al. Development and validation of a liquid chromatography—tandem mass spectrometry assay for the quantification of lurbinectedin in human plasma and urine. J Pharm Biomed Anal. vol. 158 pp. 160-165.
Subbiah et al. Efficacy and safety of lurbinectedin (PM1183) in Ewing sarcoma: Final results from a phase 2 study. ASCO American Society of Clinical Oncology, 54th Annual Meeting, Jun. 1-5, 2018. Chicago, Illinois. J Clin Oncol. vol. 36 (Supl) Abs. No. 11519 (Poster).
Subbiah et al. Efficacy and safety of lurbinectedin (PM1183) in Ewing sarcoma: Final results from a phase 2 study. ASCO American Society of Clinical Oncology, 54th Annual Meeting, Jun. 1-5, 2018. Chicago, Illinois. J Clin Oncol. vol. 36 (Supl) Abs. No. 11519 (Presentation).
Subbiah et al. Efficacy and safety of lurbinectedin (PM1183) in Ewing sarcoma: Final results from a phase 2 study. ASCO American Society of Clinical Oncology, 54th Annual Meeting, Jun. 1-5, 2018. Chicago, Illinois. J Clin Oncol. vol. 36 (Supl) Abs. No. 11519 (Abstract).
Trigio Perez et al. Efficacy and safety of lurbinectedin (PM1183) in small cell lung cancer (SCLC): Results from a phase 2 study. ASCO American Society of Clinical Oncology, 54th Annual Meeting, Jun. 1-5, 2018. Chicago, Illinois. J Clin Oncol. vol. 36 (Supl) Abs. No. 8570. (Poster).
Trigio Perez et al. Efficacy and safety of lurbinectedin (PM1183) in small cell lung cancer (SCLC): Results from a phase 2 study. ASCO American Society of Clinical Oncology, 54th Annual Meeting, Jun. 1-5, 2018. Chicago, Illinois. J Clin Oncol. vol. 36 (Supl) Abs. No. 8570. (Abstract).
Farago et al. Atlantis: Global, randomized phase III study of lurbinectedin (L) with doxorubicin (DOX) vs. CAV or topotecan (T) in small-cell lung cancer after platinum therapy. ASCO American Society of Clinical Oncology, 54th Annual Meeting, Jun. 1-5, 2018. Chicago, Illinois. J Clin Oncol. vol. 36 (Supl) Abs. N TPS8587 (Poster).
Farago et al. Atlantis: Global, randomized phase III study of lurbinectedin (L) with doxorubicin (DOX) vs. CAV or topotecan (T) in small-cell lung cancer after platinum therapy. ASCO American Society of Clinical Oncology, 54th Annual Meeting, Jun. 1-5, 2018. Chicago, Illinois. J Clin Oncol. vol. 36 (Supl) Abs. N TPS8587 (Abstract).
Takahashi et al. Phase I trial of lurbinectedin (PM1183) in Japanese patients with advanced tumors: Results of the dose escalation part. ASCO American Society of Clinical Oncology, 54th Annual Meeting, Jun. 1-5, 2018. Chicago, Illinois. J Clin Oncol. vol. 36 (Supl) Abs. N 2551 (Poster).
Takahashi et al. Phase I trial of lurbinectedin (PM1183) in Japanese patients with advanced tumors: Results of the dose escalation part. ASCO American Society of Clinical Oncology, 54th Annual Meeting, Jun. 1-5, 2018. Chicago, Illinois. J Clin Oncol. vol. 36 (Supl) Abs. N 2551 (Abstract).
Awada et al. Anti-tumor activity of PM1183 (lurbinectedin) in combination with capecitabine in metastatic breast cancer patients: Results from a phase I trial. ASCO American Society of Clinical Oncology, 54th Annual Meeting, Jun. 1-5, 2018. Chicago, Illinois. J Clin Oncol. vol. 36 (Supl) Abs. N 1072 (Poster).
Awada et al. Anti-tumor activity of PM1183 (lurbinectedin) in combination with capecitabine in metastatic breast cancer patients: Results from a phase I trial. ASCO American Society of Clinical Oncology, 54th Annual Meeting, Jun. 1-5, 2018. Chicago, Illinois. J Clin Oncol. vol. 36 (Supl) Abs. N 1072 (Abstract).
Gourd K. 2018 ASCO Annual Meeting. Lancet Oncol. vol. 19(7) pp. 865-866.
Andres et al. Phase II study to evaluate the efficacy, tolerability, and biomarkers of PM01183 with Olaparib in patients with advanced gynecological tumors. IGCS International Gynecologic Cancer Society, 17th Biennial Meeting, Sep. 14-16, 2018. Kyoto, Japan. Int J Gynecol Cancer. vol. 28( Supl 2) pp. 1146 Abs N IGCS8-0961.
Jiminez, C. Marine Natural Products in Medicinal Chemistry. ACS Med Chem Lett. vol. 9 pp. 959-961.
Cruz et al. Multicenter Phase II Study of Lurbinectedin in BRCA-Mutated and Unselected Metastatic Advanced Breast Cancer and Biomarker Assessment Substudy. J Clin Oncol. vol. 36(31) pp. 3134-3143.
Forster et al. Overall survival with Lurbinectedin Plus Doxorubicin in relapsed SCLC. Results from an expansion cohort of a phase IB trial. IASLC 19th World Conference on Lung Cancer. Sep. 23-26, 2018. Toronto, Canada. J Thorac Oncol. vol. 13 (10 Supl) pp. S581 Abs N P1.12-20. (Poster).
Forster et al. Overall survival with Lurbinectedin Plus Doxorubicin in relapsed SCLC. Results from an expansion cohort of a phase IB trial. IASLC 19th World Conference on Lung Cancer. Sep. 23-26, 2018. Toronto, Canada. J Thorac Oncol. vol. 13 (10 Supl) pp. S581 Abs N P1.12-20. (Abstract).
Gourd, E. Lurbinectedin for BRCA-mutated advanced breast cancer. Lancet oncol. vol. In press pp. 1.
Gaillard et al. Phase III trial of lurbinectedin versus PLD or topotecan in platinum-resistant ovarian cancer patients: Results of Corail trial. 43rd ESMO European Cancer Congress, Munich, Germany Oct. 19-23, 2018. Ann Oncol. vol. 29 (Supl 8) pp. 332-358 Abs N 932O (Presentation).
Gaillard et al. Phase III trial of lurbinectedin versus PLD or topotecan in platinum-resistant ovarian cancer patients: Results of Corail trial. 43rd ESMO European Cancer Congress, Munich, Germany Oct. 19-23, 2018. Ann Oncol. vol. 29 (Supl 8) pp. 332-358 Abs N 932O (Abstract).
Metaxas et al., Abstract "SAKK 17/16—Lurbinectedin as second or third line palliative chemotherapy in malignant pleural mesothelioma (MPM): A multi-center, single-arm phase II trial", 43rd ESMO European Cancer Congress, Munich, Germany Oct. 19-23, 2018. Ann Oncol, 2019, vol. 30, Supplement 5, V748 (Poster).
Yokoi et al. Lurbinectedin (PM01183), a selective inhibitor of active transcription, effectively eliminates both cancer cells and cancer stem cells in preclinical models of uterine cervical cancer. Invest New Drugs. vol. 37(5) pp. 818-827.
Lubomirov et al. Population pharmacokinetic-based targeted exome sequencing (PopPK-TES) approach to assess the impact of genetic variants on pharmacokinetics of lurbinectedin in patients with advanced cancer. 27th Annual Meeting of the Population Approach Group in Europe. May 29-Jun. 1, 2018. Montreux, Switzerland. Abs N 8489 (Poster).
Lubomirov et al. Population pharmacokinetic-based targeted exome sequencing (PopPK-TES) approach to assess the impact of genetic variants on pharmacokinetics of lurbinectedin in patients with advanced cancer. 27th Annual Meeting of the Population Approach Group in Europe. May 29-Jun. 1, 2018. Montreux, Switzerland. Abs N 8489 (Abstract).
Fernandez-Teruel et al. Population-Pharmacokinetic and Covariate Analysis of Lurbinectedin (PM01183), a New RNA Polymerase II Inhibitor, in Pooled Phase I/II Trials in Patients with Cancer. Clin Pharmacokinet. vol. 58(3) pp. 363-374.
Hendriks et al. Prospects of targeted and immune therapies in SCLC. Expert Rev Anticancer Ther. vol. 19(2) pp. 151-167.
Trigio Perez et al. Antitumor activity of single agent Lurbinectedin in patients with relapsed SCLC occurring 0 days after last platinum dose. IASLC 20th World Conference on Lung Cancer. Sep. 7-10, 2019. Barcelona, Spain. pp. 560 Abs No. P1.12-03. (Poster).
Trigio Perez et al. Antitumor activity of single agent Lurbinectedin in patients with relapsed SCLC occurring 0 days after last platinum dose. IASLC 20th World Conference on Lung Cancer. Sep. 7-10, 2019. Barcelona, Spain. pp. 560 Abs No. P1.12-03. (Abstract).
Wang et al. Current Diagnosis and Management of Small-Cell Lung Cancer. Mayo Clin Proc. vol. 94(8)pp. 1599-1622.
Yang et al. Emerging therapies for small cell lung cancer. J Hematol Oncol. vol. 12(1) pp. 47.
Pacheco and Bunn. Advancements in Small-cell Lung Cancer: The Changing Landscape Following IMpower-133. Clin Lung Cancer. vol. 20(3) pp. 148-160.
Li et al. Tumor-associated macrophages in tumor metastasis: biological roles and clinical therapeutic applications. J Hematol Oncol. vol. 12 p. 76.

(56) References Cited

OTHER PUBLICATIONS

Luvero et al. Ovarian Cancer Relapse: From the Latest Scientific Evidence to the Best Practice. Crit Rev Oncol Hematol. vol. 140 pp. 28-38.
Gedminas et al. Lurbinectedin Targets the EWS-WT1 Transcription Factor in Desmoplastic Small Round Cell Tumor. American Society of Pediatric Hematology/Oncology, ASPHO, May 1-4, 2019. New Orleans, LA, United States. Pediatr Blood Cancer. vol. 66 (Supl 2) pp. 146-147.
Aquila et al. Lurbinectedin delays the onset of splenomegaly and extends survival of C26 tumor bearing mice. 16th Meeting of the Interuniversity Institute of Myology (IIM)—Assisi . Eur J Transl Myol. vol. 30(3) pp. 40 Abs N p. 01.
Chakraborty et al. De novo and histologically transformed small cell lung cancer is sensitive to lurbinectedin treatment through the modulation of EMT and NOTCH signaling pathways. Clin Cancer Res. vol. In press pp. 1-43.
Lurbinectedin Is Safe and Active in Relapsed Small-Cell Lung Cancer. Cancer Discov. vol. 10(6) pp. 757.
Metaxas et al. Lurbinectedin as second- or third-line palliative therapy in malignant pleural mesothelioma: an international, multi-centre, single-arm, phase II trial (SAKK 17/16). Ann Oncol. vol. 31(4) pp. 495-500.
Ponce Aix et al. Lurbinectedin (LUR) in combination with Irinotecan (IRI) in patients (pts) with advanced solid tumors: Updated results from a phase Ib-II trial. ASCO American Society of Clinical Oncology, 56th Annual Meeting, virtual, May 31-Jun. 4, 2020. J Clin Oncol. vol. 38 (15 Supl) Abs N 3514. (Poster).
Ponce Aix et al. Lurbinectedin (LUR) in combination with Irinotecan (IRI) in patients (pts) with advanced solid tumors: Updated results from a phase Ib-II trial. ASCO American Society of Clinical Oncology, 56th Annual Meeting, virtual, May 31-Jun. 4, 2020. J Clin Oncol. vol. 38 (15 Supl) Abs N 3514. (Presentation).
Ponce Aix et al. Lurbinectedin (LUR) in combination with Irinotecan (IRI) in patients (pts) with advanced solid tumors: Updated results from a phase Ib-II trial. ASCO American Society of Clinical Oncology, 56th Annual Meeting, virtual, May 31-Jun. 4, 2020. J Clin Oncol. vol. 38 (15 Supl) Abs N 3514. (Abstract).
Leary et al. Pooled safety analysis of single-agent lurbinectedin versus topotecan (Results from a randomized phase III trial Corail and a phase II basket trial). ASCO American Society of Clinical Oncology, 56th Annual Meeting, virtual, May 31-Jun. 4, 2020. J Clin Oncol. vol. 38 (15 Supl) Abs No. 3635 (Poster).
Leary et al. Pooled safety analysis of single-agent lurbinectedin versus topotecan (Results from a randomized phase III trial Corail and a phase II basket trial). ASCO American Society of Clinical Oncology, 56th Annual Meeting, virtual, May 31-Jun. 4, 2020. J Clin Oncol. vol. 38 (15 Supl) Abs No. 3635 (Abstract).
Risnik et al. Immunoregulatory Effects of Lurbinectedin in Chronic Lymphocytic Leukemia. Cancer Immunol Immunother. vol. 69(5) pp. 813-824.
Markham, A. Lurbinectedin: First Approval. Drugs. vol. 80(13) pp. 1345-1353.
Subbiah et al. Activity of lurbinectedin in second-line SCLC patients candidates for platinum rechallenge. ESMO Virtual Congress 2020. Sep. 19-21, 2020. Ann Oncol. vol. 31(Suppl 4) pp. S1034-S1035 Abs N 1784P. (Poster).
Subbiah et al. Activity of lurbinectedin in second-line SCLC patients candidates for platinum rechallenge. ESMO Virtual Congress 2020. Sep. 19-21, 2020. Ann Oncol. vol. 31(Suppl 4) pp. S1034-S1035 Abs N 1784P. (Abstract).
Takahashi et al. Phase I study of lurbinectedin in Japanese patients with pretreated advanced tumours: Final results. ESMO Virtual Congress 2020. Sep. 19-21, 2020. Ann Oncol. vol. 31(Suppl 4) pp. S478 Abs N 551P (Poster).
Takahashi et al. Phase I study of lurbinectedin in Japanese patients with pretreated advanced tumours: Final results. ESMO Virtual Congress 2020. Sep. 19-21, 2020. Ann Oncol. vol. 31(Suppl 4) pp. S478 Abs N 551P (Abstract).
Subbiah et al. Antitumor Activity of Lurbinectedin in Second-line Small Cell Lung Cancer Patients Who Are Candidates for Re-challenge with the First-line Treatment. Lung Cancer. vol. 150 pp. 90-96.
Perez-Fidalgo, J. A. Cell proliferation inhibitors and apoptosis promoters. Eur J Cancer. vol. 15(Supl) pp. 73-76.
Subbiah et al. Phase 2 Basket Trial of Lurbinectedin in Second-line SCLC: Characteristics and Outcomes in Treatment Responders. IASLC 2020 North America Conference on Lung Cancer, Oct. 16-17, 2020. J Thorac Oncol. vol. 16 (1 Supl) pp. S18-S19 Abs N MO01.08. (Poster).
Subbiah et al. Phase 2 Basket Trial of Lurbinectedin in Second-line SCLC: Characteristics and Outcomes in Treatment Responders. IASLC 2020 North America Conference on Lung Cancer, Oct. 16-17, 2020. J Thorac Oncol. vol. 16 (1 Supl) pp. S18-S19 Abs N MO01.08. (Abstract).
Sands et al. Phase 2 Basket Trial of Lurbinectedin in Small-Cell Lung Cancer (SCLC): Analysis of Efficacy by Baseline Characteristics. IASLC 2020 North America Conference on Lung Cancer, Oct. 16-17, 2020. J Thorac Oncol. vol. 16(1 Supl) pp. S19 Abs N MO01.09 (Abstract).
Sands et al. Phase 2 Basket Trial of Lurbinectedin in Small-Cell Lung Cancer (SCLC): Analysis of Efficacy by Baseline Characteristics. IASLC 2020 North America Conference on Lung Cancer, Oct. 16-17, 2020. J Thorac Oncol. vol. 16(1 Supl) pp. S19 Abs N MO01.09 (Poster).
Subbiah et al. Activity of Lurbinectedin in Second-line SCLC Patients Who Are Candidates for Platinum Rechallenge. IASLC 2020 North America Conference on Lung Cancer, Oct. 16-17, 2020. J Thorac Oncol. vol. 16 (1 Supl) pp. S19-S20 Abs N MO01.10 (Poster).
Subbiah et al. Activity of Lurbinectedin in Second-line SCLC Patients Who Are Candidates for Platinum Rechallenge. IASLC 2020 North America Conference on Lung Cancer, Oct. 16-17, 2020. J Thorac Oncol. vol. 16 (1 Supl) pp. S19-S20 Abs N MO01.10 (Abstract).
Lurbinectedin. Am J Health Syst Pharm. vol. 77(22) pp. 1815-1817.
Sezran et al. Drugs in development for small cell lung cancer. J Thorac Dis. vol. 12(10) pp. 6298-6307.
Pacheco, J.M. Systemic therapy options following first-line chemoimmunotherapy in small-cell lung cancer. J Thorac Dis. vol. 12(10) pp. 6264-6274.
Cote et al. Lurbinectedin in combination with irinotecan in patients (PTS) with soft tissue sarcomas (STS). CTOS 2020 Annual Meeting. Virtual, Nov. 18-21, 2020. (Poster).
Cote et al. Lurbinectedin in combination with irinotecan in patients (PTS) with soft tissue sarcomas (STS). CTOS 2020 Annual Meeting. Virtual, Nov. 18-21, 2020. (Abstract).
Reddy et al. Emerging drugs for small cell lung cancer: a focused review on immune checkpoint inhibitors. Expert Opinion Emerg Drugs. vol. 25(3) pp. 353-366.
Devgun and Lal. Microarray data analysis, structure prediction, and in silico docking of drugs for inhibiting overexpression of high mobility group A1 in human malignant neoplasias. Int J Pharm Sci Drug Res. vol. 12(5) pp. 448-456.
Rosenmayr-Templeton, L. An industry update: Dec. 2019, what is new in the field of therapeutic delivery this month? Ther Deliv. vol. 11(5) pp. 289-296.
Menna et al. Lurbinectedin, an Anticancer drug of natural origin, Effectively reduces retinal macular edema: A Case Report. Asian J Res Rep Ophthalmol. vol. 3(2)pp. 24-31.
Fudio et al. Efect of lurbinectedin on the QTc interval in patients with advanced solid tumors: an exposure—response analysis. Cancer Chemother Pharmacol. vol. 87(1) pp. 113-124.
Singh et al. FDA Approval Summary: Lurbinectedin for the Treatment of Metastatic Small Cell Lung Cancer. Clin Cancer Res. vol. 27(9) pp. 2378-2382.
Shinn et al. Lurbinectedin: A New Treatment Option for Relapsed/Refractory Small-Cell Lung Cancer. Ann Pharmacother. vol. 55(9) pp. 1172-1179.
De Miguel Luken et al. Lurbinectedin in Combination with Pembrolizumab for Patients with Relapsed Small Cell Lung Cancer. LUPER Clinical Trial. IASLC 2020 World Conference on Lung

(56) References Cited

OTHER PUBLICATIONS

Cancer in Singapure (WCLC 2020). Jan. 28-31, 2021 J Thorac Oncol. vol. 16( 3 Supl) pp. S501-S502 Abs N P48.06.
Ponce Aix et al. Lurbinectedin With Irinotecan in Relapsed Small Cell Lung Cancer. Results From the Expansion Stage of a Phase I-II Trial. IASLC 2020 World Conference on Lung Cancer in Singapure (WCLC 2020). Jan. 28-31, 2021 J Thorac Oncol. vol. 16(3) pp. S127 Abs No. OA11.04 (Presentation).
Ponce Aix et al. Lurbinectedin With Irinotecan in Relapsed Small Cell Lung Cancer. Results From the Expansion Stage of a Phase I-II Trial. IASLC 2020 World Conference on Lung Cancer in Singapure (WCLC 2020). Jan. 28-31, 2021 J Thorac Oncol. vol. 16(3) pp. S127 Abs No. OA11.04 (Abstract).
Fudio et al. Semi-Mechanistic Models of the Time Course of Neutrophils and Platelets in Cancer Patients Treated With Lurbinectedin. IASLC 2020 World Conference on Lung Cancer in Singapure (WCLC 2020). Jan. 28-31, 2021 J Thorac Oncol. vol. 16(3 Supl) pp. S508-S509 Abs N P48.22 (Presentation).
Fudio et al. Semi-Mechanistic Models of the Time Course of Neutrophils and Platelets in Cancer Patients Treated With Lurbinectedin. IASLC 2020 World Conference on Lung Cancer in Singapure (WCLC 2020). Jan. 28-31, 2021 J Thorac Oncol. vol. 16(3 Supl) pp. S508-S509 Abs N P48.22 (Abstract).
Fudio et al. Exposure-Response Analyses and Clinical Utility Index to Justify the Dosage of Lurbinectedin in Small-cell Lung Cancer. IASLC 2020 World Conference on Lung Cancer in Singapure (WCLC 2020). Jan. 28-31, 2021 J Thorac Oncol. vol. 16 (3 Supl) pp. S509 Abs N P48.23 (Presentation).
Fudio et al. Exposure-Response Analyses and Clinical Utility Index to Justify the Dosage of Lurbinectedin in Small-cell Lung Cancer. IASLC 2020 World Conference on Lung Cancer in Singapure (WCLC 2020). Jan. 28-31, 2021 J Thorac Oncol. vol. 16 (3 Supl) pp. S509 Abs N P48.23 (Abstract).
Yu et al. Opportunities and obstacles of targeted therapy and immunotherapy in small cell lung cancer. J Drug Targeting. vol. 29(1) pp. 1-11.
Poveda et al. A phase I dose-finding, pharmacokinetics and genotyping study of olaparib and lurbinectedin in patients with advanced solid tumors. Sci Rep. vol. 11(1) 4433.
Olmedo et al. Efficacy and safety of lurbinectedin and doxorubicin in relapsed small cell lung cancer. Results from an expansion cohort of a phase I study. Invest New Drugs. vol. 39(5) pp. 1275-1283.
Baena et al. Lurbinectedin in the treatment of relapsed small cell lung cancer. Future Oncol. vol. 17(18) pp. 2279-2289.
Cortinovis et al. Novel Cytotoxic Chemotherapies in Small Cell Lung Carcinoma. Cancers. vol. 13(5) arn 1152.
Torre and Albericio the Pharmaceutical Industry in 2020. An Analysis of FDA Drug Approvals from the Perspective of Molecules. Molecules. vol. 26(3) pp. 627.
Dingemans et al. Small-cell lung cancer: ESMO Clinical Practice Guidelines for diagnosis, treatment and follow-up. Ann Oncol. vol. In press pp. 1-42.
Fernandez-Teruel et al. Population Pharmacokinetic-Pharmacodynamic Modeling and Covariate Analyses of Neutropenia and Thrombocytopenia in Patients With Solid Tumors Treated With Lurbinectedin. J Clin Pharmacol. vol. 61(9) pp. 1206-1219.
Boudin et al. Lurbinectedin for metastatic small-cell bladder carcinoma. Eur J Cancer. vol. 151 pp. 1-2.
Anobile et al. Evaluation of the Preclinical Efficacy of Lurbinectedin in Malignant Pleural Mesothelioma. Cancers. vol. 13(10) arn 2332.
Falcon Gonzalez et al. Lurbinectedin (LUR) in combination with Irinotecan (IRI) in patients (pts) with advanced endometrial carcinoma. ASCO American Society of Clinical Oncology, 57th Annual Meeting, virtual, Jun. 4-8, 2021. J Clin Oncol. vol. 39 (15 Supl) pp. 333s Abs N 5586 (Poster).
Falcon Gonzalez et al. Lurbinectedin (LUR) in combination with Irinotecan (IRI) in patients (pts) with advanced endometrial carcinoma. ASCO American Society of Clinical Oncology, 57th Annual Meeting, virtual, Jun. 4-8, 2021. J Clin Oncol. vol. 39 (15 Supl) pp. 333s Abs N 5586 (Abstract).
Patel et al. An overview of lurbinectedin as a new second-line treatment option for small cell lung cancer. Ther Adv Med Oncol. vol. 13 pp. 17588359211020529.
Wahab et al. Lurbinectedin-Induced Tumor Lysis Syndrome in Small Cell Neuroendocrine Cancer of the Cecum: A First-Ever Case Report. Am J Case Rep. vol. 22 pp. e932081.
Li et al. Lurbinectedin for the treatment of small cell lung cancer. Drugs Today. vol. 57(6) pp. 377-385.
Gros et al. Lurbinectedin in Refractory Diffuse Malignant Peritoneal Mesothelioma: Report of Two Cases. Front Oncol. vol. 11 pp. 704295.
Yakobson et al. Metastatic small cell lung cancer—an aggressive disease: a case report and literature review. Anticancer Drugs. vol. 32(10) pp. 1138-1141.
Liang et al. An update of new small-molecule anticancer drugs approved from 2015 to 2020. Eur J Med Chem. vol. 220 pp. 113473.
Kundu et al. Characterization of lurbinectedin as a single agent and in combinations with DNA damage response inhibitor for the treatment and bio-marker discovery of SCLC. AACR Annual Meeting. Apr. 9-14, 2021. Cancer Res. vol. 81(13 Supl) Abs No. 1022.
Gaillard et al. Lurbinectedin versus pegylated liposomal doxorubicin or topotecan in patients with platinum-resistant ovarian cancer: A multicenter, randomized, controlled, open-label phase 3 study (Corail). Gynecol Oncol. vol. 163(2) pp. 237-245.
Subbiah et al. Subsequent Systemic Therapy After Lurbinectedin Discontinuation in Patients With Small-cell Lung Cancer. IASLC 2021 World Conference on Lung Cancer (WCLC 2021). Sep. 8-14, 2021. J Thorac Oncol. vol. 16(10 Supl) pp. S844-S845 Abs No. MA16.01.
Hanvesakul et al. Emerge 402 Phase 4 Observational Study: Safety and Outcomes in Patients With SCLC Receiving Treatment With Lurbinectedin. IASLC 2021 World Conference on Lung Cancer (WCLC 2021).Sep. 8-14, 2021. J Thorac Oncol. vol. 16 (10 Supl) pp. S1189-S1190 Abs No. P64.02 (Presentation).
Hanvesakul et al. Emerge 402 Phase 4 Observational Study: Safety and Outcomes in Patients With SCLC Receiving Treatment With Lurbinectedin. IASLC 2021 World Conference on Lung Cancer (WCLC 2021).Sep. 8-14, 2021. J Thorac Oncol. vol. 16 (10 Supl) pp. S1189-S1190 Abs No. P64.02 (Abstract).
Dumoulin et al. Lurbinectedin in Pre-Treated Patients With Small Cell Lung Cancer and Malignant Pleural Mesothelioma in a Real World Setting. IASLC 2021 World Conference on Lung Cancer (WCLC 2021). Sep. 8-14, 2021. J Thorac Oncol. vol. 16 (10 Supl) pp. S1180 Abs N P63.01 (Presentation).
Dumoulin et al. Lurbinectedin in Pre-Treated Patients With Small Cell Lung Cancer and Malignant Pleural Mesothelioma in a Real World Setting. IASLC 2021 World Conference on Lung Cancer (WCLC 2021). Sep. 8-14, 2021. J Thorac Oncol. vol. 16 (10 Supl) pp. S1180 Abs N P63.01 (Abstract).
Paz-Ares et al. Lurbinectedin/Doxorubicin versus CAV or Topotecan in Relapsed SCLC Patients: Phase III Randomized Atlantis Trial. IASLC 2021 World Conference on Lung Cancer (WCLC 2021). Sep. 8-14, 2021. J Thorac Oncol. vol. 16(10 Supl) pp. S844-S845Abs N PL02.3 (Poster).
Paz-Ares et al. Lurbinectedin/Doxorubicin versus CAV or Topotecan in Relapsed SCLC Patients: Phase III Randomized Atlantis Trial. IASLC 2021 World Conference on Lung Cancer (WCLC 2021). Sep. 8-14, 2021. J Thorac Oncol. vol. 16(10 Supl) pp. S844-S845Abs N PL02.3 (Abstract).
Fudio et al. Exposure-Response Analysis of Lurbinectedin Alone or With Doxorubicin in Overall Survival in Small Cell Lung Cancer. IASLC 2021 World Conference on Lung Cancer (WCLC 2021). Sep. 8-14, 2021. J Thorac Oncol. vol. 16(10 Supl) pp. S1182-S1183Abs N P63.02 (Presentation).
Fudio et al. Exposure-Response Analysis of Lurbinectedin Alone or With Doxorubicin in Overall Survival in Small Cell Lung Cancer. IASLC 2021 World Conference on Lung Cancer (WCLC 2021). Sep. 8-14, 2021. J Thorac Oncol. vol. 16(10 Supl) pp. S1182-S1183Abs N P63.02 (Abstract).
Liguori et al. Absence of Biomarker-Driven Treatment Options in Small Cell Lung Cancer, and Selected Preclinical Candidates for Next Generation Combination Therapies. Front Pharmacol. vol. 12 747180.

(56) References Cited

OTHER PUBLICATIONS

Kristeleit et al. Doxorubicin plus lurbinectedin in patients with advanced endometrial cancer: results from an expanded phase I study. Int J Gynecol Cancer. vol. 31(11) pp. 1428-1436.
Das et al. Advances in Treatment of Recurrent Small Cell Lung Cancer (SCLC): Insights for Optimizing Patient Outcomes from an Expert Roundtable Discussion. Adv Ther. vol. 38(11)pp. 5431-5451.
Tariq et al. Update 2021: Management of Small Cell Lung Cancer. Lung. vol. 1999(6) pp. 579-587.
Mendonca Nogueira and Vinicius Nora de Souza. New FDA oncology small molecule drugs approvals in 2020: Mechanism of action and clinical applications. Bioorg Med Chem. vol. 46 pp. 116340.
Ponce Aix et al. 2SMALL (NCT04253145) phase I part: lurbinectidine (LUR) in combination with atezolizumab (ATZ) for second line extensive stage small cell lung cancer (ES-SCLC) patients (pts). SITC, 36th Anniversary Annual Meeting (SITC 2021), Nov. 10-14, 2021. J Immunother Cancer. vol. 9(Supl 2) pp. A493 Abs No. 464 (Poster).
Ponce Aix et al. 2SMALL (NCT04253145) phase I part: lurbinectidine (LUR) in combination with atezolizumab (ATZ) for second line extensive stage small cell lung cancer (ES-SCLC) patients (pts). SITC, 36th Anniversary Annual Meeting (SITC 2021), Nov. 10-14, 2021. J Immunother Cancer. vol. 9(Supl 2) pp. A493 Abs No. 464 (Abstract).
Kundu et al. SLFN11 biomarker status predicts response to lurbinectedin as a single agent and in combination with ATR inhibition in small cell lung cancer. Transl Lung Cancer Res. vol. 10(11) pp. 4095-4105.
Hodgkinson, L. International Association for the Study of Lung Cancer (IASLC)—22nd World Conference on Lung Cancer (WCLC 2021). Drugs Fut. vol. 46(12)pp. 1033-1036.
Loeuille et al. Physicochemical stability of lurbinectedin reconstituted at 500 μ mL and diluted at 15, 30, and 70 μ mL in 0.9% sodium chloride and 5% dextrose. Eur J Oncol Pharm. vol. 4(3) E032.
Nandini et al. Therapeutic Strategies for Metastatic Triple-Negative Breast Cancers: From Negative to Positive. Pharmaceuticals. vol. 14(5) 455.
Metaxas et al. A phase I trial of lurbinectedin in combination with cisplatin in patients with advanced solid tumors. Invest New Drugs. vol. 40(1) pp. 91-98.
Hao and Sekkath Veedu. Current Strategies for Extensive Stage Small Cell Lung Cancer Beyond First-line Therapy. Clin Lung Cancer. vol. 23(1) pp. 14-20.
Liu et al. New pharmaceuticals approved by FDA in 2020: Small-molecule drugs derived from amino acids and related compounds. Chirality. vol. 34(1) pp. 86-103.
Fernandez-Teruel et al. Integrated exposure-response analysis of efficacy and safety of lurbinectedin to support the dose regimen in small-cell lung cancer. Cancer Chemother Pharmacol. vol. 89(5) pp. 585-594.
Rajput et al. Treatment of Small Cell Lung Cancer with Lurbinectedin: A Review. Anticancer Agents Med Chem. vol. 22(5)pp. 812-820.
Chu et al. Treatment of small cell lung cancer: recent advances. Current Opin Oncol. vol. 34(1) pp. 83-88.
Aviles et al. Metabolic Disposition of Lurbinectedin, a Potent Selective Inhibitor of Active Transcription of Protein-Coding Genes, in Nonclinical Species and Patients. Drug Metab Dispos. vol. 50(4) pp. 327-340.
Cortesi et al. Exceptional response to lurbinectedin and irinotecan in BRCA-mutated platinum-resistant ovarian cancer patient: a case report. Ther Adv Chronic Dis. vol. In press pp. 1-6.
Rengarajan et al. Indirect Treatment Comparison of Lurbinectedin vs. Other Second-Line Treatments for Small-Cell Lung Cancer. Int J Radiat Oncol Biol Phys. vol. 112(2) p. E18 Abs No. 119.
Hanvesakul et al. Systemcatic Literature Review of Second-line Treatments for Small-Cell Lung Cancer. ISPOR Europe 2021. Virtual. Nov. 30-Dic 3, 2021. Value Health. vol. 25(1 Suppl) pp. S37-S38 (Abs. N POSC28).
Poveda et al. Phase 2 Trial (POLA Study) of Lurbinectedin plus Olaparib in Patients with Advanced Solid Tumors: Results of Efficacy, Tolerability, and the Translational Study . Cancers . vol. 14(4) arn 915.
Desai, A. Real-World Experience of Lurbinectedin beyond the second line in Small Cell Lung Cancer. IASLC. Targeted Therapies of Lung Cancer (TTLC). Virtual.Feb. 22-26, 2022.
Kim et al. Antibody-Drug Conjugate Targeting c-Kit for the Treatment of Small Cell Lung Cancer. Int J Mol Sci. vol. 23(4) 2264.
Lurbinectedin for small cell lung cancer. Aust Prescr. vol. 45(1) pp. 31.
Costanzo et al. Promoters of ASCL1- and NEUROD1-dependent genes are specific targets of lurbinectedin in SCLC cells. EMBO Mol Med. vol. 14(4)e14841.
Liguori et al. Preclinical studies with ONC201/TIC10 and lurbinectedin as a novel combination therapy in small cell lung cancer (SCLC). Am J Cancer Res. vol. 12(2) pp. 729-743.
Matsui et al. High mRNA expression of POU2F3 in small cell lung cancer cell lines predicts the effect of lurbinectedin. Thorac Cancer. vol. 13(8) pp. 1184-1192.
Masacchio et al. Preclinical and Clinical Evidence of Lurbinectedin in Ovarian Cancer: Current Status and Future Perspectives. Front Oncol. vol. 12 pp. 831612.
Zugazagoitia and Paz-Ares. Extensive-Stage Small-Cell Lung Cancer: First-Line and Second-Line Treatment Options. J Clin Oncol. vol. 40(6) pp. 671-680.
Papachristos and Ratain. Lurbinectedin-induced thrombocytopenia: the role of body surface area. Cancer Chemother Pharmacol. vol. 89(5) pp. 573-575.
Jorger et al. Safety profile and associated costs of therapies for relapsed small cell lung cancer in Switzerland. European Lung Cancer Congress (ELCC). Virtual. Mar. 30-Apr. 2, 2022 Ann Oncol. vol. 33(Supl 2) pp. S102 Abs N 153P.
Cantini et al. Immune modulatory functions of lurbinectedin in small cell lung cancer and malignant pleural mesothelioma patients. European Lung Cancer Congress (ELCC). Virtual. Mar. 30-Apr. 2, 2022 Ann Oncol. vol. 33(Supl 2) pp. S108 Abs No. 164P.
Rittberg et al. Real-world patient eligibility for lurbinectedin/doxorubicin in small cell lung cancer. European Lung Cancer Congress (ELCC). Virtual. Mar. 30-Apr. 2, 2022 Ann Oncol. vol. 33(Supl 2) pp. S101-S102 Abs N 151P.
Mark et al. Long-term benefit of lurbinectedin as palliative chemotherapy in progressive malignant pleural mesothelioma (MPM): final efficacy and translational data of the SAKK 17/16 study. ESMO Open. vol. 7(3) 100446.
Subbiah et al. Antitumor Activity of Lurbinectedin, a Selective Inhibitor of Oncogene Transcription, in Relapsed Ewing Sarcoma: Results of a Basket Phase II Study. Clin Cancer Res.vol. 28(13) pp. 2762-2770.
Benjamin and Prasad. Accelerated approval requirements for lurbinectedin. Lancet Oncol. vol. 23(5) pp. e206.
Kashima and Okuma. Advances in biology and novel treatments of SCLC: The four-color problem in uncharted territory. Semin Cancer Biol. vol. In press pp. 1-10.
Gedminas et al. Lurbinectedin inhibits the EWS-WT1 transcription factor in desmoplastic small round cell tumor. Mol Cancer Ther. vol. 21(8) pp. 1296-1305.
Calles et al. A phase 1/2 trial of lurbinectedin (L) in combination with pembrolizumab (P) in relapsed small cell lung cancer (SCLC): The Luper study. ASCO American Society of Clinical Oncology, 58th Annual Meeting, Jun. 3-7, 2022. Chicago, Illinois. J Clin Oncol. vol. 40 (Supl 16) p. 526 Abs No. 8581 (Poster).
Calles et al. A phase 1/2 trial of lurbinectedin (L) in combination with pembrolizumab (P) in relapsed small cell lung cancer (SCLC): The Luper study. ASCO American Society of Clinical Oncology, 58th Annual Meeting, Jun. 3-7, 2022. Chicago, Illinois. J Clin Oncol. vol. 40 (Supl 16) p. 526 Abs No. 8581 (Abstract).
Navaro et al. Analysis of patients with relapsed small cell lung cancer (SCLC) receiving single-agent lurbinectedin in the phase 3 Atlantis trial. ASCO American Society of Clinical Oncology, 58th Annual Meeting, Jun. 3-7, 2022. Chicago, Illinois. J Clin Oncol. vol. 40 (Supl 16) p. 512 Abs No. 8524. (Poster).

(56) References Cited

OTHER PUBLICATIONS

Navaro et al. Analysis of patients with relapsed small cell lung cancer (SCLC) receiving single-agent lurbinectedin in the phase 3 Atlantis trial. ASCO American Society of Clinical Oncology, 58th Annual Meeting, Jun. 3-7, 2022. Chicago, Illinois. J Clin Oncol. vol. 40 (Supl 16) p. 512 Abs No. 8524. (Abstract).
Nair et al. Efficacy and safety of second-line (2L) therapy in patients with relapsed small cell lung cancer (SCLC): A systematic literature review (SLR). ASCO American Society of Clinical Oncology, 58th Annual Meeting, Jun. 3-7, 2022. Chicago, Illinois. J Clin Oncol. vol. 40 (Supl 16) Abs N e20576.
Ganti et al. Efficacy of lurbinectedin in a clinical trial versus other standard of care in a real-world comparator arm in relapsed/refractory small cell lung cancer patients. ASCO American Society of Clinical Oncology, 58th Annual Meeting, Jun. 3-7, 2022. Chicago, Illinois. J Clin Oncol. vol. 40 (Supl 16) Abs N e20619.
Cote et al. A phase 1b lead-in to a randomized phase 2 trial of lurbinectedin plus doxorubicin in leiomyosarcoma (LMS). ASCO American Society of Clinical Oncology, 58th Annual Meeting, Jun. 3-7, 2022. Chicago, Illinois. J Clin Oncol. vol. 40 (Supl 16) p. 684 Abs N TPS11592 (Poster).
Cote et al. A phase 1b lead-in to a randomized phase 2 trial of lurbinectedin plus doxorubicin in leiomyosarcoma (LMS). ASCO American Society of Clinical Oncology, 58th Annual Meeting, Jun. 3-7, 2022. Chicago, Illinois. J Clin Oncol. vol. 40 (Supl 16) p. 684 Abs N TPS11592 (Abstract).
Leventakos et al. ASCO American Society of Clinical Oncology, 58th Annual Meeting, Jun. 3-7, 2022. Chicago, Illinois. J Clin Oncol. vol. 40 (Supl 16) p. 532 Abs N TPS8604 (Poster).
Leventakos et al. ASCO American Society of Clinical Oncology, 58th Annual Meeting, Jun. 3-7, 2022. Chicago, Illinois. J Clin Oncol. vol. 40 (Supl 16) p. 532 Abs N TPS8604 (Abstract).
Boni et al. Lurbinectedin in patients with pretreated BRCA1/2-associated metastatic breast cancer: Results from a phase II basket study. ASCO American Society of Clinical Oncology, 58th Annual Meeting, Jun. 3-7, 2022. Chicago, Illinois. J Clin Oncol. vol. 40 (Supl 16) p. 532 Abs No. 1092. (Poster).
Boni et al. Lurbinectedin in patients with pretreated BRCA1/2-associated metastatic breast cancer: Results from a phase II basket study. ASCO American Society of Clinical Oncology, 58th Annual Meeting, Jun. 3-7, 2022. Chicago, Illinois. J Clin Oncol. vol. 40 (Supl 16) p. 532 Abs No. 1092. (Abstract).
Cheng et al. Efficacy and safety of lurbinectedin as second-line therapy in Chinese patients with small cell lung cancer: Preliminary results of a phase 1 study. ASCO American Society of Clinical Oncology, 58th Annual Meeting, Jun. 3-7, 2022. Chicago, Illinois. J Clin Oncol. vol. 40 (Supl 16) p. 526 Abs No. 8580. (Poster).
Cheng et al. Efficacy and safety of lurbinectedin as second-line therapy in Chinese patients with small cell lung cancer: Preliminary results of a phase 1 study. ASCO American Society of Clinical Oncology, 58th Annual Meeting, Jun. 3-7, 2022. Chicago, Illinois. J Clin Oncol. vol. 40 (Supl 16) p. 526 Abs No. 8580. (Abstract).
Toublanc et al. Second-line lurbinectedin as a new treatment option for small-cell lung cancer: Preliminary results in real-clinical practice. Thorac Cancer. vol. 13(15) pp. 2248-2252.
Longo-Munoz et al. Lurbinectedin in patients with pretreated neuroendocrine tumours: Results from a phase II basket study. Eur J Cancer. vol. 172 pp. 340-348.
Dumoulin et al. Lurbinectedin shows clinical activity and immune-modulatory functions in patients with pre-treated small cell lung cancer and malignant pleural mesothelioma. Eur J Cancer. vol. 172 pp. 357-366.
Flick et al. Synthetic Approaches to the New Drugs Approved During 2020. J Med Chem. vol. 65(14) pp. 9607-9661.
Desai et al. Lurbinectedin in Extrapulmonary Metastatic Neuroendocrine Carcinomas. 14th Annual Multidisciplinary Neuroendocrine Tumor Medical Virtual Symposium of the North American Neuroendocrine Tumor Society, Nov. 4-6, 2021. Pancreas. vol. 51(3) pp. E38.
Oronsky et al. A 2022 Update on Extensive Stage Small-Cell Lung Cancer (SCLC). J Cancer. vol. 13(9) pp. 2945-2953.
Boni et al. Lurbinectedin, a selective inhibitor of oncogenic transcription, in patients with pretreated germline BRCA1/2 metastatic breast cancer: results from a phase II basket study. ESMO Open. vol. 7(5) pp. 100571.
Keogh et al. Emerging Biomarkers and the Changing Landscape of Small Cell Lung Cancer. Cancers. vol. 14(15) pp. 3772.
Liguori et al. Synergistic activity of Lurbinectidin plus ONC201 in SCLC is associated with ATF4, CHOP and pChk1 induction. AACR Annual Meeting. Apr. 8-13, 2022. Cancer Res. vol. 82(12 Supl) Abs N 4064.
Schultz et al. ATR inhibition augments the efficacy of the lurbinectedin in small cell lung cancer. AACR Annual Meeting. Apr. 8-13, 2022. Cancer Res. vol. 82(12 Supl) Abs No. 2153.
Hu et al. An oral and selective CDK12 inhibitor demonstrates robust anti-tumor activity. AACR Annual Meeting. Apr. 8-13, 2022. Cancer Res. vol. 82(12 Supl) Abs N 5393.
Calvo et al. Phase I study of lurbinectedin in combination with weekly paclitaxel with or without bevacizumab in patients with advanced solid tumors. Invest New Drugs. vol. 40(6) pp. 1263-1273.
Kaland et al. U.S. Food and Drug Administration analysis of newly identified adverse events with lurbinectedin: extravasation, rhabdomyolysis, and tumor lysis syndrome. Clin Lung Cancer. vol. 23(8) pp. e556-e562.
Boyne et al. Synthetic control arm (SCA) analysis of lurbinectedin compared to the standard of care (SoC) among patients with small cell lung cancer (SCLC) previously treated with platinum-based chemotherapy. ESMO Congress 2022. Sep. 9-13, 2022. Ann Oncol. vol. 33 (Supl 7) pp. S1249 Abs No. 1536P (Poster).
Boyne et al. Synthetic control arm (SCA) analysis of lurbinectedin compared to the standard of care (SoC) among patients with small cell lung cancer (SCLC) previously treated with platinum-based chemotherapy. ESMO Congress 2022. Sep. 9-13, 2022. Ann Oncol. vol. 33 (Supl 7) pp. S1249 Abs No. 1536P (Abstract).
Estrin et al. Real-world (RW) outcomes of second-line (2L) small cell lung cancer (SCLC) patients treated with lurbinectedin. ESMO Congress 2022. Sep. 9-13, 2022. Ann Oncol. vol. 33 (Supl 7) pp. 1250 Abs No. 1539P (Poster).
Estrin et al. Real-world (RW) outcomes of second-line (2L) small cell lung cancer (SCLC) patients treated with lurbinectedin. ESMO Congress 2022. Sep. 9-13, 2022. Ann Oncol. vol. 33 (Supl 7) pp. 1250 Abs No. 1539P (Abstract).
Bushunow et al. Emerge 402: Preliminary Real-world Characteristics and Safety of Lurbinectedin in Patients With Small-cell Lung Cancer. Proceedings of the American Society for Radiation Oncology. 64th Annual Meeting. San Antonio, TX, United States Aug. 6-9, 2022. J Thorac Oncol. vol. 17 (9 Supl) pp. S145-S146 Abs. No. P2.10-02.
Paz-Ares et al. Proceedings of the American Society for Radiation Oncology. 64th Annual Meeting. San Antonio, TX, United States Aug. 6-9, 2022. J Thorac Oncol. vol. 17 (9 Supl) pp. S532-S533 Abs. No. EP14.01-15.
Mccall et al. Phase I Study of Palliative Radiotherapy with Lurbinectedin in Patients with Extensive Stage Small Cell Lung Cancer. Proceedings of the American Society for Radiation Oncology. 64th Annual Meeting. San Antonio, TX, United States Aug. 6-9, 2022. J Thorac Oncol. vol. 17 (9 Supl) pp. S541 Abs. No. EP14.03-003.
Wang et al. Characterization of Real-World Use of Lurbinectedin in Adult Small Cell Lung Cancer Patients in the United States. Proceedings of the American Society for Radiation Oncology. 64th Annual Meeting. San Antonio, TX, United States Aug. 6-9, 2022. J Thorac Oncol. vol. 17 (9 Supl) pp. S553-S554 Abs. No. EP14.05-23.
Manzo et al. Lurbinectedin in small cell lung cancer. Front Oncol. vol. 12 pp. 932105.
Ponce Aix et al. Combination lurbinectedin and doxorubicin versus physician's choice of chemotherapy in patients with relapsed small-cell lung cancer (Atlantis): a multicentre, randomised, open-label, phase 3 trial. Lancet Respir Med. vol. In press pp. 1-13.
Simona et al. Lurbinectedin improves macular edema in a case of central retinal vein occlusion. Am J Ophthalmol Case Rep. Am J Ophthalmol Case Rep. vol. 28 arn 101743.

(56) References Cited

OTHER PUBLICATIONS

Lurbinectedin (Zepzelca) for Small-Cell Lung Cancer. Med Lett Drugs Ther. vol. 64 pp. e198-e199.
Bushunow et al. IASLC 2022 World Conference on Lung Cancer (WCLC 2022). Aug. 6-9, 2022. J Thorac Oncol. vol. 17(9 Supl) Abs No. P2.10-02.
Paz-Ares et al. IMforte: A Phase III Study of Lurbinectedin and Atezolizumab Versus Atezolizumab as Maintenance Therapy in ES-SCLC. IASLC 2022 World Conference on Lung Cancer (WCLC 2022). Aug. 6-9, 2022. J Thorac Oncol. vol. 17(9 Supl) Abs No. EP14.01-015.
Mccall et al. Phase I Study of Palliative Radiotherapy with Lurbinectedin in Patients with Extensive Stage Small Cell Lung Cancer. IASLC 2022 World Conference on Lung Cancer (WCLC 2022). Aug. 6-9, 2022. J Thorac Oncol. vol. 17(9 Supl) Abs No. EP14.03-003.
Wang et al. Characterization of Real-World Use of Lurbinectedin in Adult Small Cell Lung Cancer Patients in the United States. IASLC 2022 World Conference on Lung Cancer (WCLC 2022). Aug. 6-9, 2022. J Thorac Oncol. vol. 17(9 Supl) Abs No. EP14.05-023.
Awada et al. Antitumor activity of lurbinectedin in combination with oral capecitabine in patients with metastatic breast cancer. ESMO Open. vol. 7(6) arn 100651.
Cote et al. A Phase 1B lead-in to a randomized phase 2 trial of Lurbinectedin plus Doxorubicin in leiomyosarcom (LMS): Results from the phase 1B soft-tissue sarcoma (STS) lead-in. CTOS Connective Tissue Oncology Society, 27th Annual Meeting, Nov. 16-19, 2022, Vancouver, Canada. (Poster).
Cote et al. A Phase 1B lead-in to a randomized phase 2 trial of Lurbinectedin plus Doxorubicin in leiomyosarcom (LMS): Results from the phase 1B soft-tissue sarcoma (STS) lead-in. CTOS Connective Tissue Oncology Society, 27th Annual Meeting, Nov. 16-19, 2022, Vancouver, Canada. (Abstract).
Petty and Paz-Ares. Emerging Strategies for the Treatment of Small Cell Lung Cancer: A Review. JAMA Oncol. vol. In press pp. 1-11.
Fourie Zirkelbach et al. Improving Dose-Optimization Processes Used in Oncology Drug Development to Minimize Toxicity and Maximize Benefit to Patients. J Clin Oncol. vol. 40(30) pp. 3489-3500.
Schultz et al. ATR inhibition augments the efficacy of lurbinectedin in small cell lung cancer. bioRxiv. vol. In press pp. 1-37.
Meijer et al. Small cell lung cancer: Novel treatments beyond immunotherapy. Semin Cancer Biol. vol. 86(Pt 2) pp. 376-385.
Rosner and Levy. Relapsed small-cell lung cancer: a disease of continued unmet need. Lancet Respir Med. vol. 11(1) pp. 6-8.
Yu et al. Extensive-Stage Small-Cell Lung Cancer: Current Management and Future Directions. Int J Cancer. vol. 152(11) pp. 2243-2256.
Product monograph updates Health Product InfoWatch. Health Product InfoWatch. pages 1-7.
Spigel et al. Emerge-201: Phase 2 Basket Study of Lurbinectedin Monotherapy in Advanced or Metastatic Solid Tumors. NACLC 2022 North America Conference on Lung Cancer. Chicago, Illinois, United States. Sep. 23-25, 2022. J Thorac Oncol. vol. 18(3 Supl) pp. e31 Abs N PP01.50.
Schreeder et al. Emerge 402: Real-world Characteristics and Safety of Lurbinectedin in Small-cell Lung Cancer (SCLC). vol. 18(3 Supl) pp. e43 Abs N PP01.77.
Ganti et al. Lurbinectedin vs an External Control arm in Patients with Small Cell Lung Cancer. NACLC 2022 North America Conference on Lung Cancer. Chicago, Illinois, United States. Sep. 23-25, 2022. J Thorac Oncol. vol. 18(3 Supl) pp. e42-e43 Abs N PP01.76.
Sonpavde et al. Phase II trial of lurbinectedin combined with avelumab as maintenance therapy for metastatic urothelial carcinoma with stable or responding disease following platinum based chemotherapy. ASCO American Society of Clinical Oncology Genitourinary Cancers Symposium. Feb. 16-18, 2023. San Francisco, CA. J Clin Oncol. vol. 41(6 Supl) Abs N TPS590.
King et al. Quantitative determination of lurbinectedin, its unbound fraction and its metabolites in human plasma utilizing ultra-performance LC—MS/MS. PLoS One. vol. 18(3) pp. e0283783.
Chakraborty et al. Preclinical analysis identifies predictive biomarker and potential pathways of resistance to lurbinectedin treatment in small cell lung cancer. AACR American Association for Cancer Research. Annual Meeting. Apr. 14-19, 2023. Orlando, FL. Philadelphia (PA) Cancer Res. vol. 83(8 Supl) Abs N LB233.
Gupta et al. High SLFN11 expression correlates with sensitivity to lurbinectedin in small cell lung cancer (SCLC) models. AACR American Association for Cancer Research. Annual Meeting. Apr. 14-19, 2023. Orlando, FL. Philadelphia (PA) Cancer Res. vol. 83 (7 Supl) Abs No. 2145.
Martinez Diez et al. Lurbinectedin shows potent activity in all four molecular subtypes of small cell lung cancer (SCLC) and POU2F3 and SLFN11 are biomarkers for a better response. (Poster).
Martinez Diez et al. Lurbinectedin shows potent activity in all four molecular subtypes of small cell lung cancer (SCLC) and POU2F3 and SLFN11 are biomarkers for a better response. (Abstract).
Resano et al. Exportin 1 inhibition synergizes with lurbinectedin by altering the response to DNA damage in neuroendocrine lung tumors. AACR American Association for Cancer Research. Annual Meeting. Apr. 14-19, 2023. Orlando, FL. Philadelphia (PA) Cancer Res. vol. 83 (7 Supl) Abs N 6188.
Tummala et al. Synergistic combinations of lurbinectedin with irinotecan and ONC212 in pancreatic cancer. AACR American Association for Cancer Research. Annual Meeting. Apr. 14-19, 2023. Orlando, FL. Philadelphia (PA) Cancer Res. vol. 83 (7 Supl) Abs N 2674.
Uruchurtu et al. Molecular analysis of small cell lung cancer provides insights into mechanism of action underlying the novel drug combination of lurbinectedin and TIC10/ONC201. AACR American Association for Cancer Research. Annual Meeting. Apr. 14-19, 2023. Orlando, FL. Philadelphia (PA) Cancer Res. vol. 83 (7 Supl) Abs N 4909.
Vaidya et al. Lurbinectedin exhibits combinatorial activity with BCL2/BCL2L1 inhibitors in vitro and in vivo by modulation of MCL1 expression. AACR American Association for Cancer Research. Annual Meeting. Apr. 14-19, 2023. Orlando, FL. Philadelphia (PA) Cancer Res. vol. 83 (7 Supl) Abs N 6155.
Hanvesakul et al. Indirect treatment comparison of lurbinectedin versus other second-line treatments for small-cell lung cancer. J Comp Eff Res. vol. In press pp. e220098.
Shi et al. Comparison of the second-line treatments for patients with small cell lung cancer sensitive to previous platinum-based chemotherapy: A systematic review and Bayesian network analysis. Front Oncol. vol. 13 pp. 1154685.
Girard et al. IFCT-2105 lurbiclin real-world effectiveness and treatment sequences in patients (pts) with extensive-stage small cell lung cancer (ES-SCLC) who received lurbinectedin as part of the French Early Access Program (EAP-ATU). ASCO American Society of Clinical Oncology, 59th Annual Meeting, Jun. 2-6, 2023. Chicago, Illinois. J Clin Oncol. vol. 41 (Supl 16) Abs No. 8584 (Poster).
Girard et al. IFCT-2105 lurbiclin real-world effectiveness and treatment sequences in patients (pts) with extensive-stage small cell lung cancer (ES-SCLC) who received lurbinectedin as part of the French Early Access Program (EAP-ATU). ASCO American Society of Clinical Oncology, 59th Annual Meeting, Jun. 2-6, 2023. Chicago, Illinois. J Clin Oncol. vol. 41 (Supl 16) Abs No. 8584 (Abstract).
Cousin et al. Efficacy and safety of lurbinectedin in elderly patients with relapsed SCLC. ASCO American Society of Clinical Oncology, 59th Annual Meeting, Jun. 2-6, 2023. Chicago, Illinois. J Clin Oncol. vol. 41 (Supl 16) Abs No. 8591 (Poster).
Cousin et al. Efficacy and safety of lurbinectedin in elderly patients with relapsed SCLC. ASCO American Society of Clinical Oncology, 59th Annual Meeting, Jun. 2-6, 2023. Chicago, Illinois. J Clin Oncol. vol. 41 (Supl 16) Abs No. 8591 (Presentation).
Cousin et al. Efficacy and safety of lurbinectedin in elderly patients with relapsed SCLC. ASCO American Society of Clinical Oncology, 59th Annual Meeting, Jun. 2-6, 2023. Chicago, Illinois. J Clin Oncol. vol. 41 (Supl 16) Abs No. 8591 (Abstract).

(56) References Cited

OTHER PUBLICATIONS

Besse et al. A phase III study of lurbinectedin alone or in combination with irinotecan vs investigator's choice (topotecan or irinotecan) in patients with relapsed small cell lung cancer (SCLC; Lagoon trial). ASCO American Society of Clinical Oncology, 59th Annual Meeting, Jun. 2-6, 2023. Chicago, Illinois. J Clin Oncol. vol. 41 (Supl 16) Abs N TPS8613 (Poster).
Besse et al. A phase III study of lurbinectedin alone or in combination with irinotecan vs investigator's choice (topotecan or irinotecan) in patients with relapsed small cell lung cancer (SCLC; Lagoon trial). ASCO American Society of Clinical Oncology, 59th Annual Meeting, Jun. 2-6, 2023. Chicago, Illinois. J Clin Oncol. vol. 41 (Supl 16) Abs N TPS8613 (Abstract).
Wasifuddin et al. Correlations between overall response rate, progression-free survival and overall survival in refractory small cell lung cancer treated with lurbinectedin. ASCO American Society of Clinical Oncology, 59th Annual Meeting, Jun. 2-6, 2023. Chicago, Illinois. J Clin Oncol. vol. 41 (Supl 16) Abs N e20623.
Subbiah et al. Safety analysis of lurbinectedin versus topotecan in elderly patients. ASCO American Society of Clinical Oncology, 59th Annual Meeting, Jun. 2-6, 2023. Chicago, Illinois. J Clin Oncol. vol. 41 (Supl 16) Abs No. e20632.
Cote et al. Efficacy of combination lurbinectedin (LURBI) + doxorubicin (DOX) from the phase 1B soft-tissue sarcoma (STS) lead-in to a randomized phase 2 trial in leiomyosarcoma (LMS). ASCO American Society of Clinical Oncology, 59th Annual Meeting, Jun. 2-6, 2023. Chicago, Illinois. J Clin Oncol. vol. 41 (Supl 16) Abs N 11507 (Presentation).
Cote et al. Efficacy of combination lurbinectedin (LURBI) + doxorubicin (DOX) from the phase 1B soft-tissue sarcoma (STS) lead-in to a randomized phase 2 trial in leiomyosarcoma (LMS). ASCO American Society of Clinical Oncology, 59th Annual Meeting, Jun. 2-6, 2023. Chicago, Illinois. J Clin Oncol. vol. 41 (Supl 16) Abs N 11507 (Abstract).
Lee et al. Advancements in small cell lung cancer. Semin Cancer Biol. vol. 93 pp. 123-128.
Su et al. Cost-Effectiveness Modeling of Lurbinectedin as a Second-Line Therapy in Patients with Small Cell Lung Cancer (SCLC). ISPOR Europe 2023. May 7-10, 2023. Boston, MA, USA. Value Health. vol. 26(6 Supl) pp. S87 (Abs. NEE152).
Bhamidipati and Subbiah. Lurbinectedin, a DNA minor groove inhibitor for neuroendocrine neoplasms beyond small cell lung cancer. Oncoscience. vol. 10 pp. 22-23.
Arai, Tadashi et al., "New Antibiotics, Safraycins A, B, C, D and E", The Journal of Antibiotics, vol. XXX, No. 11, on. 1015-1018 (1977).
Arai, Tadashi et al., "Directed Biosynthesis of New Saframycin Derivatives with Resting Cells of Streptomyces lavendulae", Antimicrobial Agents and Chemotherapy, vol. 28, No. 1, pp. 5-11 (1985).
Arai, T. et al., "The Structure of a Novel Antitumor Antibiotic, Saframycin A", Experientia, vol. 36, pp. 1025-1027 (1980).
Arai, Tadashi et al., "Isoquinolineinones from Actinomycetes and Sponges", The Alkaloids Chemistry and Pharmacology, vol. XXI, pp. 56-100 (1983).
Arai, Tadashi et al., "Increased Production of Saframycin A and Isolation of Saframycin S", The Journal of Antibiotics, vol. XXXIII, No. 9, No. 951-960 (1980).
Asaoka, Takemitsu et al., "A New Saframycin, Saframycin R", The Journal of Antibiotics, vol. XXXV, No. 12, pp. 1708-1710 (1982).
Barton, Derek H.R. et al., "Synthesis and Properties of a Series of Sterically Hindered Guanidine Bases1", Journal of the Chemical Society Perkin Transactions I, No. 9, pp. 2085-2090 (1982).
Brown, J.M., "NCI's Anticancer Drug Screening Program May Not Be Selecting for Clinically Active Compounds," Oncol. Res. 9(5):213-215 (1997).
Cable, Karl M et al., "The Biosynthesis of Tuberin from Tyrosine and Glycine; Observations on the Stereochemistry Associated with the Conversion of Glycine through Methylenetetrahydrofolate into Methenyltetrahydrofolate", Journal of the Chemical Society Perkins Transactions I, No. 7, pp. 1593-1598 (1987).
Calabresi et al., "Chemotherapy of Neoplastic Diseases", Goodman & Gilman's The Pharmacological Basis of Therapeutics, 9th ed. New York: McGraw-Hill, 1996, pp. 1225-1229.
Cecil Textbook of Medicine (Bennet, J.C. and Plum, F., eds.) 20th Edition, vol. 1, pp. 1004-1010 (1996).
Cecil Textbook of Medicine (Goldman & Bennett, eds.) 21st Edition, Chapter 198, 2000, pp. 1060-1074.
Cooper, Raymond et al., "Structure of the Quinone Antibiotic EM5519 and the Behavior of Quinones in Fast Atom Bombardment Mass Spectrometry", The Journal of Antibiotics, vol. XXXVIII, No. 1, on. 24-30 (1985).
Corey, E.J. et al., "Enantioselective Total Synthesis ofEcteinascidin 743", Journal of the American Chemical Society, vol. 118, No. 38, pp. 9202-9203 (1996).
Cuevas, Carmen et al., "Synthesis of Ecteinascidin ET-743 and Phthalascidin Pt-650 from Cyanosafracin B", Organic Letters vol. 2, No. 16, No. 2545-2548 (2000).
Dorwald F. A. Side Reactions in Organic Synthesis, 2005, Wiley: VCH, Weinheim pg. IX of Preface.
Draetta, G. and Pagano, M., "Annual Reports in Medicinal Chemistry, vol. 31," Academic Press, San Diego, pp. 241-246 (1996).
Eckhardt, S.G. et al., "Activity of ecteinascidin, a novel marine cytotoxic, against primary human tumor colony-forming units", Proceedings of the American Association for Cancer Research, vol. 37, #2791, No. 409 (1996).
Faircloth, G. et al., "Ecteinascidin-743 (ET743): in vitro (IVT) and in vivo (INV) Results in Tumor Models", The Euro12ean Journal of Cancer, vol. 32A, Supp. 1, #24 O, pp. S5 (1996).
Flam, Faye, "Chemical Prospectors Scour the Seas for Promising Drugs", Science, vol. 266, pp. 1324-1325 (1994).
Fregeau, Nancy Louise, "Biologically Active Compounds froma Clam and a Tunicate", Thesis, University of Illinois art Urbana-Champaign, 1992.
Frincke, James M. et al., "Antimicrobial Metabolites of the Sponge *Reniera* sp.", Journal of the American Chemical Society, vol. 104, pp. 265-269 (1982).
Fukuyama, Tohru et al., "Stereocontrolled Total Synthesis of (±)-Saframycin B", Journal of American Chemical Society, vol. 104, pp. 4957-4958 (1982).
Fukuyama, Tohru et al., "Total Synthesis of (±)-Saframycin A", Journal of American Chemical Society, vol. 112, pp. 3712-3713 (1990).
Garcia-Rocha, M. et al., "Characterisation of antimitotic products from marine organisms that disorganize the microtubule network: ecteinascidin 743, isohomohalichondrin-B and LL-15", British Journal of Cancer, vol. 73, pp. 875-883 (1996).
Goldwasser, F, et al. "Characterization of ecteinascidin 743-induced DNA damages in cells", Proceedings of the American Association for Cancer Research vol. 39, #4066, pp. 598 (1998).
Greene et al., Protective Groups in Organic Systems, 1999, Table of Contents for Chapters 2 and 7.
Guan, Yue et al., "Molecular and Crystal Structures ofEcteinascidins: Potent Antitumor Compounds from the Caribbean Tunicate Ecteinascidia Turbinata", Journal of Biomolecular Structure & Dynamics, vol. 10, No. 5, pp. 793-818 (1993).
Gulavita, Nanda K., et al., "Antimicrobial Constituents of a Sponge-Nudibranch Pair from Sri Lanka", Bioactive Compounds from Marine Organisms, Oxford & IBH Publishing Co. Pvt. Ltd., pp. 229-233 (1991).
He, Hai-yin et al., "Renieramycins E and F from the Sponge *Reniera* sp.: Reassignment of the Stereochemistry of the Renieramycins", The Journal of Organic Chemistry, vol. 54, No. 24, pp. 5822-5824 (1989).
Hendriks, H.R. et al., "High antitumor activity ofET743 in human tumor xenograft models", Proceedings of the American Association for Cancer Research vol. 37, #2653, pp. 389 (1996).
Holt, Tom Grady, The Isolation and Structural Characterization of the Ecteinascidins, Thesis, University of Illinois art Urbana-Champaign, 1986.

(56) References Cited

OTHER PUBLICATIONS

Ikeda, Yoshifumi et al., "Safracins, New Antitumor Antibiotics I. Producing Organism, Fermentation and Isolation", The Journal of Antibiotics, vol. XXXVI, No. 10, pp. 1279-1283 (1983).
Ikeda, Yoshifumi et al., "Safracins, New Antitumor Antibiotics I. Producing Organism, Fermentation and Isolation", The Journal of Antibiotics, vol. XXXVI, No. 10, pp. 1284-1289 (1983).
Internal Medicine, 4th Edition, Editor-in-Chief Jay Stein, Chapters 71-72, 1994, pp. 699-715.
Ito, Yoichiro, "High-Speed Countercurrent Chromatography", Critical Reviews in Analytical Chemistry, vol. 17, No. 1, pp. 65-143 (1986).
Kania, "The first Enantioselective Total Synthesis of Dolabellatrienone and Ecteinascidin 743", Harvard University, Sep. 1997, pp. 1-225.
Koenig, Karl E., "The Applicability of Asymmetric Homogeneous Catalytic Hydrogenation", Asymmetric Synthesis Ed. Morrison, Academic Press, Inc., Orlando, FL, vol. 5, pp. 71 (1985).
Kofron, William G. et al., "A Convenient Method for Estimation of Alkyllithium Concentrations", The Journal of Organic Chemistry, vol. 41, No. 10, pp. 1879-1880 (1976).
Kubo, Akinori et al., "Structure of Saframycin D, A New Dimeric Isoquinolinequinone Antibiotic", Chem. Pharm. Bull., vol. 35, No. 1, pp. 440-442 (1987).
Kuffel, MJ. et al., "Cytochrome P450 catalyzed metabolism of Ecteinascidin 743 by rat and human liver microsomes", Proceedings of the American Association for Cancer Research, vol. 38, #4003, pp. 596 (1997).
Lichter, W. et al, "Biological Activities Exerted by Extracts ofEcteinascidia Turbinata", Food and Drugs from the Sea Proceedings, pp. 117-127 (1972).
Lown, J. William et al, "Molecular Mechanisms of Binding and Single-Strand Scission of Deoxyribonucleic Acid by the Antitumor Antibiotics Saframycins A and C", Biochemistry, vol. 21, No. 3, pp. 419-428 (1982).
Lown, J. William et al, "Structure and Confirmation ofSaframycin R Determined by High Field 1H and 13C NMR and its Interactions with DNA in Soloution", The Journal of Antibiotics, vol. XXXVI, No. 9, pp. 1184-1194 (1983).
Martinez et al, "A New, More Efficient, and Effective Process for the Synthesis of a Key Pentacyclic Intermediate for Production of Ecteinascidin and Phthalascidin Antitumor Agents", Organic Letters, 2(7):993-996 (2000).
Martinez et al, "Enantioselective Synthesis of Saframycin A and Evaluation of Antitumor Activity Relative to Ecteinascidin/Saframycin Hybirds", Organic Letters, 1(7):75-77 (1999).
Martinez, Eduardo J. et al., "Phthalascidin, a synthetic antitumor agent with potency and mode of action comparable to ecteinascidin 743", Chemistry, vol. 96, pp. 3496-3501 (1999).
Mikami, Yuzuru et al., "Structural Studies on Minor Components of Saframycin Group Antibiotics Saframycins F, G and H", The Journal of Antibiotics, vol. XLI, No. 6, pp. 734-740 (1988).
Mirsalis, J.C. et al, "Toxicity ofEcteinascidin 743 in female Fischer-344 rats administered i.v. in a multiple-dose regimen", Proceedings of the American Association for Cancer Research, vol. 38, #2073, pp. 309 (1997).
Moore, B.M. et al., "The NMR model ofan ecteinascidin 743-DNA adduct", Proceedings of the American Association for Cancer Research, vol. 38, #2105, pp. 314 (1997).
Morales, Jose Javier, "Marine Natural Products Chemistry of a Caribbean Tunicate and a Palau Sponge", University of Illinois art Urbana-Champaign, 1999.
Myers et al., "A Concise, Stereocontrolled Syntheis of (-)-Saframycin A by the Directed Condensation ofa-Amino Aldehyde Precursors", J. Am. Chem. Soc., 121:10828-10829 (1999).
Nakagawa, Masako et al., "Total Synthesis of(-)-Eudistomin Land (-)- Debromoeudistomin L", Journal of the American Chemical Society, vol. 111, No. 7, pp. 2721-2722 (1989).
Parulekar, A.H. et al., "Bioactivity and Chemical Ecology of Some Interdial Animals" Bioactivity and Chemical Ecology, pp. 29-35, 1991.
Pommier, Yves et al, "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", Biochemistry, vol. 35, pp. 13303-13309 (1996).
Pretsch et al, Tables of Spectral Data for Structure Determination of Organic Compounds, pp. H125 (1983).
Reid, Joel M. et al., "Preclinical pharmacology of ecteinascidin 729, a marine natural product with potent antitumor activity", Cancer Chemotherapy and Pharmacology, vol. 38, No. 4, pp. 329-334 (1996).
Remers, William A., "Saframycins, Renieramycins, and Safracins", The Chemistry of Antitumor Antibiotics, vol. 2, DD. 93-119 (1988).
Rinehart, Kenneth L. et al., "Ecteinascidins 729, 743, 759A, 759B, and 770: Potent Antitumor Agents from the Caribbean Tunicate Exteinascidia Turbinata", The Journal of Organic Chemistry, vol. 55, No. 15, DD. 4512-4515 (1990).
Rinehart, Kenneth L. et al., "Applications of High-Resolution Tandem FAB Mass Spectrometry", Biological Mass Spectrometry, eds. Burlingame et al., Elsevier Amsterdam, DD. 233-258 (1990).
Rinehart, Kenneth L. et al., "Bioactive Compounds from Aquatic and Terrestrial Sources", Journal of Natural Products, vol. 53, No. 4, pp. 771-792 (1990).
Rinehart, Kenneth L. et al., "Biologically active natural products", Pure and Applied Chemistry, vol. 62, No. 7, pp. 1277-1280 (1990).
Rinehart et al., "Novel Bioactive Natural Products from Marine Organisms", Topics in Pharmaceutical Sciences 1989, pp. 613-626, D.D. Breimer, D.J.A. Cromwelin, K.K. Midha, Eds., Amsterdam Medical Press B.V. Noordwijk, The Netherlands (1989).
Saito, Naoki et al., "Synthesis of Saframycins. 3. Preparation of a Key Tricyclic Lactam Intermediate to Saframycin A", The Journal of Organic Chemistry, vol. 54, No. 22, pp. 5391-5395 (1989).
Sakai, Ryuichi, "Biologically Active Compounds from Tunicates and a Sponge", Thesis, University of Illinois art Urbana-Champaign, 1991.
Sakai, Ryuichi et al., "Additional antitumor ecteinascidins from a Caribbean tunicate: Crystal structures and activities in vivo", Proceedings of the National Academy of Sciences, vol. 89, No. 23, pp. 11456-11460 (1992).
Sakai, Ryuichi et al., "Ecteinascidins: Putative Biosynthetic Precursors and Absolute Stereochemistry", Journal of the American Chemical Society, vol. 118, No. 38, pp. 9017-9023 (1996).
Shamma, Maurice et al., Carbon-13 NMR Shift Assignments of Amines and Alkaloids, pp. 206 (1979).
Sparidans Rolf W. et al., "Search for metabolites of ecteinascidin 743, a novel, marine-derived anti-cancer agent, in man." Anti-Cancer Drugs, vol. 12, pp. 653-666, 2001.
Still, W. Clark et al., "Rapid Chromatographic Technique for Preparative Separations with Moderate Resolution", Journal ofOrn:anic Chemistry, vol. 43, No. 14, DD. 2923-2925 (1978).
Takahaski, Katsuhiro, "New Antibiotics, Saframycins A, B, C, D and E", The Journal of Antibiotics, vol. XXX, No. 11, pp. 1015-1018 (1977).
Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", The Journal of Antibiotics, vol. XXXV, No. 2, DD. 196-202 (1982).
Trowitzsch-Kienast, Wolfram et al., "Isolierung und Strukturaufklarung der Saframycine Mx 1 und Mx 2, neue antitumor-aktive Antibiotika aus Myxococcus xanthus", Liebigs Ann. Chem., vol. XXXV, pp. 475-481 (1988).
Valoti et al. Clin. Cancer Res. 4(8): 1977-83 (1998).
Witten, Jane L. et al., "Structures of Two Cockroach Neuropeptides Assigned by Fast Atom bombardment Mass Spectrometry", Biochemical and Biophysical Research Communications, vol. 124, No. 2, DD. 350-358 (1984).
Wright, Amy E. et al., "Antitumor Tetrahydroisoquinoline Alkaloids from the Colonial Ascidian Ecteinascidia Turbinata", The Journal of Organic Chemistry:, vol. 55, No. 15, pp. 4508-4512 (1990).

(56) References Cited

OTHER PUBLICATIONS

Yazawa, Katsukiyo et al., "Bioconversions of Saframycin A Specific to some Genera of Actinomycetes", The Journal of Antibiotics, vol. XXXV, No. 7, pp. 915-917 (1982).
Yazawa, Katsukiyo et al., "Isolation and Structural Elucidation of New Saframycins Y3, Yd-I, Yd-2, Ad-I, Y2b and Y2b-d", The Journal of Antibiotics, vol. XXXIX, No. 12, pp. 1639-1650 (1986).
Zmijewski, Milton J., Jr. et al., "The in vitro Interaction ofNaphthyridinomycin with Deoxyribonucleic Acids", Chemico-Biological Interactions, vol. 52, No. 3, pp. 361-375 (1985).
Allavena et al., Effects of the Anti-Tumor Agents Trabectedin and Lurbinectedin on Immune Cells of the Tumor Microenvironment, Front. Oncol. 12:851790.
Aviles, et al., "Mechanism of action and antitumor activity of PM01183," AACR Annual Meeting, Abstract No. 2679, 1 page, Apr. 18-22, (2009), Denver, CO.
Aviles, et al., "Mechanism of action and antitumor activity of PM01183," Pharma Mar Grupo Zeltia, Poster corresponding to Abstract # 2679, Apr. 20, (2009).
Bray F, et al. Global cancer statistics 2018: GLOBOCAN estimates of incidence and mortality worldwide for 36 cancers in 185 countries. CA Cancer J Clin (2018) 68 (6): 394-424.
Bredberg et al., "Ciprofloxacin-induced inhibition of topoisomerase II in human lymphoblastoid cells." Antimicrobial Agents and Chemotherapy 1991, 35(3), 448-450.
Bria et al., "Gemcitabine-based combinations for inoperable pancreatic cancer: Have we made real progress? A meta-analysis of 20 phase 3 trials", Cancer 2007, 110(3), 525-533.
Tourneau et al., "Mtorci Inhibitors: Is Temsirolimus In Renal Cancer Telling Us How They Really Work?" Brit. J. Canc., vol. 99, pp. 1197-1203, Sep. 16, 2008.
Cassier et al., "Trabectedin and Its Potential in the Treatment of Soft Tissue Sarcoma," Therapeutics and Clinical Risk Management, 4(1), pp. 109-116, 2008.
Christinat et al., "Role of Trabectedin in the Treatment of Soft Tissue Sarcoma," Onco Targets and Therapy, 2, pp. 105-113, 2009.
Cuevas et al., Anticancer Agents from Natural Products, Second Edition, CRC Press, 2012, "Ecteinascidin-473 (Yondelis), Aplidin, and Irvalec", Chapter 12, pp. 291-310.
Cuevas et al, Drug Discovery from Natural Products, Section 1, Chapter 1, "Semisynthesis Approach of Ecteinascidin (ET-473, Yondelis)", Sep. 13, 2012, p. 5-12, https://doi.org/10.1039/9781849734950.
David-Cordonnier et al., "DNA and Non-DNA Targets in the Mechanism of Action of the Antitumor Drug Trabectedin", Chemistry & Biology, vol. 12, pp. 1201-1210, Nov. 2005.
Dingemans AC, et al. Small-cell lung cancer: ESMO Clinical Practice Guidelines for diagnosis, treatment and follow-up. Ann Oncol (2021) 32 (7):839-53.
Eckardt JR, et al. Phase III study of oral compared with intravenous topotecan as second-line therapy in small-cell lung cancer. J Clin Oncol (2007) 25 (15): 2086-92.
Erba et al., Ascites interferes with the activity of lurbinectedin and trabectedin: Potential role of their binding to alpha 1-acid glycoprotein, Biochem. Pharmacol. (2017).
Evans TL, et al. Cabazitaxel Versus Topotecan in Patients with Small-Cell Lung Cancer with Progressive Disease During or After First-Line Platinum-Based Chemotherapy. J Thorac Oncol (2015) 10 (8): 1221-8.
Fernandez-Teruel, Population-Pharmacokinetic and covariate analysis of lurbinectedin (PM01183) a new RNA polymerase II inhibitor, in pooled phase I/II trials in patients with cancer, Clinical Pharmacokinetics, 2019, 58, 363-374.
Fischer B, et al. Current status of clinical trials for small cell lung cancer. Rev Recent Clin Trials (2008) 3 (1 ): 40-61.
Galmarini et al., "Abstract 5499: Lurbinectedin (PM01183) Synergizes with Topoisomerase I Inhibitors in Vitro and in Vivo," Cancer Research, vol. 73, issue 8, supplement 1, Apr. 15, 2013 (Abstract).
Galmarini, "New Marine Anticancer Agents in Development," Pharma Mar Grupo Zeltia, 28 pages, 6th European Spring Oncology Conference, Jun. 22-25, 2010.
Galmarini, "New Marine Anticancer Agents in Development," PharmaMar, New Cytotoxics and Vaccines, Symposium IX, 1 page, Abstract (vol. 12 (Supl), p. 26), Cell Biology Department, PharmaMar, Madrid, Spain, Jun. 22-25, 2010.
Minotti et al., "Anthracyclines: Molecular Advances and Pharmacologic Developments in Antitumor Activity and Cardiotoxicity," Pharmacol. Rev., (Jun. 1, 2004) vol. 56, No. 2, pp. 185-229.
Gore et al., "Phase I Combination Study of Trabectedin (T) and Capecitabine (C) in Patients with Advanced Malignancies," J. of Clinical Oncology, 24(18S), 2079, 2008 ASCO Annual Meeting Proceedings (Post-Meeting edition).
Hande et al., "Topoisomerase II inhibitors," Update of Cancer Therapeutics, vol. 3, pp. 13-26, Mar. 25, 2008.
Larsen, et al., "The marine product Tryptamicidin shows activity toward platinum-resistant cells and attenuates nucleotide excision repair" Universite Pierre & Marie Curie Science A Paris, Inserm Institute National de la sante et de la recherche medicale, 20 pages, 31st EORTC-PAMM (Pharmacology and Molecular Mechanisms). Group Annual Winter Meeting held on Toulouse (France) on Jan. 27-30, 2010.
Takahashi et al., "Preclinical Investigations of PM01183 (Lurbinectedin) as a Single Agent or in Combination with Other Anticancer Agents for Clear Cell Carcinoma of the Ovary", PLOS One, Mar. 17, 2016.
Li et al., "Characterization of ARC-111 as a Novel Topoisomerase I-Targeting Anticancer Drug." Cancer Research 2003, 63(23), 8400-8407.
Paz, "Antitumor Antibiotics," Anticancer Therapeutics, Chapter 8, Jan. 1, 2008.
von Mehren et al., "A Phase I Study of the Safety and Pharmacokinetics of Trabectedin in Combination with Pegylated Liposomal Doxorubicin in Patients with Advanced Malignancies," Annals of Oncoloy, 19, pp. 1802-1809, 2008.
Messersmith et al., Phase I trial of weekly trabectedin Cancer Chemother. Pharmacol., vol. 63, pp. 181-188, 2008.
Nitiss et al., "Targeting DNA topoisomerase II in cancer chemotherapy." Nature reviews. Cancer. 2009, 9(5), 338-350.
O'Brien Me, et al. Phase III trial comparing supportive care alone with supportive care with oral topotecan in patients with relapsed small-cell lung cancer. J Clin Oncol (2006) 24 (34): 5441-7.
Pelayo Alvarez M, et al. Chemotherapy versus best supportive care for extensive small cell lung cancer. Cochrane Database Syst Rev (2013) 11:CD001990.
Perez-Ruixo et al, Population Pharmacokinetic Meta-Analysis of trabectedin in cancer patients, Clin. Pharmacokinet, 2007,46, 867-884.
Pommier, "Topoisomerase I Inhibitors: Camptothecins and Beyond," Nature Rev. Cancer, vol. 6, pp. 789-802, Oct. 1, 2006.
Puglisi M, et al. Treatment options for small cell lung cancer—do we have more choice? Br J Cancer (2010) 102 (4): 629-38.
Pujol JL, el al. A Randomized Non-Comparative Phase II Study of Anti-Programmed Cell Death-Ligand 1 Atezolizumab or Chemotherapy as Second-Line Therapy in Patients With Small Cell Lung Cancer: Results From the FCT-1603 Trial. J Thorac Oncol (2019) 14 (5): 903-13.
Reck M, et al. Efficacy and safety of nivolumab (nivo) monotherapy versus chemotherapy (chemo) in recurrent small cell lung cancer (SCLC): Results from CheckMate 331. Ann Oncol (2018) 29 (Suppl 10): x39-x43.10.1093/annonc/mdy511.
Ren et al., "NB-506, an indolocarbazole topoisomerase I inhibitor, binds preferentially to triplex DNA." Febs Letters 2000, 470(3), 355-359.
Riccardi et al., "Combination of trabectedin and irinotecan is highly effective in a human rhabdomyosarcoma xenograft", Anti-Cancer Drugs 2005, 16, 811-815.
Office Action for Russian Application No. 2018102080 dated Apr. 12, 2021, 18 pages.
Office Action for Russian Application No. 2018102080 dated Aug. 26, 2021, 20 pages.
Saulnier et al., "Discovery of a Fluoroindolo[2,3-a]carbazole Clinical Candidate with Broad Spectrum Antitumor Activity in Preclini-

(56) References Cited

OTHER PUBLICATIONS cal Tumor Models Superior to the Marketed Oncology Drug, CPT-11." Journal of Medicinal Chemistry 2005, 48(7), 2258-2261.
Scaife et al., "Antimetabolites in Cancer Therapy," Anticancer Therapeutics, Chapter 7, Jan. 1, 2008.
Schmidt et al., "Mitotic Drug Targets and the Development of Novel Anti-Mitotic Anticancer Drugs," Drug Resistance Updates, vol. 10, pp. 162-181, Aug. 1, 2007.
Scotlandi et al., "Effectiveness of Ecteinascidin-743 Against Drug-Sensitive and Resistant Bone Tumor Cells," Clinical Cancer Research, 8, pp. 3893-3903, 2002.
Seaman and Hurley, "Molecular Basis for the DNA Sequence Selectivity of Ecteinascidin 736 and 743: Evidence for the Dominant Role of Direct Readout via Hydrogen Bonding", J. Am. Chem. Soc., vol. 120, pp. 13028-13041, Dec. 3, 1998.
Sessa et al., "Phase 1 Clinical and Pharmacokinetic Study of Trabectedin and Doxorubicin in Advanced Soft Tissue Sarcoma and Breast Cancer," European Journal of Cancer, 45, pp. 1153-1161, 2009.
Simos D, et al. Third-line chemotherapy in small-cell lung cancer: an international analysis. Clin Lung Cancer (2014) 15 (2): 110-8.
Slotman B, et al. Prophylactic cranial irradiation in extensive small-cell lung cancer. N Engl J Med (2007) 357 (7): 664-72.
Soares et al., "The DNA damage response to monofunctional anticancer DNA binders", Drug Discovery Today: Disease Models, vol. 9, No. 2, pp. e59-e67, Jun. 2012.
Soares et al., "Trabectedin and Its C Subunit Modified Analogue PM01183 Attenuate Nucleotide Excision Repair and Show Activity towards Platinum-Resistant Cells", Molecular Cancer Therapeutics, vol. 10, No. 8, pp. 1481-1489, May 27, 2011.
Sundstrom S, et al. Cisplatin and etoposide regimen is superior to cyclophosphamide, epirubicin, and vincristine regimen in small-cell lung cancer: results from a randomized phase III trial with 5 years' follow-up. J Clin Oncol (2002) 20 (24): 4665-72.
Takahashi et al., "Sequence-dependent Enhancement of Cytotoxicity Produced by Ecteinascidin 743 (ET-743) with Doxorubicin or Paclitaxel in Soft Tissue Sarcoma Cells", Clinical Cancer Research, vol. 7, pp. 3251-3257, Oct. 2001.
Takahashi et al., "Sequence-dependent Synergistic Cytotoxicity of Ecteinascidin-743 and Paclitaxel in Human Breast Cancer Cell Lines in Vitro and in Vivo", Cancer Research, vol. 62, pp. 6909-6915, Dec. 1, 2002.
Valeri, et al., "Development of an in vitro model for the simultaneous study of the efficacy and hematotoxicity of antileukemic compounds," Science Direct, Toxicology Letters 199, pp. 317-322, 2010.
Vengerovsky, Farmakologicheskaya nesovmestimost [Pharmacological incompatibility], Bulleten Sibirskoi meditsiny [Bulletin of Siberian Medicine], 2003, No. 3, pp. 49-56.
Von Pawel J, et al. Randomized phase III trial of amrubicin versus topotecan as second-line treatment for patients with small-cell lung cancer. J Clin Oncol (2014) 32 (35): 4012-9.
Von Pawel J, et al. Phase II comparator study of oral versus intravenous topotecan in patients with chemosensitive small-cell lung cancer. J Clin Oncol (2001) 19 (6): 1743-9.
Von Pawel J, et al. Topotecan versus cyclophosphamide, doxorubicin, and vincristine for the treatment of recurrent small-cell lung cancer. J Clin Oncol (1999) 17 (2): 658-67.
Willis, Michael, Response to Final Office Action with Notice of Appeal filed in related U.S. Appl. No. 10/416,086, Notice of Appeal filed May 17, 2006, pp. 1-16.
Willis, Michael, Response to Final Office Action with Notice of Appeal filed in related U.S. Appl. No. 10/416,086, Response to Final Office Action filed on Apr. 4, 2008, pp. 1-20.
Willis, Michael, Response to Non-Final Office Action filed in related U.S. Appl. No. 10/416,086, response filed Aug. 23, 2005, pp. 1-7.
Willis, Michael, Response to Non-Final Office Action in related U.S. Appl. No. 10/416,086, Response to Non-Final Office Action filed on Sep. 2, 2008, pp. 1-23.
Tallarida RJ. Quantitative methods for assessing drug synergism. Genes Cancer. Nov. 2011;2(11):1003-8. doi: 10.1177/1947601912440575. PMID: 22737266; PMCID: PMC3379564.
Meco et al., "Effective combination of ET-743 and doxorubicin in sarcoma: preclinical studies," Cancer Cehmother. Pharmacol., (2003) 52, pp. 131-138.
NCCN Clinical Practice Guidelines in Oncology Small Cell Lung Cancer. Version 2.2022—Nov. 24, 2021. https://www.nccn.org/professionals/physician_gls/pdf/sclc.pdf.
Chou TC. Drug combination studies and their synergy quantification using the Chou-Talalay method. Cancer Res. Jan. 15, 2010;70(2):440-6. doi: 10.1158/0008-5472.CAN-09-1947. Epub Jan. 12, 2010. PMID: 20068163.
D'Incalci et al., "A Review of Trabectedin (ET-743): A Unique Mechanism of Action," Mol Cancer Ther; (2010) 9(8), pp. 2157-2163.
Hurwitz JL, et al. New advances in the second-line treatment of small cell lung cancer. Oncologist (2009) 14 (10): 986-94.
Chou T. Relationships between inhibition constants and fractional inhibition in enzyme-catalyzed reactions with different numbers of reactants, different reaction mechanisms, and different types and mechanisms of inhibition. Mol Pharmacol. Mar. 1974; 10(2):235-47. PMID: 4212316.
Chou TC, Talalay P. Analysis of combined drug effects: a new look at a very old problem. Trends in Pharm Sci 4, 1983,450-454. doi: 10.1016/0165-6147(83)90490-X.
Erba et al., "The Unique Biological Features of the Marine Product YondelisTM (ET-743, Trabectedin) Are Shared by its Analog ET-637, Which Lacks the C Ring," Oncology Research, (2004) vol. 14, pp. 579-587.
"IUPAC Gold Book", http://goldbook.iupac.org/A00123.html.
Moore et al., "Sequencing evaluation of ET-743 combinations with standard chemotherapy agents against a panel of human tumor cell lines," Clinical Cancer Research, vol. 6, Abstract 504 (Nov. 2000) along with Table A. (Abstract).
Moore et al., "Sequencing evaluation of ET-743 combinations with standard chemotherapy agents against a panel of human tumor cell lines," Clinical Cancer Research, vol. 6, Abstract 504 (Nov. 2000) along with Table A. (Poster).
Rinehart, Kenneth L., "Antitumor Compounds from Tunicates", Medicinal Research Reviews, vol. 20, No. 1, pp. 1-27 (2000).
Sakai, et al., Additional Antitumor Ecteinascidins from a Caribbean Tunicate: Crystal Structures and Activities in vivoProceedings of the National Academy of Sciences of the United States of America (1992), 89(23), 11456-60.
Shah et al. The relevance of drug sequence in combination chemotherapy, Drug resistance update (2000), 3, 335-356.
Topotecan United Kingdom Summary of Product Characteristics (PP-PFE-GBR-2780 / Jul. 2020). Topotecan UK SmPC—Hospira from Wayback text revision Apr. 2019.
Topotecan United Kingdom Summary of Product Characteristics (PP-PFE-GBR-2780 / Jul. 2020). Topotecan UK SmPC—Novartis hard caps—wayback—version date May 3, 2018.
Jonsson et al., Differential Activity of topotecan, irinotecan and SN-38 in fresh human tumor cells but no in cell lines, European Journal of Cancer, 36, 2000, pp. 2120-2127.
Vincenzi et al., "Wide-spectrum characterization of trabectedin: biology, clinical activity and future perspectives," Pharmacogenomics, (2010) 11(6), pp. 865-878.
Lee, Wan Chieh, Response to Non-Final Office Action filed in related U.S. Appl. No. 10/416,086, Response to Non-Final Office Action filed on Aug. 9, 2007, pp. 1-190.
Fetterolf, Brandon J., Examiner Interview Summary issued for related U.S. Appl. No. 10/416,086, Interview Summary issued on May 7, 2008, pp. 1-2.
International Preliminary Report on Patentability mailed on May 14, 2013 by the International Preliminary Examining Authority for International Application No. PCT/EP2011/069976, filed on Nov. 11, 2011 (Applicant-Pharma Mar, S.A. (18 pages).
International Search Report (mailed May 18, 2012) and Written Opinion (mailed on May 12, 2012) by the International Searching Authority for International Application No. PCT/EP2011/069976, filed on Nov. 11, 2011 (Applicant-Pharma Mar, S.A.) (25 Pages).

(56) References Cited

OTHER PUBLICATIONS

Zepzelca FDA label.
Schultz et al. ATR inhibition augments the efficacy of lurbinectedin in small-cell lung cancer. MBO Mol Med. Jul. 25, 2023:e17313.
Takahashi et al. Phase I Study of Lurbinectedin in Japanese Patients with Pretreated Advanced Solid Tumors. JJ Oncol Clin Res 4: 1-19.
Berckmans et al. Drug Repurposing for Targeting Myeloid-Derived Suppressor-Cell-Generated Immunosuppression in Ovarian Cancer: A Literature Review of Potential Candidates. s. Pharmaceutics 2023, 15, 1792.
Leary et al. Pooled Safety Analysis of Single-Agent Lurbinectedin in Patients With Advanced Solid Tumours. European Journal of Cancer. Articles in Press, 113259.
Kristeleit et al. Lurbinectedin in patients with pretreated endometrial cancer: results from a phase 2 basket clinical trial and exploratory translational study. Invest New Drugs (2023).
Boyne et al. Comparative Efectiveness of Lurbinectedin for the Treatment of Relapsed Small Cell Lung Cancer in the Post-Platinum Setting: A Real-World Canadian Synthetic Control Arm Analysis. Targ Oncol (2023).
Garcia-Cameplo et al. SEOM-GECP Clinical guidelines for diagnosis, treatment and follow-up of small-cell lung cancer (SCLC) (2022) Clinical and Translational Oncology (2023) 25:2679-2691.
Garcia-Campelo et al. Correction to: SEOM-GECP Clinical guidelines for diagnosis, treatment and follow-up of small-cell lung cancer (SCLC) (2022). Clinical and Translational Oncology (2023) 25:2760-2762.
Pharma Mar Annual report 2022.
Pharma Mar Financial statements 2022.
Pharma Mar Annual report 2021.
Pharma Mar Financial statements 2021.
Pharma Mar Annual report 2020.
Pharma Mar Financial statements 2020.
Pharma Mar Annual report 2019.
Pharma Mar Financial statements 2019.
Pharma Mar Annual report 2018.
Pharma Mar Financial statements 2018.
Pharma Mar Annual report 2017.
Pharma Mar Financial statements 2017.
Pharma Mar Annual report 2016.
Pharma Mar Annual report 2015.
Pharma Mar Annual report 2014.
Pharma Mar Annual report 2013.
Pharma Mar Annual report 2012.
Zeltia Annual report 2014.
Zeltia Annual report 2013.
Zeltia Annual report 2012.
Zeltia Annual report 2011.
Zeltia Annual report 2010.
Zeltia Annual report 2009.
Zeltia Annual report 2008.
Q1 Interim report (2023) (Apr. 26, 2023).
Q1 Interim report (2022) (Apr. 28, 2023).
H2 Interim report (2022) (Jul. 27, 2022).
H2 Periodic publication (2022) (Jul. 27, 2022).
H2 Presentation 2022 (Jul. 28, 2022).
Q3 Interim report (2022) (Oct. 27, 2022).
Q4 Report (2023) (Feb. 28, 2023).
Q4 Periodic publication (2023) (Feb. 28, 2023).
Q1 Interim report (2021) (May 5, 2021).
H2 Interim report (2021) (Jul. 29, 2021).
H2 Pperiodic publication (Jul. 29, 2021).
Q3 Interim report (2021) (Oct. 28, 2021).
Q4 Report (2022) )Feb. 28, 2022).
Q4 Periodic publication (2022) (Feb. 28, 2022).
Q1 Interim report (2020) (Apr. 23, 2020).
H1 Interim report (2020) (Jul. 30, 2020).
Q3 Interim report (2020) (Nov. 3, 2020).
Q4 Rreport (2021) (Feb. 26, 2021).
Q1 Interim report (2019) (Apr. 26, 2019).
H1 Interim report (2019) (Jul. 29, 2019).
Q3 Interim report (2019) (Oct. 23, 2019).
Q4 Report (2020) (Feb. 26, 2020).
Q1 Interim report (2018) (Apr. 26, 2018).
H1 Interim report (2018) (Jul. 26, 2018).
Q3 Interim report (2018) (Oct. 30, 2018).
Q4 Report (2019) (Feb. 28, 2019).
Consolidated non-financial information (2022).
Consolidated non-financial information (2021).
Consolidated non-financial information (2020).
Consolidated non-financial information (2019).
Consolidated non-financial information (2018).
Announcements of public presentations and meetings. Strategic plans (2017) (Apr. 24, 2017).
Strategic plans, profit forecasts and presentations (2017) (Jun. 29, 2017).
RD new licences patents and registered trademarks (2017) (Dec. 11, 2017).
Strategic plans, profit forecasts and presentations (2018) (Jan. 9, 2018).
Strategic plans, profit forecasts and presentations (2018) (Jun. 12, 2018).
Strategic plans, profit forecasts and presentations (2019) (Jun. 26, 2019).
On business and financial situation (Nov. 10, 2020).
1H 2022 Results presentation (Jul. 28, 2022).
CNMV Submissions (2017).
CNMV Submissions (2018).
CNMV Submissions (2019).
CNMV Submissions (2020).
CNMV Submissions, 2021.
CNMV Submissions (2022).
CNMV Submissions (2023).
On business and financial situation (Jul. 26, 2023).
H1 results 2023 (Jul. 27, 2023).
Corporate presentation 2023 (Aug. 1, 2023).
FY 2022 Results presentation (Mar. 1, 2023).
PharmaMar to host Conference Call and Webcast on Wednesday, Jan. 4, 2017 to discuss the License and Commercialization agreement with Chugai Pharmaceuticals for Lurbinectedin in Japan (Jan. 3, 2017).
PharmaMar continues to execute commercially in 2016, adds new partner for pipeline asset, and sees pipeline progress (Feb. 24, 2017).
The success of sarcoma treatment, seen by prestigious international oncologists (Mar. 29, 2017).
PharmaMar presents new data on the treatment of multiple myeloma and ovarian cancer at the AACR Congress (Apr. 4, 2017).
According to international oncologists, trabectedin is the therapeutic option of reference for the second line treatment of sarcoma (Apr. 7, 2017).
PharmaMar demonstrates its progress in R&D in New York (Apr. 27, 2017).
PharmaMar and Specialised Therapeutics Asia sign licensing and marketingfor lurbinectedin covering Australia, New Zealand and several Asian countries (May 17, 2017).
PharmaMar announces new data with its compounds Yondelis® and lurbinectedin during ASCO 2017 (May 18, 2017).
PharmaMar announces encouraging results in clinical trials of lurbinectedin endometrial and breast cancers (Jun. 16, 2017).
PharmaMar will commercialize PM1183 with the trade name of Zepsyre™ (Jun. 16, 2017).
FDA chooses Zepsyre™ (PM1183) from PharmaMar to explore potential development for pediatric cancers (Jun. 20, 2017).
PharmaMar will present new clinical data on PM1183 during ESMO 2017 (Aug. 31, 2017).
New positive data on PM1183 sees a response rate of 36% as single agent in patients with advanced and relapsed small-cell lung cancer (Sep. 12, 2017).
PharmaMar starts clinical studies with a new compound -PM14- in patients with solid tumors (Sep. 19, 2017).
PharmaMar will present final data on PM1183 during the 18th World Lungin Japan (Oct. 10, 2017).

(56) References Cited

OTHER PUBLICATIONS

Final data on phase I/II in small-cell lung cancer with Zepsyre® presented at the IASCLC 18th World Conference on Lung Cancer in Japan (Oct. 18, 2017).
In real-life, Yondelis® improves the results obtained in previous clinical trials in soft tissue sarcoma (Oct. 24, 2017).
PharmaMar will present at ESGO new data on Yondelis® for gynecological (Nov. 3, 2017).
PharmaMar and Boryung Pharm sign a licensing agreement for Zepsyre® (lurbinectedin) in Korea (Nov. 7, 2017).
Significant event: R&D: New licenses, patents and registered trademarks (Nov. 8, 2017).
PharmaMar presents positive results from a Phase II study of lurbinectedin in Ewing's sarcoma at the CTOS International Congress (Nov. 13, 2017).
PharmaMar to present at the Stifel 2017 Healthcare Conference (Nov. 14, 2017).
Phase III trial with Zepsyre® in small-cell lung cancer (Atlantis) to continue on the basis of positive recommendation by IDMC (Nov. 15, 2017).
Pharma Mar, S.A. announces the results of the Phase III clinical trial (Corail) with Zepsyre® (lurbinectedin) in platinum-resistant ovarian cancer patients. (Jan. 18, 2018).
PharmaMar's Lurbinectedin Atlantis trial design and data in small-cell lung cancer will be an oral presentation at the IASCLC's annual meeting (Feb. 20, 2018).
PharmaMar announces data presentations for both its molecules Yondelis® and lurbinectedin at ASCO 2018 (May 17, 2018).
Positive recommendation of IDMC to Zepsyre® to continue the Phase III trial with in small-cell lung cancer (Atlantis) (May 29, 2018).
PharmaMar presents new results with lurbinectedin as a single agent in patients with recurrent small-cell lung cancer at ASCO 2018 (Jun. 4, 2018).
PharmaMar requests the modification from primary endpoint to OS for the Atlantis trial (Jun. 12, 2018).
PharmaMar and Chugai agree to terms for early termination of the license agreement for Zepsyre® in Japan (Jun. 26, 2018).
PharmaMar announces the signature of a Memorandum of Understanding with the Indonesian Oceanographic Research Center to address the fight against cancer (Jul. 9, 2018).
The Lancet Oncology journal chooses a PharmaMar poster as one of the most relevant of the ASCO 2018 congress (Jul. 13, 2018).
PharmaMar reaches an agreement with Impilo Pharma, a part of Immedica Group, for the promotion and distribution of Yondelis® in the Nordic countries and Eastern Europe (Jul. 27, 2018).
PharmaMar announces that the Atlantis study has reached the goal of patitent recruitment (Jul. 30, 2018).
The U.S. Food and Drug Administration (FDA) has granted Orphan Drug designation to PharmaMar's Lurbinectedin (Aug. 3, 2018).
PharmaMar will present in the ESMO congress results of lurbinectedin on Ovarian Cancer (Aug. 10, 2018).
PharmaMar will present in the IASLC congress results of lurbinectedin on Small-Cell Lung Cancer (Aug. 13, 2018).
PharmaMar will present the results of the Phase I/II Study with lurbinectedin in combination with doxorubicin in relapsed small-cell lung cancer during the IASLC World Conference (Sep. 6, 2018).
Pharma Mar presents the Overall Survival data from the Phase I/II Study of lurbinectedin in combination with doxorubicin for relapsed Small Cell Lung Cancer (Sep. 24, 2018).
PharmaMar will present at ESMO results of the phase III Corail study with lurbinectedin in platinum-resistant Ovarian Cancer (Oct. 18, 2018).
Zepsyre® receives positive recommendation of the IDMC to continue with the Phase III trial in small-cell lung cancer (Atlantis) (Oct. 26, 2018).
PharmaMar announces that Zepsyre® (lurbinectedin) shows noteworthy clinical activity in metastatic breast cancer with mutations in BRCA 1/2 (Nov. 8, 2018).
PharmaMar announces the meeting of its patient recruitment target in the phase II study with lurbinectedin as a single agent in small-cell lung cancer (Nov. 14, 2018).
Phase II trial of lurbinectedin in progressive mesothelioma finalizes its patient recruitment (Dec. 17, 2018).
PharmaMar receives positive opinion from EMA (COMP) for orphan drug designation of Zepsyre® (lurbinectedin) for small-cell lung cancer (Jan. 24, 2019).
PharmaMar's Zepsyre® Atlantis trial in small-cell lung cancer will be an oral presentation at the IASLC's Targeted Therapies annual meeting (Feb. 20, 2019).
Soft Tissue Sarcoma requires a multidisciplinary approach to reduce patient relapses and improve patient survival (Mar. 21. 2019).
PharmaMar announces positive results in its lurbinectedin monotherapy trial for small cell lung cancer (Mar. 25, 2019).
ASCO selects PharmaMar's lurbinectedin monotherapy trial for an oral presentation(Apr. 1, 2019).
PharmaMar is present with its Atlantis study at the IASLC Congress on small cell lung cancer in New York (Apr. 8, 2019).
PharmaMar and Specialized Therapeutics Asia meet in Madrid to define new agreements (Apr. 17, 2019).
PharmaMar and Luye Pharma sign License agreement for Development and Commercialization of lurbinectedin in China territories (Apr. 26, 2019).
ASCO selects lurbinectedin second line small cell lung cancer abstract for "Best of ASCO" program (May 15, 2019).
ASCO releases abstracts and publishes PharmaMar's lurbinectedin data in second line small cell lung cancer (May 16, 2019).
Positive results of lurbinectedin Phase II trial (PharmaMar) for the treatment of relapsed small cell lung cancer are presented at ASCO (Jun. 1, 2019).
PharmaMar will host a conference call with investors after lurbinectedin results are presented at ASCO (Jun. 3, 2019).
IASLC publishes lurbinectedin (PharmaMar) abstracts titles for small cell lung cancer (Aug. 12, 2019).
PharmaMar will submit NDA for lurbinectedin under accelerated approval in SCLC in the USA (Aug. 19, 2019).
PharmaMar enters into a new licensing agreement with Janssen for Yondelis® (Aug. 26, 2019).
PharmaMar announces that its Phase I study on Japanese patients with lurbinectedin monotherapy has achieved its objective (Aug. 27, 2019).
PharmaMar presents at MaNaPro & ECMNP its latest advances in the development of compounds of marine origin (Sep. 2, 2019).
PharmaMar presents new lurbinectedin data at the World Conference on Lung Cancer (Sep. 9, 2013).
Phase II study results of lurbinectedin in progressive mesothelioma will be presented in an oral session at ESMO 2019 (Sep. 23, 2019).
Phase II Study results of trabectedin combined with low-dose radiation therapy for Soft Tissue Sarcoma are presented at ESMO (Sep. 30, 2019).
Lurbinectedin data in Progressive Malignant Pleural Mesothelioma presented at ESMO (Oct. 1, 2019).
PharmaMar has presented Yondelis® data in ovarian cancer at ESGO INov. 4, 2019).
PharmaMar will participate in the Solebury Trout KOL Day in New York on Nov. 15, 2019 (Novemer 7, 2019).
PharmaMar has presented results of its antitumor compounds trabectedin and plocabulin at the CTOS Congress (Nov. 18, 2019).
PharmaMar receives Orphan Drug Designation for lurbinectedin from the Swiss Agency for Therapeutic Products for Small Cell Lung Cancer (Nov. 26, 2019).
PharmaMar has filed New Drug Application for lurbinectedin with the FDA for the treatment of relapsed small cell lung cancer (Dec. 17, 2019).
PharmaMar and Jazz Pharmaceuticals Sign Exclusive License Agreement for Lurbinectedin in the U.S. (Dec. 19, 2019).
PharmaMar in San Francisco during the J.P. Morgan Annual Healthcare Conference in San Francisco (Jan. 9, 2020).
PharmaMar announces the initiation of a study of lurbinectedin in combination with immunotherapy (Jan. 14, 2020).

(56) References Cited

OTHER PUBLICATIONS

PharmaMar and Jazz Pharmaceuticals Announce the U.S. License Agreement for Lurbinectedin is Effective With the Expiration of the HSR Waiting Period (Jan. 22, 2020).
PharmaMar and Bionical Emas launch Expanded Access Program for lurbinectedin in relapsed Small Cell Lung Cancer in the U.S. (Jan. 27, 2020).
PharmaMar announces that it has received the upfront payment of $200 million from the license agreement with Jazz for lurbinectedin in the United States (Jan. 29, 2020).
PharmaMar and Jazz Pharmaceuticals Announce FDA Acceptance and Priority Review of New Drug Application for Lurbinectedin in Relapsed Small Cell Lung Cancer (Feb. 17, 2020).
Lurbinectedin receives Orphan Drug designation from the TGA for Small-Cell Lung Cancer in Australia (Feb. 19, 2020).
PharmaMar signs an agreement with Immedica Pharma to market lurbinectedin in Eastern Europe, the UK, Ireland, the Nordic countries and some Middle Eastern countries (Apr. 29, 2020).
PharmaMar and Megapharm sign a licensing agreement for lurbinectedin in Israel (May 11, 2020).
PharmaMar announces abstracts to be presented at ASCO 2020 (May 14, 2020).
Pharma Mar announces that TGA has granted the "Provisional Approval Pathway" for lurbinectedin in relapsed Small Cell Lung Cancer in Australia(Jun. 3, 2020).
PharmaMar to Host Virtual KOL Event on Lurbinectedin (Jun. 3, 2020).
PharmaMar announces the U.S. FDA approval of lurbinectedin (ZepzelcaTM) for the treatment of metastatic Small Cell Lung Cancer (Jun. 15, 2020).
PharmaMar announces that it has received payment of $100 million from Jazz Pharmaceuticals for the approval of ZepzelcaTM (lurbinectedin) in the U.S.(Jun. 29, 2020).
PharmaMar announces that lurbinectedin has received acceptance for its clinical trial application in China (Jun. 29, 2020).
PharmaMar announces that the NCCN® (National Comprehensive Cancer Network) has added Zepzelca™ (lurbinectedin) to Clinical Practice Guidelines in Oncology in the U.S.(Jul. 13, 2020).
PharmaMar has filed lurbinectedin for Temporary Marketing Authorisation with the Swiss Agency for Therapeutic Products (Jul. 20, 2020).
PharmaMar will present data for ZepzelcaTM (lurbinectedin) and Yondelis® (trabectedin) at ESMO 2020 (Sep. 14, 2020).
PharmaMar has presented new results for ZepzelcaTM (lurbinectedin) in sensitive patients with Small-Cell Lung Cancer, candidates for "re-challenge" (Sep. 17, 2020).
PharmaMar signs an agreement with Jazz Pharmaceuticals for lurbinectedin in Canada (Oct. 15, 2020).
PharmaMar will present new data for ZepzelcaTM (lurbinectedin) and Yondelis® (trabectedin) for advanced Soft-Tissue Sarcoma at CTOS 2020 ((Nov. 11, 2020).
PharmaMar and Luye Pharma have started a clinical trial with lurbinectedin in China (Dec. 1, 2020).
PharmaMar and Jazz Pharmaceuticals announce results of the Atlantis phase III study with lurbinectedin (Dec. 3, 2020).
PharmaMar will present new data for ZepzelcaTM (lurbinectedin) at rescheduled IASLC 2020 (Jan. 13, 2021).
PharmaMar presents new data on Zepzelca® (lurbinectedin) in combination with irinotecan at an oral session at (rescheduled) IASLC 2020 (Feb. 1, 2021).
PharmaMar signs a new agreement with Adium to commercialize Zepzelca® (lurbinectedin) in Latin America (Mar. 1, 20201).
ESMO includes lurbinectedin in its Clinical Practice Guidelines (Apr. 15, 2021).
PharmaMar announces abstracts to be presented at ASCO 2021 (May 20, 2021).
PharmaMar receives positive opinion from EMA (COMP) for Orphan Drug Designation of lurbinectedin for Mesothelioma (Jul. 28, 2021).
PharmaMar announces the approval of Zepzelca® (lurbinectedin) for the treatment of metastatic Small Cell Lung Cancer in the United Arab Emirates (Sep. 1, 2021).
PharmaMar announces abstracts to be presented during the IASLC 2021 World Conference on Lung Cancer (Sep. 2, 2021).
PharmaMar announces that Australia approves Zepzelca® (lurbinectedin) for the treatment of metastatic Small Cell Lung Cancer (Sep. 14, 2021).
PharmaMar announces Singapore Health Sciences Authority approval of Zepzelca® (lurbinectedin) for the treatment of metastatic Small Cell Lung Cancer (Sep. 22, 2021).
PharmaMar announces the approval of ZepzelcaTM (lurbinectedin) for the treatment of relapsed stage III or metastatic small cell lung cancer in Canada (Sep. 30, 2021).
PharmaMar signs a licensing and commercialization agreement with Lotus Pharmaceutical for lurbinectedin in Taiwan (Nov. 11, 2021).
PharmaMar and Jazz Pharmaceuticals announce initiation of confirmatory phase III clinical trial of Zepzelca® (lurbinectedin) for the treatment of patients with relapsed Small Cell Lung Cancer (Dec. 13, 2021).
PharmaMar signs a new licensing and commercialization agreement with Eczacibasi for lurbinectedin in Turkey (Dec. 22, 2021).
PharmaMar receives the first commercial milestone payment from Jazz Pharmaceuticals for US$25 million (Mar. 4, 2022).
Results of the phase II trial with lurbinectedin for the treatment of patients with relapsed Ewing Sarcoma (May 3, 2022).
PharmaMar has filed for approval of lurbinectedin for the treatment of metastatic Small Cell Lung Cancer in the UK (May 4, 2022).
PharmaMar announces abstracts to be presented at ASCO 2022 (Jun. 1, 2022).
Chinese health authorities approve lurbinectedin for "urgent clinical use" (Jul. 19, 2022).
Lurbinectedina recibe la designación de medicamento innovador de la MHRA del Reino Unido (Aug. 5, 2022).
PharmaMar announces the data to be presented at ESMO 2022 (Sep. 8, 2022).
PharmaMar announces the approval of Zepzelca® (lurbinectedin) for the treatment of metastatic Small Cell Lung Cancer in South Korea (Sep. 23, 2022).
PharmaMar receives Orphan Drug Designation for lurbinectedin from the Swiss Agency for Therapeutic Products for Malignant Mesothelioma (Dec. 27, 2022).
Lurbinectedin "Named Patient Program" for Small-Cell Lung Cancer launched in Hong Kong (Jan. 9, 2023).
PharmaMar announces the full approval of Zepzelca® (lurbinectedin) for the treatment of metastatic Small Cell Lung Cancer in Mexico (Jan. 24, 2023).
PharmaMar announces the approval of Zepzelca® (lurbinectedin) for the treatment of metastatic Small Cell Lung Cancer in Israel (Jan. 31, 2023).
PharmaMar announces the approval of Zepzelca® (lurbinectedin) for the treatment of metastatic Small Cell Lung Cancer in Switzerland (Mar. 8, 2023).
PharmaMar to present new data on its compounds at AACR 2023 Congress (Apr. 17, 2023).
European Commission grants orphan drug designation to PharmaMar's lurbinectedin for the treatment of Soft Tissue Sarcoma May 12, 2023).
PharmaMar announces abstracts to be presented at ASCO 2023 (May 26, 2023).
PharmaMar and Luye Pharma announce the acceptance of New Drug Application for lurbinectedin in China (Jun. 6, 2023).
PharmaMar announces the approval of Zepzelca® (lurbinectedin) for the treatment of metastatic Small Cell Lung Cancer in Taiwan (Jul. 11, 2023).
PharmaMar announces the approval of Zepzelca® (lurbinectedin) for the treatment of metastatic Small Cell Lung Cancer in Oman (Jul. 19, 2023).
PharmaMar to present new data on lurbinectedin at the IASLC 2023 World Lung Cancer Congress (Sep. 8, 2023).
Written Opinion of the ISA for PCT/EP2020/083061.

(56) References Cited

OTHER PUBLICATIONS

International Search Report for PCT/EP2020/074689 mailed Nov. 12, 2020.
Written Opinion of the ISA for PCT/EP2020/074689.
Examination Report for Eurasian Patent Application No. Application No. 202290761/28 dated May 2, 2023 (with English translation).
Office Action issued Apr. 12, 2023 for Chinese Patent Application No. 202080061468.5 (with English translation).
International Search Report for PCT/EP2020/063734 mailed Mar. 24, 2021.
Written Opinion of the ISA for PCT/EP2020/063734 mailed Mar. 24, 2021.
International Search Report for PCT/EP2020/065093 mailed Oct. 7, 2020.
Written Opinion of the ISA for PCT/EP2020/065093 mailed Oct. 7, 2020.
Research Report with Opinion on Patentability for Moroccan Application No. 56827 dated Dec. 8, 2022 (with English translation).
Moroccan Decision Partially rejecting Patent Application No. 56827 dated May 31, 2023 and Final Search Report with Opinion on Patentability for Application No. 56827 dated May 10, 2023 (with English translation).
International Search Report of PCT/EP2020/074860 mailed May 3, 2021.
Written Opinion of the ISA for PCT/EP2020/074860 May 3, 2021.
International Search Report of PCT/EP2021/074425 mailed Nov. 2, 2021.
Written Opinion of the ISA for PCT/EP2021/074425 mailed Nov. 2, 2021.
International Search Report for PCT/EP2021/081218 mailed Feb. 16, 2022.
Written Opinion of the ISA for PCT/EP2021/081218 mailed Feb. 16, 2022.
International Search Report for PCT/EP2022/081155 mailed Feb. 3, 2023.
Written Opinion of the ISA for PCT/EP2022/081155 mailed Feb. 3, 2023.
Office Action for Chinese Application No. 202080090766.7 May 4, 2023 (with English translation).
Examination Report for Canadian Patent Application No. 3,158,733 dated Aug. 16, 2023.
Office Action for Eurasian Patent Application No. 202291414 dated Aug. 2, 2023 (with English translation).
Office Action for Saudi Arabia Patent Application No. 522432668 dated Aug. 20, 2023 (with English translation).
Rinehart, ET743: Preclinical Antitumor Development of a Marine Derived Natural Product, Proc. Am. Assoc. Cancer Rsch., 86thAnnual Meeting, 390, Abstract No. 2322 (Mar. 18-22, 1995).
Janota, Continuous Flow Fast Atom Bombardment and Electrospray Ionization Mass Spectrometry in Natural Products Research, Ph.D. thesis, University of Illinois At Urbana-Champaign, UMI Microform No. 9543611 (1995).
NCT02448537, Protocol 15-083, Feb. 5, 2016.
Lopez-Guerrero, et al., "Trabectedin therapy as an emerging treatment strategy for recurrent platinum-sensitive ovarian cancer," Chin J Cancer 2015, 34, 1, 41-49, 2015.
Colby, et al., "High-dose carboplatin and regimen-related toxicity following autologous bone marrow transplant," Bone Marrow Transplantation 2002, 26, 467-472, 2002.
A. Soto, Lurbinectedin (PM01183) for the Treatment of Ewing Sarcoma and Neuroblastoma, Pediatric Oncology Subcommittee of the Oncology Drug Advisory Committee (ODAC), Jun. 21, 2017.
M.B. Lustberg, Management of Neutropenia in Cancer Patients, 10 Clinical Adv. Hematology Oncology 825, Dec. 2012.
Common Terminology Criteria for Adverse Events (CTCAE) Version 4.0, U.S. Dep't Health & Hum. Servs. (2009).
Physicians' Desk Reference 54th Edition 2000 ("PDR") Monograph for Velban® (vinblastine sulfate) 1647-49, 2000.
PDR Monograph for Oncovin® (vincristine sulfate) 1631-33 (PLSLURB00007314)—2000.
PDR Monograph for Purinethol® (mercaptopurine) 1255-57, 2000.
PDR Monograph for Cosemgen® (dactinomycin) 1766-67 (PLSLURB00007301), 2000.
PDR Monograph for Mutamycin® (mitomycin) 872-73 (PLSLURB00007309),2000.
PDR Monograph for Mithracin® (plicamycin) 697-98 (PLSLURB00007305), 2000.
Physicians' Desk Reference 53th Edition 1999, Monograph for Cytosar-U® (cytarabine) 2469-72 (PLSLURB00007295)—1999.
Izbicka, "In Vitro Antitumor Activity of the Novel Marine Agent, Ecteinascidin-743 (ET-743, NSC-648766)," 9 Ann. Oncology 981, 1998.
Ghielmini, "In Vitro Cytotoxicity of Ecteinascidin 743 (ET-743) Against Human Hemopoietic Progenitors," 9 Suppl. 2 Ann. Oncology 139, 1998.
Jin, "Ecteinascidin 743, a Transcription-Targeted Chemotherapeutic that Inhibits MDR1 Activation," 97 PNAS 12, 6775, 2000.
Scotto & Johnson, "Transcription of the Multidrug Resistance Gene MDR1: A Therapeutic Target," 1 Molecular Interventions 2, 117, 2001.
Garcia-Nieto, "Bending of DNA upon Binding of Ecteinascidin 743 and Phthalascidin 650," 122 J. Am. Chem. Soc. 30, 7172, 2000.
Newman, "The Influence of Natural Products upon Drug Discovery," 17 Nat. Prod. Rep. 215, 2000.
Cromie, "Potent Cancer Drugs Made—Sea Squirts Provide Recipe," Harvard University Gazette, May 4, 2000.
Seaman, "An Ecteinascidin-DNA Hydrogen Bond Network Plays a Major Role in Determining DNA Sequence Specificity," 10th NCI-EORTC Symposium, Abstract 530, 1998.
Zewail-Foote, "The Antitumor Agent Ecteinascidin 743 (Et 743): Characterization of its Covalent DNA Adducts," Ph.D. Dissertation, Univ. of Texas, 2000.
Njardarson, Top 200 Brand-Name Drugs by Retail Dollars in 2006.
Njardarson, Top 200 Generic Drugs by Retail Dollars in 2006.
McGrath, A Graphical Journey of Innovative Organic Architectures That Have Improved Our Lives, 87 J. CHEM. ED. 12, 1348-49, 1348, Dec. 2010.
Paul, "How to Improve R&D Productivity: The Pharmaceutical Industry's Grand Challenge," 9 Nature Rev. Drug Discovery 203, 2010.
DiMasi, "Innovation in the Pharmaceutical Industry: New Estimates of R&D Costs," 47 J. Health Econ. 20, 2016.
Martin, "Clinical Trial Cycle Times Continue to Increase Despite Industry Efforts," 16 Nature Rev. Drug Discovery 157, 2017.
PhRMA, "Biopharmaceutical Research & Development: The Process Behind New Medicines," 2015.
Mullin, "Drug R&D Costs Take Big Leap," 92 Chem. Eng. News 6, 2014.
U.S. Food & Drug Admin., Challenge and Opportunity on the Critical Path to New Medical Technologies, Mar. 2004.
Kola, "Can the Pharmaceutical Industry Reduce Attrition Rates?" 3 Nature Revs. Drug Discovery 711, Aug. 2004.
Kraljevic, "Accelerating Drug Discovery," 5(9) EMBO Reports 837, 2004.
Ramanjooloo, "Marine Sponge-Derived/Inspired Drugs and Their Applications in Drug Delivery Systems," 13(5) Future Medicinal Chemistry 487, 2021.
Guo, "Recent advances in the synthesis and activity of analogues of bistetrahydroisoquinoline alkaloids," 262 European Journal of Medicinal Chemistry 1, 2023.
Leal, "Molecular pharmacology and antitumor activity of Zalypsis in several human cancer cell lines," 78 Biochemical Pharmacology 162, 2009.
Newman, "Drugs and Drug Candidates from Marine Sources: An Assessment of the Current 'State of Play'," 82 Planta Med 775, 2016.
Petek, "PM00104 (Zalypsis): A Marine Derived Alkylating Agent," 19 Molecules 12328, 2014.
Hergert, "NCCN Guidelines Recommend Lurbinectedin as Second-Line Treatment in Relapsed SCLC," OncLive, Jul. 15, 2020.

(56) References Cited

OTHER PUBLICATIONS

Jazz Pharmaceuticals, Zepzelca® (lurbinectedin) and Atezolizumab (Tecentriq®) Combination Granted U.S. FDA Priority Review for First-Line Maintenance Treatment of Extensive-Stage Small Cell Lung Cancer (Jun. 10, 2025).
Yondelis label, Dec. 2025.
NCCN Clinical Practice Guidelines, Jul. 7, 2020.
Rinehart, "Didemnin and its biological properties," Peptides: Chemistry and Biology, 1988.
Mosmann, Rapid Colorimetric Assay for Cellular Growth and Survival: Application to Proliferation and Cytotoxicity Assays, Journal of Immunological Methods, 65 (1983) 55-63.
Taamma, Ecteinascidin-743 (ET-743) 24 Hour Continuous Intravenous Infusion (CI) Phase I Study in Solid Tumors (ST) Patients (pts), Proc. Am. Assoc. Cancer Rsch., 89th Annual Meeting, 323, Abstract No. 2207 (Mar. 28-Apr. 1, 1998).
Dwyer, "The use of concanavalin A to study the immunoregulation of human T cells," Clin, exp. Immunol, (1981), 46, 237-249.
Nakamura, "A Novel Method of Screening for Immunomodulating Substances, Establishment of an Assay System and its Application to Culture Broths of Microorganisms," 39 Journal of Antibiotics 1148-1154, 1986.
Tsuji, "Selective Immunosuppression of Prodigiosin 25-C and FK506 in the Murine Immune System," 43 Journal of Antibiotics 1293-1301, Oct. 1990.
Hadoux, J., Multimodal Treatment With Doxorubicin, Cisplatin, and Ifosfamide for the Treatment of Advanced or Metastatic Uterine LMS . . . , Int J Gynecol Cancer, 2015, vol. 25(2) pp. 296-302.
Bui-Nguyen, B., A phase IIb multicentre study comparing the efficacy of trabectedin to doxorubicin in patients with untreated STS: Trusts trial, Eur J Cancer, 2015, vol. 51(10) pp. 1312-1320.
Wagner, M.J., A retrospective chart review of drug treatment patterns and clinical outcomes among patients with metastatic STS . . . , BMC Cancer, 2015, 15:175.
Coleman, R.L., A phase III study of trabectedin plus pegylated liposomal doxorubicin (PLD) versus PLD for advanced-relapsed ovarian cancer., ASCO 51th Annual Meeting, 2015, Abs. No TPS5606.
Demetri, G.D., A randomized phase III study of trabectedin or dacarbazine for the treatment of patients with advanced LPS or LMS., ASCO 51th Annual Meeting, 2015, Abs Np 10503 (poster).
Demetri, G.D., A randomized phase III study of trabectedin or dacarbazine for the treatment of patients with advanced LPS or LMS., ASCO 51th Annual Meeting, 2015, Abs No. 10503 (abstract).
Wong, N.A.C.S., Abdominal monophasic synovial sarcoma is a morphological and immunohistochemical mimic of gastrointestinal stromal tumour, Histopathology, 2015, vol. 66(7) pp. 974-981.
Demetri, G., Efficacy and safety of trabectedin or dacarbazine for treatment of patients with advanced leiomyosarcoma or liposarcoma after prior chemotherapy, 18th ECCO—40th ESMO Congress, 2015, vol. 51(Supl 3) pp. 700 Abs. N 3436 (poster).
Demetri, G., Efficacy and safety of trabectedin or dacarbazine for treatment of patients with advanced leiomyosarcoma or liposarcoma after prior chemotherapy, 18th ECCO—40th ESMO Congress, 2015, vol. 51(Supl 3) pp. 700 Abs. N 3436 (abstract).
Patel, S., Final overall survival analysis of the randomized phase 3 study of trabectedin or dacarbazine for treatment of pts with advanced LMS or LPS, 18th ECCO—40th ESMO Congress, 2015, vol. 51(Supl 3) pp. 689 Abs. N 3403.
Von Mehren, M., Efficacy and safety of trabectedin or dacarbazine in an elderly patient subgroup (≥65 years) with advanced LMS or LPS . . . , 18th ECCO—40th ESMO Congress, 2015, vol. 51(Supl 3) pp. 194 Abs. No. 1321 (poster).
Von Mehren, M., Efficacy and safety of trabectedin or dacarbazine in an elderly patient subgroup (≥65 years) with advanced LMS or LPS . . . , 18th ECCO—40th ESMO Congress, 2015, vol. 51(Supl 3) pp. 194 Abs. No. 1321 (abstract).
Patel, S., A Randomized controlled Phase-3 study of travectedin or Dacarbazine for the treatment of pts with advanced LMS or LPS: Final OS analysis, CTOS 20th Annual Meeting, 2015, pp. 193-194 Abs No. 100.
Demetri, G.D., Trabectedin or Dacarbazine for treatmetn of pts with advanced LMS or LPS after prior chemotherapy: histology-specific subgroup analysis . . . , CTOS 20th Annual Meeting, 2015, pp. 220-221 Abs N 137.
von Mehren, M., Efficacy and safety of Trabectedin or Dacarbazine in advanced LMS or LPS after prior chemotherapy: Elderly patient Subgroup analysis, CTOS 20th Annual Meeting, 2015, pp. 215 Abs. N 128.
Tan, D.S., Chemotherapy for Patients with BRCA1 and BRCA2-Mutated Ovarian Cancer: Same or Different?, Am Soc Clin Oncol Educ Book, 2015, pp. 114-121.
Hollander, L., Atreus Trial: A Phase II Study on the Activity of Trabectedin in Pretreated Epithelioid or Biphasic/Sarcomatoid Malignant Pleural Mesothelioma, 17th National Congress of Medical Oncology, 2015, vol. 26(Supl 6) Abs No. H43.
Koh, A., The impact of reducing osteal macrophages and their efferocytotic function on bone turnover and bone mass, Annual Meeting of the ASBMR, 2015, vol. 30(Supl 1) Abs No. 1360.
Demetri, G.D., Efficacy and Safety of Trabectedin or Dacarbazine for Metastatic LPS or LMS After Failure of Conventional Chemotherapy: Phase III Trial., J Clin Oncol, 2016, vol. 34(8)pp. 786-793.
Lorusso, D., Prospective phase II trial of trabectedin in BRCA mutated and/or BRCAness phenotype recurrent ovarian cancer patients: MITO 15 trial, Ann Oncol, 2016, vol. 27(3) pp. 487-493.
Angarita, F.A., Trabectedin for inoperable or recurrent soft tissue sarcoma in adult patients: a retrospective cohort study., BMC Cancer, 2016, vol. 16(1) pp. 30.
Saponara, M., The safety and efficacy of Trabectedin for the treatment of liposarcoma or leiomyosarcoma, Expert Rev Anticancer Ther, 2016, vol. 16(5) pp. 473-484.
Uboldi, S., The WEE1 inhibitor AZD-1775 has synergic activity with trabectedin or lurbinectedin in ovarian cancer cells, AACR 107th Annual Meeting, 2016, Abs N 4821 (poster).
Uboldi, S., The WEE1 inhibitor AZD-1775 has synergic activity with trabectedin or lurbinectedin in ovarian cancer cells, AACR 107th Annual Meeting, 2016, Abs N 4821 (abstract).
Schoffski, P., Eribulin versus dacarbazine in previously treated patients with advanced LPS or LMS: randomized, multicentre, phase 3 trial, Lancet, 2016, vol. 387(10028) pp. 1629-1637.
Demetri, G.D., Patient-reported outcomes from randomized, phase-3 study of trabectedin (T) vs. dacarbazine (D) in advanced LMS or LPS, ASCO 52th Annual Meeting, 2016, Abs No. 11061.
Schuetze, S., Cardiac safety analysis of trabectedin (T) vs. dacarbazine (D) in pts with advanced LMS or LPS after prior anthracycline chemotherapy., ASCO 52th Annual Meeting, 2016, vol. 34 (15 Supl) Abs. No 11060.
Vincenzi, B., M1-polarized macrophages as predictor of poor response to trabectedin treatment in myxoid liposarcoma, ASCO 52th Annual Meeting, 2016, Abs. N e22537.
Zhu, X., The significance and therapeutic potential of PD-1 and its ligands in ovarian cancer: A systematic review., Gynecol Oncol, 2016, vol. 142(1) pp. 184-189.
Hensley, M.L., Efficacy and safety of tarbectedin or dacarbazine for the treatment of patients with uterine LMS after prior chemotherapy . . . , 47th Annual Meeting on Women's Cancer of the SGO, 2016, vol. 141(Supl 1) p. 3 Abs. No. 3.
Galletti, G., B cells and macrophages pursue a common path toward the development and progression of chronic lymphocytic leukemia, Leukemia, 2016, vol. 30(12) pp. 2293-2301.
Poveda, A., Os Analysis by treatments received after Trabectedin/PLD or PLD alone in patients with recurrent ovarian cancer: platinum vs non-platinum, IGCS 16th Biennial Meeting, 2016, vol. 26(Supl 3) p. 811 Abs. No IGCS-0711 (poster).
Poveda, A., Os Analysis by treatments received after Trabectedin/PLD or PLD alone in patients with recurrent ovarian cancer: platinum vs non-platinum, IGCS 16th Biennial Meeting, 2016, vol. 26(Supl 3) p. 811 Abs. No. IGCS-0711 (abstract).
Colombo, N., Randomized, non comparative, phase II trial on the efficacy and safety of bevacizumab and trabectedin with or without carboplatin in ROC pts, IGCS 16th Biennial Meeting, 2016.

(56) References Cited

OTHER PUBLICATIONS

Grosso, F., A phase II randomized—non comparative—study on the activity of trabectedin or gemcitabine + docetaxel in MLRUL . . . , CTOS 21st Annual Meeting, 2016, pp. 140-141 Abs No. 025 (poster).
Grosso, F., A phase II randomized—non comparative—study on the activity of trabectedin or gemcitabine + docetaxel in MLRUL . . . , CTOS 21st Annual Meeting, 2016, pp. 140-141 Abs No. 025 (abstract).
Chiodoni, C., Concomitant reprogramming of tumor cell differentiation and immune environment inhibits osteosarcoma metastatic potential, CTOS 21st Annual Meeting, 2016, p. 171 Abs N 015.
Tseng, W.W., A pilot feasibility study of immunotherapy with combination Trabectedin and Nivolumab in advanced soft tissue sarcoma, CTOS 21st Annual Meeting, 2016, pp. 373-374 Abs. N 128.
Fioramonti, M., M1 Macrophages as predictor of poor response to Trabectedin treatment in myxoid liposarcoma, CTOS 21st Annual Meeting, 2016, pp. 375-377 Abs. No. 130.
Stacchiotti, S., Patient-derived solitary fibrous tumour xenografts predict high sensitivity to doxorubicin/dacarbazine combination . . . , Eur J Cancer, 2017, vol. 76 pp. 84-92.
Gronchi, A., Trabectedin and radiotherapy in soft-tissue sarcoma (TRASTS) study: international, prospective, phase I/II trial . . . , ASCO 53rd Annual Meeting, 2017, vol. 35(Supl) Abs No. 11061 (poster).
Gronchi, A., Trabectedin and radiotherapy in soft-tissue sarcoma (TRASTS) study: international, prospective, phase I/II trial . . . , ASCO 53rd Annual Meeting, 2017, vol. 35(Supl) Abs No. 11061 (abstract).
Ratti, C., Trabectedin Overrides Osteosarcoma Differentiative Block and Reprograms the Tumor Immune Environment Enabling effective combo with ICIs, Clin Cancer Res, 2017, vol. 23(17) pp. 5149-5161.
Sinder, B.P., Bone Mass is Compromised by the Chemotherapeutic Trabectedin in Association with Effects on Osteoblasts and Macrophage Efferocytosis, J Bone Miner Res, 2017, vol. 32(10) pp. 2116-2127.
Hensley, M.L., Efficacy and safety of trabectedin or dacarbazine in patients with advanced uterine LMS after failure of chemotherapy: Subgroup analysis of SAR-3007, Gynecol Oncol, 2017, vol. 146(3) pp. 531-537.
Barone, A., FDA Approval Summary: Trabectedin for Unresectable or Metastatic LPS or LMS Following an Anthracycline-Containing Regimen., Clin Cancer Res, 2017, vol. 23(24) pp. 7448-7453.
Gordon, E.M., Cancer immunotherapy with sequential administration of trabectedin and nivolumab in advanced soft tissue sarcoma., 4th Immuno Therapy of Cancer Conference, 2017, vol. 5(Supl 1) pp. 17 Abs. N A42.
Poveda, A., Platinum or nonplatinum in recurrent ovarian cancer: that is the question, Future Oncol, 2017, vol. In press pp. 1-6.
Colombo, N., Randomized, non-comparative, phase II trial of bevacizumab and trabectedin with or without carboplatin in PPS ROC women, 20th International Meeting of the ESGO, 2017.
Chawla, S., Cancer Immunotherapy using Trabectedin and Nivolumab in Advanced Soft Tissue Sarcoma: A retrospective Analysis, CTOS 22nd Annual Meeting, 2017, Abs No. 020.
Schwoppe, C., Comparative PK of targeted tissue factor tTF-NGR intravenously applied alone or preceding trabectedin, AACR Annual Meeting 2025, vol. 85 (8 Supl 1) Abs No. 824, 2025.
Zielinski, R.J., Combining annamycin with azacitidine, gemcitabine, ifosfamide, or trabectedin to synergize anticancer effects . . . , AACR Annual Meeting 2025, 2025, vol. 85 (8 Supl 1) Abs N 1683.
Siontis, B.L., A Phase II Multi-Center Trial of Trabectedin in Combination with Olaparib in Patients with Advanced Unresectable or Metastatic Sarcoma, Clin Cancer Res, 2025, vol. In press pp. 1-26.
Agarwal, A.D., Phase 2 study using talimogene laherparepvec, nivolumab, and trabectedin for advanced LMS and liposaroma., ASCO 61st Annual Meeting, 2025, vol. 43 (Supl 16) Abs N e23560.
Povo-Retana, A., Correction: Trabectedin and Lurbinectedin Modulate Interplay between Cells in the Tumour Microenvironment . . . , Molecules, 2025, vol. 30(11) pp. 2472.
Giordano, G., cGAS-STING pathway is master regulator of OCT4 expression in persistent sarcoma cells and enhances cellular immunotherapy . . . , Cancer Immunol Immunother, 2025, vol. 74(10) pp. 312.
Mayasin, Y., Targeting TAMs & CAFs in melanoma: New approaches to tumor microenvironment therapy, Oncol Res, 2025, vol. 33(9) pp. 2221-2242.
D'Ambrosio, L., Trabectedin-olaparib combo or trabectedin in advanced STS after failure of anthracycline (TOMAS2): randomized phase 2 study, Ann Oncol, 2025, vol. In press pp. 1-35.
Lee, J., DCMiC: double-cylinder micro-chamber platform for high-throughput screening of microenvironmental resistance in Ewing sarcoma, Lab Chip, 2025, vol. In press pp. 1-16.
Ballon, J., Phase 2 Study Using Talimogene Laherparepvec, Nivolumab, and Trabectedin for Advanced LMS and LPS, 28th Annual Meeting ASGCT, 2025, vol. 33(4 Supl 1) Abs No. 1704.
Berdel, W.E., Trabectedin plus CD13-targeted tissue factor tTF-NGR against advanced relapsed STS: Translational data and safety, ESMO Congress, Berlin, 2025, vol. 36(Supl 2) pp. S1445 Abs No. 2711P.
Li, Y., Interaction Between Tumor-Associated Macrophages and T Cells Reshapes Paradigm of Cancer Immunotherapy, Immunology, 2026, vol. In press pp. 1-22.
Yondelis label 2015—Oct. 23, 2015.
Yondelis approval letter—Oct. 23, 2015.
Yondelis Summary review—Oct. 23, 2015.
Yondelis approval package—Oct. 23, 2015.
Yondelis printed labeling—Oct. 23, 2015.
Yondelis Officer/Employee list—Oct. 23, 2015.
Yondelis Office director memo—Oct. 23, 2015.
Yondelis Cross discipline team leader review—Oct. 23, 2015.
Yondelis medical review(s)—Oct. 23, 2015.
Yondelis Chemistry review(s)—Oct. 23, 2015.
Yondelis Pharmacology review(s)—Oct. 23, 2015.
Yondelis Statistical review(s)—Oct. 23, 2015.
Yondelis Clinical pharmacology and biopharmaceutics review(s)—Oct. 23, 2015.
Yondelis assessment and risk mitigation review(s)—Oct. 23, 2015.
Yondelis proprietary name review(s)—Oct. 23, 2015.
Yondelis Other review(s)—Oct. 23, 2015.
Yondelis Administrative and Correspondence documents—Oct. 23, 2015.
Yondelis approval letter—Dec. 23, 2025.
Yondelis label 2025—Dec. 23, 2025.
Yondelis approval letter 2020—Jun. 3, 2020.
Yondelis label—Jun. 3, 2020.
Yondelis approval letter 2018—Dec. 28, 2018.
Yondelis label 2018—Dec. 28, 2018.
Yondelis approval letter 2018—Jun. 29, 2018.
Yondelis label 2018—Jun. 29, 2018.
Yondelis approval letter—May 18, 2017.
Yondelis label—May 18, 2017.
Yondelis approval letter 2016—Jul. 20, 2016.
Yondelis label 2016—Jul. 20, 2016.
History of Changes for Study: NCT04358237—Apr. 20, 2020.
Record History: NCT04358237—Apr. 20, 2020.
History of Changes for Study: NCT05091567—Oct. 12, 2021.
Record History: NCT05091567—Oct. 12, 2021.
PharmaMar presents new results for lurbinectedin at ASCO Genitourinary Cancers symposium, published Jan. 29, 2024.
PharmaMar receives US$10 million milestone payment from Janssen, published Nov. 6, 2023.
Q3 results 2023, published Oct. 26, 2023.
Reagan Shaw Dose translation from animal to human studies revisited (FASEBJ vol. 22.pp. 659-661, published 2007).
REEC 2013-000548-25 Clinical Trial Information, Published Pre 2019.
REEC 2014-003773-42 Clinical Trial Information, Published Pre 2019.

(56) References Cited

OTHER PUBLICATIONS

REEC 2014-005251-39 Clinical Trial Information, Published Pre 2019.
REEC 2015-000206-18 Clinical Trial Information, Published Pre 2019.
REEC 2015-001141-80 Clinical Trial Information, Published Pre 2019.
REEC 2015-001641-89 Clinical Trial Information, Published Pre 2019.
REEC 2015-003602-16 Clinical Trial Information, Published Pre 2019.
Reguart et al. A cross-sectional analysis of treatment patterns in small-cell lung cancer in five European countries. Future oncology, published Nov. 30, 2023.
Saida et al. Extensive-Stage Small-Cell Lung Cancer: Current Landscape and Future Prospects. OncoTargets and Therapy 2023:16 657-671, published Aug. 2, 2023.
Sands and Subramanian Treating patients with platinum-sensitive extensive-stage small-cell lung cancer in a real-world setting. Front. Oncol. vol. 13, published Dec. 22, 2023.
Supplement to: Trigo J, Subbiah V, Besse B, et al. Lurbinectedin as second-line treatment for patients with small-cell lung cancer: a single-arm, open-label, phase 2 basket trial. Lancet Oncol 2020; published online Mar. 27. http://dx.doi.org/10.1016/S1470-2045(20)30068-1.
Tambaro et al. An escalating dose finding study of liposoma; doxorubicin and vinorelbine for the treatment of refractory or resistant epithelial ovarian cancer. Ann Oncol. Sep. 2003;14(9):1406-11, published Sep. 1, 2003.
Tina Kristensen, "Anti-Vascular Endothelial Growth Factor Therapy in Breast Cancer", International Journal of Molecular Sciences, published Dec. 11, 2014.
Tummala et al. Preclinical Synergistic Combination Therapy of Lurbinectedin with Irinotecan and 5-Fluorouracil in Pancreatic Cancer. Current Oncology 30(11):9611-9626, published Oct. 31, 2023.
Usach et al. Subcutaneous Injection of Drugs: Literature Review of Factors Influencing Pain Sensation at the Injection SiteAdv Ther. 2019; 36(11): 2986-2996, published Oct. 5, 2019.
Wasifuddina et al. Review of real-world experience with lurbinectedin in relapsed/refractory small cell lung cancer. Journal of Chemotherapy, published Jan. 17, 2024.
Lowe E., and Balis, F, "Dose-Effect and Concentration-Effect Analysis", Chapter 18, p. 289-300, 296, Principles of Clinical Pharmacology, second edition, 2007.
Plana et al., Independent Drug Action in Combination Therapy: Implications for Precision Oncology, Cancer Discov., 2022;12:606-24 at p. 610.
Mokhtari et al., Combination therapy in combating cancer, ONCOTARGET, 2017, vol. 8, (No. 23), pp. 38022-38043.
Le Tourneau, C., Lee, J. J., & Siu, L. L. (2009). Dose escalation methods in phase I cancer clinical trials. JNCI: Journal of the National Cancer Institute, 101(10), 708-720.
Office Action for Chinese Patent Application No. 202080061468.5 dated Dec. 20, 2023.
Office Action for Israel Patent Application No. 182776 dated Aug. 8, 2023.
Office Action for Canadian Patent Application No. 3,148,690 mailed Oct. 13, 2023.
Office Action for U.S. Appl. No. 18/448,144 mailed Nov. 13, 2023.
Office Action for U.S. Appl. No. 18/448,124 mailed Nov. 28, 2023.
Office Action for U.S. Appl. No. 18/456,385 mailed Nov. 1, 2023.
Office Action for U.S. Appl. No. 18/456,379 mailed Oct. 17, 2023.
Office Action for Chile Patent Application No. 2022-00522 mailed Nov. 3, 2023.
Office Action for U.S. Appl. No. 18/448,097 mailed Dec. 18, 2023.
Office Action for U.S. Appl. No. 18/448,122 mailed Nov. 15, 2023.
Office Action for U.S. Appl. No. 18/095,877 mailed Dec. 28, 2023.
Office Action for Saudi Arabian Application No. 522432668 mailed Oct. 8, 2023.
Heilig, Ch.E., Top-Art / PMO-1603: Randomized Phase 2 Study of Trabectedin/Olaparib in subjects with DNA Repair Deficiencies, ESMO Congress, Barcelona, 2019, vol. 30 (Supl 5) pp. v795-v796 Abs N 1979TiP (abstract).
Aldinucci, D., Formation of the Immunosuppressive Microenvironment of Classic Hodgkin Lymphoma and Therapeutic Approaches to Counter It, Int J Mol Sci, 2019, vol. 20(10) pp. E2416.
Martin-Broto, J., Trabectedin with concurrent low-dose of radiation therapy for metastatic STS (TRASTS): Multicenter phase II trial . . . , CTOS 24th Annual Meeting, 2019, Abs N 3255113 (poster).
Martin-Broto, J., Trabectedin with concurrent low-dose of radiation therapy for metastatic STS (TRASTS): Multicenter phase II trial . . . , CTOS 24th Annual Meeting, 2019, Abs N 3255113 (abstract).
Gordon, E.M., The SAINT: Results of a Phase 1/2 study of safety/efficacy using ipilimumab, nivolumab and trabectedin in advanced STS, CTOS 24th Annual Meeting, 2019, Abs N 3255343.
Takeyama, M., The clinical results of trabectedin or eribulin chemotherapy in advanced soft tissue sarcoma, CTOS 24th Annual Meeting, 2019, Abs N 3255227.
Li, X., Harnessing tumor-associated macrophages as aids for cancer immunotherapy, Mol Cancer, 2019, vol. 18(1) arn 177.
Gronchi, A., Trabectedin and radiotherapy in STS (TRASTS) study: phase II trial in localized myxoid liposarcoma—collaborative Spanish, Italian, French groups study., ASCO 56th Annual Meeting, 2020, vol. 38 (15 Supl) Abs No. 11514 (poster).
Gronchi, A., Trabectedin and radiotherapy in STS (TRASTS) study: phase II trial in localized myxoid liposarcoma—collaborative Spanish, Italian, French groups study., ASCO 56th Annual Meeting, 2020, vol. 38 (15 Supl) Abs No. 11514 (abstract).
Moura, D.S., Immune-checkpoint genes as predictive biomarkers of trabectedin in advanced soft tissue sarcoma (STS): GEIS translational study., ASCO 56th Annual Meeting, 2020, vol. 38 (15 Supl) Abs N 11546 (poster).
Moura, D.S., Immune-checkpoint genes as predictive biomarkers of trabectedin in advanced soft tissue sarcoma (STS): GEIS translational study., ASCO 56th Annual Meeting, 2020, vol. 38 (15 Supl) Abs N 11546 (abstract).
Pink, D., Which pts with pre-treated locally advanced or metastatic sarcoma benefit most from trabectedin: GISG-14—ReTraSarc Results., ASCO 56th Annual Meeting, 2020, vol. 38 (15 Supl) Abs N 11554.
Aquila, G., Trabectedin and Lurbinectedin Extend Survival of Mice Bearing C26 Colon Adenocarcinoma . . . , Cancers, 2020, vol. 12(8) 2312.
Muller et al., A non-randomized, open-label phase II trial evaluating feasiability of combined treatment with trabectedin and nivolumab in advanced STS . . . , ESMO Virtual Congress 2020, 2020, vol. 31(Suppl 4) pp. S991 Abs N 1669TiP (poster).
Muller et al., A non-randomized, open-label phase II trial evaluating feasiability of combined treatment with trabectedin and nivolumab in advanced STS . . . , ESMO Virtual Congress 2020, 2020, vol. 31(Suppl 4) pp. S991 Abs N 1669TiP (abstract).
Toulmonde, M., Tramune, a phase Ib study combining trabectedin and durvalumab, results of expansion cohort in pts with pretreated STS, ESMO Virtual Congress 2020, vol. 31(Suppl 4) pp. 1199 Abs N LBA67, 2020 (poster).
Toulmonde, M., Tramune, a phase Ib study combining trabectedin and durvalumab, results of expansion cohort in pts with pretreated STS, ESMO Virtual Congress 2020, vol. 31(Suppl 4) pp. 1199 Abs N LBA67 (abstract), 2020.
Bailly, C., Combined cytotoxic chemotherapy and immunotherapy of cancer: modern times, NAR Cancer, 2020, vol. 2 (1) pp. 1-20.
Corbellari, R., The immunocytokine L19-TNF eradicates sarcomas in combination with chemotherapy agents or with immune checkpoint inhibitors, Anticancer Drugs, 2020, vol. 31(8) pp. 799-805.
Zhang, S.Y., Tumor-associated macrophages: A promising target for a cancer immunotherapeutic strategy, Pharmacol Res, 2020, arn 105111.
Povo-Retana, A.., Specific Effects of Trabectedin and Lurbinectedin on Human Macrophage Function and Fate—Novel Insights, Cancers, 2020, vol. 12(10) pp. 3060.

(56) References Cited

OTHER PUBLICATIONS

Moura, D.S., Immune-checkpoint genes as predictive biomarkers of trabectedin in advanced STS: GEIS translational study., CTOS 2020 Annual Meeting, 2020 (poster).
Moura, D.S., Immune-checkpoint genes as predictive biomarkers of trabectedin in advanced STS: GEIS translational study., CTOS 2020 Annual Meeting, 2020 (abstract).
Pink, D., The NiTraSarc Trial—combined treatment with trabectedin and nivolumab in pts with metastatic STS: Interim Safety Analysis, CTOS 2020 Annual Meeting, 2020 (poster).
Pink, D., The NiTraSarc Trial—combined treatment with trabectedin and nivolumab in pts with metastatic STS: Interim Safety Analysis, CTOS 2020 Annual Meeting, 2020 (abstract).
Chawla, S.P., TNT: A phase 2 study using Talimogene Laherparepvec, Nivolumab and Trabectedin for advanced STS, chordoma . . . , CTOS 2020 Annual Meeting, 2020.
Gordon, E.M., Saint: An expanded phase 2 study using ipilimumab, Nivolumab, and Trabectedin as first-line treatment of advanced STS, CTOS 2020 Annual Meeting, 2020.
Wagner, M., A phase I/II trial combining avelumab and trabectedin for advanced liposarcoma and leiomyosarcoma, 35th Annual Meeting SITC 2020, 2020, vol. 8 (Supl 3) p. A476 Abs N 796.
Chawla, S.P., The TNT protocol: A phase II study using talimogene laherparepvec, nivolumab and trabectedin for advanced sarcoma . . . , ASCO 56th Annual Meeting, 2020, vol. 38 (15 Supl) Abs N TPS11572.
Keisling, S., Effects of acoustic immune priming with LOFU and trabectedin on a murine model of osteosarcoma, 35th Annual Meeting SITC 2020, 2020, vol. 8 (Supl 3) p. A348-349 Abs N 581.
Gundle, K.R., Multiplexed Evaluation of Microdosed Antineoplastic Agents in Situ in the TME of Patients with Soft Tissue Sarcoma, Clin Cancer Res, 2020, vol. 26(15) pp. 3958-3968.
Casagrande, N., Trabectedin overcomes doxorubicin-resistance and counteracts tumor-immunosuppressive reprogramming of monocytes in HL, Cancer Lett, 2021, vol. 500 pp. 182-193.
Jones, R.L., Cardiac safety of trabectedin monotherapy or in combination with PLD in patients with sarcomas and ovarian cancer, Cancer Med, 2021, vol. 10(11) pp. 3565-3574.
Gordon, E.M., A phase 2 study using ipilimumab, nivolumab, and trabectedin for previously untreated metastatic soft tissue sarcoma., ASCO 57th Annual Meeting, 2021, vol. 39 (15 Supl) pp. 588s Abs No. 11562.
Gordon, E.M., A phase 2 study using ipilimumab, nivolumab, and trabectedin for previously untreated metastatic soft tissue sarcoma., ASCO 57th Annual Meeting, 2021, vol. 39 (15 Supl) pp. 588s Abs No. 11562 (Poster).
Chawla, N.S., A phase 2 study of talimogene laherparepvec, nivolumab, and trabectedin (TNT) in advanced sarcoma., ASCO 57th Annual Meeting, 2021, vol. 39 (15 Supl) pp. 589s Abs N 11567 (abstract).
Pink, D., Efficacy and safety of nivolumab and trabectedin in pretreated patients with advanced STS: GISG-15 (NitraSarc) results, ASCO 57th Annual Meeting, 2021, vol. 39 (15 Supl) pp. 584s Abs No. 11545 (poster).
Pink, D., Efficacy and safety of nivolumab and trabectedin in pretreated patients with advanced STS: GISG-15 (NitraSarc) results, ASCO 57th Annual Meeting, 2021, vol. 39 (15 Supl) pp. 584s Abs No. 11545 (abstract).
Reichardt, P., Uncertainties that threaten the benefit/risk balance in early treatment lines for advanced soft tissue sarcoma, Future Oncol, 2021, vol. 17(21 Supl) pp. 7-10.
Gronchi, A., Surgery in soft tissue sarcoma: The thin line between a surgical or more conservative approach, Future Oncol, 2021, vol. 17(21 Supl) pp. 3-6.
Lambden, J.P., Metastatic Myxofibrosarcoma with Durable Response to Temozolomide Followed by Atezolizumab: A Case Report, Oncologist, 2021, vol. 26(7) pp. 549-553.
Zhao, Y.D., Nanomedicine enables spatiotemporally regulating macrophage-based cancer immunotherapy, Biomaterials, 2021, vol. 268 arn 120552.
Ahmad, R.S., Immune Cell Modulation of the Extracellular Matrix Contributes to the Pathogenesis of Pancreatic Cancer, Biomolecules, 2021, vol. 11(6) arn 901.
Toscaa, E.M., Modeling approaches for reducing safety-related attrition in drug discovery and development., Expert Opin Drug Discov, 2021, pp. 1-26.
Ozaniak, A., Novel Insights into the Immunotherapy of Soft Tissue Sarcomas: Do We Need a Change of Perspective?, Biomedicines, 2021, vol. 9(8) 935.
Dolmatova, L.S., Tumor-Associated Macrophages as Potential Targets for Anti-Cancer Activity of Marine-Derived Compounds, Curr Pharm Des, 2021, vol. 27(28) pp. 3139-3160.
Pautier, P., LMS-04 study: randomized phase III comparing doxorubicin alone vs doxorubicin with trabectedin in metastatic/unresectable LMS, ESMO Virtual Congress 2021, 2021, vol. 32(Suppl 5) pp. S1335-S1336 Abs N LBA59.
Belgiovine, C., Inhibition of Tumor-Associated Macrophages by trabectedin improves anti-tumor adaptive immunity in response to anti-PD-1 therapy, Eur J Immunol, 2021, vol. 51(11) pp. 2677-2686.
Leblond, M.M., Tumor-Associated Macrophages in Bladder Cancer: Biological Role, Response and Perspectives for Immunotherapy, Cancers, 2021, vol. 13(18) 4712.
Tang, F., Targeted and immuno-based therapies in sarcoma: mechanisms and advances in clinical trials, Biochim Biophys Acta cancer, 2021, vol. 1876(2) Arn 188606.
National Center for Biotechnology Information, PubChem Compound Summary for CID 5284373, Cyclosporin A, Jul. 31, 2025.
Herman, "Effect of cyclosporin A on DNA repair and cancer incidence in kidney transplant recipients," 137 Journal of Laboratory and Clinical Medicine 14-20, 2001.
Hojo, "Cyclosporine induces cancer progression by a cell-autonomous mechanism," 397 Nature 530-534, 1999.
Hakala & Rustum, "The Potential Value of in Vitro Screening," XVI Methods in Cancer Research 247-284, 1979.
Schabel, "Testing Therapeutic Hypotheses in Mice and Man: Observations on the Therapeutic Activity Against Solid Tumors of Mice Treated with Anticancer Drugs that have Demonstrated or Potential Clinical Utility for Treatment of Advanced Solid Tumors of Man," XVII Methods in Cancer Research 4-50, 1979.
Manzanares, "Advances in the Chemistry and Pharmacology of Ecteinascidins, A Promising New Class of Anticancer Agents," Current Medicinal Chemistry—Anticancer Agents 257-276, 2001.
Zewail-Foote, Differential Rates of Reversibility of Ecteinascidin 743-DNA Covalent Adducts from Different Sequences Lead to Migration to Favored Bonding Sites, J. Am. Chem. Soc. 2001, 123, 6485-6495.
Williams, "Drug Metabolism," 4 Principles of Medicinal Chemistry 83-140, 1995.
Wilkinson, "The Dynamics of Drug Absorption, Distribution, and Elimination," 10 The Pharmacological Basis of Therapeutics 3-29, 2001.
Low, "Metabolic Changes of Drugs and Related Organic Compounds," 10 Textbook of Organic Medicinal and Pharmaceutical Chemistry 43-122, 1998.
Meunier, "Mechanism of Oxidation Reactions Catalyzed by Cytochrome P450 Enzymes," 104 Chemical Reviews 3947-3980, 2004.
Silverman, "Drug Metabolism," The Organic Chemistry of Drug Design and Drug Action 405-495, 2004.
Sanchez, "Challenges of Cancer Drug Design: A Drug Metabolism Perspective," Current Cancer Drug Targets 1-32, 2001.
Sanwald, Drug Metabolism and Disposition: the biological fate of chemicals, vol. 24, No. 5, May 1996.
Gillam, "Oxidation of Indole by Cytochrome P450 Enzymes," 39 Biochemistry 13817-13824, 2000.
Shen, "The reactions of indoles in aqueous solution initiated by one-electron oxidation," Journal of the Chemical Society, Perkin Transactions 2 597-603, 1990.
Goyal, "Oxidation chemistry and biochemistry of indole and effect of its oxidation product in albino mice," 45 Bioelectrochemistry and Bioenergetics 47-53, 1998.
Burd, "Oxidation of Indole and Indole Derivatives Catalyzed by Nonheme Chloroperoxidases," 37 Applied Biochemistry and Microbiology 248-250, 2000.

(56) References Cited

OTHER PUBLICATIONS

Kawakami, "Synthesis and Evaluation of Novel Rhodacyanine Dyes That Exhibit Antitumor Activity," 40 J. Med. Chem. 3151-3160, 1997.
Provencher, "Characterization of Four Novel Epithelial Ovarian Cancer Cell Lines," 36 In Vitro Cell. Dev. Biol. 357-361, 2000.
Modica-Napolitano, "Selective Damage to Carcinoma Mitochondria by the Rhodacyanine MKT-077," 56 Cancer Research 544-550, Feb. 1, 1996.
Cinar, "Androgen Receptor Mediates the Reduced Tumor Growth, Enhanced Androgen Responsiveness, and Selected Target Gene Transactivation in a Human Prostate Cancer Cell Line," 61 Cancer Research 7310-7317, 2001.
Meunier, Peroxidase-catalyzed O-demethylation Reactions, The Journal of Biological Chemistry, vol. 260, No. 19, 1985.
Sato, "Oxidation of 1,2,4,5-Tetramethoxybenzene to a Cation Radical by Cytochrome P450," 122 Journal of the American Chemical Society 8099-8100 (2000).
Simon & Schindler, "Cell biological mechanisms of multidrug resistance in tumors," 91 Proceedings of the National Academy of Sciences of the United States of America 3497-3504, Apr. 1994.
Ford & Hait, "Pharmacology of Drugs That Alter Multidrug Resistance in Cancer," 42 Pharmacological Reviews 155-199 (1990).
Kartner & Ling, "Multidrug Resistance in Cancer," Scientific American 44-51 (1989).
Shtil, "Signal Transduction Pathways and Transcriptional Mechanisms as Targets for Prevention of Emergence of Multidrug Resistance in Human Cancer Cells," 2 Current Drug Targets 57-77 (2001).
Li, "Sensitivity of Soft Tissue Sarcoma Cell Lines to Chemotherapeutic Agents: Identification of Ecteinascidin-743 as a Potent Cytotoxic Agent," 7 Clinical Cancer Research 2908-2911, Sep. 2001.
"Chapter 1: Cell Membranes, Epithelial Barriers, and Drug Absorption," from Physiological Pharmaceutics: Barriers to Drug Absorption 1, 12-16 (2d Edition, Washington et al. eds. 2001).
Byfield & Calabro-Jones, "Carrier-Dependent and Carrier-Independent Transport of Anti-Cancer Alkylating Agents," 294(5838) Nature 281, 281 (1981).
Vistica, "Cytotoxicity as an Indicator for Transport Mechanism: Evidence that Murine Bone Marrow Progenitor Cells Lack a High-Affinity Leucine Carrier that Transports Melphalan in Murine L1210 Leukemia Cells," 56(3) Blood 427, Sep. 1980.
Laznicek, "The Effect of Lipophilicity on the Protein Binding and Blood Cell Uptake of Some Acidic Drugs," 13 J. Pharmaceutical & Biomedical Analysis 823 (1995).
Wang, "Molecular Recognition of DNA Minor Groove Binding Drugs," Crystallographic and Modeling Methods in Molecular Design (1990).
Reedijk, "The Relevance of Hydrogen Bonding in the Mechanism of Action of Platinum Antitumor Compounds," 198-200 Inorganica Chimica Acta 873-881 (1992).
Neidle, "Crystallographic Insights into DNA Minor Groove Recognition by Drugs," Biopolymers (1997).
Traxler, "Use of a Pharmacophore Model for the Design of EGFR Tyrosine Kinase Inhibitors: Isoflavones and 3-Phenyl-4(1H)-quinolones," 42 J. Med. Chem. 1018 (1999).
Widler, "7-Alkyl- and 7-Cycloalkyl-5-aryl-pyrrolo[2,3-d]pyrimidines-Potent Inhibitors of the Tyrosine Kinase c-Src," 11 Bioorganic & Med. Chem. Lett. 849 (2001).
Witherington, "6-Aryl-pyrazolo[3,4-b]pyridines: Potent Inhibitors of Glycogen Synthase Kinase-3 (GSK-3)," 13 Bioorganic & Med. Chem. Lett. 3055-3057 (2003).
Liechti, "Salicylanilides as Inhibitors of the Protein Tyrosine Kinase Epidermal Growth Factor," 39 Eur. J. Med. Chem. 11 (2004).
McCauley, "NR2B-Selective N-Methyl-D-aspartate Antagonists: Synthesis and Evaluation of 5-Substituted Benzamidazoles," 47 J. Med. Chem. 2089 (2004).
Woll, "Phase II Trial of Ralitrexed ('Toludex') in Advanced Small-Cell Lung Cancer," 76(2) Brit. J. Cancer 264, 264 (1997).
ESMO Minimum Clinical Recommendations for Diagnosis, Treatment and Follow-Up of Small-Cell Lung Cancer (SCLC), 12 Annals of Oncology 1051, (2001).
SmithKline Beecham, "Hycamtin® (topotecan hydrochloride) for Injection," FDA Approved Labeling (1998).
Dr. Pellini on the Challenges of Using Topotecan as a Comparator Arm in Recurrent ES-SCLC, Onclive (May 19, 2021), https://www.onclive.com/view/dr-pellini-on-the-challenges-of-using-topotecan-as-a-comparatorarm-in-recurrent-es-sclc—May 19, 2021.
Chute, "Twenty Years of Phase IIII Trials for Patients with Extensive-Stage Small Cell Lung Cancer," 17(6) J. Clin. Oncology 1794, 1799 (1999).
FDA Approves Genentech's Tecentriq in Combination With Chemotherapy for the Initial Treatment of Adults With Extensive-Stage Small Cell Lung Cancer, (Mar. 18, 2019).
Mansfield, "First-Line Atezolizumab Plus Chemotherapy in Extensive-Stage Small Cell-Lung Cancer," 379 N. Eng. J. Med. 2220, Dec. 6, 2018.
Schenk, "A Randomized Double-Blind Phase II Study of the Seneca Valley Virus (NTX-010) vs Placebo for Patients with Extensive Stage SCLC (ESCLC) Who Were Stable or Responding after at Least 4 Cycles of Platinum-Based Chemotherapy: NCCTG (Alliance) N0923 Study," 15(1) J. Thoracic Oncology 110, 111, Jan. 2020.
Jazz Pharmaceuticals Announces Zepzelca® (lurbinectedin) and Atezolizumab (Tecentriq®) Combination Significantly Improves Survival as First-Line Maintenance Therapy for Extensive-Stage Small Cell Lung Cancer, (Jun. 2, 2025).
Brunetto et al., Modest Reductions in Dose Intensity and Drug-Induced Neutropenia have No Major Impact on Survival of Patients with Non-small Cell Lung Cancer Treated with Platinum-Doublet Chemotherapy: J. Thoracic Oncology, 5, 1397, Sep. 2010.
"Camptosar Prescribing Information", rev. Feb. 2019.
"Doxil Prescribing Information", rev. Aug. 2019.
"The Clinical Trial of Lurbinectedin (PM01183) in Selected Advanced Solid Tumors" NCT02454972, Feb. 16, 2018.
"FDA Briefing Presentation, 'Lurbinectedin (PM01183) for the Treatment of Ewing Sarcoma and Neuroblastoma,' Pediatric Oncology Subcommittee . . . ", Jun. 21, 2017, 1-27.
"Gemzar Prescribing Information", rev. May 2019.
Ixempra NDA, Oct. 16, 2007.
Ixempra supplemental approval letter, Oct. 18, 2011.
Owonikoko et al., A Systematic Analysis of Efficacy of Second Line Chemotherapy in Sensitive and Refractory Small Cell Lung Cancer. J. Thoracic Oncology. 7, 866, May 2012.
"Taxol® Prescribing Information", rev. Mar. 2015.
"Taxotere Prescribing Information", rev. Jun. 2019.
"Topotecan Prescribing Information", rev. Feb. 2014.
Devita VT Jr., Hellman S, Rosenberg SA., Cancer: Principles & Practice of Oncology, Lippincott Williams & Wilkins eds., 5th ed., 17, 336, Mar. 19, 1997.
Boyer & Tannock., "The Basic Science of Oncology", lan F. Tannock & Richard P. Hill eds., 3d ed., 15, 350, 1998.
Erlichman & Moore., "The Basic Science of Oncology", lan F. Tannock & Richard P. Hill eds., 3d ed., 16, 370, 1998.
Akazawa et al., Chemotherapy Sensitivity for Recurrent Small-Cell Lung Cancer Based on Chemotherapy-Free Interval and Treatment Regimens, J. Thoracic Oncology, 19, S668, Oct. 2024.
Zepsyre proprietary name review, May 20, 2020.
"FDA Briefing Transcript, Pediatric Subcommittee of the Oncologic Drugs Advisory Committee Meeting", Topic 2, Jun. 21, 2017, 1-86.
Monaca et al. Antibody-Drug Conjugates in Small-Cell Lung Cancer: DLL3, B7-H3, TROP2 and Beyond. Journal of Thoracic Oncology, 2026.
Feng et al. Lambert-Eaton Myasthenic Syndrome During Immunotherapy in Extensive-Stage Small-Cell Lung Cancer: A Case Report. Br. J. Hosp. Med. (Lond) 2026, 87(4), 53025.
Alexander et al. Lurbinectedin in small cell lung cancer: real-world experience of a multicentre national early access programme. Internal Medicine Journal (2024) 1-10, published Feb. 18, 2024.
Caliman et al. Challenges in the treatment of small cell lung cancer in the era of immunotherapy and molecular classification. Lung Cancer vol. 175, P88-100, published Nov. 22, 2022.

(56) References Cited

OTHER PUBLICATIONS

Chemotherapy-induced thrombocytopenia: Amgen. Published Jan. 1, 2010.
Cheng et al. A pivotal bridging study of lurbinectedin as second-line therapy in Chinese patients with small cell lung cancer. Scientific reports (2024) 14:3598, published Feb. 13, 2024.
Desai et al . Real-World Outcomes with Lurbinectedin in second-line setting and beyond for Extensive Stage Small Cell Lung Cancer S1525-7304(23)00183-3, published Sep. 16, 2023.
EUCTR 2010-024292-30 Clinical Trial Information, Published Mar. 10, 2011.
EUCTR 2011-002172-16 Clinical Trial Information, Published Aug. 9, 2011.
EUCTR 2011-006108-11 Clinical Trial Information, Published Apr. 3, 2012.
EUCTR 2013-000548-25 Clinical Trial Information, Published Apr. 9, 2013.
EUCTR 2014-003773-42 Clinical Trial Information, Published Jul. 29, 2015.
EUCTR 2014-005251-39 Clinical Trial Information, Published Jul. 17, 2015.
EUCTR 2015-000206-18 Clinical Trial Information, Published Jul. 10, 2015.
EUCTR 2015-001141-80 Clinical Trial Information, Published Aug. 13, 2015.
EUCTR 2015-001641-89 Clinical Trial Information, Published Oct. 21, 2016.
Gomez-Randulfe. Recent advances and future strategies in first-line treatment of ES-SCLC. EJC—vol. 200, 113581, published Jan. 28, 2024.
Gutiérrez et al. Actionable Driver Events in Small Cell Lung Cancer. Lung Cancer. Int. J. Mol. Sci. 2024, 25, 105, published Dec. 20, 2023.
Jiminez et al Pharmacology of marine drugs: Pattern-, purpose- and prudence-driven innovations. Annual Reports in Medicinal Chemistry vol. 61, 2023, pp. 101-131, Nov. 19, 2023.
Judith A. Seidel, "Anti-PD-1 and Anti-CTLA-4 Therapies in Cancer: Mechanisms of Action, Efficacy, and Limitations", National Library of .Medicine, Mar. 28, 2018.
Kasper and Gerhard Winter, Recent advances and further challenges in lyophilization. Eur J Pharm Biopharm. Oct. 2013;85(2):162-9, published Oct. 1, 2013.
Khoury et al. A Comprehensive Review on the Role of Lurbinectedin in Soft Tissue Sarcomas. Curr Treat Options Oncol . Feb. 2024;25(2):176-190, published Feb. 7, 2024.
Matera and Chiang. What Is New in Small Cell Lung Cancer Hematol Oncol Clin N Am 37 (2023) 595-607, published Jun. 1, 2023.
NCT00877474 Clinical Trial Information, Published Apr. 6, 2009.
NCT01314599 Clinical Trial Information, Published Mar. 11, 2011.
NCT01405391 Clinical Trial Information, Published Jul. 27, 2011.
NCT01525589 Clinical Trial Information, Published Feb. 2, 2012.
NCT01831089 Clinical Trial Information, Published Apr. 9, 2013.
NCT01951157 Clinical Trial Information, Published Sep. 23, 2013.
NCT01970540 Clinical Trial Information, Published Oct. 22, 2013.
NCT01970553 Clinical Trial Information, Published Oct. 22, 2013.
NCT01980667 Clinical Trial Information, Published Nov. 4, 2013.
NCT02210364 Clinical Trial Information, Published Aug. 5, 2014.
NCT02421588 Clinical Trial Information, Published Apr. 15, 2015.
NCT02448537 Clinical Trial Information, Published May 15, 2015.
NCT02451007 Clinical Trial Information, Published May 18, 2015.
NCT02454972 Clinical Trial Information, Published May 21, 2015.
NCT02566993 Clinical Trial Information, Published Oct. 1, 2015.
NCT02611024 Clinical Trial Information, Published Nov. 18, 2015.
NCT02684318 Clinical Trial Information, Published Feb. 11, 2016.
NCT03213301 Clinical Trial Information, Published Jul. 7, 2017.
P1285CN OA2, Official Action, dated Dec. 20, 2023.
P1357USD, Official Action, dated Dec. 28, 2023.
Peters et al. Lurbinectedin in patients with small cell lung cancer with chemotherapy-free interval ?30 days and without central nervous metastases. Lung Cancer. vol. 188, 107448, Feb. 2024, published Nov. 27, 2023.
PharmaMar announces the approval of Zepzelca® (lurbinectedin) for the treatment of relapsed Small Cell Lung Cancer in Hong Kong, published Dec. 12, 2023.
PharmaMar announces the full approval of Zepzelca® (lurbinectedin) for the treatment of metastatic Small Cell Lung Cancer in Peru, published Nov. 7, 2023.
PharmaMar gets the approval of Zepzelca® (lurbinectedin) for the treatment of metastatic Small-Cell Lung Cancer in Macao, China, published Dec. 4, 2023.
PharmaMar Group reports financial results to Sep. 30, 2023, published Oct. 26, 2023.
PharmaMar increased R&D investment in oncology by 23% in 2022, published Sep. 22, 2023.
PharmaMar initiates a Phase IIb/III clinical trial of Zepzelca® (lurbinectedin) for the treatment of patients with metastatic Leiomyosarcoma, published Oct. 31, 2023.
PharmaMar licences lurbinectedin to Key Oncologics (Pty) Ltd for its marketing and distribution in Africa, published Sep. 12, 2023.
PharmaMar presents new data on lurbinectedin for Small Cell Lung Cancer at ESMO 2023, published Oct. 18, 2023.
Guo, H.Z., Leukemic progenitor cells enable immunosuppression and post-chemotherapy relapse via IL-36-inflammatory monocyte axis, Sci Adv, vol. 7(41) pp. eabg4167, Oct. 2021.
Shimada, E., Use of Peripheral Immune-Related Markers to indicate whether to Administer Pazopanib, Trabectedin, or Eribulin to STS Pts, J Clin Med, (2021), vol. 10, 4972.
Hourani, T., Tumor Associated Macrophages: Origin, Recruitment, Phenotypic Diversity, and Targeting, Front Oncol, (2021), vol. 11, 788365.
Fujiwara, T., Role of Tumor-Associated Macrophages in Sarcomas, Cancers, (2021), vol. 13(5),1086.
Cendrowicz, E., The Role of Macrophages in Cancer Development and Therapy, Cancers, (2021), 13, 1946.
Heymann, M.F., Bone sarcomas in the immunotherapy era, Br J Pharmacol, (2021), vol. 178(9) pp. 1955-1972.
An & Yang, Tumor-associated macrophage-targeted therapeutics in ovarian cancer, Int J Cancer, (2021), vol. 149(1) pp. 21-30.
Preusser, M., Trabectedin for recurrent WHO grade 2 or 3 meningioma: randomized phase 2 study of the EORTC Brain Tumor Group, Neuro oncol, (2022), vol. 24(5) pp. 755-767.
Toulmonde, M., Trabectedin plus durvalumab in patients with advanced pretreated STS and ovarian carcinoma (Tramune): phase Ib study, Clin Cancer Res, (2022), vol. 28(9) pp. 1765-1772.
Alvarez-Breckenridge, C.A., Trabectedin for recurrent WHO grade 2 or 3 meningiomas-paving the road for new opportunities, Neuro Oncol, (2022), vol. In press pp. 1-5.
Digklia, A., Trabectedin and Durvalumab Combination is Feasible—and Active in Relapsing Ovarian Cancer., Clin Cancer Res, 2022, vol. 28(9) pp. 1745-1747.
Schroeder, B.A., Immunologic Gene Signature Analysis Correlates M2 Macrophages with Time to Trabectedin Failure in Sarcoma Patients, Cancers, 2022, vol. 14(5) pp. 1290.
Allavena, P., Effects of the Anti-Tumor Agents Trabectedin and Lurbinectedin on Immune Cells of the Tumor Microenvironment, Front Oncol, 2022, vol. 12 pp. 851790.
Wagner, M.J., A Phase 1/2 Trial Combining Avelumab and Trabectedin for Advanced Liposarcoma and Leiomyosarcoma, Clin Cancer Res, 2022, vol. 28(11) pp. 2306-2312.
Zhang, X.Y., Anlotinib treatment in elderly patients with unresectable or metastatic soft tissue sarcoma: a retrospective study, Anticancer Drugs, 2022, vol. 33(1) pp. E519-524.
Chamseddine, A.N., Modulating tumor-associated macrophages to enhance the efficacy of immune checkpoint inhibitors: A TAM-pting approach, Pharmacol Ther, 2022, vol. 231 pp. 107986.
Gordon, E.M., Five-year results of a phase 2 trial using ipilimumab, nivolumab, and trabectedin for previously untreated advanced STS., ASCO 58th Annual Meeting, 2022, vol. 40 (Supl 16) p. 680 Abs No. 11573 (poster).

(56) References Cited

OTHER PUBLICATIONS

Gordon, E.M., Five-year results of a phase 2 trial using ipilimumab, nivolumab, and trabectedin for previously untreated advanced STS., ASCO 58th Annual Meeting, 2022, vol. 40 (Supl 16) p. 680 Abs No. 11573 (abstract).
Scambia, G., Randomized phase III trial on trabectedin agent vs clinician's choice chemo in BRCA-mutated recurrent ovarian cancer (MITO23)., ASCO 58th Annual Meeting, 2022, vol. 40 (Supl 16) Abs N LBA5504 (poster).
Scambia, G., Randomized phase III trial on trabectedin agent vs clinician's choice chemo in BRCA-mutated recurrent ovarian cancer (MITO23), ASCO 58th Annual Meeting, (2022), vol. 40 (Supl 16) Abs N LBA5504 (abstract).
Casagrande, N., Current and Emerging Approaches to Study Microenvironmental Interactions and Drug Activity in Classical Hodgkin Lymphoma, Cancers, (2022), vol. 14(10), 2427.
Pautier, P., Doxorubicin alone vs doxorubicin with trabectedin as first-line therapy for metastatic or unresectable LMS (LMS-04): randomized phase 3, Lancet Oncol, (2022), vol. 23(8) pp. 1044-1054.
Gordon, E., Results of a phase I/II combination regimen with ipilimumab, nivolumab and trabectedin as first line therapy for advanced LMS, ESMO Congress 2022, 2022, vol. 33 (Supl 7) pp. S1225 Abs No. 1483O.
Heilig, C.E., Randomized phase II study of trabectedin/olaparib compared to physician's choice in solid tumors harboring DNA repair deficiencies, ESMO Congress 2022, 2022, vol. 33 (Supl 7) pp. S762-S763 Abs N 487P.
Lima, M.F., Consecutive Inhibition of Telomerase and Alternative Lengthening Pathway Promotes Hodgkin's Lymphoma Cell Death, Biomedicines, 2022, vol. 10(9) pp. 2299.
Sasi, A., Doxorubicin plus trabectedin for metastatic or unresectable leiomyosarcoma, Lancet Oncol, 2022, vol. 23(10) pp. e442.
Chib, S., Doxorubicin plus trabectedin for metastatic or unresectable leiomyosarcoma, Lancet oncol, 2022, vol. 23(10) pp. e443.
Sutcuoglu, O., Doxorubicin plus trabectedin for metastatic or unresectable leiomyosarcoma, Lancet Oncol, 2022, vol. 23(10) pp. e444.
Pautier, P., Doxorubicin plus trabectedin for metastatic or unresectable leiomyosarcoma—Authors' reply, Lancet Oncol, 2022, vol. 23(10) pp. e445.
Kantidakis, G., benchmarks to design clinical trials with advanced metastatic LPS or synovial sarcoma: EORTC meta-analysis . . . , Eur J Cancer, 2022, vol. 174 pp. 261-276.
Lorusso D, Efficacy and safety of trabectedin for treatment of advanced uterine or ovarian carcinosarcoma: phase II trial (MITO-26), Gynecol Oncol, 2022, vol. 167(3) pp. 436-443.
Meftahpour, V., Prognostic significance and therapeutic potentials of immune checkpoints in osteosarcoma, Excli J, 2022, vol. 21 pp. 250-268.
Lynch, M.M., Combinations of Chemotherapy and PD-1/PD-L1 Inhibitors in Sarcoma, Curr Treat Options Oncol, 2022, vol. 23(12) pp. 1861-1876.
Chekerov, R., comparison of quality of life in recurrent ovarian cancer treated with trabectedin plus PLD or platinum therapy: Noggo S16/Compass, 23rd European Congress on Gyn Oncology, 2022, vol. 32(Supl 2) pp. A252-A253 Abs N RA-672 (poster).
Chekerov, R., comparison of quality of life in recurrent ovarian cancer treated with trabectedin plus PLD or platinum therapy: Noggo S16/Compass, 23rd European Congress on Gyn Oncology, 2022, vol. 32(Supl 2) pp. A252-A253 Abs N RA-672 (abstract).
Alvarez, R., Trabectedin with concomitant radiation therapy for pts with resectable retroperitoneal LPS or LMS: phase I/II trial . . . , CTOS 27th Annual Meeting, 2022, Abs No. 1301234 (poster).
Alvarez, R., Trabectedin with concomitant radiation therapy for pts with resectable retroperitoneal LPS or LMS: phase I/II trial . . . , CTOS 27th Annual Meeting, 2022, Abs No. 1301234 (abstract).
Siontis, B.L., Phase II Multi center, single arm trial of Trabectedin in combination with Olaparib in advanced unresectable or metastatic sarcoma, CTOS 27th Annual Meeting, 2022 (poster).
Siontis, B.L., Phase II Multi center, single arm trial of Trabectedin in combination with Olaparib in advanced unresectable or metastatic sarcoma, CTOS 27th Annual Meeting, 2022 (Abstract).
Jang, H.J., Therapeutic Targeting of Macrophage Plasticity Remodels the Tumor-Immune Microenvironment, Cancer Res, 2022, vol. 82(14) pp. 2593-2609.
Bednarek, A., Liver metastasis or a pseudocyst? A rare presentation of leiomyosarcoma's metastasis in the liver., Contemp Oncol, 2022, vol. 26(4) pp. 306-309.
Tian, Z., PD-1/L1 inhibitor plus chemotherapy in the treatment of sarcomas, Front Immunol, (2022), vol. 13, 898255.
Assi, T., Trabectedin and immune checkpoint inhibitors: a blissful combination or another failure in soft tissue sarcomas?, Immunotherapy, 2023, vol. 15(1) pp. 5-8.
Gordon, E.M., Saint: A Phase I/Expanded Phase II Study Using ipilimumab, Nivolumab and Trabectedin in First-Line advanced STS, Cancers, 2023, vol. 15(3) pp. 906.
Peraza, D.A., Trabectedin modulates macrophage polarization in the tumor-microenvironment. Role of KV1.3 and KV1.5 channels, Biomed Pharmacother, 2023, vol. 161 pp. 114548.
Chawla, S.P., Activity of TNT: a phase 2 study using talimogene laherparepvec, nivolumab and trabectedin for previously treated pts with advanced sarcomas, Front Oncol, 2023, vol. 13 pp. 1116937.
Reichardt, P., Efficacy and safety of nivolumab and trabectedin in pretreated patients with advanced STS: Results of NitraSarc trial, ASCO 59th Annual Meeting, 2023, vol. 41 (Supl 16) Abs N 11500 (poster).
Reichardt, P., Efficacy and safety of nivolumab and trabectedin in pretreated patients with advanced STS: Results of NitraSarc trial, ASCO 59th Annual Meeting, 2023, vol. 41 (Supl 16) Abs N 11500 (abstract).
Chawla, N.S., Interim results of a phase 2 study using talimogene laherparepvec, nivolumab, and trabectedin for advanced leiomyosarcoma., ASCO 59th Annual Meeting, 2023, vol. 41 (Supl 16) Abs No. 11556 (poster).
Chawla, N.S., Interim results of a phase 2 study using talimogene laherparepvec, nivolumab, and trabectedin for advanced leiomyosarcoma., ASCO 59th Annual Meeting, 2023, vol. 41 (Supl 16) Abs No. 11556 (abstract).
PharmaMar study of the combination of lurbinectedin and irinotecan on Small Cell Lung Cancer has been selected for a presentation at ASCO, Apr. 25, 2024.
Results presented at ASCO demonstrating the synergy of PharmaMar's combination of lurbinectedin with irinotecan in patients with relapsed small cell lung cancer, Jun. 4, 2024.
PharmaMar Group Presents Financial Results for the First Half of 2024, Jul. 30, 2024.
PharmaMar Announces Positive and Statistically Significant Overall Survival and Progression-Free Survival Results for Zepzelca® (lurbinectedin) and Atezolizumab Combination in First-Line Maintenance Therapy for Extensive-Stage Small Cell Lung Cancer, Oct. 15, 2024.
PharmaMar Group presents its financial results as of Sep. 30, 2024, Oct. 29, 2024.
PharmaMar's Zepzelca® (lurbinectedin) receives approval in China for the treatment of Small Cell Lung Cancer, Dec. 3, 2024.
PharmaMar completes enrollment for phase III Lagoon study with Zepzelca® (lurbinectedin) for the treatment of small cell lung cancer, Dec. 19, 2024.
FY 2023 result, Feb. 28, 2024.
Financial information, Dec. 31, 2023.
Directors report, Jan. 1, 2024.
Financial statements 2023, Feb. 28, 2024.
Consolidated non-financial information statement 2023, Feb. 28, 2024.
Q1 results 2024, Apr. 23, 2024.
Periodic public information 2024.
Q2 results 2024, Jul. 30, 2024.
Annual Report 2023.
Q3 results 2024, Apr. 29, 2024.
Hang Leung et al. Comparison of target agent treatment strategies for platinum-resistant recurrent ovarian cancer A Bayesian network meta-analysis. Medicine 2024; 103:21(e38183).

(56) References Cited

OTHER PUBLICATIONS

Jesús Gullón Sanz, BSc, MSc, Ines Perez Roman, PhD Costs Associated With the Administration, Postinfusion Monitoring, and Management of Adverse Events (AEs) Related to Novel Drugs for Second-Line (2L+) Treatment of Small-Cell Lung Cancer (SCLC). Nov. 2025, ISPOR Europe 2025, Glasgow, Scotland Value in Health, vol. 28, Issue S2. EE289.
Drewinko et al. Combination chemotherapy in vitro with adriamycin. Observations of additive, antagonistic, and synergistic effects when used in two-drug combinations on cultured human lymphoma cells. Cancer Biochem Biophys. May 1976; 1(4):187-95., 1976.
Lazo et al. Antiproliferative actions of tamoxifen to human ovarian carcinomas in vitro. Cancer Research Jun. 1, 1984 Medicine—Jun. 1984.
Neelam et al. Combination of flavone acetic acid (FAA) with adriamycin, cis-platinum and difluoromethylornithine (DFMO) in vitro against human colon cancer cells. Invest New Drugs. Aug. 1990;8(3):263-8.
Kano et al. Effects of CPT-11 in combination with other anti-cancer agents in culture. Int J Cancer. Feb. 20, 1992;50(4):604-10.
Hahn et al. Taxol in Combination with Doxorubicin or Etoposide. Cancer Nov. 1, 1993, vol. 72, No. 9, Nov. 1, 1992.
Woods et al. Antagonism between tamoxifen and doxorubicin in the MCF-7 human breast tumor cell line Biochemical Pharmacology vol. 47, Issue 8, Apr. 20, 1994, pp. 1449-1452.
Viallet et al. Etoposide and doxorubicin antagonize the in vitro activity of paclitaxel in human non-small cell lung cancer cell lines. Lung Cancer. Aug. 1996;15(1):93-101.
Borbe et al. Failure of taxol-based combination chemotherapy for malignant glioma cannot be overcome by G2/M checkpoint abrogators or altering the p53 status. Cancer Chemother Pharmacol . 1999; 44(3):217-27.
"Drugs Future," 22(11):1279, 1997.
Le et al. Ecteinascidins. A Review of the Chemistry, Biology and Clinical Utility of Potent Tetrahydroisoquinoline Antitumor Antibiotics. Nat Prod Rep. Feb. 2015; 32(2): 328-347.
Nat'l Cancer Institute, FDA Approves Trabectedin to Treat Two Types of Soft Tissue Sarcoma, Dec. 4, 2015.
Rudin et al. Ifinatamab Deruxtecan in Patients With Extensive-Stage Small Cell Lung Cancer: Primary Analysis of the Phase II IDeate-Lung01 Trial. J Clin Oncol 44, 261-273(2026)—Oct. 14, 2025.
PharmaMar Q1 results 2025 dated Apr. 24, 2025.
PharmaMar Separate Financial Statements for 2024 dated Feb. 27, 2025.
PharmaMar Q2 Results 2025 dated Jul. 30, 2025.
Q2 PharmaMar Periodic public information dated Jun. 30, 2025.
PharmaMar Q3 Results 2025 dated Sep. 30, 2025.
PharmaMar Group announces financial results for first quarter 2025—Apr. 24, 2025.
PharmaMar Group Announces Financial Results as of Sep. 30, 2025-Oct. 30, 2025.
Swiss medical authority approves PharmaMar's Zepzelca® (lurbinectedin) and Atezolizumab (Tecentriq®) combination as first-line maintenance therapy for extensive-stage small cell lung cancer—Nov. 24, 2025.
Chawla the TNT protocol: A phase II study using talimogene laherparepvec (TVEC), nivolumab (N) and trabectedin (T) as first, second/third line therapy for advanced sarcoma, including desmoid tumor and chordoma. Journal of Clin Onc. vol. 31, No. Issue 15_sup.
Chawla et al. Interim results of a phase 2 study using talimogene laherparepvec, nivolumab, and trabectedin for advanced leiomyosarcoma. ASCO American Society of Clinical Oncology, 59th Annual Meeting, Jun. 2-6, 2023. Chicago, Illinois. J Clin Oncol. vol. 41 (Supl 16) Abs No. 11556 (abstract).
Chawla et al. Interim results of a phase 2 study using talimogene laherparepvec, nivolumab, and trabectedin for advanced leiomyosarcoma. ASCO American Society of Clinical Oncology, 59th Annual Meeting, Jun. 2-6, 2023. Chicago, Illinois. J Clin Oncol. vol. 41 (Supl 16) Abs No. 11556 (poster).
Tian, Zhichao, and Weitao Yao. "PD-1/L1 inhibitor plus chemotherapy in the treatment of sarcomas." Frontiers in Immunology 13 (2022): 898255.
Cojocaru et al. What's the latest with investigational drugs for soft tissue sarcoma? Expert Opin Investig Drugs. vol. 31 (11) pp. 1239-1253, 2022.
Lynch et al. Combinations of Chemotherapy and PD-1/PD-L1 Inhibitors in Sarcoma. Curr Treat Options Oncol. vol. In press pp. 1-16, Nov. 16, 2022.
Loi et al. Radiosensitizing Effect of Trabectedin on Human Soft Tissue Sarcoma Cells. Int J Mol Sci. Nov. 18, 2022.
Meftahpour et al. Prognostic significance and therapeutic potentials of immune checkpoints in osteosarcoma. Excli J. vol. 21 pp. 250-268, Jan. 12, 2022.
Wagner et al. A Phase 1/2 Trial Combining Avelumab and Trabectedin for Advanced Liposarcoma and Leiomyosarcoma. Clin Cancer Res. vol. 28(11) pp. 2306-2312, 2022.
Schroeder et al. Immunologic Gene Signature Analysis Correlates Myeloid Cells and M2 Macrophages with Time to Trabectedin Failure in Sarcoma Patients. Cancers. vol. 14(5) pp. 1290, Mar. 2, 2022.
Toulmonde et al. Trabectedin plus durvalumab in patients with advanced pretreated soft tissue sarcoma and ovarian carcinoma (Tramune): an open-label, multicenter phase lb study. Clin Cancer Res. vol. 28(9) pp. 1765-1772, May 1, 2022.
Pink et al. Efficacy and safety of nivolumab and trabectedin in pretreated patients with advanced soft tissue sarcomas (STS): Preliminary results of a phase II trial of the German Interdisciplinary Sarcoma Group (GISG-15, NitraSarc) for the non-L sarcoma cohort.ASCO American Society of Clinical Oncology, 57th Annual Meeting, virtual, Jun. 4-8, 2021. J Clin Oncolvol 39 (15 Supl) pp. 584s Abs No. 11545 (abstract).
Pink et al. Efficacy and safety of nivolumab and trabectedin in pretreated patients with advanced soft tissue sarcomas (STS): Preliminary results of a phase II trial of the German Interdisciplinary Sarcoma Group (GISG-15, NitraSarc) for the non-L sarcoma cohort.ASCO American Society of Clinical Oncology, 57th Annual Meeting, virtual, Jun. 4-8, 2021. J Clin Oncolvol 39 (15 Supl) pp. 584s Abs No. 11545 (poster).
Casagrande et al. Trabectedin overcomes doxorubicin-resistance, counteracts tumor-immunosuppressive reprogramming of monocytes and decreases xenograft growth in Hodgkin lymphomac. Cancer Lett. vol. 500 pp. 182-193, 2020.
Wagner et al. A phase I/II trial combining avelumab and trabectedin for advanced liposarcoma and leiomyosarcoma. 35th Annual Meeting and Pre-Conference Programs of the Society for Immunotherapy of Cancer, SITC 2020. virtual Nov. 9-14, 2020. J Immunother Cancer. vol. 8 (Supl 3) p. A476 Abs No. 796.
Moura et al. Immune-checkpoint genes as predictive biomarkers of trabectedin in advanced soft tissue sarcoma (STS): A Spanish Group for Research on Sarcomas (GEIS) translational study. CTOS 2020 Annual Meeting. Virtual, Nov. 18-21, 2020. (abstract).
Moura et al. Immune-checkpoint genes as predictive biomarkers of trabectedin in advanced soft tissue sarcoma (STS): A Spanish Group for Research on Sarcomas (GEIS) translational study. CTOS 2020 Annual Meeting. Virtual, Nov. 18-21, 2020. (poster).
Povo-Retana et al. Specific Effects of Trabectedin and Lurbinectedin on Human Macrophage Function and Fate—Novel Insights. Cancers. vol. 12(10) pp. 3060, Oct. 20, 2020.
Bailly et al. Combined cytotoxic chemotherapy and immunotherapy of cancer: modern times. NAR Cancer. vol. 2(1) pp. 1-20, Feb. 17, 2020.
Chukwueke and Wen. Medical management of meningiomas. Handbook Clin Neurol. vol. 170 pp. 291-302, 2020.
Moura et al. Immune-checkpoint genes as predictive biomarkers of trabectedin in advanced soft tissue sarcoma (STS): A Spanish Group for Research on Sarcomas (GEIS) translational study. ASCO American Society of Clinical Oncology, 56th Annual Meeting, virtual, May 31-Jun. 4, 2020. J Clin Oncol. vol. 38 (15 Supl) Abs No. 11546 (abstract).

(56) References Cited

OTHER PUBLICATIONS

Moura et al. Immune-checkpoint genes as predictive biomarkers of trabectedin in advanced soft tissue sarcoma (STS): A Spanish Group for Research on Sarcomas (GEIS) translational study. ASCO American Society of Clinical Oncology, 56th Annual Meeting, virtual, May 31-Jun. 4, 2020. J Clin Oncol. vol. 38 (15 Supl) Abs No. 11546 (poster).
Banerjee et al. Trabectedin reveals a strategy of immunomodulation in chronic lymphocytic leukemia. Cancer Immunol Res. vol. 7(12) pp. 2036-2051, Dec. 2019.
Sebio et al. The current landscape of early drug development for patients with sarcoma in immunotherapy era. Future Oncol. vol. 14(12) pp. 1197-1211, 2018.
Casagrande et al. Trabectedin Inhibits Classical Hodgkin Lymphoma Growth, Monocytes Immunosuppressive Polarization by Tumor Cells and Synergizes with the CCR5-Antagonist Maraviroc. 11th International Symposium on Hodgkin Lymphoma, ISHL 2018. Cologne, Germany. Oct. 27-29, 2018. HemaSphere. vol. 2(Supl 3) Abs No. T005 (0077).
Gordon et al. Phase 1/2 study of safety/efficacy using trabectedin, ipilimumab and nivolumab triple therapy as first line treatment of advanced soft tissue sarcoma. ASCO American Society of Clinical Oncology, 54th Annual Meeting, Jun. 1-5, 2018. Chicago, Illinois. J Clin Oncol. vol. 36 (Supl) Abs. No. TPS11591 (abstract).
Gordon et al. Phase 1/2 study of safety/efficacy using trabectedin, ipilimumab and nivolumab triple therapy as first line treatment of advanced soft tissue sarcoma. ASCO American Society of Clinical Oncology, 54th Annual Meeting, Jun. 1-5, 2018. Chicago, Illinois. J Clin Oncol. vol. 36 (Supl) Abs. No. TPS11591 (poster).
Pham et al. The Role of Macrophage/B-Cell Interactions in the Pathophysiology of B-Cell Lymphomas. Front Oncol. vol. 8, Article 147, May 8, 2018.
Zu and Lang. The significance and therapeutic potential of PD-1 and its ligands in ovarian cancer: A systematic review. Gynecol Oncol. vol. 142(1) pp. 184-189, 2016.
Guo et al. Combined Trabectedin and anti-PD1 antibody produces a synergistic antitumor effect in a murine model of ovarian cancer. J Transl Med. vol. 13(1) pp. 247, 2015.
History of Changes for Study:NCT06203210—Jan. 2, 2024.
History of Changes for Study:NCT06217536—Jan. 19, 2024.
History of Changes for Study:NCT06228066—Jan. 26, 2024.
History of Changes for Study: NCT06385548—Apr. 23, 2024.
History of Changes for Study:NCT06406673—May 6, 2024.
Pharma Mar clinical trial protocol version 4.0 PM1183-A-003-10—Phase I Multicenter, Open-label, Clinical and Pharmacokinetic 2010-024291-25 NCT01970540—Feb. 24, 2020.
Pharma Mar Statistical analysis plan PM1183-A-003-10 (NCT01970540) 2010-024291-25—Feb. 12, 2018.
Pharma Mar clinical trial protocol version 4.0 PM1183-B-003-11 2011-006108-11 NCT01525589—Sep. 4, 2020.
Pharma Mar statistical analysis plan PM1183-B-003-11 version 3.0 2011-006108-11 NCT01525589—Dec. 10, 2018.
Pharma Mar statistical analysis plan PM1183-B-005-14 version 5.0 2014-003773-42 NCT02454972—Nov. 11, 2020.
Pharma Mar clinical trial protocol version 8.0—PM1183-B-005-14 2014-003773-42 NCT02454972—Jun. 5, 2020.
Pharma Mar clinical trial protocol version 4.0 PM1183-C-003-14 2015-001641-89 NCT02566993—May 3, 2018.
Pharma Mar statistical analysis plan PM1183-C-003-14 version 3.0 2015-001641-89 NCT02566993—Sep. 4, 2020.
Pharma Mar clinical trial protocol version 1.0 PM1183-C-004-14 2014-005251-39 NCT02421588—Dec. 4, 2014.
Pharma Mar statistical analysis plan PM1183-C-004-14 version 2.0 2014-005251-39 NCT02421588—Aug. 30, 2017.
Mino R. Caira. Crystalline Polymorphism of Organic Compounds. Topics in Current Chemistry, vol. 198—Nov. 28, 2024.
Auernhammer et al. Personalized drug screening and risk assessment in patient-derived gastroenteropancreatic neuroendocrine neoplasms. J Clin Endocrinol Metab. Jan. 10, 2026-Jan. 10, 2026.
Navarro et al. A phase II, multicenter, open-label, single-arm study of berzosertib plus topotecan in patients with relapsed platinum-resistant small-cell lung cancer (DDRiver SCLC 250). ESMO Open, vol. 11, Issue 1, 105918—2026.
Hella Bartsch et al., Growth-Inhibiting Effect of Crude Pineal Extracts on Human Melanoma Cells in vitro is Different from That of Known Synthetic Pineal Substances, 69 J. Neural Transmission 299-311 (1987).
J. K. Buolamwini, Novel anticancer drug discovery, 3 Current Opin Ions in Chem. Biology 500-09 (1999).
E. Erba et al., Mode of action of ecteinascidin 743, a natural marine compound with antitumoral activity, 9 Annals of Oncology Abstract 535 132-43 (1998)—1998.
E. Erba et al., Isolation and characterization of an IGROV-1 human ovarian cancer cell line made resistant to Ecteinascidin-743 (ET-743), 82 Brit. J. of Cancer 1732-39 (2000).
Peter J. Ferguson et al., Differential Cellular Retention of Vincristine and Vinblastine by Cultured Human Promyelocytic Leukemia HL 60/CI Cells: The Basis of Differential Toxicity, 45 Cancer Rsch. 5480-88 (1985).
Richard A. Glennon et al., 2-Substituted Tryptamines: Agents with Se lectivity for 5-HT6 Serotonin Receptors, 43 J. Med. Chem. 1011-18 (2000).
H. R. Hendriks, High antitumour activity of ET743 against human tu mour xenografts from melanoma, non-small-cell lung and ovarian can cer, 10 Annals of Oncology 1233-40 (1999).
Eva Hofsli and Jon Nissen-Meyer, Reversal of Multidrug Resistance by Lipophilic Drugs, 50 Cancer Rsch. 3997-4002 (1990).
Felix Kratz and Ulrich Beyer, Serum Proteins as Drug Carriers of An ticancer Agents: A Review, 5 Drug Delivery 281-99 (1998).
Mack et al., Dissociation Constants and Lipophilicity of Catechola mines and Related Compounds, 310 Naunyn-Schmiedeberg's AR Chives of Pharmacology 1-9 (1979).
Bob M. Moore II et al., NMR-Based Model of an Ecteinascidin 743-DNA Adduct, 119 J. Am. Chem. Soc'y 5475-76 (1997).
Bob M. Moore II et al., Mechanism for the Catalytic Activation of Ec teinascidin 743 and Its Subsequent Alkylation of Guanine N2, 120 J. Am. Chem. Soc'y 2490-91 (1998).
David E. Nichols et al., Synthesis and Evaluation of 2,3-Dihydrobenzo furan Analogues of the Hallucinogen I-(2,5-Dimethoxy-4-methylphenyl)-2-aminopropane: Drug Discrimination Studies in Rats, 29 J. Med. Chem. 302-04 (1986).
J. F. Riou et al., Cellular uptake, and efflux of docetaxel (Taxotere®) and paclitaxel (Taxol®) in P388 cell line, 35 Proc. Am. Ass'n Cancer Rsch., 2292 (1994).
Daryl A. Roston et al., Liquid chromatographic determination of phe nolic acids of vegetable origin, 5 J. Liquid Chromatography 75-103 (1982).
David P. Ryan et al., Phase I and Pharmacokinetic Study of Ecteinas cidin 743 Administered as a 72-Hour Continuous Intravenous Infusion in Patients with Solid Malignancies, 7 Clin. Cancer Rsch. 231-42 (2001).
P. Sanwald et al., Simultaneous measurement of the major metabolites of dolasetron mesilate in human urine using solid-phase extraction and high-performance liquid chromatography, 661 J. Chromatography B101-07 (1994).
Alexander T. Shulgin et al., Structure-Activity Relationships of One Ring Psychotomimetics, 221 Nature 537-41 (1969).
A. Taamma, Phase I and Pharmacokinetic Study of Ecteinascidin-743, a New Marine Compound, Administered as a 24-hour Continuous in fusion in Patients with Solid Tumors, 19:5 J. Clin. Oncology 1256-65 (2001).
Kit-Sum Wong, Properties and Reaction of Tryptamine-4,5-Dione with Glutathione and Central Toxicity and Potential Mechanisms of Action of Their Reaction Product 7-S-Glutathionyl-Tryptamine-4,5-Dione (Ph.D. Dissertation, University of Oklahoma)—1992.
G. J. R. Zaman et al., The human multidrug resistance-associated pro tein MRP is a plasma membrane drug-efflux pump, 91 Proc. Nat'l. Acad. Sci. 8822-26 (1994).
Maha Zewail-Foote and Laurence H. Hurley, Ecteinascidin 743: A Mi nor Groove Alkylator That Bends DNA toward the Major Groove, 42:14 J. Med. Chem. 2493-97 (1999).

(56) References Cited

OTHER PUBLICATIONS

Yeping Zhao, Simultaneous determination of SU5416 and its phase I and phase II metabolites in rat and dog plasma by LC/MS/MS, 25 J. Pharmaceutical and Biomedical Analysis 821-32 (2001).
Xiao-Jian Zhou et al., Uptake and Metabolism of Vinca Alkaloids by Freshly Isolated Human Hepatocytes in Suspension, 14 Anticancer Rsch. 1017-22 (1994).
A. Ghose, et al., Prediction of Hydrophobic (Lipophilic) Properties of Small Organic Molecules Using Fragmental Methods: An Analysis of ALOGP and CLOGP Methods, 102 J. Phys. Chem. A 21, 3762-72 (1998).
Timmerman & Levy, Dendritic Cell Vaccines for Cancer Immunotherapy, 50 Annual Review of Medicine 507 (1999).
Carbone, Molecular Modalities in the Treatment of Lung Cancer, 13(10) Oncology (Suppl. 5) 142 (1999).
Murphy, Infusion of Dendritic Cells Pulsed with HLA-A2-Specific Prostate-Specific Membrane Antigen Peptides: A Phase II Prostate Cancer Vaccine Trial Involving Patients with Hormone Refractory Metastatic Disease, 38 The Prostate 73 (1999).
Disis, Cancer Vaccines for the Treatment and Prevention of Non-Small-Cell Lung Cancer, 1(4) Clinical Lung Cancer 294 (2000).
Ballen & Stewart, Adoptive Immunotherapy, 9 Current Opinion in Oncology 579, 582 (1997).
Kimura & Yamaguchi, Adjuvant Immunotherapy with Interleukin 2 and Lymphokine-Activated 11 Killers Cells after Noncurative Resection of Primary Lung Cancer, 13 Lung Cancer 31, 31 (1995).
Suzuki, Intermittent Adjuvant Chemo-Immunotherapy After Resection of Non-Small Cell Lung Cancer with Multilevel Mediastinal Lymph Node Metastasis, 7 Oncology Reports 545, 545 (2000).
Halmos et al. Efficacy and Safety of Lurbinectedin for Small Cell Lung Cancer in a Real-World Setting: Jazz Emerge 402 Study. IASLC 2024 World Conference on Lung Cancer (WCLC 2024). Sep. 7-10, San Diego. 2024. J Thorac Oncol. vol. 19(10 Supl) pp. S210-S211 Abs No. P1.13A.10.
Halmos et al. Efficacy and Safety of Lurbinectedin for Small Cell Lung Cancer in a Real-World Setting: Jazz Emerge 402 Study. IASLC 2024 World Conference on Lung Cancer (WCLC 2024). Sep. 7-10, San Diego. 2024. J Thorac Oncol. vol. 19(10 Supl) pp. S210-S211 Abs No. P1.13A. 10 (Poster).
Gupta et al. High SLFN11 Expression Predicts Response but is not Required to Confer Sensitivity to Lurbinectedin. IASLC 2024 World Conference on Lung Cancer (WCLC 2024). Sep. 7-10, San Diego. 2024. J Thorac Oncol. vol. 19(10 Suppl) pp. S458 Abs No. EP.03G.04 (Abstract).
Gupta et al. High SLFN11 Expression Predicts Response but is not Required to Confer Sensitivity to Lurbinectedin. IASLC 2024 World Conference on Lung Cancer (WCLC 2024). Sep. 7-10, San Diego. 2024. J Thorac Oncol. vol. 19(10 Suppl) pp. S458 Abs No. EP.03G.04 (Poster).
Libre et al. Lurbinectedin vs. Platinum Rechallenge in Extensive Stage Small Cell Lung Cancer after Platinum Doublet, A Multicenter Retrospective Study. IASLC 2024 World Conference on Lung Cancer (WCLC 2024). Sep. 7-10, San Diego. 2024. J Thorac Oncol. vol. 19(10) pp. S213 Abs No. P1.13B.01.
Shim et al. Real-world outcomes with lurbinectedin in second-line and beyond for small cell lung cancer in Korea. ASCO Breakthrough: A Global Summit for Oncology Innovators. Aug. 8-10, 2024. Yokohama, Japan. J Clin Oncol. vol. 42 (23 Supl) pp. 211.
Cigrang et al. Targeting Transcriptional addiction in melanoma with a new marine derived drug. 21st Science Day of "La ligue contre le cancer" Nov. 9, 2021 Strasbourg, France.
Scattolin et al. 14P SLFN11 detection in patients with small cell lung cancer treated with lurbinectedin: A retrospective translational analysis. Molecular Analysis for Precision Oncology Congress (MAP), Oct. 16-18, 2024, London, Uk. Ann Oncol. vol. 9 (Supl 6) pp. 3-4 Abs No. 14P.
A. Iñañez et al. Modulation of EMT Increases the Activity of Lurbinectedin in Small Cell Lung Cancer. IASLC 2024 World Conference on Lung Cancer (WCLC 2024). Sep. 7-10, San Diego. 2024. J Thorac Oncol.
Mirzapoiazova et al. Teriflunomide in Vitro or Leflunomide in Vivo Treatment Increases the Efficacy of Lurbinectedin in SCLC. IASLC 2024 World Conference on Lung Cancer (WCLC 2024). Sep. 7-10, San Diego. 2024. J Thorac Oncol. vol. 19(10) pp. S314 Abs No. MA19.04.
Xiang et al. Efficacy and safety of lurbinectedin in Chinese patients with extensive-stage small cell lung cancer (ES-SCLC): A multicenter, retrospective real-world study. European Society for Medical Oncology Asia Congress, ESMO 2024. Singapore. Dec. 6-8, 2024. Ann Oncol. vol. 35 (Supl 4) pp. S1667 Abs No. 703P.
Collins, C.; Hellyer, J. Lurbinectedin in relapsed extensive stage small cell lung cancer demonstrates similar efficacy to phase II basket trial. Western Medical Research Conference. Jan. 16-18, 2025. Carmel, California. J Invest Med. vol. 73 (1) pp. 199-200 Abs No. 157.
Shi, X.; Pietropaoli, A.P.; Nagel, D. Lurbinectedin-induced Pneumonitis and DAH in Recurrent Stage IV SCLC: Possible Pulmonary Toxicity From a Novel Alkylating Agent. American Thoracic Society International Conference. May 16-21, San Francisco 2025. Am J Respir Crit Care Med. vol. 211 p. A2751 Abs N A80-1.
Krayim et al. Lurbinectedin for small cell lung cancer (SCLC): Response patterns and survival outcomes by line of therapy. ASCO American Society of Clinical Oncology, 61st Annual Meeting, May 30-Jun. 3, 2025. Chicago, Illinois. J Clin Oncol. vol. 43 (Supl 16) Abs No. e20128.
Laharwal et al. Real-world effectiveness of lurbinectedin in extensive stage small cell lung cancer (ES-SCLC). ASCO American Society of Clinical Oncology, 61st Annual Meeting, May 30-Jun. 3, 2025. Chicago, Illinois. J Clin Oncol. vol. 43 (Supl 16) Abs No. e20133.
Shi, X.; Pietropaoli, A.P.; Nagel, D. Lurbinectedin-induced Pneumonitis and DAH in Recurrent Stage IV SCLC: Possible Pulmonary Toxicity From a Novel Alkylating Agent. American Thoracic Society International Conference, ATS 2025. San Francisco, CA, United States May 16-21, 2025. Am J Respir Crit Care Med. vol. 211 Abs No. A2751.
Sanchez Sevilla Uruchurtu et al. Chk1/2 inhibition enhances response to lurbinectedin treatment in small cell lung cancer. AACR American Association for Cancer Research. Annual Meeting. Apr. 5-10, 2024. San Diego. CA. Philadelphia (PA) Cancer Res. vol. 84 (6 Supl) Abs No. 3191.
Redin et al. Lurbinectedin Synergizes with Selinexor by Inhibiting DNA Damage Repair and Enhancing Immune Cell Infiltration in Neuroendocrine Lung Tumors. IASLC 2024 World Conference on Lung Cancer (WCLC 2024). Sep. 7-10, San Diego. 2024. J Thorac Oncol. vol. 19(10 Supl) pp. S159 Abs No. P1.03G.01.
Redin et al. Lurbinectedin synergizes with selinexor by inhibiting DNA damage repair and enhancing immune cell infiltration in neuroendocrine lung and prostate tumors. AACR American Association for Cancer Research. Annual Meeting. Apr. 25-30, 2025. Chicago, IL. Cancer Res. vol. 85 (8 Supl 1) Abs No. 1166.
Nie Y, Chiang AC. Small-Cell Lung Cancer Updates. Semin Respir Crit Care Med., Aug. 2025.
Cheng and Zhang IMforte: A new starting point and new challenges. Med, vol. 6, Aug. 8, 2025.
Lu and Liu Aligning organ-specific toxicities with formulation strategies: a rational design approach to chemotherapy optimization. International Journal of Pharmaceuticsvol. 684, Sep. 2, 2025.
Anonymous, Atezolizumab Approved for Initial Treatment of Metastatic Lung Cancer, NCI, Jan. 7, 2019.
Guo et al. Combined Trabectedin and anti-PD1 antibody produces a synergistic antitumor effect in a murine model of ovarian cancer. Guo et al. J Transl Med (2015) 13:247.
Alsheimer et al. The Effect of Lurbinectedin as a Monotherapy and in Combination with Ionizing Radiation on Sarcoma Cell Lines. Cancers 2025, 17(17), 2930.
Behrouzi R, Blackhall F. State of the art in treatment of small cell lung cancer. Therapeutic Advances in Medical Oncology. 2025;17.
Florez et al. Clinical strategies for lung cancer management: Recommendations from the Bridging the Gaps Lung Cancer Consensus Conference 2024. Cancer. 2025;e70060, Apr. 28, 2025.

(56) References Cited

OTHER PUBLICATIONS

Dowalti et al. Phase 2 Open-Label Study of Sacituzumab Govitecan as Second-Line Therapy in Patients With Extensive-Stage SCLC: Results From TROPiCS-03. Small Cell Lung Cancer, vol. 20, Issue 6, p. 799-808, Jan. 2, 2025.
Anusha, M., Godela, R., & Gubbiyappa, K. S. (2025). Stability Indicating LC—ESI-MS/MS Method Development and Validation for the Quantitation of Lurbinectedin in Biological Matrices. International Journal of Applied Pharmaceutics, 17(5), 465-470.
Srivastava et al. Therapeutic Effects of Lurbinectedin in PARP Inhibitor-Resistant High-Grade Serous Ovarian Cancer Using Patient-Derived Cell Lines and Organoid Models. Int. J. Mol. Sci. 2025, 26, 8866, Sep. 11, 2025.
Annika Simon, Lung carcinoma: Combination with lurbinectedin beats antibody monotherapy. Pneumology 2025; 79 (09): 611-612.
Huang et al. Cost-effectiveness analysis of lurbinectedin plus atezolizumab as first-line treatment for extensive-stage small-cell lung cancer. Sec. Cancer Immunity and Immunotherapy vol. 16, Sep. 23, 2025.
Sawyer et al. Review of outcomes in a veteran treated with lurbinectedin long-term for extensive-stage small cell lung cancer: A case report. Current Problems in Cancer: Case Reports vol. 17, 100350, 2025.
Owonikoko et al. IDeate-Lung02: a Phase 3 study of second-line ifinatamab deruxtecan in patients with relapsed small cell lung cancer. Future Oncology, 1-8, Oct. 7, 2025.
Andreas et at. Second-line treatment strategies and clinical outcomes after progression on chemoimmunotherapy in extensive-stage small-cell lung cancer. Lung Cancer vol. 209108786 Oct. 2025.
Wade Iams et al. HSD69 Patient Characteristics and Treatment Patterns in Extensive-Stage Small Cell Lung Cancer (ES-SCLC). Value in Health, vol. 28, Issue 6, S238 Abstract, 2025.
Wade Iams et al. HSD69 Patient Characteristics and Treatment Patterns in Extensive-Stage Small Cell Lung Cancer (ES-SCLC). Value in Health, vol. 28, Issue 6, S238 Poster, 2025.
Cuevas. Development of Lurbinectedin for the Treatment of SCLC. IL3. European conference on marine natural products, 2025.
NDABLA Multi-disciplinary Review and Evaluation NDA 213702 Zepzelca (Lurbinectedin). Apr. 2, 2018.
Falcón et al. Phase I results on the efficacy, safety and pharmacokinetics of lurbinectedin and irinotecan in advanced solid tumors. Invest New Drugs 43, 955-967 (2025).
Zhang and Gay. Sacituzumab govitecan: another emerging treatment option for patients with relapsed small cell lung cancer. TLCR vol. 14, No. 9, Sep. 11, 2025.
Jeffrey et al. Clinical benefit analysis of a phase I/II study using lurbinectedin combined with ipilimumab and nivolumab as first-line therapy for advanced soft tissue sarcoma (NCT05876715). EMSO 2025. Abstract.
Jeffrey et al. Clinical benefit analysis of a phase I/II study using lurbinectedin combined with ipilimumab and nivolumab as first-line therapy for advanced soft tissue sarcoma (NCT05876715). Emso 2025. Poster.
Paz-Ares et al. Patterns of disease progression (PD) and eU'icacy associated with tumour burden from the phase III IMforte study of lurbinectedin (lurbi) + atezolizumab (atezo) as first-line (1L) maintenance treatment (tx) in ES-SCLC. EMSO 2025. Abstract.
Paz-Ares et al. Patterns of disease progression (PD) and eU'icacy associated with tumour burden from the phase III IMforte study of lurbinectedin (lurbi) + atezolizumab (atezo) as first-line (1L) maintenance treatment (tx) in ES-SCLC. EMSO 2025. Poster.
PharmaMar Group announces financial resultsfor fiscal year 2024, Feb. 28, 2025.
PharmaMar signs a new licensing, development and commercialization agreement with Merck for lurbinectedin in Japan, Apr. 3, 2025.
PharmaMar's lurbinectedin transformative data in combination with atezolizumab for small cell lung cancer will be shared as oral presentation at ASCO 2025.
PharmaMar's Zepzelca® (lurbinectedin) receives commercialization approval for the treatment of relapsed small cell lung cancer in Argentina, May 19, 2025.
PharmaMar has submitted EU marketing authorization application for lurbinectedin in combination with atezolizumabin first-line maintenance therapy for extensive-stage small cell lung cancer, May 21, 2025.
Moreno et al. Impact of a Moderate CYP3A4 Inducer (Bosentan) on Lurbinectedin Pharmacokinetics and Safety in Patients with Advanced Solid Tumors: An Open-Label, Two-Way, Crossover, Phase Ib Drug—Drug Interaction Study. Pharmaceuticals 2024, 17, 182.
Huang et al. Tumor-associated macrophages in non-small-cell lung cancer: From treatment resistance mechanisms to therapeutic targets. Critical Reviews in Oncology / Hematology 196 (2024) 104284.
Jo et al. The novel ATR inhibitor M1774 induces replication protein overexpression and broad synergy 2 with DNA-targeted anticancer drugs. Mol Cancer Ther (2024).
Badin. Considerations for selecting second-line treatment in patients with progressive small cell lung cancer and the use of Lurbinectedin in this setting. Cancer Treatment and Research Communications 39 (2024) 100803.
Li et al. Post-marketing safety evaluation of lurbinectedin: a pharmacovigilance analysis based on the FAERS database. Front. Pharmacol. vol. 15—2024.
Carlisle and Leal. Advancing immunotherapy in small cell lung cancer. Cancer. 2023; 129:3525-3534.
Moreno et al. Pharmacokinetics and Safety of Lurbinectedin Administrated with Itraconazole in Cancer Patients: A Drug—Drug Interaction Study. Mar. Drugs 2024, 22, 178.
Cote et al. Safety and Efficacy of Combination Lurbinectedin Plus Doxorubicin From a Phase 1B Trial in Patients With Advanced/ Metastatic STS. Clin Cancer Res OF1-OF7, 2024.
Spigel et al. Resilient Part 2: A Randomized, Open-Label Phase III Study of Liposomal Irinotecan Versus Topotecan in Adults With Relapsed Small Cell Lung Cancer. J Clin Oncol. Jul. 1, 2024;42(19):2317-2326.
Pons-Tostivint et al. Second-line treatment outcomes after first-line chemotherapy plus immunotherapy in Extensive-Stage small cell lung cancer (ES-SCLC) patients: A large French multicenter study. Lung Cancer. vol. 194, 107887, 2024.
Andrini et al. Challenges and future perspectives for the use of temozolomide in the treatment of SCLC. Cancer Treat Rev. 3:129:102798, 2024.
Mirzapoiazova et al. Teriflunomide/leflunomide synergize with chemotherapeutics by decreasing mitochondrial fragmentation via DRP1 in SCLC. iScience vol. 27, Issue 6, 2024.
Scattolin et al. The emerging role of Schlafen-11 (SLFN11) in predicting response to anticancer treatments: Focus on small cell lung cancer. Cancer Treat Rev. 128:102768, 2024.
Moussa et al. Durable Objective Response to Lurbinectedin in Small Cell Bladder Cancer with TP53 Mutation: A Molecular-Directed Strategy. y. Curr. Oncol. 2024, 31,3342-3349, 2024.
Solta et al. Small cells—big issues: biological implications and preclinical advancements in small cell lung cancer. Molecular Cancer vol. 23, Article No. 41 (2024).
Liao et al. Functionalized graphene oxide NPs as a nanocarrier for drug delivery system in quercetin/ lurbinectedin as dual sensitive therapeutics for A549 lung cancer treatment. Heliyon 10 (2024).
Ghalib et al. A phase I safety and efficacy clinical trial of plocabulin and gemcitabine in patients with advanced solid tumors. Invest New Drugs (2024).
Oronky et al. Lost at SCLC: a review of potential platinum sensitizers. Cancer Metastasis Rev (2024).
Byrne et al. Phase II study of nab-paclitaxel with gemcitabine for relapsed/refractory small cell lung cancer. Front. Oncol. 14:1303268, 2024.
Meyer et al. The Use of Lurbinectedin for the Treatment of Small Cell and Neuroendocrine Carcinoma of the Prostate. Clinical Genitourinary Cancer, vol. 22, 102172, 2024.
Cigrang et al. Novel synthetic ecteinascidins exhibit potent anti-melanoma activity by suppressing superenhancer-driven oncogenic trans. https://doi.org/10.1101/2024.03.26.586754, 2024.

(56) References Cited

OTHER PUBLICATIONS

Xing et al Phase 2 dose-ranging study to evaluate the efficacy and safety of liposomal irinotecan (LY01610) as a second-line treatment for patients with relapsed small cell lung cancer. eClinicalMedicine 2024;75: 102791, 2024.
Shaw et al Recent treatment patterns and real-world survival following first-line anti-PD-L1 treatment for extensive-stage small cell lung cancer. The Oncologist, 2024, XX, 1-11.
Anusha Stability Indicating LC—ESI-MS/MS Method Development and Validation for the Quantitation of Lurbinectedin in Biological Matrices. IJPQA, vol. 15 Issue 3, Jul-Sep. 2024.
Becerra et al Promising Response to Lurbinectedin in NUT Carcinoma: a case report and review of emerging therapeutic strategies. Annals of Oncology. Articles in Press, Oct. 11, 2024.
Guo et al FZ-AD005, a Novel DLL3-Targeted Antibody-Drug Conjugate with Topoisomerase I Inhibitor, Shows Potent Antitumor Activity in Preclinical Models. Mol Cancer Ther (2024) 23 (10): 1367-1377.
Tang et al Efficacy and toxicity of lurbinectedin in subsequent systemic therapy of extensivestage small cell lung cancer: a met analysis BMC Cancer (2024) 24:1351.
Sung Shim et al Real-World Outcomes with Lurbinectedin in Second Line and Beyond for Extensive Stage Small Cell Lung Cancer in Korea. Lung Cancer: Targets and Therapy 2024:15 149-159.
Girard et al Lurbinectedin in extensive-stage small-cell lung cancer: a brief report of the IFCT-2105 Lurbiclin study. ESMO vol. 9, Issue 12103968Dec. 2024.
Zugazagoitia et al Facts and Hopes on Cancer Immunotherapy for Small Cell Lung Cancer. Clin Cancer Res 2024:30:2872-B3.
Tumini E, Herrera-Moyano E, San Martín-Alonso M, Barroso S, Galmarini CM, Aguilera A. The Antitumor Drugs Trabectedin and Lurbinectedin Induce Transcription-Dependent Replication Stress and Genome Instability. Mol Cancer Res. Mar. 2019;17(3):773-782. doi: 10.1158/1541-7786.MCR-18-0575. Epub Dec. 14, 2018. PMID: 30552231; PMCID: PMC6398590.
Kuter—Managing Thrombocytopenia Associated With Cancer Chemotherapy Oncology vol. 29 No. 4, 2015.
Calles et al. Unveiling the Mechanism of Lurbinectedin's Action and Its Potential in Combination Therapies in Small Cell Lung Cancer. Mol Cancer Ther. 2024.
Vince et al. Real-world comparison of the efficacy and safety of atezolizumab versus durvalumab in extensive-stage small cell lung cancer. Lung Cancer 198 (2024) 107999.
Chakraborty et al. Lurbinectedin sensitizes PD-L1 blockade therapy by activating STING-IFN signaling in small-cell lung cancer. Cell Reports Medicine 5, 101852, 2024.
Gomez et al. Lurbinectedin is an effective alternative to platinum rechallenge and may restore platinum sensitivity in patients with sensitive relapsed small cell lung cancer. Expert Review of Anticancer Therapy, 25(1), 27-40, 2024.
Ren et al. Recent advances in immunotherapy for small cell lung cancer Curr Opin Oncol 2025, 37:17-26.
Salarolio et al. Ecteinascidin synthetic analogues: a new class of selective inhibitors of transcription, exerting immunogenic cell death in refractory malignant pleural mesothelioma. Journal of Experimental & Clinical Cancer Research (2024) 43:327.
Da Hyun Kang et al. Navigating the Complexity of Resistance in Lung Cancer Therapy: Mechanisms, Organoid Models, and Strategies for Overcoming Treatment Failure. Cancers 2024, 16, 3996.
Cigrang et al. Pan-inhibition of super-enhancer-driven oncogenic transcription by next-generation synthetic ecteinascidins yields potent anti-cancer activity. Nature Communications | (2025) 16:512.
Kalemkerian et al. Systemic Therapy for Small Cell Lung Cancer: ASCO Guideline Rapid Recommendation Update. J Clin Oncol 43:101-105, 2024.
Gómez-Puerto et al. Emerging treatments for sarcoma: from 2024 onward Expert Opin Emerg Drugs. 2025.
Fudio et al. A model-based head-to-head comparison of single-agent lurbinectedin in the pivotal Atlantis Study. Front. Oncol., Jun. 15, 2023.
Chakraborty et al. De Novo and Histologically Transformed Small-Cell Lung Cancer Is Sensitive to Lurbinectedin Treatment Through the Modulation of EMT and NOTCH Signaling Pathways. Clin Cancer Res. Sep. 1, 2023;29 (17):3526-3540.
Damiano et al. Real-world evidence in extensive disease small cell lung cancer: The missing piece of the puzzle. Critical Reviews in Oncology/Hematology vol. 207, Mar. 2025, 104618.
Calles et al. Lurbinectedin plus pembrolizumab in relapsed small cell lung cancer (SCLC): the phase I/II Luper study J Thorac Oncol Feb. 10, 2025:S1556-0864(25)00064-4, 2025.
Cote et al. Saludo: a randomized phase IIb/III study oflurbinectedin plus doxorubicin as first-line treatment inleiomyosarcoma. Future Oncology, 1-9, 2025.
PharmaMar Group reports 2023 annual results, Feb. 28, 2024.
The PharmaMar Group presents financial results for the first quarter of 2024, Apr. 23, 2024.
Jazz Pharmaceuticals Provides Update on Zepzelca® (lurbinectedin) Phase 3 LAGOON Trial in Second-Line Small Cell Lung Cancer, https://www.prnewswire.com/news-releases/jazz-pharmaceuticals-provides-update-on-zepzelca-lurbinectedin-phase-3-lagoon-trial-in-second-line-small-cell-lung-cancer-302798651.html, Jun. 12, 2026.
PharmaMar Press Release—PharmaMar Reports Update on Phase III Lagoon Trial in Second Line for Small Cell Lung Cancer, Jun. 12, 2026.

* cited by examiner

METHOD OF TREATING SCLC AND MANAGING NEUTROPENIA

FIELD OF THE INVENTION

Provided are methods for the treatment of SCLC patients by administering therapeutic amounts of lurbinectedin by intravenous infusion. Also provided are methods of treating cancer by administering lurbinectedin in combination with other anticancer drugs, in particular topoisomerase inhibitors. The invention further relates to the administration of lurbinectedin in combination with anti-emetic agents for effective control of symptoms related to nausea and vomiting, reduced lurbinectedin dosages to achieve a safer administration and an increase in the number of treatment cycles. Stable lyophilized formulations of lurbinectedin are also provided.

BACKGROUND TO THE INVENTION

Lung cancer is the leading cause of cancer death in both men and women in the United States. In 1998, an estimated 171,500 new cases were diagnosed, and about 160,100 deaths resulted from this disease. More women die from lung cancer than breast, ovarian, and uterine cancer combined, and 4 times as many men die from lung cancer than from prostate cancer.

Lung cancer is a disease in which malignant (cancer) cells form in the tissues of the lung. The two major types of lung cancer are small cell lung cancer (SCLC) and non-small cell lung cancer (NSCLC). SCLC comprises only about 13-15% of all lung cancers at diagnosis; however, SCLC is the more aggressive form of lung cancer. With SCLC, the cancer cells tend to grow quickly and travel to other parts of the body, or metastasize, more easily. Its incidence is associated with smoking, almost two thirds of patients present with advanced disease, and although response rates to chemotherapy are high, the benefit is short-lived. The median survival of patients with untreated SCLC is two to four months (Clark, 1998; Glisson, 2003; Davies, 2004). The most common regimens include cisplatin or carboplatin and etoposide. Unfortunately, despite the 40-90% response rate to first-line chemotherapy, long-term survival is unusual because patients develop resistance to chemotherapy and relapse (Sundstrom, 2005; Jackman, 2005). The overall expected mean survival after disease relapse without treatment is two to four months (Huisman, 1999).

Treatment and survival have not changed substantially during the past two decades. Even limited-stage disease is rarely cured with radical local therapy (surgery or radiotherapy) and systemic chemotherapy (platinum plus etoposide) remains a cornerstone of first-line treatment in SCLC.

Topotecan is the only approved drug for second-line treatment of patients with a chemotherapy-free interval longer than 60 days. Topotecan monotherapy improves survival and quality of life, as well as cancer-related symptoms in the second-line setting. Alternatively, doxorubicin-based combination therapy can be administered with a similar outcome but a slightly lower rate of symptom control. In refractory patients no standard therapy exists. Amrubicin, a novel anthracyline, showed promising activity in refractory and relapsed patients. Phase Ill trials are ongoing. Other agents with activity include paclitaxel, docetaxel, gemcitabine, bendamustine and vinorelbine.

During the past few years, several clinical trials have evaluated the effect of addition of immunotherapy to conventional chemotherapy in patients with extensive SCLC. Checkpoint inhibitors are currently under investigation, especially the CTLA-4 and PD-1/PD-L1 inhibitors. Nivolumab and Pembrolizumab were the first immunotherapeutic agents to be approved by the FDA for patients with metastatic SCLC with disease progression on or after platinum-based chemotherapy and at least one other prior line of chemotherapy.

Lurbinectedin (PM01183) is a synthetic tetrahydropyrrolo [4, 3, 2-de]quinolin-8(1H)-one alkaloid analogue with antineoplastic activity. Lurbinectedin is a selective inhibitor of oncogenic transcription, induces DNA double-strand break generating apoptosis, and modulates the tumor microenvironment. For example, by inhibiting active transcription in tumor-associated macrophages, lurbinectedin downregulates IL-6, IL-8, CCL2, and VEGF.

Lurbinectedin has demonstrated a highly potent in vitro activity against solid and non-solid tumor cell lines as well as a significant in vivo activity in several xenografted human tumor cell lines in mice, such as those for breast, kidney and ovarian cancer. Preliminary clinical results have shown that lurbinectedin has activity as a second line therapeutic as a single agent in SCLC. There is a need for treatment for SCLC and other solid tumors.

SUMMARY OF THE INVENTION

Phase 2 clinical trial results demonstrate an at least 30% (35.2%) overall response rate for SCLC patients with lurbinectedin as a second line agent administered as single agent. Results from a phase 1b-2 trial in solid tumor patients demonstrated activity of a combination of lurbinectedin and irinotecan, particularly in SCLC, endometrial carcinoma, soft tissue sarcoma and glioblastoma. Accordingly, provided herein are methods of treating SCLC, including metastatic SCLC, in patients in need thereof, especially those patients whose SCLC has progressed after prior therapy, such as platinum-containing therapy or immunotherapy, including among others patients who have failed to respond or to respond adequately to prior treatment, those who may have responded to prior treatment but then experienced progression of the disease, and those who may have had such response followed by progression more than once. Also provided are methods of treating solid tumors, particularly SCLC, endometrial carcinoma, soft tissue sarcoma, and glioblastoma, in patients in need thereof administering lurbinectedin in combination with a topoisomerase inhibitor, particularly irinotecan or SN-38. Stable lyophilized formulations are further provided.

The methods provided herein involve administering to a patient, including an adult patient, suffering from SCLC, including metastatic SCLC, particularly an SCLC patient who has progressed after prior platinum-based chemotherapy, an effective amount of lurbinectedin by intravenous infusion. In certain embodiments, provided are methods of administering to a patient suffering from SCLC, including metastatic SCLC, who has progressed after prior immunotherapy, particularly atezolizumab, including in combination with carboplatin and etoposide, or nivolumab, an effective amount of lurbinectedin by intravenous infusion. Lurbinectedin is preferably administered at a dose of 3.2 $mg/m^2$ every 21 days (or 3 weeks), typically over a period of multiple months, and in most cases until disease progression and death or the patient experiences unacceptable toxicity, depending upon the patient's response to the administration.

In certain embodiments, treatment effective amounts of lurbinectedin may be administered every 21 days or 3 weeks to the patient as a 1-hour IV infusion using dosing levels of 3.2 $mg/m^2$, to achieve mean total plasma Cmax of about 85.6 μg/L to 133.75 μg/L, preferably 107 μg/L, and mean AUC∞ of about 440.8 μg*h/L to 688.75 μg*h/L, preferably 551 μg*h/L. Treatment results in an overall response rate of greater than 30%, progression free survival for a median 3.5 months, (a range of 2.6 months to 4.3 months), including a median of 2.6 months in resistant patient population (CFTI less than 90 days for prior chemotherapy treatment) and a median of 4.6 months in sensitive patient populations (CFTI greater than or equal to 90 days for prior chemotherapy treatment). Overall survival for a median of 9.3 months (resistant patient population of 5.0 months and sensitive patient population of 11.9 months) may be achieved according to the methods disclosed herein.

In an embodiment, provided is a method of managing hematological adverse events associated with lurbinectedin treatment regimen by dose reduction and/or administration of G-CSF. The method provided relates to administering to an SCLC patient a lurbinectedin formulation by IV infusion at a dose of 3.2 $mg/m^2$; assessing, after administering the lurbinectedin, whether the patient experiences an adverse reaction associated with the lurbinectedin administration that is a ≥Grade 3 (severe) non hematological toxicity, Grade 4 thrombocytopenia (platelet count less than 25,000 cells/mm3), Grade 3 thrombocytopenia (platelet count less than 50,000 $cells/mm^3$) with bleeding that requires transfusion, Grade 4 neutropenia (Neutrophil count less than 500 $cells/mm^3$), or any grade neutropenia (Neutrophil count <LLN) that is associated with infection/sepsis or any other of the adverse reactions. At the next scheduled dose, preferably 3 weeks after the prior dose, and once the patient's neutrophil count is greater than 1500 $cells/mm^3$; platelet count is greater than about 100,000 $mm^3$; and hemoglobin levels are greater than about 9 g/d, (i) if the adverse reaction consists of an isolated Grade 4 neutropenia, then administering to the patient a dose of G-CSF and a dose of lurbinectedin that is the same as the previous dose, for example, 3.2 $mg/m^2$, or (ii) if the adverse reaction is a hematological abnormality that is not solely isolated Grade 4 neutropenia, then administering a dose that is reduced compared to the prior dose, for example is 80 to 85% of the prior dose, for example, 2.6 $mg/m^2$ if the prior dose is 3.2 $mg/m^2$. Optionally, if the adverse reaction is isolated Grade 4 neutropenia, then the dose may be reduced at the next scheduled dose, in particular, to 80 to 85% of the prior dose, for example, 2.6 $mg/m^2$ if the prior dose is 3.2 $mg/m^2$.

In the event that after receiving a reduced dosage of lurbinectedin, a patient experiences an adverse event that is a ≥Grade 3 (severe) non hematological toxicity, Grade 4 thrombocytopenia (Platelet count less than 25,000 cells/mm3), Grade 3 thrombocytopenia (Platelet count less than 50,000 cells/mm3) with bleeding that requires transfusion), or any grade neutropenia (Neutrophil count <LLN) that is associated with infection/sepsis or any other of the adverse reactions (but, in certain embodiments, not isolated Grade 4 neutropenia), then at the next scheduled dosage, preferably 3 weeks after the prior dose, and once the patient's neutrophil count is greater than 1500 $cells/mm^3$; platelet count is greater than about 100,000 $mm^3$; and hemoglobin levels are greater than about 9 g/d, administering a second reduced dosage to the patient which is 60 to 65% of the first, unreduced dose, particularly 2.0 $mg/m^2$ (60-65% of the 3.2 mg/m2 dosage). Optionally, if the adverse reaction after the administration of a reduced dosage of lurbinectedin is isolated Grade 4 neutropenia, then the dose may be reduced at the next scheduled dose, in particular, to 60 to 65% of the first, unreduced dose, for example, 2.6 $mg/m^2$ if the initial dose is 3.2 $mg/m^2$.

In another embodiment, provided is a method of managing hematological toxicity, myleosupressive effects and/or hepatotoxicity that may be associated with lurbinectedin administration in the treatment of SCLC, including metastatic SCLC, in a patient, including an adult patient, by dose reduction and/or dose delay. Provided are methods of treating SCLC, including metastatic SCLC, by administering to a patient in need thereof with an absolute neutrophil count of at least 1500 $cells/mm^3$ and a platelet count of at least $100,000/mm^3$, a dose of 3.2 $mg/m^2$ lurbinectedin, preferably by infusion over 60 minutes. In a further embodiment, 21 days after the previous dose, the patient has an absolute neutrophil count of at least 1500 $cells/mm^3$ and a platelet count of at least $100,000/mm^3$ and is administered 3.2 $mg/m^2$ dose of lurbinectedin, preferably by infusion over 60 minutes. In embodiments, the patient is monitored for and has no hepatotoxicity prior to administration of lurbinectedin. Subsequent treatments are administered at 21 day (3 week) intervals to the patient having an absolute neutrophil count of at least 1500 $cells/mm^3$ and a platelet count of at least $100,000/mm^3$, and preferably, does not have any Grade 2 or greater adverse reaction.

In certain embodiments, provided are methods of treating SCLC, including metastatic SCLC, in a patient in need thereof by administering lurbinectedin at a dose of 3.2 $mg/m^2$, including by infusion over 60 minutes, then monitoring the patient for adverse hematological or hepatic reactions or other adverse reaction that is Grade 2 or greater. In the event a patient having been administered a dose of 3.2 $mg/m^2$ lurbinectedin exhibits grade 4 neutropenia (neutrophil count less than 500 $cells/mm^3$) or any febrile neutropenia, then the subsequent dose of lurbinectedin is not administered until the later of 21 days after the prior dose or when the patient exhibits less than grade 1 neutropenia (at least 1500 $cells/mm^3$), which may be greater than 21 days past the previous dose, and then either administering lurbinectedin at a reduced dose of 2.6 $mg/m^2$ every three weeks or administering lurbinectedin at a dose of 3.2 $mg/m^2$ every three weeks with G-CSF prophylaxis. In the event, a patient having been administered a 3.2 $mg/m^2$ dose of lurbinectedin exhibits Grade 3 thrombocytopenia (25,000-50,000 $platelets/mm^3$) with bleeding or Grade 4 thrombocytopenia (less than 25,000 $platelets/mm^3$), then the subsequent dose of lurbinectedin is not administered until the later of 21 days after the previous dose or when the patient exhibits a platelet count of greater than or equal to $100,000/mm^3$ and the subsequent dose is a reduced dose of 2.6 $mg/m^2$ every three weeks (21 days). In the event, a patient having been administered a 3.2 $mg/m^2$ dose of lurbinectedin exhibits hepatotoxicity or other adverse reaction that is either Grade 2 or Grade 3 or 4, then the subsequent dose of lurbinectedin is not administered until the later of 21 days after the previous dose or when the patient exhibits less than or equal to Grade 1 hepatotoxicity (or Grade 1 or less of the other adverse reaction), and the subsequent dose is a dose of 3.2 $mg/m^2$ every three weeks (21 days) if the patient had exhibited Grade 2 hepatotoxicity (or other adverse reaction) and the subsequent dose is a reduced dose of 2.6 $mg/m^2$ every three weeks (21 days) if the patient had exhibited Grade 3 or 4 hepatotoxicity or other adverse reaction. If after dose reduction, the patient exhibits one of Grade 4 neutropenia, or any grade febrile neutropenia, Grade 3 thrombocytopenia with bleeding or Grade 4 thrombocytopenia, or hepatotoxicity or other adverse reaction at Grade 3 or 4, then the subsequent dose is not administered until the later of 21 days or when the patient has recovered as detailed above and then administered a further reduced dose of 2 mg/$m^2$ lurbinectedin every three weeks or, in the case of Grade 4 neutropenia, is administered the same dose of lurbinectedin as the prior dose with G-CSF prophylaxis. If the patient ceases to tolerate (that is exhibits, after lurbinectedin administration, one of Grade 4 neutropenia, or any grade febrile neutropenia, Grade 3 thrombocytopenia with bleeding or Grade 4 thrombocytopenia, or hepatotoxicity or other adverse reaction at Grade 3 or 4) at a dose of 2 mg/$m^2$ lurbinectedin or if delay in administration is greater than 2 weeks past the scheduled dose (at 21 days after the prior dose) for the patient to recover and meet the criteria for lurbinectedin administration, then treatment is discontinued.

Provided are methods of treating SCLC or solid tumor in a patient in need thereof by administration of a dose of 2 to 3.2 mg/$m^2$ lurbinectedin and avoiding co administration with a strong or a moderate CYP3A inhibitor or a strong or moderate CYP3A inducer. In certain embodiments, provided are methods of treating SCLC or solid tumor in a patient in need thereof where the patient is also administered a moderate CYP3A inhibitor, then administering a reduced dose of lurbinectedin, for example a dose of 2.6 mg/$m^2$ or a dose of 2 mg/$m^2$ to said patient every 3 weeks (21 days).

Also provided are embodiments in which an antiemetic is prophylactically administered prior to administration of lurbinectedin-associated (acute and delayed-phase) nausea and/or vomiting comprising administering an antiemetic prophylaxis on the day of and prior to administering a dose of 2 to 3.2 mg/$m^2$ lurbinectedin to the patient, particularly where the antiemetic agents comprise a corticosteroid and a serotonin antagonist. The treatment may be for SCLC, including metastatic SCLC, or any other solid tumor in a patient in need of such treatment. In certain embodiments, the corticosteroid is dexamethasone, preferably a dose of 8 mg administered intravenously, or a dose of a corticosteroid that is equivalent to 8 mg dexamethasone intravenously and where the serotonin antagonist is ondansetron, preferably a dose of 8 mg administered intravenously, or a dose of serotonin antagonist that is equivalent to 8 mg ondansetron administered intravenously. In certain embodiments, antiemetic therapy is administered post-infusion on the day of, or for 2, 3, or 4 days after administration of lurbinectedin, preferably comprising administering a corticosteroid, a serotonin antagonist and metoclopramide. In specific embodiments, the corticosteroid is dexamethasone administered orally at a dose of 4 mg, or a dose of corticosteroid equivalent to 4 mg oral dexamethasone; the serotonin antagonist is ondansetron administered orally at a dose of 8 mg, or a serotonin antagonist equivalent to 8 mg oral ondansetron; and metoclopramide is administered at a dose of 10 mg either intravenously or orally, or the dose equivalent to oral or intravenous 10 mg metoclopramide, wherein the metoclopramide is administered every 8 hours.

One aspect of the invention is a method of treating patients with solid tumors in need thereof by administering lurbinectedin in combination with a topoisomerase inhibitor, particularly irinotecan. In particular embodiments, the solid tumor patient is treated with a treatment regimen in which lurbinectedin is administered at a dose of 1 to 2.5 mg/$m^2$ on day 1 with a dose of 75 mg/$m^2$ irinotecan administered on day 1 and day 8 of the treatment cycle, and the irinotecan is administered with G-CSF. The treatment cycle is generally 21 days such that, in the second treatment cycle, a dose of 1 to 2.5 mg/$m^2$ lurbinectedin is administered with a dose of 75 mg/$m^2$ irinotecan is administered on day 22 and a dose of 75 mg/$m^2$ irinotecan is administered 7 days later on day 29 after the initial treatment. Subsequent treatments are administered generally every three weeks with the combination of 1 to 2.5 mg/$m^2$ lurbinectedin and 75 mg/$m^2$ irinotecan administered on day 1 of the cycle and 75 mg/$m^2$ irinotecan administered on day 8, with G-CSF. In certain embodiments, if the patient exhibits hematologic toxicity following the day 1 combination dosage, the dose of irinotecan is not administered at day 8. In some embodiments, the solid cancer is selected from endometrial cancer, SCLC, soft tissue sarcoma (including Ewing and synovial sarcoma), glioblastoma, pancreatic adenocarcinoma, mesothelioma, colorectal carcinoma, and epithelial ovarian cancer. In preferred embodiments, the solid tumor is endometrial cancer, SCLC, soft tissue sarcoma (including Ewing or synovial sarcoma), or glioblastoma.

In one aspect, provided is a stable, lyophilized formulation of lurbinectedin comprising lurbinectedin, a buffer derived from an organic acid (e.g., an organic carboxylic acid, such as lactate buffer) and a disaccharide, which formulation has a pH of 3.8 to 4.5 when reconstituted with 8 mL of water. Reference to reconstitution of 4 mg lurbinectedin in 8 mL having a concentration of 0.5 mg/mL may be based on a calculated concentration of 0.47 mg/mL in 8.55 mL.

In some embodiments, the lyophilized composition comprises or consists of 4 mg lurbinectedin, 22.1 mg lactic acid, 5.1 mg sodium hydroxide and 800 mg sucrose (or comprises or consists of these ingredients in this ratio). The composition is preferably packaged in a 30 ml vial and may be reconstituted in 8 mL water, to yield a solution containing 0.5 mg/ml lurbinectedin.

In some embodiments, the lyophilized formulation may be stored for 24 months or 36 months or more at 5° C.±3° C., during which time the lurbinectedin retains its therapeutic effectiveness and exhibits minimal chemical degradation. For example, after 24 months or 36 months of storage, the amount of Impurity D (lurbinectedin degradation product resulting from deacetylation of lurbinectedin) present in the composition is not more than 0.8% wt./wt. of the total lurbinectedin weight. In certain embodiments, the stored formulation does not contain more than 2.0%, 1.5%, or 1.3% (area or wt/wt) total degradation products.

Also provided are methods of storing the lurbinectedin lyophilized formulation and methods of treating SCLC and solid tumors by administration of a lurbinectedin infusion solution prepared from a stored, stable lyophilized lurbinectedin formulation.

The present invention identifies methods of treatment using lurbinectedin alone or in combination with further agents. Where reference is made to a method of treatment the present invention also encompasses lurbinectedin and/or said further agents in the manufacture of a medicament for the treatment of cancer and also lurbinectedin and/or said further agents for use in the treatment of cancers as disclosed herein.

FIG. **7*a***: IR of Form A of lurbinectedin (Batch P04).

FIG. **7*b***: IR of Form B of lurbinectedin (Batch 1711182-2).

Figure 8:
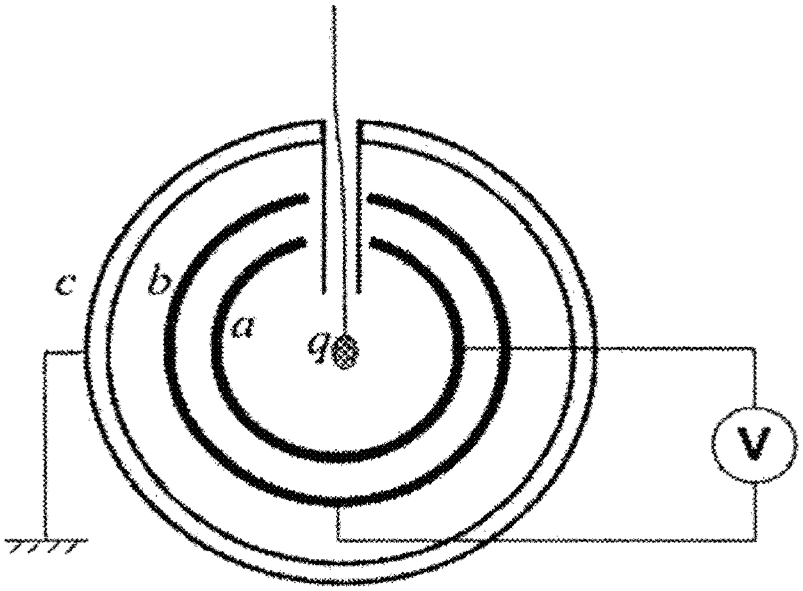

FIG. 8: Scheme of the Faraday cage.

FIG. **9*a***: Electrostatic charge (nC) of different amounts of Form A of lurbinectedin (Batch P04) and Form B of lurbinectedin (Batch 1924129-LT).

FIG. **9*b***: Electrostatic charge (nC) of different amounts of Form A of lurbinectedin (Batch R05) and Form B of lurbinectedin (Batch 1924128-LT).

FIG. **10*a***: Charge density of Form A of lurbinectedin (Batch P04) and Form B of lurbinectedin (Batch 1924129-LT).

FIG. **10*b***: Charge density of Form A of lurbinectedin (Batch R05) and Form B or lurbinectedin (Batch 1924128-LT).

DETAILED DESCRIPTION OF THE INVENTION

Provided herein are methods of for the efficacious treatment of small cell lung cancer (SCLC) based on the administration of lurbinectedin as monotherapy. Also provided are methods of treating solid tumors by administration of a combination of lurbinectedin and irinotecan. Such methods may be carried out by administration of lurbinectedin prepared from stable, lyophilized formulations disclosed herein.

Lurbinectedin

Lurbinectedin is a synthetic alkaloid and an ecteinascidin analog having the following chemical structure:

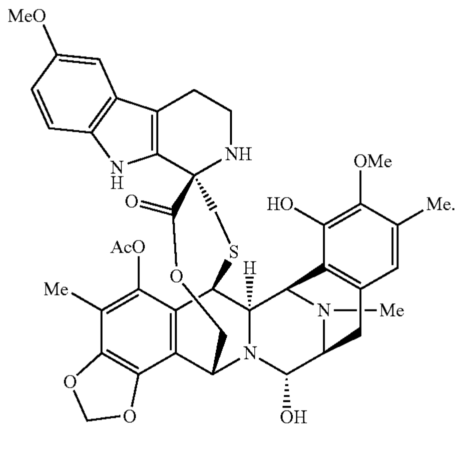 [SMILES: COc1ccc2[nH]c3c(c2c1)CCN[C@]31CS[C@@H]2c3c(OC(C)=O)c(C)c4c(c3[C@H](COC1=O)N1[C@@H]2[C@H]2c3c(cc(C)c(OC)c3O)C[C@@H]([C@@H]1O)N2C)OCO4]

It is described for example, in U.S. Pat. No. 7,763,615, incorporated by reference herein in its entirety. Lurbinectedin may be prepared according to methods known in the art, for example, the process disclosed in International Application Publication PCT WO 2003/014127, which is incorporated herein by reference.

Any lurbinectedin compound referred to herein is intended to represent hydrates, solvates, amorphous and crystalline or partially crystalline forms, and mixtures thereof when such forms exist in the medium. In addition, lurbinectedin compounds referred to herein may exist in isotopically-labelled forms. All geometric hydrates, solvates, and isotopically labelled forms of the compounds referred to herein, and mixtures thereof, are considered within the scope of the formulations and methodologies of this invention.

In the present application, by "cancer" it is meant to include tumors, neoplasias, and any other malignant disease having as cause malignant tissue or cells.

The term "treating", as used herein, unless otherwise indicated, means reversing, alleviating, or inhibiting the progress of the disease or condition to which such term applies, or one or more symptoms of such disorder or condition. The term "treatment", as used herein, unless otherwise indicated, refers to the act of treating as "treating" is defined immediately above. In particular, the methods of "treatment" or "treating" herein may be used for alleviating one or more symptoms of solid tumors, delaying progression of solid tumors, shrinking tumor size in a solid tumor patient, inhibiting solid tumor growth, prolonging overall survival, prolonging progression free survival, preventing or delaying solid tumor metastasis, reducing (such as eradicating) preexisting solid tumor metastasis, reducing incidence or burden of preexisting solid tumor metastasis, or preventing recurrence of solid tumors.

The term "immunotherapy," as used herein, means therapy that modulates the immune response, including promoting an immune response or blocking inhibition of an immune response, to cancer cells, for example, but not limited to, antibodies, proteins or other agents that bind to a checkpoint inhibitor, such as, CTLA-4, PD-1, PD-L1 and others with like activity that promote immune response to cancer cells. Examples of immunotherapies include, but are not limited to, atezolizumab, nivolumab, pembrolizumab, ipilimumab, cemiplimab, durvalumab, avelumab and the like.

The grades of adverse events, such as neutropenia, thrombocytopenia, hepatotoxicity and other adverse reactions are according to the criteria set forth in the National Cancer Institute Common Terminology Criteria for Adverse Events (NCI CTCAE), version 4.0 (May 28, 2009). Generally the Grades are as follows: Grade 1: Mild; asymptomatic or mild symptoms; clinical or diagnostic observations only; intervention not indicated; Grade 2: Moderate; minimal, local or noninvasive intervention indicated; limiting age-appropriate instrumental activities of daily living, such as food preparation, etc.; Grade 3: Severe or medically significant but not immediately life-threatening; hospitalization or prolongation of hospitalization indicated; disabling; limiting self care activities of daily living, such as dressing, toileting, etc. but not bed ridden; Grade 4: Life-threatening consequences; urgent intervention indicated; Grade 5: Death related to adverse event.

Treatment of SCLC

Embodiments of this invention include methods of treating small cell lung cancer (SCLC), including metastatic SCLC, in a patient suffering therefrom by administering to the patient a therapeutically effective amount of lurbinectedin according to dosing regimen of one or more treatment cycles using pharmaceutical formulations of lurbinectedin described herein. Lurbinectedin therapy, in certain embodiments, is second line therapy, such that patients have previously been administered, and disease has progressed in response to, therapies such as platinum-containing therapy or platinum-based chemotherapy and/or immune-oncology therapy. Such treatment regimens are preferably administering to the SCLC patient a dose of 2.0 to 3.2 $mg/m^2$ lurbinectedin, in preferred embodiments at least for an initial dose, 3.2 $mg/m^2$, by intravenous infusion, preferably over 1 hour, every three weeks (or 21 days), provided that dose may be reduced and/or delayed depending upon the occurrence of adverse events, particularly hematological abnormalities and hepatotoxicity as disclosed herein. In some embodiments, the SCLC patient is administered 3.2 $mg/m^2$ by intravenous infusion over 60 minutes repeated every 3 weeks until disease progression or unacceptable toxicity (for example, when a patient does not recover to meet criteria for dosing greater than 5 weeks after the prior dose or ceases to tolerate a second reduced dose of 2.0 $mg/m^2$). In aspects of the invention, treatment results in an overall response rate of greater than 30%, including greater than 35% or 35.2%; progression free survival for a median of 3.5 months, including 2.6 to 4.6 months, or 2.6 months (in resistant patient population (chemotherapy free interval (CTFI) less than 90 days)) to 4.6 months (in sensitive patient populations (CTFI greater than or equal to 90 days)); and overall survival for a median of 9.3 months (resistant patient population (CTFI less than 90 days) of 5.0 months and sensitive patient population (CTFI greater than or equal to 90 days) at 11.9 months).

In various embodiments, the invention provides methods for treating SCLC, including metastatic SCLC, in a patient in need thereof, especially those whose SCLC has progressed after prior therapy such as platinum-containing therapy or platinum-based chemotherapy, immunotherapy, or both, including among others patients who have failed to respond or to respond adequately to prior treatment, those who may have responded to prior treatment but then experienced progression of the disease, and those who may have had such response followed by progression more than once.

In some embodiments, the present disclosure provides methods for treating metastatic SCLC. In some embodiments, the present disclosure provides methods for treating adult patients with metastatic SCLC with disease progression after platinum-based chemotherapy.

SCLC Patients

Patients with SCLC, including metastatic SCLC, who fail to respond or progress through first-line platinum containing chemotherapy and/or immunotherapy are considered to be "refractory." Patients who initially respond to initial or "first-line" chemotherapy comprising platinum agents and then relapse/progress within 90 days (3 months) are considered to be "resistant." Patients who respond to initial treatment but then relapse or whose tumors progress within about 91 to 180 days (3-6 months) after the cessation of first-line therapy with platinum agents are considered sensitive and considered herein to have a "91 to 180 day progressive" SCLC. Patients who respond to initial relapse or whose tumors progress after 180 days are "sensitive"

The lurbinectedin therapy can be second-line therapy wherein the SCLC patient has been previously treated with one or more other chemotherapeutic agents such as carboplatin or cisplatin (platinum-based chemotherapy) and etoposide. In particular, the treatments are suited for SCLC patients who are relapsing or refractory to previous chemotherapy. In some embodiments, the SCLC patient ceased to respond or ceased to respond adequately to prior platinum-containing therapy or had no response to prior platinum-containing therapy. More specifically, lurbinectedin therapy can be used when a SCLC patient is refractory, resistant, or relapsed/progressive, including in certain embodiments, within 0 to 90 days, or within 91 to 180 days, after cessation of first-line platinum-containing chemotherapy, and, optionally, radiation treatment. SCLC patients that progress within 0 to 90 days or within the 91 to 180 day period after cessation of the first-line therapy, as well as patients whose SCLC is refractory to treatment and progress, including within 90 days, 180 days or at any time, or whose SCLC responds to initial treatment and then progresses within 90 days, 180 days or at any time of cessation of initial treatment, can advantageously be treated with lurbinectedin so as to increase one or more of their lengths of progression-free survival, overall survival, or duration of response. In some embodiments, the SCLC patient had a chemotherapy-free interval of at least 90 days, at least 120 days, at least 150 days, or at least 180 days after prior administration of the prior platinum containing therapy. In specific embodiments, the patient had not received platinum-containing therapy in at least 30 days or at least 60 days or at least 90 days prior to administration of lurbinectedin. In some embodiments, the present disclosure provides methods of treating patients with SCLC who have progressed after prior platinum-containing therapy. In some embodiments, the present disclosure provides methods of treating adult patients with metastatic SCLC with disease progression after platinum-based chemotherapy.

The lurbinectedin therapy can also be administered following first-line platinum-based chemotherapy, such as carboplatin or cisplatin and etoposide, in combination with checkpoint inhibitors, such as atezolizumab, pembrolizumab, ipilimumb, durvalumab, or a combination thereof, or following second-line therapy with nivolumab or other immunotherapy, such as atezolizumab, pembrolizumab, ipilimumab or durvalumab. In particular, the treatments are suited for SCLC patients who are relapsing or refractory to prior immunotherapy. For example, in some embodiments, lurbinectedin treatment is suited for SCLC patients who are relapsing or refractory to prior first-line carboplatin/etoposide/atezolizumab combination therapy or second-line immunotherapy with nivolumab. In some embodiments, the SCLC patient ceased to respond or ceased to respond adequately to prior immunotherapy or had no response to prior immunotherapy. More specifically, lurbinectedin therapy can be used when a SCLC patient is refractory, resistant, sensitive or relapsed/progressive within 91 to 180 days, after cessation of first-line platinum-containing chemotherapy in combination with immunotherapy or second-line nivolumab, and, in certain embodiments, the patient has received radiation treatment. SCLC patients that progress after cessation of the first-line immunotherapy (including in combination with platinum-containing therapy) or second-line immunotherapy at any time after therapy (including in certain embodiments within 90 days or within 180 days of treatment), as well as patients whose SCLC is refractory to treatment (has a chemotherapy free interval less than 90 days) and progresses within 180 days, or whose SCLC responds to initial treatment and then progresses within 180 days of cessation of initial treatment, can advantageously be treated with lurbinectedin so as to increase one or more of their progression-free survival, overall survival, or duration of response. In some embodiments, the SCLC patient had, with respect to prior treatment, a chemotherapy-free interval, including immunotherapy, of less than 90 days, and in other embodiments, the SCLC had a chemotherapy-free interval of at least 90 days, at least 120 days, at least 150 days, or at least 180 days, but in certain embodiments, no more than 120 days, 150 days or 180 days. In specific embodiments, the patient had not received first-line immunotherapy (in combination with platinum-containing therapy) or second-line immunotherapy in at least 30 days or at least 60 days or at least 90 days prior to administration of lurbinectedin.

It is expected that when a treatment disclosed herein is administered to a SCLC patient, including a metastatic SCLC patient, in need of such treatment, said treatment will produce an effect as measured by the extent of the anticancer effect, the (overall) response rate, the time to disease progression, or the survival rate. In one embodiment, the overall response rate is at least 30%, at least 35%, at least 40%, at least 45%, at least 50%, or at least 60%. In some embodiments, the overall response rate is at least 11%, or at least 20%, or at least 25%, or at least 30%, or at least 35% for patients with a chemotherapy-free interval of less than 90 days or wherein the overall response rate is at least 30% or at least 40% or at least 45%, or at least 50% or at least 55% for patients with a chemotherapy-free interval of at least 90 days. In some embodiments, the duration of response is at least 5.3 months (from 4.1 months to 6.4 months) or at least 4.7 months (from 2.6 months to 5.6 months) for the resistant patient (chemotherapy-free interval of less than 90 days) or wherein the duration of response is at least 6.2 months (from 3.5 months to 7.3 months) for the sensitive patient with a chemotherapy-free interval of at least 90 days.

In certain embodiments, the SCLC patient treated with lurbinectedin as disclosed herein has a progression free survival of at least 3.5 months (from 2.6 months to 4.3 months), and, for resistant patients, a progression free survival of 2.6 months (from 1.3 months to 3.9 months), and for sensitive patients, a progression free survival of 4.6 months (from 2.8 months to 6.5 months). In other embodiments, the SCLC patient treated with lurbinectedin as disclosed herein as an overall survival of 9.3 months (from 6.3 to 11.8 months), and, for resistant patients, an overall survival of 5.0 months (from 4.1 months to 6.3 months), and for sensitive patients, an overall survival of 11.9 months (from 9.7 months to 16.2 months).

Alternatively, the treatment can be a second-line therapy for SCLC with extensive or limited disease that is refractory to initial chemotherapy or progressive within less than 90 days (3 months) of completing first line, platinum-containing therapy. SCLC patients that progress after cessation of the first-line therapy (including within 30 to 90 days of treatment, but may be at anytime), as well as patients whose SCLC is refractory to treatment and progress within 90 days, or whose SCLC responds to initial treatment and then progress within 90 days of cessation of initial treatment, can advantageously be treated with lurbinectedin so as to increase one or more of their progression-free survival, overall survival, or duration of response. In some embodiments, the SCLC patient had a chemotherapy-free interval for the prior treatment of less than 90 days, such as less than 30 days, less than 60 days, or less than 90 days.

In various embodiments, the SCLC patient is first treated with platinum-based chemotherapy therapy and immunotherapy, wherein the platinum-based chemotherapy and the immunotherapy were either given concurrently or consecutively, followed by administering to the patient an effective amount of lurbinectedin or cycles of lurbinectedin treatment as disclosed herein, including administering 3.2 $mg/m^2$ every three weeks (or as delayed or reduced in patients exhibiting hematologic toxicity). For example, in some embodiments, a SCLC patient had received prior immunotherapy comprising administering antibodies targeting PD-L1, CTLA-4, or PD-1, wherein the antibodies are selected from atezolizumab, nivolumab, pembrolizumab, ipilimumb, durvalumab, or a combination thereof. In some embodiments, the patient has previously been administered atezolizumab in combination with platinum-containing therapy and etoposide. In some embodiments, the patient has been administered nivolumab. Thus, provided are methods of treating a SCLC patient who has progressed on atezolizumab (including in combination with carboplatin and etoposide) or on nivolumab with lurbinectedin at 3.2 $mg/m^2$ every three weeks (or as delayed or reduced in patients exhibiting hematologic toxicity).

In some embodiments, the patient administered lurbinectedin is an adult.

Treatment Cycles

Administration of the pharmaceutical compositions comprising lurbinectedin is preferably by intravenous infusion. Infusion times of up to 72 hours can be used, but are preferably between 1 and 24 hours, and generally about 1 hour. Short infusion times which allow treatment to be carried out without an overnight stay in hospital are especially desirable. In a preferred embodiment, lurbinectedin is administered by infusion over 1 hour (60 minutes).

Preferably, the administration of lurbinectedin is performed in cycles. In a preferred administration schedule, an intravenous infusion of lurbinectedin is given to the patient the first day of each cycle and the patient is allowed to recover for the remainder of the cycle. The preferred duration of each cycle is 3 weeks or 21 days. The treatment cycle can, however, be increased or decreased, for example by 1 to 6 days, one week, or two weeks, or longer than 3 weeks, such as 22, 23, 24, 25, 26, 27, 28, 29, 30, 31, 32, 33, 34, 35 or more days depending on patient response to the treatment. In certain embodiments, if the treatment cycle is delayed by more than 2 weeks because the patient has not recovered from an adverse event and does not meet hematological criteria for lurbinectedin treatment, then treatment with lurbinectedin may be discontinued. Administration of lurbinectedin by intravenous infusion during about 1 hour once every 3 weeks is the most preferred administration schedule, although other protocols can be devised as variations. Multiple cycles can be given as needed. Over the course of treatment of SCLC, 1 to 24 doses of lurbinectedin can be administered, with 4 to 8 doses being typically administered, at intervals of about 21 days (three weeks). Intervals of up to six weeks, e.g., 3 to 4 weeks, can be employed if, for example, it is necessary to modify the treatment schedule to reduce or manage side-effects (as discussed in detail below). Over the course of treatment of the cancer, 1 to 24 treatments of lurbinectedin can be administered, with 4 to 8 treatments being typically administered, at intervals of about 21 days (three weeks). In some embodiments, one dose of lurbinectedin is administered per treatment cycle and the patient undergoes at least 1, 2, 3, 4, 5, 6, 7, 8, 9, 10, 11, 12, 13, 14, 15, 16, 17, 18, 19, 20, 21, 22, 23, or 24 treatment cycles. In embodiments, lurbinectedin is administered in 3 week treatment cycles, or as delayed to permit the patient to recover from an adverse event, until disease progression or unacceptable toxicity.

Bioavailability of a drug is defined as the proportion of a drug or other substance that enters the circulation when introduced into the body and so is able to have an active effect. Measures of bioavailability well known in the art include the area under the plasma concentration-time curve (AUC) and the concentration maximum (Cmax). Cmax is the maximum plasma concentration achieved after drug administration.

Provided herein are methods for lurbinectedin dosing by one or more pharmacokinetic parameters, wherein administration of said dosage is effective to treat resistant, refractory or progressive SCLC. In exemplary embodiments, the one or more pharmacokinetic parameters is peak concentration (Cmax) or area-under-the-curve (AUC). In one embodiment, 3.2 $mg/m^2$ of lurbinectedin is administered to a SCLC patient in need thereof as a 1-hour infusion, to achieve mean total plasma Cmax within 80% to 125% of about 107 μg/L and mean AUC∞ within 80% to 125% of about 551 μg*h/L. In some embodiments, lurbinectedin is administered to a SCLC patient on a 1 day on and 20 days off cycle (1/20 cycle). In one embodiment, the administration cycle is a 1/20 cycle and the target mean AUC∞ is about 551 μg*h/L. In one embodiment, the administration cycle is a 1/20 cycle and the target mean AUC∞ is about 551 μg*h/L±5%, about 551 μg*h/L±10%, about 551 μg*h/L±20%, or about 551 μg*h/L±25%, In a preferred embodiments, the administration cycle is a 1/20 cycle and the target mean AUC∞ is within 80% to 125% of about 551 μg*h/L. In one embodiment, the administration cycle is a 1/20 cycle and the mean target Cmax is about 107 μg/L. In one embodiment, the administration cycle is a 1/20 cycle and the mean target Cmax is about 107 μg/L±5%, about 107 μg/L±10%, about 107 μg/L±20%, or about 107 μg/L±25%. In a preferred embodiments, the administration cycle is a 1/20 cycle and the mean target Cmax is within 80% to 125% of about 107 μg/L.

Renal, hepatic, and hematologic impairment need to be ruled out prior to administration lurbinectedin to a patient afflicted with SCLC. In one embodiment, a patient afflicted with SCLC, determined to have an absolute neutrophil count of at least 1500 $cells/mm^3$, a platelet count of at least $100,000/mm^3$, and, optionally, hemoglobin levels of at least 9 g/dL (with transfusion if necessary), is administered a first dose of about 3.2 $mg/m^2$ lurbinectedin. In another embodiment, a patient afflicted with SCLC, determined to have a calculated hepatic clearance of greater than 30 mL/min and an AST or ALT less than 3×ULN or bilirubin less than 1.5×ULN, and a calculated creatinine clearance greater than 30 mL/min, is administered a first dose of about 3.2 $mg/m^2$ lurbinectedin. A second dose of 3.2 $mg/m^2$ lurbinectedin is administered to the patient about 21 days after the first dose, and further dosing at this level is continued if hematological, renal, and hepatic parameters remain stable. In a particular embodiment, the patient is administered a dose of lurbinectedin, particularly, an initial dose or scheduled dose 3 weeks after a prior dose, at 3.2 $mg/m^2$, or a reduced dose, if the patient has an absolute neutrophil count of at least 1500 $cells/mm^3$ and a platelet count of at least $100,000/mm^3$. To achieve the preferred dosing, preferably about 3.2 $mg/m^2$ of lurbinectedin is administered per dose, e.g., per intravenous infusion. Dosing of lurbinectedin can include about 3.2 $mg/m^2$ lurbinectedin per dose, e.g., per intravenous infusion or a reduced dose thereof as discussed below.

Antiemetic Treatment

Best supportive care for SCLC, including metastatic SCLC, and in adult patients, and solid tumor treatment comprises a number of palliative treatments. For example, in one embodiment of the invention, best supportive care includes one or more, and preferably all, administration of analgesics to control pain, management of constipation, and treatment of dyspnea and treatment of anemia, e.g., by transfusions, so as to maintain hemoglobin levels (i.e., >9 g/dL).

In other embodiments, therapies are administered to specifically prevent and treat or manage nausea and/or vomiting associated with lurbinectedin administration, are set forth below.

Chemotherapeutics differ in their emetogenicity. In the absence of antiemetic prophylaxis, agents associated with >90% risk of emesis are classified as highly emetogenic chemotherapy and those associated with 30%-90% risk of emesis classified as moderately emetogenic chemotherapy.

Aspects include methods of prevention and treatment of lurbinectedin-induced (acute and delayed-phase) nausea and/or vomiting, wherein an effective antiemetic amount of a serotonin antagonist or corticosteroid, or a combination thereof, are administered to the patient prior to administration of lurbinectedin, particularly immediately prior to lurbinectedin administration, in order to reduce the side effects of nausea and vomiting that can accompany administration of lurbinectedin. A preferred embodiment is the treatment of SCLC, including metastatic SCLC in a patient in need thereof, or otherwise reducing the side effects of administering lurbinectedin to a patient, comprising: (1) administering one or more antiemetic agents effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion. In certain embodiments, the lurbinectedin is administered as a single agent chemotherapeutic agent and/or is not administered in combination with doxorubicin. In other embodiments, the patient may be administered the anti-emetic therapy on the same day and prior to administration of of 2 $mg/m^2$ lurbinectedin in combination with 75 $mg/m^2$ irinotecan and, in certain embodiments, on day 8 of a treatment cycle with a dose of 75 $mg/m^2$ irinotecan.

In some embodiments, antiemetic agents are given intravenously or orally. If the one or more antiemetic agents are given intravenously, the one or more agents are administered between 30 and 90 minutes before administration of lurbinectedin, or at about 30 minutes, about 45 minutes, about 60 minutes, about 75 minutes, or about 90 minutes, before administration of lurbinectedin, preferably 30 or 60 minutes. If the one or more antiemetic agents are given orally, the one or more agents are administered between 30 to 60 minutes before administration of lurbinectedin, about 3 hours and 9 hours before administration of lurbinectedin, or about 4 hours, about 5 hours, about 6 hours, about 7 hours, about 8 hours, or about 9 hours before administration of lurbinectedin. In some embodiments, the antiemetic agents consist of a corticosteroid and a serotonin antagonists, wherein the corticosteroid is selected from the group consisting of dexamethasone, hydrocortisone, or methylprednisolone and the serotonin antagonist is selected from a group consisting of ondansetron, granisetron, and palonosetron. The dose of the corticosteroid is or is equivalent to about 4 mg to 20 mg of dexamethasone delivered intravenously, preferably 8 mg delivered intravenously. The dose of the serotonin antagonist is or is equivalent to about 8 mg to 16 mg of ondansetron delivered intravenously, preferably 8 mg delivered intravenously. If given orally, the dose can be increased to a dose equivalent of up to 24 mg of ondansetron. In preferred embodiments, the prophylactic antiemetic agents comprise dexamethasone intravenously administered at 8 mg, ondansetron intravenously administered at 8 mg, or a combination thereof.

In some embodiments, the method further comprises administering one or more antiemetic agents within 2, 3, or 4 days after administration of lurbinectedin to the patient, for example, administered on the same day after lurbinectedin administration, for example, within 2, 3, 4, 5, 6, 7 or 8 hours of lurbinectedin administration and/or on day 1, 2, 3, or 4 after lurbinectedin administration. The one or more antiemetic agents administered after lurbinectedin administration are selected from the group consisting of a corticosteroid, wherein the corticosteroid is selected from dexamethasone, hydrocortisone, and methylprednisolone, a serotonin antagonist, wherein the serotonin antagonist is selected from ondansetron, granisetron, and palonosetron, and metoclopramide. In preferred embodiments, the post-infusion antiemetic treatment is 4 mg dexamethasone (oral), 8 mg ondansetron (oral), or 10 mg metoclopramide (oral or as infusion), or a combination thereof. The metoclopramide may be administered at 8 hour intervals. In some embodiments, post-infusion antiemetic agents are administered intravenously. In some embodiments, the first dose of post-infusion antiemetic agents are given on the evening of, or 1, 2, 3, 4, 5, 6, 7 or 8 hours after lurbinectedin administration and continued for up to 1, 2, 3, or 4 days post infusion. In some embodiments, a corticosteroid, e.g. dexamethasone, is given at a dose equivalent to 4 mg of dexamethasone on the evening after, or 1, 2, 3, 4, 5, 6, 7 or 8 hours after chemotherapy and then twice per day for up to 1, 2, 3, or 4 days. In some embodiments, metoclopramide is administered at a dose of 10 to 20 mg, orally, every 8 hours post-chemotherapy for up to 1, 2, 3, or 4 days. In other embodiments, a serotonin antagonist, e.g. ondansetron, is given orally at a dose equivalent to 8 mg or 16 mg of ondansetron every 12 hours or 24 hours, respectively, for up to 1, 2 or 3 days after lurbinectedin administration.

In some embodiments, the antiemetic prophylaxis and optionally the post-infusion antiemetic treatment is administered to a SCLC patient who is given about 2.0 $mg/m^2$, about 2.6 $mg/m^2$, or about 3.2 $mg/m^2$ of lurbinectedin by intravenous infusion. The antiemetic prophylaxis and optionally the post-infusion antiemetic treatment is administered to a solid tumor patient who is administered 1.0 to 2.0 $mg/m^2$ lurbinectedin in combination with irinotecan.

Dosage and Dose Reduction

Additional embodiments of the invention include a dose modification in the event of identifying a ≥Grade 2 adverse event (AE) in a SCLC patient, particularly a metastatic SCLC adult patient, upon administration of a first dose of 3.2 $mg/m^2$ of lurbinectedin (for example, greater than 2 weeks) dose delays beyond the 21 day treatment cycle for lurbinectedin dosing on day 1.

In some embodiments, a lower amount of lurbinectedin is used as compared to the amount generally used for individual therapy. In some embodiments, the same or greater therapeutic benefit is achieved using a smaller amount (e.g., a lower dose or a less frequent dosing schedule) of lurbinectedin than the amount generally used for individual therapy. For example, the use of a smaller amount of lurbinectedin may result in a reduction in the number, severity, frequency, or duration of one or more side-effects associated with lurbinectedin infusion. For example, in preferred embodiments, the first dose modification is a dose reduction from about 3.2 $mg/m^2$ to about 2.6 $mg/m^2$ (or 80 to 85% of the initial dose) of lurbinectedin and the second dose modification is a dose reduction from about 2.6 $mg/m^2$ to about 2.0 $mg/m^2$ (or 60 to 65% of the initial dose) of lurbinectedin. If after the second dose reduction, the patient experiences an adverse event that would require further dose reduction, then treatment may be stopped. Adverse events which require frequent or prolonged (>2 weeks) dose delays include, but are not limited to, any hematologic toxicity that is Grade 3 or Grade 4, or any Grade 2, Grade 3 or Grade 4 non-hematologic toxicity or adverse reaction, such as hepatotoxicity. In the event of non-hematologic toxicities of Grade 2, Grade 3 or Grade 4, the following cycle is delayed until non-hematologic parameters have improved to Grade 1 or 0. Administration of two doses of lurbinectedin are always spaced apart by at least 21 days.

A treatment cycle is not initiated until hematologic parameters, such as neutrophil count, platelet count, and, optionally, hemoglobin level have improved such that absolute neutrophil count is greater than or equal to 1500 cells/$mm^3$, and platelet counts are greater than 100,000/$mm^3$, and, optionally, in certain embodiments hemoglobin levels are greater than or equal to 9 g/dL (with transfusion if necessary). For example, at first occurrence of greater than Grade 3 (severe) non-hematological toxicity, Grade 4 thrombocytopenia (platelet count less than 25,000 cells/$mm^3$), Grade 3 thrombocytopenia (platelet count less than 50,000 cells/$mm^3$) with bleeding that requires transfusion, Grade 4 neutropenia (neutrophil count less than 500 cells/$mm^3$), or of any grade neutropenia (neutrophil count <LLN) that is associated with infection/sepsis or any adverse reaction that requires frequent or prolonged (greater than 2 weeks) dose delay, the lurbinectedin dose is reduced from 3.2 $mg/m^2$ to 2.6 $mg/m^2$ (or 80 to 85% of the initial dose) and the next cycle is delayed until the patient's neutrophil count is greater than 1500 cells/$mm^3$; platelet count is greater than about 100,000/$mm^3$; and hemoglobin levels are greater than about 9 g/dL. In a certain embodiment, if the identified adverse event consists of isolated Grade 4 neutropenia, the method comprises administration to the patient a dose of G-CSF ("secondary G-CSF prophylaxis") as prophylaxis to manage the isolated Grade 4 neutropenia and then a dose of lurbinectedin that is equal to the previous dose rather than reducing the lurbinectedin dose. If after the first dose reduction, the patient suffers from one of the adverse events that requires a dose reduction (greater than Grade 3 (severe) non-hematological toxicity, Grade 4 thrombocytopenia (platelet count less than 25,000 cells/$mm^3$), Grade 3 thrombocytopenia (platelet count less than 50,000 cells/$mm^3$) with bleeding that requires transfusion, Grade 4 neutropenia (neutrophil count less than 500 cells/$mm^3$), or of any grade neutropenia (neutrophil count <LLN) that is associated with infection/sepsis or any adverse reaction that requires frequent or prolonged (greater than 2 weeks) dose delay), then the subsequent dose 3 weeks later is reduced to 2.0 $mg/m^2$ (60 to 65% of the initial dose), once the patient has recovered with neutrophils greater than or equal to 1500 cells/$mm^3$, platelet counts greater or equal to 100,000/$mm^3$ and hemoglobin levels greater than or equal to 9 g/dL (with transfusion if necessary). After the second dose reduction, the patient again has an adverse reaction which would require a dose reduction, the treatment is terminated. If a dose would be delayed by greater than 2 weeks because the patient has not recovered such that absolute neutrophil count is greater than or equal to 1500 cells/$mm^3$ and platelet count is greater than or equal to 100,000/$mm^2$, then treatment may be terminated.

If the identified adverse reaction is not solely isolated Grade 4 neutropenia, the method comprises administering to the patient a reduced dose of lurbinectedin. Administration of two doses of lurbinectedin must be spaced apart by at least 21 days regardless of the dose of lurbinectedin.

A preferred embodiment is the treatment of small cell lung cancer (SCLC), including metastatic SCLC, in a patient in need thereof, comprising: (1) administering a first dose of 3.2 $mg/m^2$ of lurbinectedin to the patient by intravenous infusion; (2) identifying an adverse reaction in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions; and (3) after the adverse reaction is identified and after the patient's neutrophil count is greater than 1500 cells/$mm^3$; platelet count is greater than about 100,000/$mm^3$; and hemoglobin levels are greater than about 9 g/dL: (i) if the identified adverse reaction consists of isolated Grade 4 neutropenia (Neutrophil count less than 500 cells/$mm^3$), administering to the patient a dose of G-CSF and a dose of lurbinectedin that is equal to the previous dose; or (ii) if the identified adverse reaction is not solely isolated Grade 4 neutropenia, administering to the patient a reduced dose of lurbinectedin, wherein administration of two doses of lurbinectedin are spaced apart by 21 days or 20 to 23 days or at least 18, 19, 20, 21, 22, or 23 days.

In some embodiments, the first dose reduction is 80 to 85% of the first dose after first occurrence of the adverse reaction that it not solely isolated Grade 4 neutropenia or wherein a first reduced dose is 2.6 mg/$m^2$ after a first occurrence of the adverse reaction that is not solely isolated Grade 4 neutropenia. In some embodiments, a second reduced dose is 60-65% of the first dose after a second occurrence of the adverse reaction that is not solely isolated Grade 4 neutropenia or wherein a second reduced dose is to 2.0 mg/$m^2$ after a second occurrence of the adverse reaction that is not solely isolated Grade 4 neutropenia, wherein the second reduced is administered to the patient. Administration of lurbinectedin is discontinued after identification of the adverse reaction after administration of the second reduced dose.

Prior to administration of an initial or subsequent dose of lurbinectedin, the patient, including an adult patient, suffering from SCLC, particularly metastatic SCLC, has an absolute neutrophil count of at least 1,500 cells/$mm^3$ and a platelet count of at least 100,000/$mm^3$. Accordingly, provided is a method of treating a patient who has an absolute neutrophil count of at least 1,500 cells/$mm^3$ and a platelet count of at least 100,000 $mm^3$ for SCLC, including metastatic SCLC by administration of lurbinectedin at a dose of 3.2 mg/$m^2$ every 3 weeks, subject to dose delays or dose reductions if the patient experiences an adverse event.

Methods are provided for managing hematological toxicity, myleosupressive effects and/or hepatotoxicity that may be associated with lurbinectedin administration in the treatment of SCLC, including metastatic SCLC by dose reduction and/or dose delay. The adverse events that could trigger a dose delay or reduction include Grade 4 or any grade febrile neutropenia (Grade 4 neutropenia is neutrophil count less than 500 cells/$mm^3$), Grade 3 thrombocytopenia with bleeding or Grade 4 thrombocytopenia (Grade 3 thrombocytopenia being 25,000-50,000 platelets/$mm^3$ and Grade 4 thrombocytopenia is less than 25,000 platelets/$mm^3$), Grade 2 or greater hepatotoxicity or other adverse reaction. In the case of all of these adverse reactions, the subsequent dose may be delayed until the patient has recovered such that the patient exhibits are less than or equal to Grade 1 neutropenia (greater than 1500 cells/$mm^3$), have a platelet count of 100,000/$mm^3$, or hepatotoxicity or the other adverse reaction that is Grade 1 or less. Patients exhibiting Grade 4 neutropenia or any grade febrile neutropenia, Grade 3 with bleeding or Grade 4 thrombocytopenia or Grade 3 or greater hepatotoxicity or other adverse reaction, after recovery, are administered a reduced dose for subsequent treatment cycles. If the prior dose was 3.2 mg/$m^2$, then the reduced dose is 2.6 mg/$m^2$, and if the prior dose was 2.6 mg/$m^2$ then the reduced dose is 2.0 mg/$m^2$ every three weeks. If the patient experiences an adverse event that would indicate a dose reduction after a dose of 2.0 mg/$m^2$, then treatment may be terminated. For patients exhibiting Grade 4 neutropenia, the subsequent dose, once the patient has recovered, may not be reduced, that is may be the same as the prior dose every three weeks, if the patient is administered G-CSF prophylaxis. For patients exhibiting Grade 2 hepatotoxicity or other adverse reaction, the subsequent dose, after the patient has recovered to Grade 1 or less toxicity, is the same as the prior dose every three weeks.

Accordingly, provided are methods of treating SCLC, including metastatic SCLC, by administering to a patient in need thereof with an absolute neutrophil count of at least 1500 cells/$mm^3$ and a platelet count of at least 100,000/$mm^3$, a dose of 3.2 mg/$m^2$ lurbinectedin, preferably by infusion over 60 minutes. In a further embodiment, 21 days after the previous dose, the patient has an absolute neutrophil count of at least 1500 cells/$mm^3$ and a platelet count of at least 100,000/$mm^3$ and is administered 3.2 mg/$m^2$ dose of lurbinectedin, preferably by infusion over 60 minutes. In embodiments, the patient is monitored for and has no hepatotoxicity prior to administration of lurbinectedin. Subsequent treatments are administered at 21 day (3 week) intervals to the patient having an absolute neutrophil count of at least 1500 cells/$mm^3$ and a platelet count of at least 100,000/$mm^3$.

In certain embodiments, provided are methods of treating SCLC, including metastatic SCLC, in a patient in need thereof by administering lurbinectedin at a dose of 3.2 mg/$m^2$, including by infusion over 60 minutes, then monitoring the patient for adverse hematological or hepatic reactions. In the event a patient having been administered a dose of 3.2 mg/$m^2$ lurbinectedin exhibits grade 4 neutropenia (neutrophil count less than 500 cells/$mm^3$) or any febrile neutropenia, then the subsequent dose of lurbinectedin is not administered until the later of 21 days after the prior dose or when the patient exhibits less than grade 1 neutropenia (at least 1500 cells/$mm^3$), which may be greater than 21 days past the previous dose, and then either administering lurbinectedin at a reduced dose of 2.6 mg/$m^2$ every three weeks or administering lurbinectedin at a dose of 3.2 mg/$m^2$ every three weeks with G-CSF prophylaxis. In the event, a patient having been administered a 3.2 mg/$m^2$ dose of lurbinectedin exhibits Grade 3 thrombocytopenia (25,000-50,000 platelets/$mm^3$) with bleeding or Grade 4 thrombocytopenia (less than 25,000 platelets/$mm^3$), then the subsequent dose of lurbinectedin is not administered until the later of 21 days after the previous dose or when the patient exhibits a platelet count of greater than or equal to 100,000/$mm^3$ and the subsequent dose is a reduced dose of 2.6 mg/$m^2$ every three weeks (21 days). In the event, a patient having been administered a 3.2 mg/$m^2$ dose of lurbinectedin exhibits hepatotoxicity or other adverse reactions that is either Grade 2 or Grade 3 or 4, then the subsequent dose of lurbinectedin is not administered until the later of 21 days after the previous dose or when the patient exhibits less than or equal to Grade 1 hepatotoxicity (or other adverse reaction), and the subsequent dose is a dose of 3.2 mg/$m^2$ every three weeks if the patient had exhibited Grade 2 hepatotoxicity (or Grade 2 of other adverse reaction) and the subsequent dose is a reduced dose of a reduced dose of 2.6 mg/$m^2$ every three weeks (21 days) if the patient had exhibited Grade 3 or 4 hepatotoxicity or other adverse reaction. If, after dose reduction, the patient exhibits one of Grade 4 neutropenia, or any grade febrile neutropenia, Grade 3 thrombocytopenia with bleeding or Grade 4 thrombocytopenia, or hepatotoxicity or other adverse reaction at Grade 3 or 4, then the subsequent dose is not administered until the later of 21 days or when the patient has recovered as detailed above and then administered a further reduced dose of 2 $mg/m^2$ lurbinectedin every three weeks or, in the case of Grade 4 neutropenia, is administered the same dose or lurbinectedin as the prior dose with G-CSF prophylaxis. If the patient ceases to tolerate (that is exhibits, after lurbinectedin administration, one of Grade 4 neutropenia, or any grade febrile neutropenia, Grade 3 thrombocytopenia with bleeding or Grade 4 thrombocytopenia, or hepatotoxicity or other adverse reaction at Grade 3 or 4) at a dose of 2 $mg/m^2$ lurbinectedin or if delay in administration is greater than 2 weeks past the scheduled dose (at 21 days after the prior dose), then treatment is discontinued.

Co-administration with a strong or a moderate CYP3A inhibitor increases lurbinectedin systemic exposure and thus, patients taking a CYP3A inhibitor are either taken off of the CYP3A inhibitor or advised to stop taking the CYP3A inhibitor, or, alternatively, the dose of lurbinectedin is reduced, for example, from a dose of 3.2 $mg/m^2$ or a dose of 2.6 $mg/m^2$ or 2.0 $mg/m^2$. Examples of CYP3A inhibitors include clarithromycin, erythromycin, diltiazem, itraconazole, ketoconazole, ritonavir, verapamil, goldenseal and grapefruit. Accordingly, provided are methods of treating patients for SCLC, particularly, metastatic SCLC, or solid tumors by administration of a dose of lurbinectedin, including 3.2 $mg/m^2$ lurbinectedin every 3 weeks where the patient is not taking a CYP3A inhibitor (and may have been taken off the CYP3A inhibitor in advance of lurbinectedin dosing to avoid drug interaction) or a dose less than 3.2 $mg/m^2$, including 2.6 $mg/m^2$ or 2.0 $mg/m^2$) if the patient is also taking a CYP3A inhibitor.

Coadministration with a strong CYP3A inducer decreases lurbinectedin systemic exposure which may reduce efficacy. Examples of CYP3A inducers include phenobarbital, phenytoin, rifampicin, St. John's Wort and glucocorticoids. Accordingly, provided are methods of treating patients for SCLC, particularly, metastatic SCLC, or solid tumors by administration of a dose of lurbinectedin, including 3.2 $mg/m^2$ lurbinectedin every 3 weeks, where the patient is not taking a strong or moderate CYP3A inducer.

Combination Therapy for Solid Tumors

In other embodiments, the invention is directed to the combination of lurbinectedin with a topoisomerase I and/or II inhibitor in the treatment of cancer, and more particularly in the treatment of solid tumors, particularly endometrial cancer, SCLC, soft tissue sarcoma (including Ewing and synovial sarcoma), glioblastoma (including supratentorial or intratentorial tumors), pancreatic adenocarcinoma, mesothelioma, colorectal carcinoma, and epithelial ovarian cancer. In preferred embodiments, the solid tumor is endometrial cancer, SCLC, soft tissue sarcoma (including Ewing and synovial sarcoma) or glioblastoma. In some embodiments, the method of treating patients with solid tumors comprises administering lurbinectedin at a dose of 1 to 2.5 $mg/m^2$ in combination with other anticancer agents, such as a topoisomerase inhibitor selected from SN-38 or irinotecan, wherein the lurbinectedin is administered at a dose of 1 to 2.5 $mg/m^2$, particularly 2.0 $mg/m^2$, and wherein the topoisomerase inhibitor is administered at a dose equivalent to 50 to 75 mg of irinotecan/$m^2$. The chemotherapeutic group of topoisomerase I and/or II inhibitors includes, but is not limited to topotecan, SN-38, irinotecan, camptothecin, rubitecan, etoposide, amsacrine and teniposide. Particularly preferred is the combination of lurbinectedin with irinotecan in the treatment of cancer, particularly, solid tumors, and more particularly in the treatment of endometrial cancer, SCLC, soft tissue sarcoma (including, Ewing and synovial sarcoma), glioblastoma, pancreatic adenocarcinoma, mesothelioma, colorectal carcinoma, and epithelial ovarian cancer.

In some embodiments, lurbinectedin is administered at a dose of 1, 1.5, 2, or 2.4 $mg/m^2$ and the topoisomerase inhibitor is administered at a dose equivalent to 50 to 75 $mg/m^2$ of irinotecan. In preferred embodiments, lurbinectedin is administered at a dose of 2 $mg/m^2$ and irinotecan is administered at a dose of 75 $mg/m^2$. G-CSF is administered to the patient with the combination.

In some embodiments, lurbinectedin and the topoisomerase inhibitor are administered on day one of a treatment cycle. In some embodiments, the method further comprises administering G-CSF to the patient to manage the myelosuppressive effects of the therapy. In another embodiment, the topoisomerase inhibitor is further administered to the patient on day 7, 8, 9, or 10 of the treatment cycle. In some embodiments, the treatment cycle is a 18, 19, 20, 21, 22, 23, 24, or 25 day cycle.

In particular embodiments, provided are methods of treating solid tumors in a patient in need thereof by administration on day 1 of a treatment cycle a dose of lurbinectedin, particularly, a dose of 2.0 $mg/m^2$ and a dose of irinotecan at a dose of 75 $mg/m^2$ and then on day 8 of the treatment cycle a dose of 75 $mg/m^2$ irinotecan, with G-CSF administration to manage myelosuppressive effects of the therapy. The treatment cycle may be a 3 week (21 day) cycle, such that a subsequent treatment cycle is initiated at day 22. In certain embodiments, patients who exhibit hematologic toxicity (including grade 3-4 adverse event) after the combination dose administered on day 1 of the treatment cycle may not be administered the irinotecan dose on day 8 (or any other time in that treatment cycle) or may be administered a reduced dose of irinotecan on day 8 of the treatment cycle or at any other time during the treatment cycle. The treatment may include multiple treatment cycles until disease progression or unacceptable toxicity. In particular, the patient may be administered 1, 2, 3, 4, 5 or more, including 8, 10, 12, 15, 20 or 30 or more cycles of the combination treatment.

In particular embodiments, the combination treatment method results in reduction in tumor size, a median progression free survival of at least 4.3 months (particularly for SCLC), of at least 7.1 months (particularly, for endometrial cancer), of at least 2.6 months (particularly, for soft tissue sarcoma), or of at least 1.4 months (particularly, for glioblastoma).

In one embodiment, the method further comprises administering one or more antiemetic agents on day one of a treatment cycle (as described in detail above for treatment of SCLC with lurbinectedin) and post-infusion anti-emetic treatment as described herein for treatment of SCLC.

Pharmaceutical Compositions and Methods of Preparation

Pharmaceutical compositions of lurbinectedin that can be used include solutions, lyophilized compositions, etc., with suitable excipients for intravenous administration.

In one aspect, lurbinectedin is supplied and stored as a stable and sterile lyophilized product comprising lurbinectedin, a buffer derived from an organic acid (e.g. an organic carboxylic acid buffer), a disaccharide, and a sufficient base to provide an appropriate pH for injection when the composition is reconstituted in an appropriate solvent.

In some embodiments, the organic carboxylic acid buffer is derived from an organic acid selected from the group consisting of lactic acid, butyric acid, propionic acid, acetic acid, succinic acid, citric acid, ascorbic acid, tartaric acid, malic acid, maleic acid, fumaric acid, glutamic acid, aspartic acid, gluconic acid, and α-ketoglutaric. In some embodiments, the organic carboxylic acid buffer is derived from an organic acid selected from lactic acid or succinic acid. In some embodiments, the organic carboxylic acid buffer is derived from lactic acid. In certain embodiments, the buffer is not a phosphate buffer.

In some embodiments, the disaccharide is selected from the group consisting of sucrose, trehalose or lactose, or a combination thereof. In some embodiments, the disaccharide is sucrose.

In some embodiments, the base is selected from the group consisting of carbonates, hydroxides, hydrogen carbonates and ammonium salts. Particularly preferred bases are sodium carbonate, potassium carbonate, calcium carbonate, $NH_4OH$, sodium hydroxide, potassium hydroxide, calcium hydroxide, sodium hydrogen carbonate, potassium hydrogen carbonate and calcium hydrogen carbonate. In some embodiments, the base is sodium hydroxide.

In some embodiments, the pH of the reconstituted lyophilized composition is about 4. In some embodiments, the pH of the reconstituted lyophilized composition is about from about 3 to about 5. In some embodiments, the pH of the reconstituted lyophilized composition is about from about 3.5 to about 4.5. In some embodiments, the pH of the reconstituted lyophilized composition is 3.8 to 4.1.

In some embodiments, the stable lyophilized product comprises lurbinectedin; lactic acid; sodium hydroxide and sucrose and the pH of the reconstituted lyophilized composition is 3.8 to 4.1. In some embodiments, the stable lyophilized product comprises 4 mg lurbinectedin; 22.1 mg lactic acid; 5.1 mg sodium hydroxide (or, including, about 0.25 mmol lactate); and 800 mg sucrose. In some embodiments, the stable lyophilized product consists essentially of 4 mg lurbinectedin; 22.1 mg lactic acid; 5.1 mg sodium hydroxide (or, including, about 0.25 mmol lactate); and 800 mg sucrose.

The lurbinectedin-containing formulations of this invention can be made by freeze-drying a composition of this invention in the form of a buffered bulk solution including lurbinectedin, a buffer derived from an organic acid, such as a lactate buffer or a succinate buffer, and a disaccharide. The disaccharide is preferably sucrose. Usually the bulk solution will be buffered, for example to a pH of about 3 to 5, preferably about 3.5 to 4.5, more preferably pH 3.8 to 4.1. The preferred buffering agent is a sodium lactate buffer. In preferred embodiments, the lactate buffer comprises lactic acid and a base, preferably an inorganic, pharmaceutically accepted base such as sodium hydroxide.

As such, in embodiments of the present invention there is provided a buffered lyophilized composition including lurbinectedin, a buffer derived from an organic acid, such as a lactate buffer or a succinate buffer, and a disaccharide; wherein the buffer is configured such that upon reconstitution the pH of the reconstituted lyophilized composition is from about 3 to about 5, about 3.5 to about 4.5, or 3.8 to 4.1

The present invention has identified methodologies that allow for complete dissolution of lurbinectedin in desired buffers whilst minimizing impurity generation. In embodiments, the use of an organic acid buffer allows for direct dissolution of lurbinectedin in the organic acid buffer (preferably at pH about 1 to 5, about 2 to 4.5, about 3 to 4.5 or about 4) followed by addition of bulking agent such as disaccharide, preferably sucrose. Such a formulation strategy enables direct dissolution into the bulk formulation and avoids the need for a pre-dissolution step. In an embodiment, there is provided direct dissolution of lurbinectedin, comprising dissolving lurbinectedin in an organic acid buffer (preferably at pH about 1 to 5, about 2 to 4.5, about 3 to 4.5 or about 4), followed by addition of bulking agent such as disaccharide, preferably sucrose, to form a bulk solution. The bulk solution may undergo sterilizing filtration. The bulk solution may then be filled in vials according to the desired dose. The bulk solution in vials may then be lyophilized to form a lyophilized buffered lurbinectedin formulation. The lyophilized formulation may then be reconstituted to form a reconstituted solution. The reconstituted solution may be diluted to form an injection solution. Preferably, with direct dissolution the lurbinectedin is amorphous or substantially amorphous.

As explained herein, lurbinectedin has limited aqueous solubility. It was found that lurbinectedin solubility is improved in the bulk solution by first forming a concentrated pre-solution of the lurbinectedin in a buffer derived from an organic acid, for example lactic acid, succinic acid, citric acid, or acetic acid which is further diluted with water for injection. A disaccharide is then dissolved in an aqueous solution containing a basic ingredient, for example an aqueous sodium hydroxide solution, and upon adjusting the pH to a set value, the pre-solution of the lurbinectedin and the buffer solution containing a disaccharide are mixed to obtain the lurbinectedin bulk solution in an organic buffer, pH=4 containing a disaccharide (for example, sucrose). Following this process, the lurbinectedin concentration can be increased in the bulk solution enabling the vial fill volume to be reduced. In these embodiments of the present invention, the fill volume is usually reduced by about 80% with respect to that of the conventional fill volume. By way of illustration, but not as a limitation, embodiments of this invention provide a fill volume of 1 mg lurbinectedin in 2 ml solution within a 10 ml vial; or 4 mg lurbinectedin in 8 ml solution within a 30 ml vial. The fill volume can optionally be reduced further in other embodiments of this invention by increasing the lurbinectedin concentration.

Provided are processes useful for improving the solubility of lurbinectedin in the bulking solution that comprise dissolving lurbinectedin in lactic acid, for example 0.31M lactic acid (25 mg/mL), and subsequent dilution of the solution with water for injection to yield a lurbinectedin concentrated solution in 0.1M lactic acid, mixing the solution containing pre-dissolved lurbinectedin with a buffer salt solution comprising sodium lactate buffer and a disaccharide, and, optionally, adjusting the pH. In some illustrative, but not limiting, embodiments of this invention, pH adjustment is accomplished with a lactate buffer.

Illustrative embodiments of bulk solution for freeze drying according to the present invention are provided by a solution of lurbinectedin buffered at pH 4 with sodium hydroxide and lactic acid with sucrose as bulking agent.

An illustrative embodiment of the methodology according to this invention provides as follows: lurbinectedin is dissolved in 0.31M lactic acid, pH~3 and subsequently diluted with water for injection to yield a lurbinectedin concentrated solution of 8.3 mg/mL lurbinectedin in 0.1M lactic acid, pH~3. Sodium lactate buffer salt solution is prepared by mixing 0.31M lactic acid solution with 0.01M sodium hydroxide solution to create a 0.05M lactate buffer salt solution. Sucrose is then added to the sodium lactate buffer salt solution. The 0.05M lactate buffer salt solution containing sucrose is diluted with water for injection to yield a 0.04M sodium lactate buffer, pH~4.2 containing 17% sucrose. Both solutions, 8.3 mg/mL lurbinectedin in 0.1M lactic acid, pH~3 and 0.04M sodium lactate buffer, pH~4.2 containing 17% sucrose are then mixed. Dissolution is visually checked at all steps before continuing, and dissolution is considered complete when it is so appreciated visually The pH of the solution is checked and adjusted to a value in the range from about 1 to about 5, more preferably in the range from about 2 to about 4.5, even more preferably in the range from about 3 to about 4.5, and most preferably to a pH of about 4.0 by slow addition of a suitable acid or base. A preferred embodiment of such acid is lactic acid, in which case a preferred concentration is about 0.1M. A suitable base is optionally added for pH control. A preferred embodiment of such base is sodium hydroxide, preferably in solution, in which case a preferred concentration is about 0.1M. The volume is finally adjusted by addition of a suitable, biocompatible fluid, preferably water for injection. The resulting bulk solution preferably comprises 0.5 mg lurbinectedin in 0.03M sodium lactate buffer, pH=4, with 10% (w/v) sucrose. The bulk solution is then filled in vials according to the desired dose.

In embodiments, the lurbinectedin to be dissolved is at least partially crystalline. The lurbinectedin to be dissolved may be in the solid state form(s) described herein. Crystalline lurbinectedin (including partially crystalline) lurbinectedin has been found to be less soluble than amorphous lurbinectedin. By way of example, while the direct dissolution of amorphous lurbinectedin at 0.5 mg/mL in 0.03 M sodium lactate buffer pH 4 was completed in approximately 30 minutes, partly crystalline lurbinectedin reached only 60-70% of the target concentration in 2 hours, meaning that it had much slower dissolution kinetics.

It has been found that decreasing the pH accelerates the dissolution kinetics of partly crystalline lurbinectedin. As such, in embodiments, a concentrated lurbinectedin solution is prepared in organic acid before addition of other excipients. In preferred embodiments, the organic acid has a pH less than 4, preferably less than 3.5, more preferably less than 3, or around 3. The maximum solubility of lurbinectedin was investigated in different molarities of the organic acid lactic acid. Solubility was high and increased linearly ranging from 7.2 mg/ml for 0.05M lactic acid to 90.4 mg/ml for 0.5M lactic acid. In a preferred embodiment, lurbinectedin is dissolved in an organic acid with a molarity of around 0.1M to 0.5M, preferably around 0.2M to 0.4M, more preferably around 0.3M organic acid. An exemplary molarity is 0.31M organic acid.

Lurbinectedin may be pre-dissolved in high concentration organic acid. In a preferred embodiment, the pre-dissolution step is at least 30 minutes, at least 60 minutes or at least 90 minutes, between 30-90 minutes, between 60-90 minutes, between 60-70 minutes or around 60 minutes. Following dissolution, the pre-dissolution solution can be diluted to form the required concentration of, for example 8.3 mg/ml. Dilution may involve ×1, ×2, ×3 or more dilutions with WFI to obtain the target concentration. In embodiments, dilutions are carried out to achieve the desired concentration at appropriate molarity. By way of example, ×3 dilutions to add 2× the initial volume of organic acid may achieve 8.3 mg/mL in 0.1M organic acid (for example lactic acid).

During manufacture, there may be limited volume capacity for the dissolution step, and therefore lurbinectedin dissolution is advantageously achieved with limited organic acid. As such, using high molarity organic acid can achieve a high lurbinectedin concentration in a limited organic acid volume.

In embodiments, a multi-step compounding strategy is used to prepare lurbinectedin. Step 1 is the pre-dissolution step described above, for example: pre-dissolving partly crystalline lurbinectedin in lactic acid 0.31M at 25 mg/mL and diluting 3× with WFI to obtain the concentrated solution at 8.3 mg/mL in 0.1M lactic acid. To avoid precipitation of lurbinectedin, the remaining excipients should have acid pH when added to the compounding formulation. It has been found that the high concentration lurbinectedin solution can be mixed with a buffer solution at pH of 5.6 or less, for example between 4 to 5.6 or 4.2 to 5.6 without precipitation of lurbinectedin. As such, in Step 2, an organic buffer solution containing the bulking agent (eg disaccharide) may be prepared at suitable pH. By way of example, this may comprise the preparation of a 0.04 M sodium lactate buffer at pH of around 4.2 containing sucrose. In step 3, the solutions from step 1 and step 2 are combined to form the final bulk solution. The final bulk solution may be adjusted with WFI to achieve the final target weight. By way of example, in step 3, the 8.3 mg/mL lurbinectedin concentrated solution in 0.1M lactic acid with pH=3 is diluted with 0.04M sodium lactate buffer pH=4.2 containing sucrose. The final bulk solution composition after adjustment of WFI to final weight may be, by way of example, 0.5 mg/mL lurbinectedin in 0.03M sodium lactate buffer pH=4+10% (w/v) sucrose. The present invention therefore identifies a compounding strategy to formulate partially crystalline lurbinectedin.

In one embodiment, the lyophilized composition comprises or consists of 4 mg of lurbinectedin, 800 mg of sucrose, 22.1 mg of lactic acid and 5.1 mg of sodium hydroxide. In some embodiments, the weight ratio in the lyophilized composition is between 0.4% and 0.6% (w/w) of active compound, 96% to 98% (w/w) of sucrose, 2% to 3% (w/w) of lactic acid, and 0.5% to 0.7% (w/w) sodium hydroxide. In preferred embodiments, the weight ratio in the lyophilized composition is 0.5% (w/w) active compound, 96.2% (w/w) sucrose, 2.7% (w/w) lactic acid, and 0.6% (w/w) sodium hydroxide. The lyophilized formulation contains about 0.25 mmol of lactate ion for 4 mg of lurbinectedin. When reconstituted to 8 ml in the vial, the resulting solution is 0.5 mg/ml lurbinectedin, 0.03M sodium lactate buffer, 10% w/v sucrose at about pH 4.0 (range of pH 3.5 to 4.5, preferably 3.8 to 4.5).

The lyophilized material is usually present in a vial which contains a specified amount of lurbinectedin. Preferably the lyophilized composition of lurbinectedin is provided in a 30 mL vial. The specified amount of lurbinectedin in a lyophilized composition can be from between 0.2 to 5 mg, or about 1 mg, about 2 mg, about 3 mg, or about 4 mg. The specified amount of lurbinectedin in a lyophilized composition is preferably 4 mg. In lyophilized embodiments, the composition contains between 0.4% and 0.6% by weight of lurbinectedin, preferably it is 0.5%.

It is necessary to ensure the lurbinectedin is sterile and is aseptically filled into vials. This is critical for parenteral drugs. According to embodiments of the present invention, terminal sterilization by heat or gamma irradiation are not used to avoid degradation of lurbinectedin. Instead, according to embodiments of the present invention, a sterilization filtration of the bulk lurbinectedin solution is carried out before aseptic vial filling. In embodiments, the filter may be filters such as PVDF or PES. In embodiments the filter may be a 0.2 μm filter.

Storage of Pharmaceutical Lurbinectedin Formulations

Embodiments of this invention also provide a method of storing a lyophilized lurbinectedin composition. It is necessary to ensure the lurbinectedin is stable during at least 24 months. The lurbinectedin lyophilized formulations are storage stable such that after prolonged storage at 5° C.±3° C., the lurbinectedin retains its therapeutic effectiveness and exhibits minimal chemical degradation (e.g., degradation is minimized and within acceptable tolerance; for example, the impurity and degradation products profile of the lurbinectedin, amount of each impurity and degradation product, lurbinectedin content, as determined by HPLC analysis, are substantially the same before and after prolonged storage).

In one aspect, the lyophilized lurbinectedin compositions of the present disclosure minimize the amount of a lurbinectedin degradation product resulting from deacetylation of lurbinectedin ("Impurity D") (having a relative retention time of 0.87 to 0.88 by commercial HPLC assay) when the composition is stored for prolonged times (e.g., at least 24 months). In some embodiments, the amount of impurity D present is less than 0.3%, 0.4%, 0.5%, 0.6%, 0.7% or 0.8% wt/wt of the total lurbinectedin weight in the formulation after prolonged storage at 5° C.±3° C. Impurity B, D and G have the following structures:

B

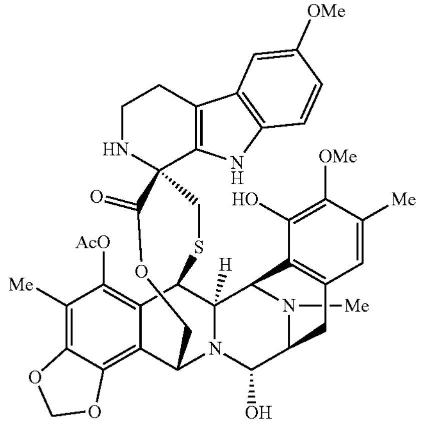

D

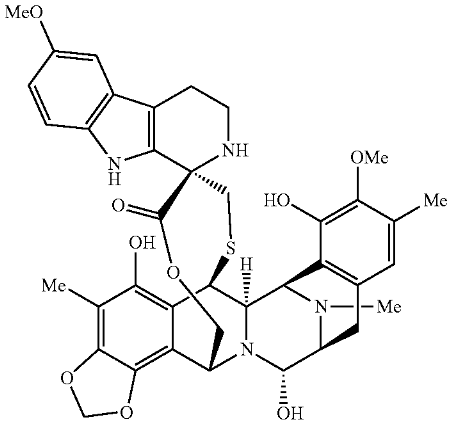

-continued

G

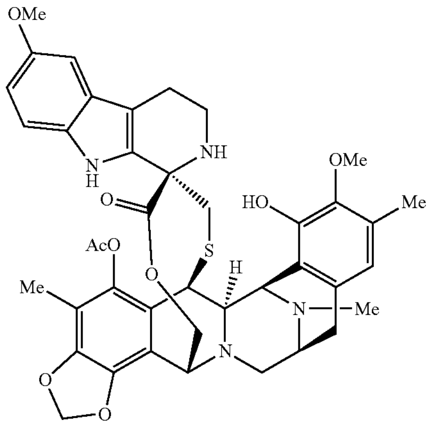

In a preferred embodiment the method of storing a lyophilized lurbinectedin composition comprises storing a lyophilized composition comprising 4 mg lurbinectedin; lactate buffer; and a disaccharide at a temperature of 5° C.±3° C. for at least 24 months, wherein the lyophilized composition is formulated such that reconstitution with 8 mL of water will yield a solution having a pH of 3.5 to 4.5 and a lurbinectedin concentration of 0.5 mg/ml and wherein after the at least 24 months storage, the amount of Impurity D present in the composition is not more than 0.8% wt./wt. of the total lurbinectedin weight. In some embodiments, the lyophilized lurbinectedin composition is stored at a temperature of 5° C.±3° C. for, or for at least, 24 months, 30 months, 36 months, 42 months, 48 months or 60 months, wherein after 24 months, 30 months, 36 months, 42 months, 48 months or 60 months of storage, the amount of a lurbinectedin degradation product Impurity D present in the composition is not more than 0.8% wt./wt. of the total lurbinectedin weight. In some embodiments, the amount of Impurity D present in the composition after storage at about 5° C.±3° C. for 60 months is not more than 0.8% wt./wt, or is less than 0.7% wt./wt., less than 0.6% wt./wt., less than 0.5% wt./wt., or less than 0.4% wt./wt. of the total lurbinectedin weight. In one embodiment, the amount of lurbinectedin degradation product Impurity D present in the composition is not more than 0.8% wt./wt. of the total lurbinectedin weight after at least 36 months of storage. In some embodiments, the total % impurities and degradation products (as % area) after storage at about 5° C.±3° C. for 24 months, 30 months or 36 months is not more than 0.6%, 0.7%, 0.8% 0.9% or 1.0% (% area). In some embodiments, the initial amount of Impurity D present in the composition (i.e., one day of lyophilization) is less than 0.4% wt./wt. of the total lurbinectedin weight. In some embodiments, the initial amount of Impurity D present in the composition is at least 0.05% wt./wt. or at least 0.1% wt./wt. of the total lurbinectedin weight. In some embodiments, the initial amount of Impurity D present in the composition is not more than 0.8% wt./wt., not more than 0.5% wt./wt. or not more than 0.1% wt./wt. of the total lurbinectedin weight. In some embodiments, after storage at about 5° C.±3° C. for 24 months, 30 months, 36 months, 48 months or 60 months the stable, lyophilized, lurbinectedin formulation shows negligible degradation of lurbinectedin assay content, for example, a decrease in the amount of lurbinectedin as compared to the amount of lurbinectedin within 1.0%, 0.5%, or 0.2% of the total amount of lurbinectedin as compared to the bulk solution from which the formulation is made.

Accordingly, provided are stable, lyophilized lurbinectedin formulations comprising a buffer derived from an organic acid (e.g., an organic carboxylic acid buffer, such as, succinate, citrate, acetate or lactate buffer) at a molar ratio of buffer to lurbinectedin of about 48, including the molar ratio 52 to 46, 54 to 44, 50 to 48, 52 to 58, or the molar ratio 51 to 48, and sucrose as a bulking agent, which, when reconstituted in 8 mL of water has a pH of about 4.0, including pH 3.5-4.5 or pH 3.8-4.1, which comprises Impurity D at no more than 0.8% wt/wt, or is less than 0.7% wt./wt., less than 0.6% wt./wt., less than 0.5% wt./wt., or less than 0.4% wt./wt of the total weight of lurbinectedin and, preferably, the Impurity D does not increase to more than 0.8% wt/wt of the total weight of lurbinectedin after storage at 5° C.±3° C. for 12 months, 24 months, 30 months, 36 months, 48 months or 60 months; or storage at 25° C./60% RH for 3 months, 6 months, 9 months, 12 months or 18 months; or 40° C./60% RH for 1 month, 3 months, 6 months or 12 months. In these embodiments, the lurbinectedin is 95 to 105%, or 97 to 103% of 4 mg lurbinectedin or of the amount of lurbinectedin by assay at day 1.

Also provided are methods of reducing lurbinectedin degradation in a lyophilized formulation by incorporating a buffer derived from an organic acid, preferably a lactate or succinate buffer, in the lyophilized formulation with the lurbinectedin such that the Impurity D in the formulation does not exceed 0.5% wt/wt, 0.6% wt/wt, 0.7% wt/wt or 0.8% wt/wt of the total lurbinectedin weight after storage at 5° C.±3° C. for 12 months, 24 months, 30 months, 36 months, 48 months or 60 months; or storage at 25° C./60% RH for 3 months, 6 months, 9 months, 12 months or 18 months; or 40° C./60% RH for 1 month, 3 months, 6 months or 12 months, particularly when the amount of lurbinectedin is 95 to 105%, or 97 to 103% of 4 mg lurbinectedin or of the amount of lurbinectedin by assay at day 1.

Other impurities or degradation products that may be minimized in the storage of the stable, lyophilized lurbinectedin formulation may be the degradation products with the following relative retention time on the commercial HPLC method: rrt 0.68, rrt 0.80, rrt 1.11 (Impurity G), and rrt 1.12.

In further embodiments, the total residual water content for the lyophilized lurbinectedin formulation is not more than 3% (w/w), preferably not more than 1.5% (w/w), preferably not more than 1% (w/w), is preferably between 0.5-0.7% (w/w).

Embodiments of this invention further provide a pharmaceutical product comprising a vial containing a lyophilized lurbinectedin composition. In a preferred embodiment, the pharmaceutical product comprises a vial containing a lyophilized composition consisting of 4 mg lurbinectedin; 22.1 mg lactic acid; 5.1 mg sodium hydroxide (or, including, about 0.25 mmol lactate); and 800 mg sucrose; and a label affixed to the vial comprising an expiration date that is at least 48 months from the date of manufacture. In some embodiments, the label affixed to the vial comprises an expiration date that is at least 24 months, at least 30 months, at least 36 months, at least 42 months, or at least 48 months from the date of manufacture. In some embodiments, the vial has a size of 30 mL to 50 mL, such as 30 mL, 35 mL, 40 mL, 45 mL, or 50 mL. In a preferred embodiment, the vial is a 30 mL vial. A vial size of 30 mL is optimized to overcome limitations of larger vial sizes which lead to production capacity reduction due to reduced freeze dryer capacity and also adequate extractable volumes due to size. A vial size of 30 mL overcomes both of these limitations.

Lurbinectedin Solid State Forms and Uses Thereof

In embodiments according to the present invention, the pre-lyophilized lurbinectedin comprises at least some crystalline material. The pre-lyophilized lurbinectedin may be partially crystalline. Using partly crystalline pre-lyophilized lurbinectedin leads to advantages, including better control of impurities and/or degradation products.

The present invention has identified a novel solid state form of lurbinectedin that is easier to handle under typical pharmaceutical processing conditions than the known amorphous form, hereinafter Form A. The amorphous Form A can be obtained by the process described in WO 03/014127. Form A becomes electrostatically charged during its manipulation causing production problems. Therefore there is the need to obtain a form of lurbinectedin that is easier to handle under typical pharmaceutical processing conditions.

In embodiments according to the present invention there is provided a novel solid state form of lurbinectedin, in the following named Form B of lurbinectedin. Form B shows advantageous physical properties compared to the known Form A. For example, Form B shows improved triboelectric properties over existing known forms of lurbinectedin. Triboelectric charging is the process by which certain materials become electrically charged after contact with a different material through friction. In many pharmaceutical operations uncontrolled static electricity can cause serious production problems. These problems may include product contamination, product loss, cleaning and safety, and the problems can be exacerbated in a nanomolar cytotoxic drug such as lurbinectedin. Even in the most stringent cleanrooms, static charge attracts particulates from people, processes and equipment, so it is important to take appropriate measures to ensure it is kept to a minimum.

Form B shows a lower average charge density over the known form of lurbinectedin. Form B also shows a narrower dispersion of charge density over the known form of lurbinectedin. Form B of lurbinectedin has lower residual solvents over the known form of lurbinectedin. Form B also has a simplified impurity profile compared to the known form of lurbinectedin. These characteristics make it especially suitable for the preparation of a medicament. The pre-lyophilisation lurbinectedin may comprise Form B. The amount of Form B may vary and can be considered a crystalline mixture (partially crystalline). In other embodiments, the crystalline mixture may comprise other crystalline lurbinectedin (e.g. non form-B crystalline lurbinectedin).

In further embodiments, the present invention relates to a process for preparing Form B of lurbinectedin comprising: a) preparing an acidic aqueous solution comprising lurbinectedin or a protonated form thereof; and b) basifying the resulting acid aqueous solution with a base or a basic buffer to precipitate Form B of lurbinectedin. The Form B of lurbinectedin may be subsequently converted into a different physical form, preferably an amorphous form. The Form B may be used in the manufacturing process to prepare lyophilized bulk product.

In further embodiments, the present invention relates to pharmaceutical compositions comprising Form B of lurbinectedin and a pharmaceutically acceptable carrier. Such compositions may be pre-lyophilisation compositions.

In further embodiments, the present invention relates to a pharmaceutical composition comprising lurbinectedin manufactured using Form B of lurbinectedin and a pharmaceutically acceptable carrier. The pharmaceutical composition may no longer contain any Form B lurbinectedin, however the composition manufacturing process utilized at least some Form B in one or more steps. In further embodiments, the present invention relates to Form B of lurbinectedin for use in the manufacture of a pharmaceutical composition comprising lurbinectedin. In yet further embodiments, the present invention relates to the use of Form B of lurbinectedin in the manufacture of a pharmaceutical composition comprising lurbinectedin. In yet further embodiments, the present invention relates to Form B of lurbinectedin for use as a medicament. Again, Form B may no longer be present in the final composition but may be utilized during manufacturing.

In further embodiments, the present invention relates to compositions comprising Form B of lurbinectedin and a pharmaceutically acceptable carrier for use as a medicament. In further embodiments, the present invention relates to Form B of lurbinectedin for use as a medicament for the treatment of cancer. In further embodiments, the present invention relates to compositions comprising Form B of lurbinectedin and a pharmaceutically acceptable carrier for use as a medicament for the treatment of cancer.

In further embodiments, the present invention relates to processes for the manufacture of pharmaceutical compositions comprising lurbinectedin that employ Form B of lurbinectedin, preferably as starting material.

In further embodiments, the present invention is also directed to the use of Form B of lurbinectedin, or the use of a pharmaceutical composition comprising Form B of lurbinectedin and a pharmaceutically acceptable carrier in the treatment of cancer. In further embodiments, the present invention is also directed to the use of Form B of lurbinectedin, or the use of a pharmaceutical composition comprising Form B of lurbinectedin and a pharmaceutically acceptable carrier in the preparation of a medicament for the treatment of cancer. Other embodiments of the invention are methods of treatment, and Form B of lurbinectedin for use in these methods. Therefore, the present invention further provides a method of treating any mammal, notably a human, affected by cancer which comprises administering to the affected individual a therapeutically effective amount of Form B of lurbinectedin or of a pharmaceutical composition comprising Form B of lurbinectedin and a pharmaceutically acceptable carrier; or a pharmaceutical composition made from a process utilizing Form B of lurbinectedin.

The present invention further provides a method of treating any mammal, notably a human, affected by cancer which comprises administering to the affected individual a therapeutically effective amount of lurbinectedin which has been manufactured via Form B of lurbinectedin. The present invention further provides a method of treating any mammal, notably a human, affected by cancer which comprises administering to the affected individual a therapeutically effective amount of a pharmaceutical composition comprising lurbinectedin which has been manufactured via Form B of lurbinectedin, and a pharmaceutically acceptable carrier.

In a further embodiment, the present invention relates to lurbinectedin having residual solvents of not more than 1%, 0.5%, 0.1% or substantially not detected. In a further embodiment, the present invention relates to lurbinectedin having a water content of above 1.6% w/w, or of 1.7-5% w/w. In a further embodiment, the present invention relates to lurbinectedin having a water content of not more than 5%, 4% or 3% w/w.

In the context of solid state forms of lurbinectedin, alkanes in the present invention may be branched or unbranched, and have from about 5 to about 10 carbon atoms. One more preferred class of alkanes has from 5 to 9 carbon atoms. Even more preferred are alkanes having 5, 6 or 7 carbon atoms. Particularly preferred alkanes of this invention are n-pentane, n-hexane, n-heptane, cyclohexane, and methylcyclohexane. As used herein, the term alkane, unless otherwise stated, refers to both cyclic and noncyclic alkanes.

Pharmaceutically acceptable solvents in the context of solid state forms of lurbinectedin are those classified under classes 2 and 3 of the guideline "Impurities: Guideline for residual solvents Q3C(R6)" of the International Conference on Harmonisation of Technical Requirements for Registration of Pharmaceuticals for Human Use.

In an embodiment, the present invention relates to Form B of lurbinectedin.

Form B of lurbinectedin can be characterized by showing an X-ray powder diffractogram pattern comprising four or more characteristic peaks at 2-theta angles selected from 6.2±0.2°, 7.6±0.2°, 9.0±0.2°, 10.9±0.2°, 14.9±0.2° and 15.3±0.2°. Form B may alternatively be characterized by showing an X-ray powder diffractogram pattern comprising five or more of said characteristic peaks. Alternatively, Form B may be characterized by showing an X-ray powder diffractogram pattern comprising all six of said characteristic peaks.

Particularly, Form B of lurbinectedin can be characterized by an X-ray powder diffractogram pattern comprising peaks and intensities as shown in the following table:

| Angle [2-theta] | Relative intensity [%] |
|---|---|
| 6.2 ± 0.2° | 79 ± 6 |
| 7.6 ± 0.2° | 100 ± 3 |
| 9.0 ± 0.2° | 63 ± 3 |
| 10.9 ± 0.2° | 100 ± 3 |
| 14.9 ± 0.2° | 76 ± 3 |
| 15.3 ± 0.2° | 75 ± 3 |

In a preferred embodiment further peaks may be found at 2-theta angles of 12.4±0.2°, 19.2±0.2° and 26.5±0.2°. Particularly, Form B of lurbinectedin can be characterized by an X-ray powder diffractogram pattern comprising characteristic peaks and intensities as shown in the following table:

| Angle [2-theta] | Relative intensity [%] |
|---|---|
| 6.2 ± 0.2° | 79 ± 6 |
| 7.6 ± 0.2° | 100 ± 3 |
| 9.0 ± 0.2° | 63 ± 3 |
| 10.9 ± 0.2° | 100 ± 3 |
| 12.4 ± 0.2° | 40 ± 3 |
| 14.9 ± 0.2° | 76 ± 3 |
| 15.3 ± 0.2° | 75 ± 3 |
| 19.2 ± 0.2° | 34 ± 3 |
| 26.5 ± 0.2° | 33 ± 3 |

In a more preferred embodiment, further peaks may be found at 2-theta angles of 18.4±0.2°, 20.7±0.2° and 24.9±0.2°. Particularly, Form B of lurbinectedin can be characterized by an X-ray powder diffractogram pattern comprising characteristic peaks and intensities as shown in the following table:

| Angle [2-theta] | Relative intensity [%] |
|---|---|
| 6.2 ± 0.2° | 79 ± 6 |
| 7.6 ± 0.2° | 100 ± 3 |
| 9.0 ± 0.2° | 63 ± 3 |
| 10.9 ± 0.2° | 100 ± 3 |
| 12.4 ± 0.2° | 40 ± 3 |
| 14.9 ± 0.2° | 76 ± 3 |
| 15.3 ± 0.2° | 75 ± 3 |
| 18.4 ± 0.2° | 29 ± 3 |
| 19.2 ± 0.2° | 34 ± 3 |
| 20.7 ± 0.2° | 32 ± 3 |
| 24.9 ± 0.2° | 26 ± 3 |
| 26.5 ± 0.2° | 33 ± 3 |

Figure 2A:
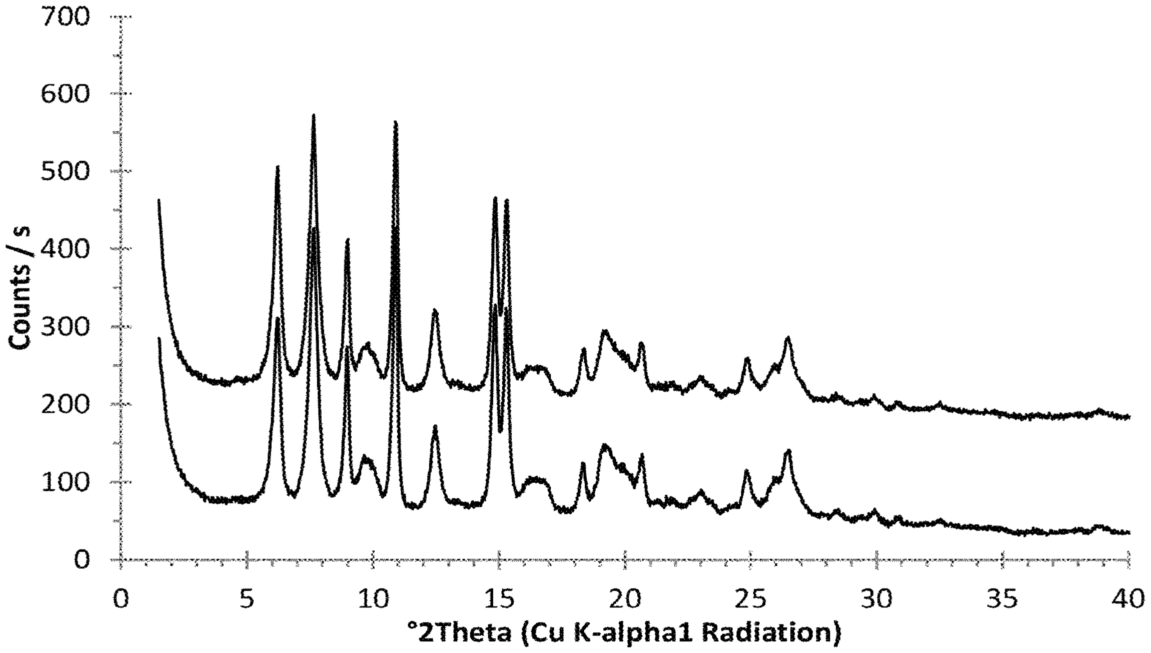
FIG. 2*a*: X-ray powder diffractograms (XRPD) of two batches of Form B of lurbinectedin (Batches 1924128-LT (overlaid) and 1924129-LT)
Figure 2B:
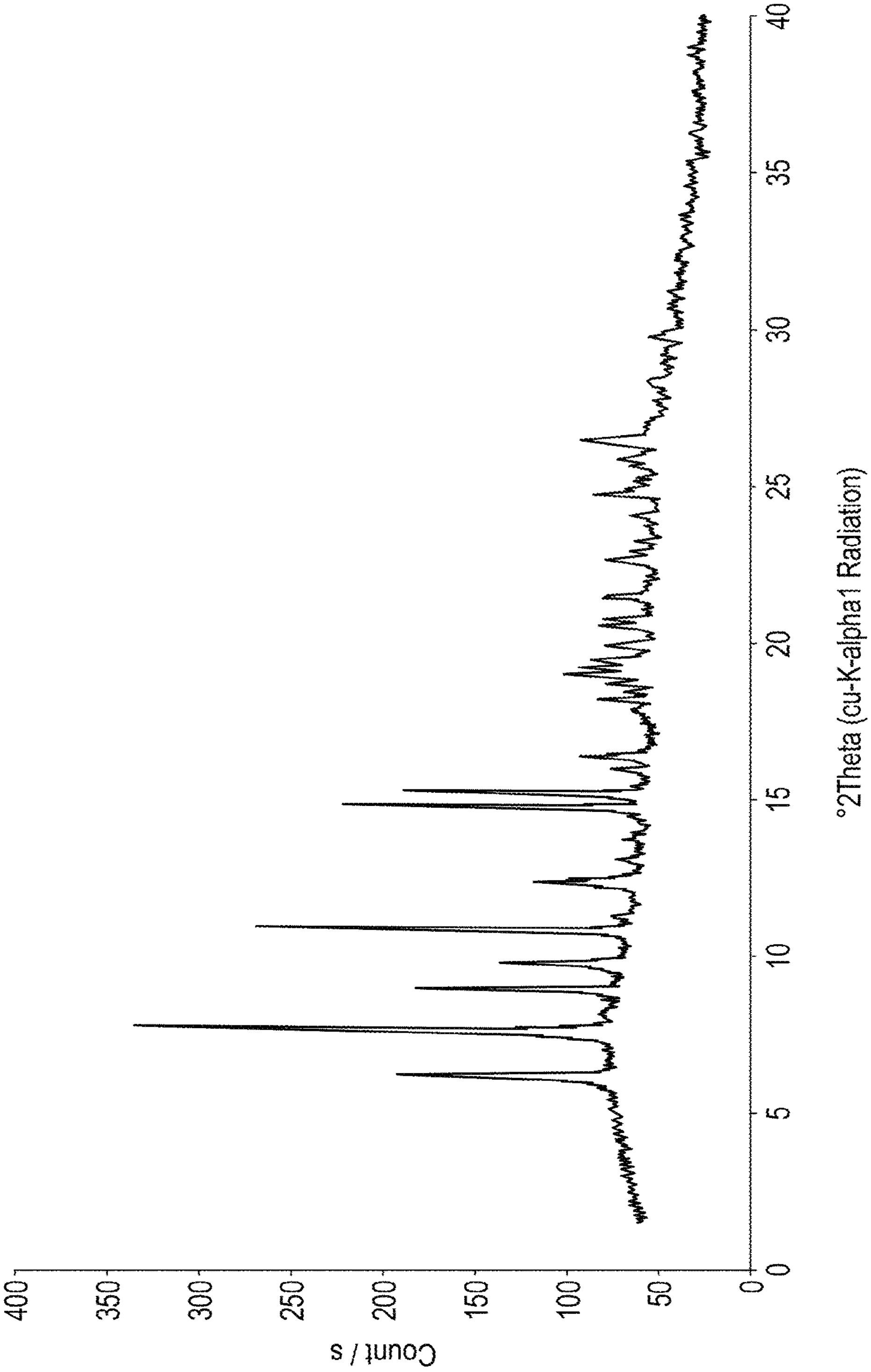
FIG. 2*b*: X-ray powder diffractograms (XRPD) of Form B of lurbinectedin made by mixing 15 mg Batch 1711182-2 (Form B partly crystalline) and 15 mg Batch P02 (amorphous) with 1 ml water. The suspension was stirred at r.t. for 24 hours. The resulting solid was filtered off).

In a most preferred embodiment, the present invention relates to Form B of lurbinectedin that exhibits an X-ray powder diffraction pattern substantially the same as any one of the X-ray powder diffraction patterns shown in FIG. 2*a* or 2*b*.

In addition, Form B of lurbinectedin can be characterized by showing an IR spectrum comprising peaks at wavelengths of 2928, 1755, 1626, 1485, 1456, 1370, 1197, 1150, 1088, 1003, 959, 916, and 587. An illustrative IR spectrum is displayed in FIG. 7*b*.

Figure 3:
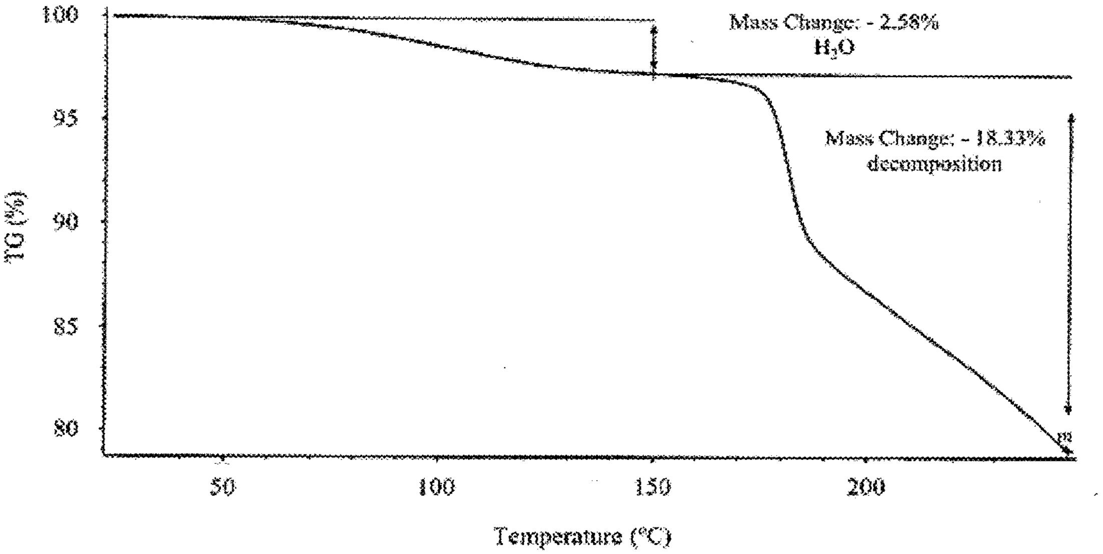
FIG. 3: TG-FTIR of Form B of lurbinectedin (Batch 1711182-2).

In addition, Form B of lurbinectedin can be characterized by TG-FTIR degradation above 150° C. Alternatively, or in addition, Form B of lurbinectedin can be characterized by a TG-FTIR mass change to 150° C. being due to the loss of water. The loss due to water may be less than about 5%, less than about 4%, or less than about 3%. Alternatively, or in addition, Form B of lurbinectedin can be characterized by TG-FTIR indicating a loss of water, preferably around 2-3% water by weight, more preferably 2.6% water by weight. An illustrative TG-FTIR is displayed in FIG. 3.

Figure 4:
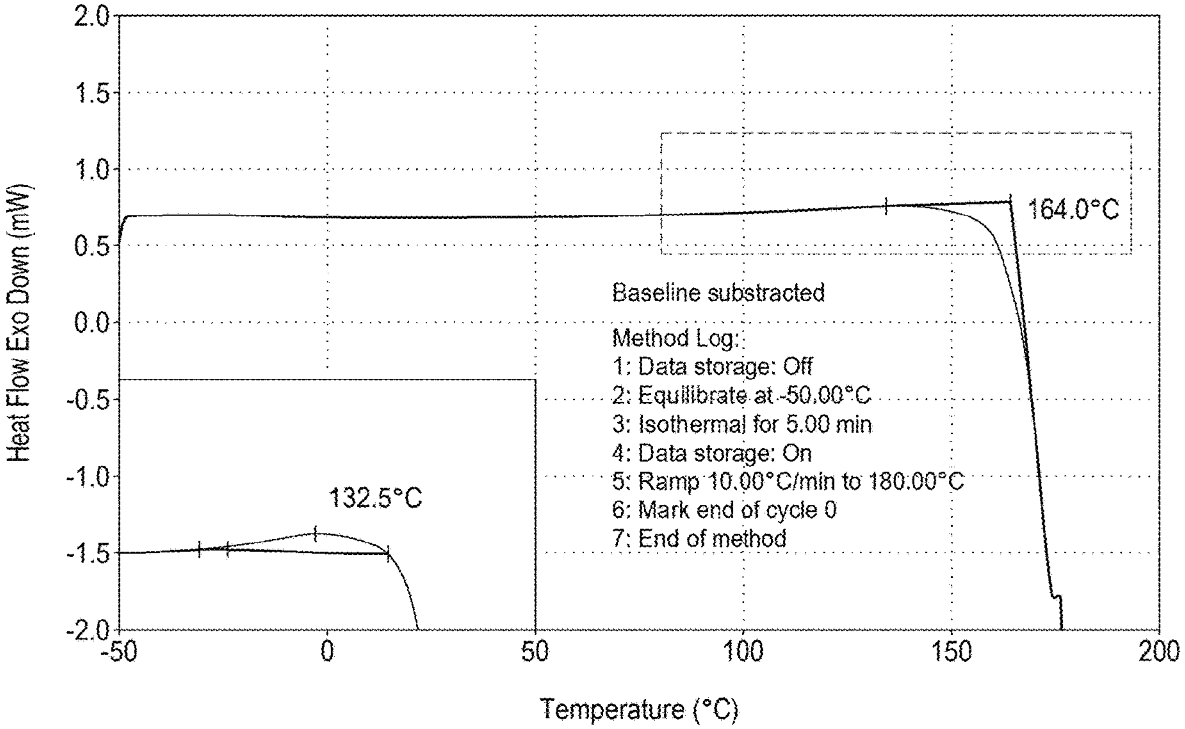
FIG. 4: DSC of Form B of lurbinectedin (Batch 1711182-2).

In addition, Form B of lurbinectedin can be characterized by DSC wherein degradation begins above 130° C. An illustrative DSC thermogram is displayed in FIG. 4.

In an embodiment, Form B of lurbinectedin has an average charge density of not more than about 30 nC/g, not more than about 20 nC/g, not more than about 10 nC/g, not more than about 6 nC/g, not more than about 5 nC/g, about 5±2 nC/g, about 4±2 nC/g, about 4-5 nC/g, about 5 nC/g, or about 4 nC/g. In an embodiment, Form B of lurbinectedin has a dispersion of charge density of less than 4.8 nC/g, of between about 0.7 nC/g to less than 4.8 nC/g, or 2.4±2 nC/g. In an embodiment, Form B of lurbinectedin has a water content of above 1.6% w/w, or of 1.7-5% w/w. In an embodiment, Form B of lurbinectedin has residual solvents of not more than 1%, 0.5%, 0.1% or substantially not detected.

The present invention encompasses lurbinectedin comprising at least a detectible amount of Form B, up to 1% w/w Form B, up to 5% w/w Form B, up to 10% w/w Form B, up to 20% w/w Form B, up to 30% w/w Form B, up to 40% w/w Form B, up to 50% w/w Form B, up to 60% w/w Form B, up to 70% w/w Form B, up to 80% w/w Form B, up to 90% w/w Form B, up to 95% w/w Form B, up to 98% w/w Form B, or be substantially pure Form B. In an embodiment, partially crystalline lurbinectedin as described herein may comprise at least a detectible amount of Form B, up to 1% w/w Form B, up to 5% w/w Form B, up to 10% w/w Form B, up to 20% w/w Form B, up to 30% w/w Form B, up to 40% w/w Form B, up to 50% w/w Form B, up to 60% w/w Form B, up to 70% w/w Form B, up to 80% w/w Form B, up to 90% w/w Form B, up to 95% w/w Form B, up to 98% w/w Form B, or be substantially pure Form B. w/w is intended to mean the amount of lurbinectedin which is in the Form B state. As such, purely by way of example, 50% w/w means the lurbinectedin API comprises 50% by weight Form B and 50% by weight another form, for example amorphous Form A.

In an embodiment, the invention relates to a process for preparing Form B of lurbinectedin comprising:

a) preparing an acidic aqueous solution comprising lurbinectedin or a protonated form thereof; and b) basifying the resulting acid aqueous solution with a base or a buffer to precipitate Form B of lurbinectedin.

In step a), a solution of lurbinectedin in acid water is provided. Examples of methods for preparing such solution include, but are not limited to: dissolving any solid form of lurbinectedin in acidic water; or extracting lurbinectedin from a solution comprising lurbinectedin in a water-immiscible organic phase to acidic water. In a preferred embodiment the acidic aqueous solution of lurbinectedin is obtained by dissolving lurbinectedin in acidic water.

Any form of lurbinectedin may be used e.g. amorphous lurbinectedin to form crystalline lurbinectedin. The concentration of lurbinectedin in acid water may range from about 10 to about 50 g/L. Particularly preferred are concentrations from about 15 to about 40 g/L, being more preferred concentrations from about 20 to about 30 g/L. Most preferred concentration of lurbinectedin in acid water is about 26 g/L.

The preferred pH of the acid water may range from about 1 to about 4, more preferably from about 1 to about 3, even more preferably from about 1 to about 2 and most preferably is about 1. The acid condition may be provided by an acid or by a buffer. Suitable pharmaceutically acceptable acids include hydrochloric acid, phosphoric acid, sulfuric acid, carboxylic acids such as aliphatic and aromatic carboxylic acids. More preferred acids include hydrochloric acid, phosphoric acid, sulfuric acid, trifluoroacetic acid, nitrobenzoic acid and citric acid. Suitable acid buffering agents provide a pH between about 1 to about 4. Examples of suitable acid buffering agents include but are not limited to phosphate buffer, citrate buffer, lactate buffer, ascorbate buffer, tartaric/citrate buffer, bicarbonate/hydrochloric acid buffer, acetate buffer, succinate buffer and glycine/hydrochloric acid buffer. More preferably the acid condition is provided by an acid and most preferably the acid is hydrochloric acid. The preferred pH of the solution of lurbinectedin in acidic water may range from about 1 to about 4, from about 1 to about 3, or about 2 to about 3.

In step b), the resulting acid aqueous solution is treated with an excess of base or buffer to basify it and precipitate Form B of lurbinectedin. The basification may be carried out with a base or with a buffer. The preferred pH of the resulting basic solution may range from about 8 to about 11, most preferably from about 9 to about 11. Suitable pharmaceutically acceptable bases include carbonates, hydroxides, hydrogen carbonates and ammonium salts. Particularly preferred bases are sodium carbonate, potassium carbonate, $NH_4OH$, lithium hydroxide, sodium hydroxide, potassium hydroxide, sodium hydrogen carbonate and potassium hydrogen carbonate. Suitable basic buffers provide a pH between about 8 to about 11. Examples of suitable basic buffers include ammonium and phosphate buffers such as $KH_2PO_4$ buffer, $Na_2HPO_4$/citric acid, and $NH_4Cl$—$NH_4OH$. In a preferred embodiment the basification is carried out with a buffer and in a most preferred embodiment the basification is carried out with a $NH_4Cl$—$NH_4OH$ buffer.

The obtained Form B of lurbinectedin can be separated by isolation operations such as filtration or centrifugation, preferably by filtration. Moreover, after separation, the separated solid may be subjected to a drying treatment by any known method. The precipitate can be dried preferably under vacuum at a temperature preferably ranging from about 15 to 35° C., more preferably from about 20 to 30° C., and most preferably at about 25° C. for a time preferably ranging from about 10 to 24 hours, more preferably from about 16 to 20 hours and most preferably for about 18 hours.

In a preferred embodiment the acid aqueous solution obtained after step a) is washed one or more times with a pharmaceutically acceptable, water-immiscible, polar solvent and one or more times with a pharmaceutically acceptable, water-immiscible, non-polar solvent, before treating it with an excess of base or buffer in step b).

Examples of pharmaceutically acceptable, water immiscible, polar solvents suitable for this washing include chloroform, 1-butanol, 2-butanol, butyl acetate, ethyl acetate, methyl acetate, 1-pentanol, propyl acetate and dichloromethane. More preferred pharmaceutically acceptable, water-immiscible, polar solvents for this washing are chloroform, ethyl acetate and dichloromethane, with dichloromethane the most preferred.

Preferred pharmaceutically acceptable, water-immiscible, non-polar solvents suitable for this washing include C5-C7 alkanes such as n-heptane, n-hexane, n-pentane, cyclohexane and methylcyclohexane; being n-pentane the most preferred.

In an embodiment, the present invention relates to pharmaceutical compositions comprising Form B of lurbinectedin and a pharmaceutically acceptable carrier or manufactured from lurbinectedin comprising Form B. The lurbinectedin used in the compositions or used during the manufacture of the compositions may comprising lurbinectedin comprising at least a detectible amount of Form B, up to 1% w/w Form B, up to 5% w/w Form B, up to 10% w/w Form B, up to 20% w/w Form B, up to 30% w/w Form B, up to 40% w/w Form B, up to 50% w/w Form B, up to 60% w/w Form B, up to 70% w/w Form B, up to 80% w/w Form B, up to 90% w/w Form B, up to 95% w/w Form B, up to 98% w/w Form B, or be substantially pure Form B.

Partially crystalline lurbinectedin as disclosed herein may in embodiments comprise at least a detectible amount of Form B, up to 1% w/w Form B, up to 5% w/w Form B, up to 10% w/w Form B, up to 20% w/w Form B, up to 30% w/w Form B, up to 40% w/w Form B, up to 50% w/w Form B, up to 60% w/w Form B, up to 70% w/w Form B, up to 80% w/w Form B, up to 90% w/w Form B, up to 95% w/w Form B, up to 98% w/w Form B, or be substantially pure Form B. In alternative embodiments, other non-Form B crystalline lurbinectedin may form partially crystalline lurbinectedin at the same w/w amounts.

The partially crystalline lurbinectedin as disclosed herein may be used to form pharmaceutical compositions according to the present invention. Accordingly, in embodiments, partially crystalline lurbinectedin is used in the manufacture of a bulk lurbinectedin solution which is thereafter lyophilized to form the lyophilized lurbinectedin formulation. The partially crystalline lurbinectedin may comprise Form B as disclosed herein.

Although the partially crystalline lurbinectedin may not be present in the final dosage form (due to the dissolution and subsequent lyophilisation steps), it nevertheless may affect the properties of the final dosage form. By way of example, using partially crystalline lurbinectedin can reduce and/or simplify the total impurities including degradation products. Characteristic impurity profiles may demonstrate the use of partially crystalline lurbinectedin during manufacture. According to an embodiment, the total degradation products in the final lyophilized product may be not more than (NMT) 1.9%, 1.8%, 1.7%, 1.6%, 1.5%, 1.4%, or 1.3%. In a preferred embodiment, the total degradation products are NMT than 1.3%. According to a further embodiment, the final lyophilized product comprises NMT 0.8% of impurity D. According to a further embodiment, the final lyophilized product comprises NMT 0.3% of any unspecified impurity.

Using partially crystalline lurbinectedin may also advantageously control residual solvents. In an embodiment, the lurbinectedin comprises not more than 0.2% residual solvents, preferably not more than 0.1% residual solvents, preferably residual solvents are substantially not detected.

In an embodiment, the partially crystalline lurbinectedin used in the manufacture of the compositions disclosed herein may have an assay (%) in the range 94.0-102.0% and an impurities level lower than 1.0%. Specified impurities and their limits may be are impurity B (50.20%), impurity D (50.50%) and/or impurity G (50.50%). Any other individual non-specified impurity may have a limit of 50.20%.

Use of Pharmaceutical Lurbinectedin Formulations

The present invention identifies a number of methods of treatment using lurbinectedin alone or in combination with further agents. Where reference is made to a method of treatment, the present invention also encompasses lurbinectedin and/or said further agents in the manufacture of a medicament for the treatment of cancer and also lurbinectedin and/or said further agents for use in the treatment of cancer. The methods below may utilize compositions of the invention as defined herein.

In some embodiments the method of treating SCLC in a patient in need therefore comprises: (1) administering to the patient lurbinectedin at a dose of 3.2 mg/m$^2$ (or a reduced dose of 2.6 mg/m$^2$ or 2.0 mg/m$^2$) by intravenous infusion of a lurbinectedin infusion solution, wherein the lurbinectedin infusion solution administered to the patient is prepared from a lyophilized composition comprising 4 mg lurbinectedin, a lactate buffer, and a disaccharide reconstituted to form a reconstituted solution at a pH of 3.8 to 4.5. In preferred embodiments, the disaccharide is sucrose. In a preferred embodiment, the lyophilized composition comprises 4 mg lurbinectedin, a lactate buffer (preferably resulting from a solution comprising 22.1 mg lactic acid and 5.1 mg sodium hydroxide, including about 0.25 mmol of lactate), and a disaccharide (preferably sucrose, particularly 800 mg sucrose), wherein reconstitution of the lyophilized composition in about 8 mL of an aqueous solution provides a lurbinectedin solution at 0.5 mg/mL lurbinectedin having a pH of about 3.8 to about 4.5. In some embodiments, a lurbinectedin infusion solution is prepared by diluting the reconstituted solution with an isotonic solution, wherein the isotonic solution is a 0.9% sodium chloride solution or a 5% dextrose solution. In some embodiments, the reconstituted solution is diluted with at least 100 mL or at least 250 mL of the isotonic solution to prepare a lurbinectedin infusion solution. In some embodiments, after reconstitution or dilution, the solution can be stored for up to 24 hours following reconstitution, including infusion time, at either room temperature (i.e., about 23° C.)/light or under refrigerated (5° C.±3° C.) conditions. In particular embodiments, the % wt/wt of Impurity D relative to lurbinectedin does not increase by more than 0.1%, 0.2% or 0.3% wt/wt upon storage of the reconstituted or diluted solution for 24, 48 or 72 hours at either room temperature (i.e., about 23° C.)/light or under refrigerated (5° C.±3° C.) conditions.

Some embodiments provide a method of administering a pharmaceutical composition to a patient in need thereof, for example, a patient suffering from SCLC refractory to first line treatment, comprising (1) reconstituting a lyophilized pharmaceutical composition in a vial after the composition has been stored for 30 to 36, or 48 months, wherein the lyophilized pharmaceutical composition was prepared by lyophilizing a stock solution comprising lurbinectedin, lactic acid, sodium hydroxide, and sucrose at a ratio of 4 mg lurbinectedin:22.1 mg lactic acid:5.1 mg sodium hydroxide: 800 mg sucrose:8 mL water; and (2) administering the reconstituted solution to a patient, wherein the reconstituted solution may be diluted with an isotonic solution, such as a 0.9% sodium chloride solution or a 5% dextrose solution, from 100 ml to 250 ml volume for administration to the patient as an infusion solution.

In a further aspect, there is provided the use of lurbinectedin in the manufacture of a medicament for the treatment of small cell lung cancer (SCLC), wherein said treatment comprises:

(1) administering a prophylactic dose of a corticosteroid and a serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided the use of corticosteroid in the manufacture of a medicament for the treatment of small cell lung cancer (SCLC), wherein said treatment comprises:

(1) administering a prophylactic dose of said corticosteroid and a serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided the use of a serotonin antagonist in the manufacture of a medicament for the treatment of small cell lung cancer (SCLC), wherein said treatment comprises:

(1) administering a prophylactic dose of a corticosteroid and said serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided the use of lurbinectedin in the manufacture of a medicament for the treatment of small cell lung cancer (SCLC), wherein said method comprises:

(1) administering a first dose of 3.2 $mg/m^2$ of lurbinectedin to the patient by intravenous infusion; and (2) identifying an adverse reaction in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;

(3) after the adverse reaction is identified and after the patient's neutrophil count is greater than 1500 cells/$mm^3$; platelet count is greater than about 100,000 $mm^3$; and hemoglobin levels are greater than about 9 g/dL: (i) if the identified adverse reaction consists of Grade 4 neutropenia (Neutrophil count less than 500 cells/$mm^3$), administering to the patient a dose of G-CSF and a dose of lurbinectedin that is equal to the first dose; or (ii) if the identified adverse reaction is not solely Grade 4 neutropenia, administering to the patient a reduced dose of lurbinectedin compared to the first dose, wherein administration of two doses of lurbinectedin are spaced apart by at least 21 days.

In a further aspect, there is provided the use of G-CSF in the manufacture of a medicament for the treatment of small cell lung cancer (SCLC), wherein said method comprises:

(1) administering a first dose of 3.2 $mg/m^2$ of lurbinectedin to the patient by intravenous infusion; and (2) identifying an adverse reaction in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;

(3) after the adverse reaction is identified and after the patient's neutrophil count is greater than 1500 cells/$mm^3$; platelet count is greater than about 100,000 $mm^3$; and hemoglobin levels are greater than about 9 g/dL:

(i) if the identified adverse reaction consists of Grade 4 neutropenia (Neutrophil count less than 500 cells/$mm^3$), administering to the patient a dose of G-CSF and a dose of lurbinectedin that is equal to the first dose; or (ii) if the identified adverse reaction is not solely Grade 4 neutropenia, administering to the patient a reduced dose of lurbinectedin compared to the first dose, wherein administration of two doses of lurbinectedin are spaced apart by at least 21 days.

In a further aspect, there is provided the use of lurbinectedin in the manufacture of a medicament for the treatment of small cell lung cancer (SCLC), wherein said method comprises:

administering to the patient lurbinectedin at a dose of 3.2 $mg/m^2$ by intravenous infusion of a lurbinectedin infusion solution, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.

In a further aspect, there is provided the use of lurbinectedin in the manufacture of a medicament for the treatment of endometrial cancer, SCLC, soft tissue sarcoma, glioblastoma, pancreatic adenocarcinoma, mesothelioma, colorectal carcinoma, or epithelial ovarian cancer, wherein said treatment comprises:

administering to the patient lurbinectedin and a topoisomerase inhibitor selected from SN-38 and irinotecan on day one of a treatment cycle;

wherein the lurbinectedin is administered at a dose of 1 to 2.5 $mg/m^2$ and wherein the topoisomerase inhibitor is administered at a dose equivalent to 50 to 75 mg of irinotecan/$m^2$.

In a further aspect, there is provided the use of a topoisomerase inhibitor selected from SN-38 and irinotecan in the manufacture of a medicament for the treatment of endometrial cancer, SCLC, soft tissue sarcoma, glioblastoma, pancreatic adenocarcinoma, mesothelioma, colorectal carcinoma, or epithelial ovarian cancer, wherein said treatment comprises:

administering to the patient lurbinectedin and said topoisomerase inhibitor selected from SN-38 and irinotecan on day one of a treatment cycle;

wherein the lurbinectedin is administered at a dose of 1 to 2.5 $mg/m^2$ and wherein the topoisomerase inhibitor is administered at a dose equivalent to 50 to 75 mg of irinotecan/$m^2$.

In a further aspect, there is provided the use of lurbinectedin in the manufacture of a medicament for the treatment of cancer, the treatment comprising reconstituting a lyophilized pharmaceutical composition in a vial after the composition has been stored for 30 to 60 months, wherein the lyophilized pharmaceutical composition was prepared by lyophilizing a stock solution comprising 4 mg of lurbinectedin, a buffer derived from an organic carboxylic acid, and sucrose, wherein the composition comprises lurbinectedin and disaccharide at a ratio of 1 mol lurbinectedin:455 to 465 mol sucrose, wherein the lyophilized composition is formulated such that reconstitution with 8 mL of water will yield a solution having a pH of 3.5 to 4.5; and administering the reconstituted solution to a patient.

In a further aspect, there is provided the use of lurbinectedin in the manufacture of a medicament for the treatment of small cell lung cancer (SCLC), wherein said treatment comprises:

administering lurbinectedin at a dose of 2 to 3.2 $mg/m^2$ to the patient by intravenous infusion;

wherein the patient was administered an immunotherapeutic antibody for treating SCLC prior to beginning the treatment cycle and wherein the duration of response is at least 2 months, 3 months, 4 months, 5 months or 6 months or wherein the overall response rate is at least 40%.

In a further aspect, there is provided the use of lurbinectedin in the manufacture of a medicament for the treatment of small cell lung cancer (SCLC), wherein said treatment comprises:

administering lurbinectedin at a dose of 2 to 3.2 $mg/m^2$ to a patient by intravenous infusion every 3 weeks, wherein the lurbinectedin is provided in a lyophilized formulation comprising lurbinectedin, a buffer derived from lactic acid, and sucrose, wherein the ratio of lurbinectedin:lactic acid:sucrose is between 1 mol:46 mol:455 mol and 1 mol:50 mol:465 mol, wherein the formulation is stable at 5 degree C.±3 degree C. for at least 24 months or at least 36 months or at least 48 months or at least 60 months such that the lurbinectedin degradation product from deacetylation does not exceed 0.8% wt./wt. of the total lurbinectedin weight.

In a further aspect, there is provided the use of lurbinectedin in the manufacture of a medicament for the treatment of small cell lung cancer (SCLC), wherein said treatment comprises:

1) dissolving a packaged, lyophilized composition comprising 4 mg lurbinectedin, a buffer derived from an organic acid and disaccharide in about 8 mL of water to provide a lurbinectedin solution having a pH of about 3.5 to about 4.1, and 2) administering about 2 to 3.2 $mg/m^2$ of lurbinectedin to a patient whose SCLC has progressed after prior platinum-containing therapy by intravenous infusion every 3 weeks and wherein the lyophilized composition comprises less than about 0.3% of Impurity D (w/w based on lurbinectedin) when the composition is packaged, and wherein upon storage at about 5 degrees C. for about 24, 36 or 48 months the composition comprises less than about 0.8% of Impurity D (w/w based on lurbinectedin).

In a further aspect, there is provided lurbinectedin for use in the treatment of small cell lung cancer (SCLC), wherein said treatment comprises:

(1) administering a prophylactic dose of a corticosteroid and a serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided a corticosteroid for use in the treatment of small cell lung cancer (SCLC), wherein said treatment comprises:

(1) administering a prophylactic dose of said corticosteroid and a serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided a serotonin antagonist for use in the treatment of small cell lung cancer (SCLC), wherein said treatment comprises:

(1) administering a prophylactic dose of a corticosteroid and said serotonin antagonist effective to reduce nausea associated with administration of lurbinectedin to the patient on the day of and prior to administration of lurbinectedin to the patient; and (2) administering lurbinectedin at a dose of 2 to 3.2 $mg/m^2$ to the patient by intravenous infusion.

In a further aspect, there is provided lurbinectedin for use in the treatment of small cell lung cancer (SCLC), wherein said method comprises:

(1) administering a first dose of 3.2 $mg/m^2$ of lurbinectedin to the patient by intravenous infusion; and (2) identifying an adverse reaction in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;

(3) after the adverse reaction is identified and after the patient's neutrophil count is greater than 1500 cells/$mm^3$; platelet count is greater than about 100,000 $mm^3$; and hemoglobin levels are greater than about 9 g/dL:

(i) if the identified adverse reaction consists of Grade 4 neutropenia (Neutrophil count less than 500 cells/$mm^3$), administering to the patient a dose of G-CSF and a dose of lurbinectedin that is equal to the first dose; or (ii) if the identified adverse reaction is not solely Grade 4 neutropenia, administering to the patient a reduced dose of lurbinectedin compared to the first dose, wherein administration of two doses of lurbinectedin are spaced apart by at least 21 days.

In a further aspect, there is provided G-CSF for use in the treatment of small cell lung cancer (SCLC), wherein said method comprises:

(1) administering a first dose of 3.2 $mg/m^2$ of lurbinectedin to the patient by intravenous infusion; and (2) identifying an adverse reaction in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;

(3) after the adverse reaction is identified and after the patient's neutrophil count is greater than 1500 cells/$mm^3$; platelet count is greater than about 100,000 $mm^3$; and hemoglobin levels are greater than about 9 g/dL:

(i) if the identified adverse reaction consists of Grade 4 neutropenia (Neutrophil count less than 500 cells/$mm^3$), administering to the patient a dose of G-CSF and a dose of lurbinectedin that is equal to the first dose; or (ii) if the identified adverse reaction is not solely Grade 4 neutropenia, administering to the patient a reduced dose of lurbinectedin compared to the first dose, wherein administration of two doses of lurbinectedin are spaced apart by at least 21 days.

In a further aspect, there is provided lurbinectedin for use in the treatment of small cell lung cancer (SCLC), wherein said method comprises:

administering to the patient lurbinectedin at a dose of 3.2 $mg/m^2$ by intravenous infusion of a lurbinectedin infusion solution, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.

In a further aspect, there is provided lurbinectedin for use in the treatment of endometrial cancer, SCLC, soft tissue sarcoma, glioblastoma, pancreatic adenocarcinoma, mesothelioma, colorectal carcinoma, or epithelial ovarian cancer, wherein said treatment comprises:

administering to the patient lurbinectedin and a topoisomerase inhibitor selected from SN-38 and irinotecan on day one of a treatment cycle;

wherein the lurbinectedin is administered at a dose of 1 to 2.5 $mg/m^2$ and wherein the topoisomerase inhibitor is administered at a dose equivalent to 50 to 75 mg of irinotecan/$m^2$.

In a further aspect, there is provided a topoisomerase inhibitor selected from SN-38 and irinotecan for use in the treatment of endometrial cancer, SCLC, soft tissue sarcoma, glioblastoma, pancreatic adenocarcinoma, mesothelioma, colorectal carcinoma, or epithelial ovarian cancer, wherein said treatment comprises:

administering to the patient lurbinectedin and said topoisomerase inhibitor selected from SN-38 and irinotecan on day one of a treatment cycle;

wherein the lurbinectedin is administered at a dose of 1 to 2.5 $mg/m^2$ and wherein the topoisomerase inhibitor is administered at a dose equivalent to 50 to 75 mg of irinotecan/$m^2$.

In a further aspect, there is provided lurbinectedin for use in the treatment of cancer, the treatment comprising reconstituting a lyophilized pharmaceutical composition in a vial after the composition has been stored for 30 to 60 months, wherein the lyophilized pharmaceutical composition was prepared by lyophilizing a stock solution comprising 4 mg of lurbinectedin, a buffer derived from an organic carboxylic acid, and sucrose, wherein the composition comprises lurbinectedin and disaccharide at a ratio of 1 mol lurbinectedin:455 to 465 mol sucrose, wherein the lyophilized composition is formulated such that reconstitution with 8 mL of water will yield a solution having a pH of 3.5 to 4.5; and administering the reconstituted solution to a patient.

In a further aspect, there is provided lurbinectedin for use in the treatment of small cell lung cancer (SCLC), wherein said treatment comprises:

administering lurbinectedin at a dose of 2 to 3.2 $mg/m^2$ to the patient by intravenous infusion;

wherein the patient was administered an immunotherapeutic antibody for treating SCLC prior to beginning the treatment cycle and wherein the duration of response is at least 2 months, 3 months, 4 months, 5 months or 6 months or wherein the overall response rate is at least 40%.

In a further aspect, there is provided lurbinectedin for use in the treatment of small cell lung cancer (SCLC), wherein said treatment comprises:

administering lurbinectedin at a dose of 2 to 3.2 $mg/m^2$ to a patient by intravenous infusion every 3 weeks, wherein the lurbinectedin is provided in a lyophilized formulation comprising lurbinectedin, lactic acid, and sucrose, wherein the ratio of lurbinectedin:lactic acid:sucrose is between 1 mol:46 mol:455 mol and 1 mol:50 mol:465 mol, wherein the formulation is stable at 5 degree C.±3 degree C. for at least 24 months or at least 36 months or at least 48 months or at least 60 months such that the lurbinectedin degradation product from deacetylation does not exceed 0.8% wt./wt. of the total lurbinectedin weight.

In a further aspect, there is provided lurbinectedin for use in the treatment of small cell lung cancer (SCLC), wherein said treatment comprises:

1) dissolving a packaged, lyophilized composition comprising 4 mg lurbinectedin, a buffer derived from an organic acid and disaccharide in about 8 mL of water to provide a lurbinectedin solution having a pH of about 3.5 to about 4.1, and 2) administering about 2 to 3.2 $mg/m^2$ of lurbinectedin to a patient whose SCLC has progressed after prior platinum-containing therapy by intravenous infusion every 3 weeks and wherein the lyophilized composition comprises less than about 0.3% of Impurity D (w/w based on lurbinectedin) when the composition is packaged, and wherein upon storage at about 5 degrees C. for about 24, 36 or 48 months the composition comprises less than about 0.8% of Impurity D (w/w based on lurbinectedin).

In a further aspect, there is provided the use of lurbinectedin in the manufacture of a medicament for the treatment of solid tumors, including SCLC, endometrial carcinoma, soft tissue sarcoma or glioblastoma wherein said treatment comprises:

(1) administering a prophylactic dose of a corticosteroid and a serotonin antagonist effective to reduce nausea associated with administration of lurbinectedin to the patient on the day of and prior to administration of lurbinectedin to the patient; and (2) administering lurbinectedin at a dose of 2 $mg/m^2$ and 75 $mg/m^2$ of irinotecan to the patient by intravenous infusion.

In a further aspect, there is provided the use of corticosteroid in the manufacture of a medicament for the treatment of solid tumor, wherein said treatment comprises:

(1) administering a prophylactic dose of said corticosteroid and a serotonin antagonist effective to reduce nausea associated with administration of lurbinectedin to the patient on the day of and prior to administration of lurbinectedin to the patient; and (2) administering lurbinectedin at a dose of 2 $mg/m^2$ and irinotecan at a dose of 75 $mg/m^2$ to the patient by intravenous infusion.

In a further aspect, there is provided the use of a serotonin antagonist in the manufacture of a medicament for the treatment of solid tumors, including SCLC, endometrial carcinoma, soft tissue sarcoma or glioblastoma, wherein said treatment comprises:

(1) administering a prophylactic dose of a corticosteroid and said serotonin antagonist effective to reduce nausea associated with administration of lurbinectedin to the patient on the day of and prior to administration of lurbinectedin to the patient; and (2) administering lurbinectedin at a dose of 2 $mg/m^2$ and irinotecan at a dose of 75 $mg/m^2$ to the patient by intravenous infusion.

In a further aspect, there is provided the use of lurbinectedin in the manufacture of a medicament for the treatment of solid tumors, including SCLC, endometrial carcinoma, soft tissue sarcoma or glioblastoma, wherein said treatment comprises:

(1) administering lurbinectedin at a dose of 2 $mg/m^2$ and irinotecan at a dose of 75 $mg/m^2$ to the patient by intravenous infusion;

(2) after 7 days administering ininotecan at a dose of 75 $mg/m^2$ irinotecan to the patient by intravenous infusion; and (3) administering G-CSF to the patient to manage the myelosuppressive effect of the administration.

In a further aspect, there is provided the use of lurbinectedin in the manufacture of a medicament for the treatment of solid tumors, including SCLC, endometrial carcinoma, soft tissue sarcoma or glioblastoma wherein said method comprises:

(1) administering lurbinectedin at a dose of 2 $mg/m^2$ and ininotecan at a dose of 75 $mg/m^2$ irinotecan to the patient by intravenous infusion; and (2) identifying if the patient exhibits a hematological toxicity of Grade 3 or 4 after said administration;

(3) if there is no Grade 3 or 4 hematological toxicity in the patient, then administering 7 days after step 1 a dose of 75 $mg/m^2$ irinotecan to the patient by intravenous infusion.

In a further aspect, there is provided the use of lurbinectedin in the manufacture of a medicament for the treatment of solid tumor, wherein said method comprises:

administering to the patient lurbinectedin at a dose of 2.0 $mg/m^2$ by intravenous infusion of a lurbinectedin infusion solution and a dose of 75 $mg/m^2$ irinotecan to the patient by intravenous infusion, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.

EXAMPLES

Example 1: Preparation of Lurbinectedin in Different Buffers

A bulk lurbinectedin solution containing 0.5 mg/mL (the calculated reconstituted concentration is 0.47 mg/mL based on the final volume of 8.55 mL) was prepared in an acetate, citrate, lactate, and succinate buffered solution with the buffer concentrations of 0.02 to 0.05 M buffered to pH 3, 4, and 5 with sodium hydroxide. An example of a lurbinectedin formulation with lactate buffered to a pH=4 is provided in Table 1 below.

TABLE 1

Composition of lurbinectedin 4 mg reconstituted solution

| Component | Concentration per vial (mg/mL) | Function |
|---|---|---|
| Lurbinectedin | 0.5 | Active ingredient |
| Sucrose | 100 | Bulking agent |
| Lactic acid | 2.76 | Buffering agent |
| Sodium hydroxide | 0.64 | Buffering agent |

Example 2: Solubility of Lurbinectedin in Different Buffers

Bulk solutions of phosphate, acetate, citrate, lactate and succinate buffers were prepared to determine maximum solubility of lurbinectedin. Table 2 shows the maximum solubility of lurbinectedin in the 0.02M-0.05 M or 0.06-0.1 M buffers at pH=4. The results show that lurbinectedin was poorly solubilized in a phosphate buffer. The results also suggest that the molarity of the buffer does not have a significant impact on solubility.

TABLE 2

Lurbinectedin maximum solubility in various buffers pH = 4. Impact of buffer molarity

| | Lurbinectedin maximun solubility (mg/mL) | |
|---|---|---|
| Buffer pH = 4 | 0.02-0.05M | 0.06-0.1M |
| Monopotasium phosphate | 0.21 | 0.32 |
| Sodium acetate | 0.94 | 0.86 |
| Sodium citrate | 0.93 | 0.93 |
| Sodium lactate | 0.90 | 0.92 |
| Sodium succinate | 0.97 | 0.95 |

Example 3: Stability of Lurbinectedin Formulations with Different Organic Carboxylic Buffers at Different pH Values Stability and solubility studies were conducted to determine a pH wherein lurbinectedin exhibits good stability. Table 3 shows the solubility and the impurities and degradation products profile of lurbinectedin in the alternative 0.02M-0.05 M buffers at pH 3, pH 4 and pH 5. The solubility was similar for pH 3 and pH 4 and drastically decreased at pH 5. This decrease in solubility is accompanied by an increase in degradation products as the buffer pH increases.

TABLE 3

Solubility and degradation products profile of lurbinectedin in different organic carboxylic buffers in the pH range 3 to 5

| | | Sodium acetate | | | Sodium citrate | | | Sodium lactate | | | Sodium succinate | | |
|---|---|---|---|---|---|---|---|---|---|---|---|---|---|
| | | pH 3 | pH 4 | pH 5 | pH 3 | pH 4 | pH 5 | pH 3 | pH 4 | pH 5 | pH 3 | pH 4 | pH 5 |
| Solubility (mg/mL) | | 0.95 | 0.94 | 0.03 | 0.94 | 0.93 | 0.50 | 0.94 | 0.90 | 0.03 | 0.96 | 0.97 | 0.04 |
| Degradation products[1] (%) | | | | | | | | | | | | | |
| individual[2] | 0.26-0.27 | — | — | 0.52 | — | — | — | — | — | 0.22 | — | — | — |
| (rrt) | 0.47 | — | — | 0.12 | — | — | — | — | — | — | — | — | — |
| | 0.69 | — | — | 0.71 | — | — | — | — | — | 0.56 | — | — | 0.74 |
| | 0.69-0.71 | — | — | 0.24 | — | — | — | — | — | 0.18 | — | — | 0.14 |
| | 0.71-0.75 | 0.10 | — | 0.18 | 0.12 | — | 0.10 | 0.12 | 0.12 | 0.16 | 0.11 | 0.10 | 0.18 |
| | 0.99 | — | — | 0.19 | — | — | — | — | — | 0.11 | — | — | 0.12 |
| | 1.03-1.10 | 0.35 | 0.40 | 0.60 | 0.14 | 0.12 | 0.13 | 0.15 | 0.15 | 0.58 | 0.35 | 0.39 | 0.40 |
| | 1.15-1.16 | — | — | — | — | 0.11 | 0.16 | — | 0.10 | — | — | — | — |
| | 1.22 | — | — | — | — | — | — | — | — | — | — | — | 0.18 |
| | 1.26-1.31 | 0.13 | 0.11 | 0.39 | — | — | — | — | — | 0.18 | — | — | 0.26 |
| | 1.29-1.34 | — | — | 0.84 | — | — | — | — | — | 0.79 | — | — | 0.84 |
| | 1.79-1.91 | — | — | 0.84 | — | — | — | — | — | 0.70 | — | — | 1.1 |
| Total[3] | | 0.8 | 0.8 | 4.6 | 0.6 | 0.6 | 0.7 | 0.7 | 0.7 | 3.5 | 0.7 | 0.8 | 4.1 |

rrt: Relative retention time.

[1]HPLC Developinent method: IANA-072 Ed02.

[2]Main degradation products. Area ≥0.10%

[3]Total % degradation products calculated as 100% − % area lurbinected in main peak The stability of lurbinectedin in the different buffers was further evaluated at 14 days with 25° C./60% RH conditions. While lurbinectedin is relatively stable at pH 3 and 4, a significant decrease in assay and purity at pH=5 is observed (Table 4).

TABLE 4

Effect of pH on the solubility and stability (25° C./60% RH 14 days) of lurbinectedin in different 0.02M-0.05M organic carboxylic buffers in the pH range 3 to 5

| | | Concentration[1] (mg/mL) | | Concentration | Purity[1] (%) | | |
|---|---|---|---|---|---|---|---|
| Buffer | pH | t = 0 h | t = 14 d | decrease (%) | t = 0 h | t = 14 d | Degradation (%) |
| Sodium acetate | 3 | 0.95 | 0.88 | 6.8 | 99.2 | 98.0 | 1.2 |
| | 4 | 0.94 | 0.89 | 5.7 | 99.2 | 98.0 | 1.2 |
| | 5 | 0.03 | 0.03 | 8.2 | 95.4 | 93.7 | 1.7 |
| Sodium citrate | 3 | 0.94 | 0.92 | 1.2 | 99.4 | 97.9 | 1.6 |
| | 4 | 0.93 | 0.88 | 6.0 | 99.4 | 96.2 | 3.2 |
| | 5 | 0.50 | 0.11 | 78.5 | 99.3 | 95.0 | 4.3 |
| Sodium lactate | 3 | 0.94 | 0.93 | 0.9 | 99.3 | 98.6 | 0.7 |
| | 4 | 0.90 | 0.87 | 3.0 | 99.3 | 97.8 | 1.5 |
| | 5 | 0.03 | 0.03 | 6.9 | 96.5 | 93.9 | 2.6 |
| Sodium Succinate | 3 | 0.96 | 0.93 | 3.2 | 99.3 | 97.7 | 1.5 |
| | 4 | 0.97 | 0.89 | 7.6 | 99.2 | 96.8 | 2.4 |
| | 5 | 0.04 | 0.03 | 8.1 | 95.9 | 94.2 | 1.8 |

[1]HPLC Development method: IANA-072 Ed02.

These results showed that an organic carboxylic buffer with pH not more than pH 4.5 is the most adequate to increase the concentration of lurbinectedin in solution and to maintain an adequate stability. Sodium lactate and sodium citrate buffers were considered the most appropriate.

Example 4: Stability of Lyophilized Vials Formulated in Sodium Lactate and Sodium Citrate Buffers with pH=4.0 Under Stress Conditions (50° C.)

In order to determine which of the two buffers was the optimal for lurbinectedin, batches of lyophilized vials containing 1 mg lurbinectedin/vial were manufactured at a laboratory scale with lurbinectedin formulated at 0.5 mg/mL in 0.03M sodium lactate pH=4 and 0.05M sodium citrate pH=4. The pH 4 was chosen because of its greater physiological compatibility compared to pH 3. Sucrose was included as a bulking agent at 10% (w/v). The stability of the active principle in the lyophilized product under stress conditions of temperature (50° C.) was evaluated. Freeze-dried vials formulated in 0.05M monopotassium phosphate buffer pH=4 were also included in these studies for comparison. The stability results of lyophilized vials after 1 month at 50° C. are shown in Table 5. Due to the large number of degradation products that appear under these conditions, only those with an area 0.20% are reported.

The three formulations showed comparable characteristics at t=0. After storage at 50° C. for 1 month, quality attributes such as the appearance of the lyophilized solid, color and pH of the reconstituted solution and water content were not modified.

Lurbinectedin assay decreased significantly (between 11% and 17%) with respect to the initial content for the three compositions being the % degradation products the major differences observed. The vials formulated in sodium lactate buffer or monopotassium phosphate buffer showed very similar behavior, however sodium citrate buffer promoted larger degradation after storage for 1 month at 50° C. In all cases, the main degradation product was an impurity eluting at rrt 0.49-0.50 (HPLC Development method), being significantly higher in the lyophilized vial formulated in the sodium citrate buffer. Other degradation products that also appeared in very significant percentages were impurity D (rrt 0.73-0.74) and impurities with rrt 0.25, rrt 0.28 and rrt 1.09-1.10.

Based on the solubility and stability results, it was concluded that the most suitable dissolution medium for an optimized lurbinectedin formulation was 0.03M sodium lactate buffer pH 4.

TABLE 5

Stability under stress conditions (1 month, 50° C.) of lurbinectedin freeze-dried vials formulated with 0.05M monopotassium buffer pH = 4 containing 10% (w/v) sucrose citrate buffer pH = 4 or 0.03M sodium lactate i phosphate buffer pH = 4, 0.05M sodium as bulking agent

| | Monopotassium phosphate 0.05M pH = 4 Batch 1317-127 | | Sodium citrate 0.05M pH = 4 Batch 1317-136 | | Sodium lactate 0.03M pH = 4 Batch 1317-139 | |
|---|---|---|---|---|---|---|
| Quality attribute | t = 0 | 1 month 50° C. | t = 0 | 1 month 50° C | t = 0 | 1 month 50° C. |
| Appearance | White lyophilized cake | Contracted cake of irregular shape. Sticky appearance and greenish-yellow color | White lyophilized cake | Contracted cake of irregular shape. Sticky appearance and greenish-yellow color | White lyophilized cake | Contracted cake of irregular shape Sticky appearance and yellowish color |
| Identification | Consistent with standard | Consistent with standard | Consistent with standard | Consistent with standard | Consistent with standard | Consistent with standard |
| Reconstitution time | ≤1 min | ≤3 min | ≤1 min | ≤1 min | ≤1 min | ≤1 min |
| Appearance of reconstitued solution | Clear solution, free of visible particles | Clear solution, free of visible particles | Clear solution, free of visible particles | Clear solution, free of visible particles | Clear solution, free of visible particles | Clear solution, tree of visible particles |
| Color of reconstituted solution | Colorless solution | Yellowish solution | Colorless solution | Yellowish solution | Colorless solution | Slighty yellowish solution |
| pH of reconstituted solution | 4.0 | 4.1 | 4.0 | 4.2 | 3.9 | 4.1 |
| Water content (% w/w) | 1.7 | 1.7 | 1.7 | 2.2 | 1.1 | 1.6 |
| Impurities and degradation and degradation products[1] (%) | | | | | | |
| Total[2] | 0.7 | 9.0 | 0.7 | 15.0 | 0.7 | 8.5 |
| Individual[3] (rrt) | | | | | | |
| 0.20-0.21 | — | 0.39 | — | 0.60 | — | 0.25 |
| 0.23 | — | — | — | 0.35 | — | — |
| 0.24 | — | — | — | 0.39 | — | 0.26 |
| 0.25 | — | 0.60 | — | 2.0 | — | 1.2 |
| 0.25-0.26 | — | 0.34 | — | 1.1 | — | 0.71 |
| 0.28 | — | 0.84 | — | 1.2 | — | 0.54 |
| 0.29-0.30 | — | — | — | 0.35 | — | 0.21 |
| 0.37-0.38 | — | 0.20 | — | 0.29 | — | — |
| 0.49-0.50 | — | 1.9 | — | 5.5 | — | 2.2 |
| 0.63 | — | 0.20 | — | — | — | — |
| 0.73-0.74 (Imp. D) | — | 1.4 | — | 0.94 | — | 0.60 |

TABLE 5-continued

Stability under stress conditions (1 month, 50° C.) of lurbinectedin freeze-dried vials formulated with 0.05M monopotassium buffer pH = 4 containing 10% (w/v) sucrose citrate buffer pH = 4 or 0.03M sodium lactate i phosphate buffer pH = 4, 0.05M sodium as bulking agent

| | Monopotassium phosphate 0.05M pH = 4 Batch 1317-127 | | Sodium citrate 0.05M pH = 4 Batch 1317-136 | | Sodium lactate 0.03M pH = 4 Batch 1317-139 | |
|---|---|---|---|---|---|---|
| Quality attribute | t = 0 | 1 month 50° C. | t = 0 | 1 month 50° C | t = 0 | 1 month 50° C. |
| 1.09-1.10 | — | 0.34 | — | 0.37 | — | 1.2 |
| 1.28-1.29 | — | 0.42 | — | | — | — |
| Assay (% nominal) | 96.8 | 85.8 | 97.5 | 81.0 | 102.0 | 89.4 |
| Assay ( initial) | NA | 88.6 | NA | 83.1 | NA | 87.6 |

[1]HPLC Development method: IANA-090 Ed05

[2]% total impurities and degradation products calculated as 100% − % area lurbinectedin main peak.

[3]Reported impurities and degradation products: Area ≥ 0.20%

NA; Not applicable

Example 5: Effect of Bulk Solution pH on Lyophilized Product Stability

The stability of 4 mg of lyophilized product produced from various 0.03M sodium lactate buffer lurbinectedin bulk solutions was studied. The bulk solutions had a concentration of 0.5 mg lurbinectedin/mL at pH 3.6, pH 4.0 and pH 4.5, using 10% sucrose (w/v) as bulking agent (8 mL filling in 30 mL glass vials). The stability of these batches was evaluated under 25° C./60% RH to determine if small variations in pH could have a significant effect on the stability of the product.

The stability results of lyophilized vials after 6 months at 25° C. are shown in Table 6. All the batches showed similar behavior. Quality attributes such as the appearance of the lyophilized, appearance, color and pH of the reconstituted solution, water content (%) and assay were kept constant. Total degradation products did not undergo significant changes, As conclusion and based on the solubility and stability data, the lurbinectedin solution and a freeze-dried presentation, 0.03M sodium lactate buffer pH 4.0 was selected as the most suitable dissolution medium for lurbinectedin presentations.

TABLE 6

Stability at 25° C./60% RH of lurbinectedin 4 mg vial 30 mL at different pH

| | Batch 2021-79 (pH 3.6) Time at 25° C./60% RH | | | Batch 2021-52 (pH 4.0) time at 25° C./60% RH | | | Batch 2021-86 (pH 4.5) Time at 25° C./60% RH | | |
|---|---|---|---|---|---|---|---|---|---|
| Quality attribute | 0 | 3 months | 6 months | 0 | 3 months | 6 months | 0 | 3 months | 6 months |
| Appearance | White lyophilized cake | White lyophilized cake | White lyophilized cake | White lyophilized cake | White lyophilized cake | White lyophilized cake | White lyophilized cake | White lyophilized cake | White lyophilized cake |
| Identification by HPLC (RT) | Consistent with standard | Consistent with standard | Consistent with standard | Consistent with standard | Consistent with standard | Consistent with standard | Consistent with standard | Consistent with standard | Consistent with standard |
| Reconstitution time in water | NMT 3 min | NMT 3 min | NMT 3 min | NMT 3 min | NMT 3 min | NMT 3 min | NMT 3 min | NMT 3 min | NMT 3 min |
| Appearance of reconstituted solution | Clear solution free of visible particles | Clear solution free of visible particles | Clear solution free of visible particles | Clear solution free of visible particles | Clear solution free of visible particles | Clear solution free of visible particles | Clear solution free of visible particles | Clear solution free of visible particles | Clear solution free of visible particles |
| Color of reconstituted solution | Colorless solution | Colorless solution | Colorless solution | Colorless solution | Colorless solution | Colorless solution | Colorless solution | Colorless solution | Colorless solution |
| pH of reconstituted solution | 3.6 | 3.6 | 3.7 | 4.0 | 4.0 | 4.0 | 4.5 | 4.5 | 4.6 |
| Water (% w/w) | 1.4 | 1.6 | 1.4 | 1.2 | 1.4 | 1.2 | 1.3 | 1.4 | 1.4 |
| Impurities and degradation products (% w/w) | | | | | | | | | |
| Total[2] | 0.3 | 0.3 | 0.4 | 0.3 | 0.4 | 0.4 | 0.3 | 0.4 | 0.4 |
| Individual[3] (rrt) | | | | | | | | | |
| 0.87-0.88 (Imp D) | 0.27 | 0.29 | 0.30 | 0.27 | 0.24 | 0.29 | 0.25 | 0.26 | 0.30 |

TABLE 6-continued

| Stability at 25° C./60% RH of lurbinectedin 4 mg vial 30 mL at different pH | | | | | | | | | |
|---|---|---|---|---|---|---|---|---|---|
| | Batch 2021-79 (pH 3.6) Time at 25° C./60% RH | | | Batch 2021-52 (pH 4.0) time at 25° C./60% RH | | | Batch 2021-86 (pH 4.5) Time at 25° C./60% RH | | |
| Quality attribute | 0 | 3 months | 6 months | 0 | 3 months | 6 months | 0 | 3 months | 6 months |
| Assay (% nominal) | 100.7 | 101.1 | 100.8 | 99.4 | 99.4 | 100.3 | 99.6 | 100.3 | 100.1 |

rrt: relative retention time.
[1]HPLC Commercial method: MPI-00769 6.0 [26]
[2]Total impurities and degradation products calculated as the sum of individual impurities ≥ 0.05 (% w/w)
[3]Impurities and degradation products: % w/w ≥ 0.20%

Example 6: Bulking Agent Concentration

The stability of 4 mg of lyophilized product produced from various 0.03M sodium lactate buffer lurbinectedin bulk solutions was studied. The bulk solutions had a concentration of 0.5 mg lurbinectedin/mL at pH 3.6, pH 4.0 and pH 4.5, using 10% sucrose (w/v) as bulking agent (8 mL filling in 30 mL glass vials). The stability of these batches was evaluated under 25° C./60% RH to determine if small variations in pH could have a significant effect on the stability of the product.

Once the dissolution medium was selected, different bulking agents were screened at different concentrations: sucrose (5%, 7.5% and 10%), mannitol (5%), and combination of sucrose and mannitol (5% sucrose+2.5% mannitol).

For that purpose, several freeze-dried batches of lurbinectedin were manufactured with a strength of 4 mg/vial incorporating the different bulking agents at various concentrations. Lurbinectedin was dissolved at 0.5 mg/mL in 0.03M sodium lactate buffer pH 4. The batches composition is detailed in Table 7. Batches were characterized and their stability under stress conditions evaluated (40° C./75% RH).

TABLE 7

| Composition of batches of lurbinectedin 4 mg vial 30 mL manufactured with different contents of sucrose and mannitol | | | | | |
|---|---|---|---|---|---|
| | Vial composition | | | | |
| Component | 10% Sucrose Batch 2021-52 | 7.5% Sucrose Batch 2021-51 | 5% Sucrose Batch 2021-50 | 5% Mannitol Batch 2021-53 | 5% Sucrose/ 2.5% Mannitol Batch 2021-54 |
| Lurbinectedin | 4 mg | 4 mg | 4 mg | 4 mg | 4 mg |
| Lactic acid | 22.08 mg | 22.08 mg | 22.08 mg | 22.08 mg | 22.08 mg |
| Sodium hydroxide | 5.12 mg | 5.12 mg | 5.12 mg | 5.12 mg | 5.12 mg |
| Mannitol | N.A. | N.A. | N.A. | 400 mg | 200 mg |
| Sucrose | 800 mg | 600 mg | 400 mg | N.A. | 400 mg |
| Water[1] | q.s. 8 mL | q.s. 8 mL | q.s. 8 mL | q.s. 8 mL | q.s. 8 mL |

[1]Evaporates during lyophilization
N.A.: No applicable

Table 8 below shows the stability results of lyophilized batches with the different bulking agents after 3 months stored at 40° C./75% RH.

The batch formulated with 5% sucrose was stable, since it did not undergo changes in the appearance of the freeze-dried cake nor in the reconstituted solution, maintained the lurbinectedin assay, and only showed a slight increase in degradation products, being impurity D the main degradation product observed (rrt 0.88 HPLC commercial method).

However, batches formulated with sucrose and mannitol mixtures or only mannitol degraded significantly during storage at 40° C. In both cases, the appearance of the freeze-dried cake differed from batches bearing only sucrose (5% or 10%). The formulation containing 5% mannitol suffered a very significant decrease in lurbinectedin assay (43% of the nominal target). In addition, the % degradation products increased in both formulations (up to 57% in the formulation containing 5% mannitol). The two major degradation products in formulations containing mannitol are those eluting at rrt 0.67-0.68 and rrt 1.06).

TABLE 8

Stress stability of lurbinectedin batches containing different bulking agents

| | 5% Sucrose Batch 2021-50 | | 5% Sucrose + 2.5% Mannitol Batch 2021-54 | | 5% Mannitol Batch 2021-53 | |
|---|---|---|---|---|---|---|
| CQAs | t = 0 | 3 months at 40° C. | t = 0 | 3 months at 40° C. | t = 0 | 3 months at 40° C. |
| Appearance | White lyophilized cake | White lyophilized cake | White lyophilized cake | Very slightly yellow, shrinked and contracted cake | White lyophilized cake | Slightly yellow, cracked lyophilized cake |
| Identification | Consistent with standard | Consistent with standard | Consistent with standard | Consistent with standard | Consistent with standard | Consistent with standard |
| Reconstitution time in water | NMT 3 min | NMT 3 min | NMT 3 min | NMT 3 min | NMT 3 min | NMT 3 min |
| Appearance of reconstituted solution | Clear solution free of visible particles | Clear solution free of visible particles | Clear solution free of visible particles | Clear solution free of visible particles | Clear solution free of visible particles | Clear solution free of visible particles |
| Color of reconstituted solution | Colorless solution | Colorless solution | Colorless solution | Very slightly yellow solution | Colorless solution | Yellow solution |
| pH of reconstituted solution | 4.0 | 4.0 | 4.0 | 4.1 | 4.0 | 4.0 |
| Water content (% w/w) | 0.8 | 1.0 | 1.6 | 1.8 | 0.6 | 0.7 |
| | Impurities and degradation products[1] (% w/w) | | | | | |
| Total[2] | 0.3 | 0.8 | 0.3 | 14.5 | 0.3 | 57.3 |
| Individual[3] (RRT) | | | | | | |
| 0.23-0.24 | — | 0.10 | — | — | — | 5.3 |
| 0.29 | — | — | — | — | — | 3.6 |
| 0.5 | — | — | — | 1.7 | — | — |
| 0.67-0.68 | — | 0.10 | — | 2.9 | — | 2.5 |
| 0.70-0.71 | — | — | — | — | — | 1.7 |
| 0.72 | — | — | — | — | — | 1.5 |
| 0.73 | — | — | — | — | — | 1.7 |
| 0.77 | — | — | — | — | — | 1.0 |
| 0.78 | — | — | — | — | — | 1.0 |
| 0.87-0.88 (D) | 0.26 | 0.39 | 0.27 | 0.67 | 0.26 | 0.27 |
| 1.06 | — | — | — | — | — | 12.9 |
| 1.12 | — | 0.12 | — | — | — | — |
| 1.19-1.20 | — | — | — | — | — | 6.7 |
| Assay (% nominal) | 98.8 | 98.7 | 99.3 | 85.5 | 98.9 | 42.7 |

[1]HPLC Commercial Method: MPI-00769 6.0 [26]

[2]Total impurities and degradation products calculated as sum of all individual impurities with % w/w ≥0.05%.

[3]Reported individual impurities and degradation products: 5% Sucrose: (% w/w ≥0.10%; 5% Sucrose + 2.5% Mannitol and 5% Mannitol: t = 0 (% w/w) ≥0.10% and t = 3 months (% w/w) ≥1.0%.

Table 9 shows the results of stability of lyophilized vials formulated in 0.03M sodium lactate buffer pH=4 with sucrose at different concentrations in the range 5%-10% under stress conditions (40° C./75% RH)

TABLE 9

Stress stability of lurbinectedin freeze-dried vials formulated in 0.03M lactate buffer pH 4 with sucrose as bulking agent at different concentrations

| | 5% Sucrose Batch 2021-50 | | 7.5% Sucrose Batch 2021-51 | | 10% Sucrose Batch 2021-52 | |
|---|---|---|---|---|---|---|
| CQAs | t = 0 | 3 months at 40° C. | t = 0 | 3 months at 40° C. | t = 0 | 3 months at 40° C. |
| Appearance | White lyophilized cake | White lyophilized cake | White lyophilized cake | White lyophilized cake | White lyophilized cake | White lyophilized cake |
| Identification by HPLC (RT) | Consistent with standard | Consistent with standard | Consistent with standard | Consistent with standard | Consistent with standard | Consistent with standard |
| Reconstitution time in water | NMT3min | NMT 3 min | NMT 3 min | NMT 3 min | NMT 3 min | NMT 3 min |
| Appearance of reconstituted solution | Clear solution free of visible particles | Clear solution free of visible particles | Clear solution free of visible particles | Clear solution free of visible particles | Clear solution free of visible particles | Clear solution free of visible particles |
| Color of reconstituted solution | Colorless solution | Colorless solution | Colorless solution | Colorless solution | Colorless solution | Colorless solution |
| pH of reconstituted solution | 4.0 | 4.0 | 4.0 | 4.1 | 4.0 | 4.0 |
| Water content (% w/w) | 0.8 | 1.0 | 1.1 | 1.2 | 1.2 | 1.5 |

TABLE 9-continued

Stress stability of lurbinectedin freeze-dried vials formulated in 0.03M lactate buffer pH 4 with sucrose as bulking agent at different concentrations

| CQAs | 5% Sucrose Batch 2021-50 t = 0 | 5% Sucrose Batch 2021-50 3 months at 40° C. | 7.5% Sucrose Batch 2021-51 t = 0 | 7.5% Sucrose Batch 2021-51 3 months at 40° C. | 10% Sucrose Batch 2021-52 t = 0 | 10% Sucrose Batch 2021-52 3 months at 40° C. |
|---|---|---|---|---|---|---|
| | Impurities and degradation products (% w/w)[1] | | | | | |
| Total[1] | 0.3 | 0.8 | 0.3 | 0.8 | 0.3 | 0.7 |
| Individual[3] (RRT) | | | | | | |
| 0.24 | — | 0.10 | — | — | — | — |
| 0.68 | — | 0.10 | — | 0.11 | — | 0.10 |
| 0.87-0.88 (D) | 0.26 | 0.39 | 0.26 | 0.39 | 0.27 | 0.40 |
| 1.12 | — | 0.12 | — | — | — | — |
| Assay (% nominal) | 98.8 | 98.7 | 90.5 | 98.1 | 99.4 | 99.2 |

[1]HPLC Commercial Method: MPI-007696.0 [26]
[2]Total impurities and degradation products calculated as sum of all individual impurities with % w/w ≥0.05%
[3]Reported individual impurities and degradation products: % w/w ≥0.10%

The batches containing sucrose at 3 different concentrations showed similar behavior and remained stable. They did not undergo significant changes in the appearance of the freeze-dried cake and lurbinectedin assay (%). A slight increase in the % degradation products was observed. In particular, Impurity D (rrt 0.88, HPLC commercial method) was the main degradation product. The percentage of sucrose does not significantly affect the stability of the product, although 10% sucrose showed the lowest degradation.

As a conclusion, sucrose showed a protective effect to prevent lurbinectedin degradation during storage at high temperature. Based on these results, sucrose was selected as the most appropriate bulking agent being the concentration of 10% (w/v) an optimal quantity for a suitable and stable lurbinectedin presentation.

Example 7: Stability of Lurbinectedin at Long-Term Storage Conditions

The stability of lyophilized lurbinectedin composition (4 mg) at the conditions proposed for long-term storage (5° C.±3° C.) was evaluated during 36 months. A batch with high residual water content was chosen as it is considered as a worst case.

The product remained stable during the 36 months of the study (Table 10). None of the quality attribute underwent significant changes. The content of lurbinectedin suffered small variations attributed to the analytical variability during the first 24 months. The total degradation products did not change throughout the storage time. The related substance observed at reportable levels was Impurity D that remained constant and at the levels present in the active ingredient used to manufacture the batch.

TABLE 10

Stability Study of Lurbinectedin 4 mg at 5° C. ± 3° C.

| Test[a] | Acceptance Criteria | Time (months) 0 | 3 | 6 | 9 | 12 | 18 | 24 | 36 | 48 | 60 |
|---|---|---|---|---|---|---|---|---|---|---|---|
| Appearance | White to off-white lypophilized cake | Complies | Complies | Complies | Complies | Complies | Complies | Complies | Complies | Complies | Complies |
| Identification by HPLC (RT) | Consistent with standard | Complies | Complies | Complies | Complies | Complies | Complies | Complies | Complies | Complies | Complies |
| Reconstitution time in water | NMT 3 min | <3 min | <3 min | <3 min | <3 min | <3 min | <3 min | <3 min | <3 min | <3 min | <3 min |
| Appearnnce of reconstituted solution | Clear solution essentially free of visible particles | Complies | Complies | Complies | Complies | Complies | Complies | Complies | Complies | Complies | Complies |
| Color of reconstituted solution | Colorless or slightly yellowish solution | Complies | Complies | Complies | Complies | Complies | Complies | Complies | Complies | Complies | Complies |
| pH of reconstituted solution | 3.8 to 4.5 | 4.1 | 4.0 | 4.0 | 4.0 | 4.0 | 4.0 | 4.0 | 4.1 | 4.0 | 4.0 |

TABLE 10-continued

| Stability Study of Lurbinectedin 4 mg at 5° C. ± 3° C. | | | | | | | | | | | |
|---|---|---|---|---|---|---|---|---|---|---|---|
| | Acceptance | Time (months) | | | | | | | | | |
| Test[a] | Criteria | 0 | 3 | 6 | 9 | 12 | 18 | 24 | 36 | 48 | 60 |
| Subvisible particles (per vial) | | | | | | | | | | | |
| Larger than 10 μm | NMT 6000 | 16 | NA | NA | NA | NA | NA | 66 | 54 | NA | 52 |
| Larger than 25 μm | NMT 600 | 1 | NA | NA | NA | NA | NA | 0 | 0 | NA | 1 |
| Moisture (% w/w) | NMT 3.0 | 0.7 | 0.6 | 0.8 | 0.6 | 0.8 | 0.8 | 0.8 | 0.7 | 1.5 | 0.8 |
| | | Degradation products (% w/w) | | | | | | | | | |
| Total | NMT 1.3 | 0.4 | 0.4 | 0.5 | 0.4 | 0.5 | 0.5 | 0.5 | 0.5 | 0.5 | 0.5 |
| Specified Impurity D | NMT 0.8 | 0.3 | 0.3 | 0.3 | 0.3 | 0.3 | 0.3 | 0.3 | 0.3 | 0.3 | 0.3 |
| Unspecified, individual | NMT 0.3 | <0.1 | <0.1 | 0.1 | <0.1 | 0.1 | <0.1 | 0.1 | 0.1 | 0.1 | 0.2 |
| Assay (% of label claim) | 90.0 to 100.0 | 99.1 | 98.8 | 100.0 | 100.3 | 99.9 | 98.5 | 100.7 | 98.8 | 98.2 | 99.4 |
| Sterility | Sterile | Sterile | NA | NA | NA | NA | NA | NA | Sterile | Sterile | Sterile |

NA: No applicable

Example 8: Clinical Study—Treatment of SCLC Patients with Lurbinectedin

A clinical study of lurbinectedin monotherapy for patients collectively afflicted with SCLC who have refractory or resistant disease, as defined herein, was carried out. In this clinical single-arm, multi-center, open-label, phase 2 trail, a cohort of 105 patients, who had measurable disease, including patients whose SCLC was unresponsive to first-line platinum-containing chemotherapy (cisplatin, carboplatin or oxaliplatin) (refractory) and patients whose SCLC recurred within or equal to 90 days after cessation of first-line therapy (resistant), were treated with lurbinectedin at a dosage of 3.2 mg/m$^2$ given intravenously over a period of 1 hour every 21 days. Lurbinectedin was provided as a sterile isotonic aqueous solution for IV infusion as described below.

Study Population

Adult patients aged at least 18 years with a pathologically proven diagnosis of SCLC were included if they had: pre-treatment with only one previous chemotherapy-containing treatment line (immunotherapy was allowed, combined with chemotherapy or alone); measurable response as per the Response Criteria in Solid Tumors (RECIST version 1.1), and documented progression before study entry; and an Eastern Cooperative Oncology Group (ECOG) performance status of 2 or lower. Patients were required to have adequate bone marrow function (evaluated by laboratory tests for absolute neutrophil count, platelet count, and hemoglobin), kidneys (evaluated by serum creatinine and creatinine kinase), liver (evaluated by total bilirubin, albumin, and aminotransferases). The minimum interval between any previous treatment and study commencement had to be 3 weeks for chemotherapy, 4 weeks for immunotherapy or radiotherapy, and 2 weeks for any investigational or palliative therapy. Only patients with grade 1 or lower toxicities from any previous therapies were included, except for cases with alopecia and peripheral sensory neuropathy (both grade 2), which were also allowed. Women of child-bearing age had to receive adequate contraception during the study and for at least 3 months after study conclusion.

Patients were excluded if they have: previously received lurbinectedin or trabectedin; previous or concurrent malignant disease unless in complete remission for than 5 years; known CNS involvement (screening of CNS metastasis at baseline are mandatory); concomitant unstable or serious medical condition within the past year (history or presence of unstable angina, myocardial infarction, congestive heart failure, valvular heart disease, arrhythmia, severe dyspnoea, or active infection, such as hepatitis or HIV); impending need for radiotherapy; or inability or restricted ability to comply with the study protocol. More details on inclusion and exclusion criteria can be found in Table 11.

| Inclusion | Exclusion |
|---|---|
| Age ≥18 years.<br>Voluntary signs informed consent of the patient before any study-specific procedure.<br>Pathologically proven diagnosis of small cell lung cancer.<br>Patients must have received one prior chemotherapy-containing line.<br>Measurable disease as defined by the RECIST v.1.1, and documented progression before study entry.<br>Eastern Cooperative Oncology group performance status ≤2. | Prior treatment with lurbinectedin or trabectedin.<br>Prior or concurrent malignant disease unless in complete remission for more than five years, except treated in situ carcinoma of the cervix, basal or squamous cell skin carcinoma, and in situ transitional cell bladder carcinoma.<br>Known central nervous system involvement. Brain computed tomography-scan or magnetic resonance imaging results has to be provided at baseline. |

-continued

| Inclusion | Exclusion |
|---|---|
| Adequate major organ function: Hemoglobin ≥9 g/dL, prior red blood cell transfusions is allowed if clinically indicated; absolute neutrophil counts ≥2.0 × $10^9$/L; and platelet count ≥100 × $10^9$/L. Alanineaminotransferaseandaspartate aminotransferase <3.0 × ULN. Total bilirubin <1.5 × ULN, or direct bilirubin <ULN. Albumin ≥3 g/dL. Serum creatinine ≤1.5 × ULN or creatinine clearance ≥30 mL/min. Creatine phosphokinase ≤2.5 × ULN. Washout periods prior to Day 1 of Cycle 1: At least three weeks since the last chemotherapy (six weeks if therapy contained nitrosureas or systemic mitomycin C). At least four weeks since the last monoclonal antibody-containing therapy, or radiotherapy >30 gray At least two weeks since the last biological/investigational therapy (excluding monoclonal antibodies) or palliative radiotherapy (≤10 fractions or ≤30 Gy total dose). Grade ≤1 toxicity due to any previous cancer therapy according to the National Cancer Institute Common Terminology Criteria for Adverse Events, v.4. Grade 2 is allowed in case of alopecia and/or peripheral sensory neuropathy. Women of childbearing potential must have pregnancy excluded by appropriate testing before study entry. Fertile women have to agree to use a medically acceptable method of contraception throughout the treatment period and for at least three months after treatment discontinuation. Fertile men had to agree to refrain from fathering a child or donating sperm during the trial and for four months after the last infusion. | Relevant diseases or clinical situations which may increase the patient's risk: History within the last year or presence of unstable angina, myocardial infarction, congestive heart failure, or clinically relevant valvular heart disease or symptomatic arrhythmia or any asymptomatic ventricular arrhythmia requiring ongoing treatment. Grade ≥3 dyspnea or daily intermittent oxygen requirement within two weeks prior to the study treatment onset. Active infection. Unhealed wounds or presence of any external drainage. Known chronic active hepatitis or cirrhosis. Immunocompromised patients, including known infection by human immunodeficiency virus. Women who are pregnant or breast feeding and fertile patients (men and women) who are not using an effective method of contraception.* Impending need for radiotherapy (e.g., painful bone metastasis and/or risk of spinal cord compression). Limitation of the patient's ability to comply with the treatment or to follow-up the protocol. |

*Women of childbearing potential have to agree to use an effective contraception method to avoid pregnancy during the course of the trial (and for at least three months after the last infusion). Fertile men have to agree to refrain from fathering a child or donating sperm during the trial and for four months after the last infusion.

Study Drug Formulation—Preparation and Administration

Lurbinectedin was presented as lyophilized powder for concentration for solution for infusion in 4 mg vials. Before use, the 4 mg vials were reconstituted with 8 mL of water for injection to give a solution containing 0.5 mg/mL of lurbinectedin. For administration to patients as an i.v. infusion, reconstituted vials were diluted with glucose 50 mg/mL (5%) solution for infusion or sodium chloride 9 mg/mL (0.9%) solution for infusion. The full composition and the reconstituted solution per mL was as shown in Table 12.

TABLE 12

Composition of 4 mg lurbinectedin vials

| Component | Concentration/ vial | Concentration/ vial after reconstitution |
|---|---|---|
| PM01183 | 4.0 mg | 0.5 mg/ml |
| Sucrose | 800 mg | 100 mg/ml |
| Lactic acid | 22.08 mg | 2.76 mg/ml |
| Sodium hydroxide | 5.12 mg | 0.64 mg/ml |

Dosage and Administration

Lurbinectedin was administered over a minimum total volume of 100 mL of solution for infusion (either on 5% glucose or 0.9% sodium chloride), through a central catheter, or over a minimum total volume of 250 mL if administered through a peripheral line, always over one hour at a fixed infusion rate.

Starting dose was 3.2 mg/m$^2$. Dose was capped at body surface area of 2.0 mg/m$^2$ (e.g. dose not allowed to exceed 6.4 mg). Patients received lurbinectedin i.v. as a one-hour infusion on Day 1 every three weeks until disease progression or unacceptable toxicity. Three weeks was defined as one treatment cycle.

Premedication

All patients received antiemetic prophylaxis before each treatment infusion. The i.v. formulations of these agents were used in this setting: Corticosteroid (dexamethasone 8 mg or equivalent), serotonin antagonists (ondansetron 8 mg or equivalent), extended treatment with oral serotonin antagonists, and oral dexamethasone for two consecutive days. If necessary, and in addition to the above, administration of 10 mg of oral or i.v. metoclopramide (or equivalent)

every 8 hours. Aprepitant and equivalent agents were forbidden in patients treated with lurbinectedin.

Criteria for Treatment Continuation

Further treatment cycles were administered q3wk (±48 hours) if the patient fulfilled all the treatment criteria described in Table 13.

TABLE 13

| Variable | Re-treatment (Day1) |
|---|---|
| ECOG PS | ≤2 |
| Hemoglobin* | ≥8.0 g/dl |
| ANC | ≥1.5 × $10^9$/l |
| Platelets | ≥100 × $10^9$/l |
| AST/ALT | ≤3.0 × ULN |
| Total bilirubin or Albumin | ≤1.5 × ULN or ≥3 g/dl |
| Serum creatinine | ≤1.5 × ULN or creatinine clearance ≥30 ml/min |
| CPK | Grade ≤1 |
| Other non-hematological drug-related AEs (except isolated increased GGT and/or AP; grade 2 asthenia, constipation, alopecia, peripheral neuropathy, or non-optimally treated nausea and/or vomiting | Grade ≤1 |
| Active infection (including sepsis) and/or bleeding (any grade) | Absence |

AE(s), adverse event(s);
ANC, absolute neutrophil count;
AP, alkaline phosphatase;
AST/ALT, aspartate aminotransferase/alanine aminotransferase;
CPK, creatinine phosphokinase;
ECOG, Eastern Cooperative Oncology Group;
GGT, gamma-glutamyltransferase;
PS, performance status;
ULN, upper limit of normal.

Patients received packed red blood cells transfusion and/or erythropoietin treatment, if clinically indicated, to increase/maintain adequate hemoglobin levels. If a patient did not meet the requirements for re-treatment on Day 1 of any following cycle, regardless of the reason, reassessments were performed at least every 48-72 hours. Treatment was then withheld, up to a maximum of three weeks beyond its due date, until appropriate recovery. Patients not meeting re-treatment criteria after a maximum 3-week delay had to withdraw from trial. For any delay due to treatment-related adverse events lasting for more than one week, a dose reduction was implemented upon recovery, following the rules explained in the next section.

Dose Modifications for Adverse Reactions

Patients continued the treatment if they presented with any of the following: (1) Grade 3 treatment-related non-hematological toxicity. Exceptions were: Grade 3 nausea and/or vomiting not optimally treated, grade 3 asthenia lasting s 3 days, grade 3 diarrhea lasting s 2 days or not optimally treated, grade 3 transient ALT/AST elevations which are rapidly reversible and not leading to subsequent delays, and non-clinically relevant biochemical abnormalities. (2) Grade 4 thrombocytopenia or Grade 3 thrombocytopenia concomitantly with grade ≥3 bleeding. (3) Grade 4 neutropenia, any grade febrile neutropenia or neutropenia associated with infection/sepsis. (4) Frequent of prolonged (>1 week) dose delays due to treatment-related adverse events. Patients who experienced Grade 3 or 4 hypersensitivity reactions were discontinued from study treatment.

Previous analysis with lurbinectedin administered following a dose based on body surface area showed that the incidence of febrile neutropenia with lurbinectedin use was lower than 10%. Therefore, according to guidelines from the American Society of Clinical Oncology and European Society for Medical Oncology, primary prophylaxis with granulocyte colony-stimulating factors (G-CSF) was not allowed (secondary prophylaxis with G-CSF for neutropenia was allowed).

Dose reduction levels are shown in Table 14 below:

TABLE 14

| Dose Modification | |
|---|---|
| Dose Reduction | Lurbinectedin Dose (mg/m2) |
| 1 (starting dose) | 3.2** |
| −1 | 2.6 |
| −2 | 2.0 |

**Dose will be capped at BSA of 2.0 m2 (i.e. dose will not exceed 6.4 mg) BSA, body surface area.

Up to 2 dose reductions were allowed per patient. Patients who continued to experience treatment-related toxicity and/or frequent dose delays after permitted dose reductions were withdrawn from the study. They could continue receiving the study medication if objective clinical benefit is adequately documented. Once a dose had been reduced for an individual patient, the dose was not re-escalated under any circumstances.

Efficacy Evaluations

The primary objective of this study was to assess the antitumor activity of lurbinectedin in terms of overall response rate (ORR) as primary endpoint and supported by duration of response (DOR) as secondary endpoint. ORR was assessed using RECIST v1.1. on a set of measurable lesions identified at baseline as target lesions or as non-target lesions (if any), and followed until disease progression (PD) by an appropriate method.

Radiological tumor assessment (CT scan or MRI) was performed at baseline, and every 6 weeks from the onset of the study treatment until cycle 6 or evidence of PD, and every 9 weeks thereafter. If an objective response was observed, according to RECIST v1.1., it had to be confirmed by the same method at least four weeks after the date of the first documentation of response.

ORR was defined as the percentage of evaluable patients with a confirmed response, either complete (CR) or partial response (PR), from the start of treatment to the date of progression or the start of a subsequent therapy or end of patients follow-up according to RECIST v1.1. DOR was calculated from the date of first documented PD, recurrence, or death due to any cause in the responder patients. The date of response, the date of radiological or clinical PD, according to the investigator assessment and the independent assessment by an independent review committee (IRC), and the date of death was registered and documented, as appropriate. The IRC determined the patient's best response and assigned the date of first documentation of response and progression/censoring according to RECIST v1.1.

Counts and percentages, with their corresponding exact 95% confidence intervals were calculated for the binominal endpoints (i.e. ORR, clinical benefit). Time-to-event variables (OS, PFS, and DOR) and their set time estimates (i.e. PFS4/6 and OS6/12) were analyzed according to Kaplan-Meier method. The evaluation of the efficacy endpoints evaluated by IA and IRC were analyzed and compared.

Pharmacokinetic Evaluations

The plasma PK of lurbinectedin was evaluated during Cycles 1 and 2 in all treated patients. The sampling schedule is shown in Table 15 and Table 16, respectively.

PK analysis of plasma-concentration-time data of lurbinectedin was performed using non-linear mixed-effects modeling and/or non-compartment analysis.

TABLE 15

Blood samples from PK evaluations-Cycle 1

| Sample No. | Day | Sampling time | Sampling window |
|---|---|---|---|
| #1 | D1 | Before infusion start | — |
| #2 * | D1 | 5 min before EOI | +/−4 min |
| #3 | D1 | 30 min after EOI | +/−4 min |
| #4 | D1 | 1 hour after EOI | +/−10 min |
| #5 | D1 | 3 hours after EOI | +/−10 min |
| #6 | D2 | 24 hours after EOI | +/−2 hours |
| #7 | D4 | 72 hours after EOI | +/−24 hours |
| #8 | D8 | 168 hours after EOI | +/−24 hours |

* Sample #2 must be collected before EOI.
D, day; EOI, end of infusion.

TABLE 16

Blood samples from PK evaluations-Cycle 2

| Sample No. | Day | Sampling time | Sampling window |
|---|---|---|---|
| #9 | D1 | Before infusion start | — |
| #10 * | D1 | 5 min before EOI | +/− 4 min |
| #11 | D1 | 30 min after EOI | +/− 4 min |
| #12 | D1 | 1 hour after EOI | +/− 10 min |
| #13 | D1 | 3 hours after EOI | +/− 10 min |
| #14 | D8 | 168 hours after EOI | +/− 24 hours |

* Sample #10 must be collected before EOI D, day; EOI, end of infusion.

Safety Evaluation

Patients were evaluated for safety if they had received any partial or complete infusion of lurbinectedin. All adverse events were graded according to the National Cancer Institute-Common Toxicity Criteria for Adverse Events (NCI-CTCAE, v4). The safety profile of patients was monitored throughout the treatment and up to 30 days after the last lurbinectedin infusion (end of treatment), or until the patient started a new anti-tumor therapy or until the date of death, whichever occurred first. Treatment delays, dose reduction requirements, transfusions, and reason for treatment discontinuation was monitored throughout the study. Any treatment-related adverse events were followed until recovery to at least grade 1 or stabilization of symptoms or until the start of a new anti-tumor therapy, whichever occurred first.

Study Endpoints

| Primary Endpoint | |
|---|---|
| Overall Response Rate (ORR) | ORR is defined as the percentage of patients with a confirmed response, either complete (CR) or partial (PR), according to the RECIST (v. 1.1). |
| **Secondary Endpoints** | |
| Duration of Response (DR) | DR is defined as the time between the date when the response criteria (PR or CR, whichever one is first reached) are fulfilled to the first date when PD, recurrence or death is documented. |
| Clinical Benefit | Clinical Benefit is defined as ORR or stable disease lasting over four months (SD ≥4 months) |
| Progression-free Survival (PFS) | PSF is defined as the period of time from the date of first infusion to the date of PD, death (of any cause), or last tumor evaluation. |
| PFS4/PFS6 | PFS4/PFS6 is defined as the Kaplan-Meier estimates of the probability of being free from progression and death after the first infusion at these time points (4 and 6 months). |
| Overall Survival (SO) | OS is defined as the period of time from the date of first infusion to the date of death or last contact in case of patients lost to follow-up or alive at the clinical cut-off established for the cohort. |
| OS6/OS12 | OS6/OS12 is defined as the Kaplan-Meier estimates of the probability of being alive after the first infusion at these time points (6 and 12 months) |
| Plasma Pharmacokinetics (PK) | Non-compartmental (NCA) PK parameters: area under the curve (AUC), $C_{max}$, clearance (CL) and half-life (t1/2) Population PK parameters of the compartment model to be developed (initially based on Volumes and Clearance), and PK/PD correlation parameters, if applicable. |
| Safety Profile | Clinical examinations. Clinical assessment of AEs and serious adverse events (SAEs). Changes in laboratory parameters (hematological and biochemical, including liver function tests). Reasons for treatment discontinuations. Reasons for dose reduction and treatment delays. |

Statistical Methods

This phase II trial was designed to assess the antitumor activity of lurbinectedin in terms of ORR according to the RECIST v.1.1 assessed by IA and tumor evaluation was also done by IRC.

Up to 100 evaluable patients were recruited to test the null hypothesis that 15% or less patients get a response ($p<0.15$) versus the alternative hypothesis that 30% or more patients get a response (p 0.30). The variance of the standardized test was based on the null hypothesis. The type I error (alpha) associated with this one-sided test is 0.025 and the type II error (beta) is 0.051 (normal approximation; ~0.05 if exact binomial distribution); hence, statistical power is 95% (normal approximation; ~95% if exact binomial distribution). With these assumptions, if the number of patients who achieved a confirmed response is 23, then this would allow the rejection of the null hypothesis. The judgement of patient's evaluability and replacement of non-evaluable patients in each cohort for the interim analyses was guided by the investigator assessment.

Duration of Study Period

Patients were evaluated at scheduled visits within three study periods: (1) Pre-treatment: from signature of IC to the first infusion of the study treatment; (2) Treatment: from the first infusion of the study treatment to the end of treatment; and (3) Follow-up: after end of treatment; patients were followed-up every 4 weeks until resolution or stabilization of all drug-related adverse events, if any, or until start of new anti-tumor therapy. Patients were followed up for at least 1 year after their first lurbinectedin infusion. Patients who finished treatment without PD were followed every 2 months during the first six months and every 3 months thereafter until PD, start of a new anti-tumor therapy, death, or until end of study date.

Results

105 SCLC patients were enrolled into the study. All 105 patients were treated and included in the analysis for the primary endpoint. Of the 105 treated patients, 60% were male, 75% were white, 92% had ECOG PS 0 or 1, and the median age was 60 years (range, 40-83 years; 35.2% were ≥65 years old). Two of the 105 treated patients (1.9%) had previously undergone surgery (curative resection in one patient). Prior radiotherapy had been administered to 75 patients (71.4%). The patients had received a median of one prior line of chemotherapy for advanced disease (range, 1-2 lines). The chemotherapy-free interval was less than 30 days in 21 (21%) patients, less than 90 days in 45 (43%) patients, and 90 days or longer in 60 (57%) patients. One patient with CNS metastases at baseline was included, and another patient had rechallenge with carboplatin plus etoposide and atezolizumab as previous line of therapy; these two cases were considered protocol deviations, but they were minor and were included in the primary analysis.

618 treatment cycles in total were administered, with a median of four cycles per patient, and 46 (44%) patients received six cycles or more. The median relative dose intensity of the study drug was 97.4% of the planned maximum dose. Dose administration was delayed in 23 (22%) patients and reduced in 28 (26%) because of treatment-related adverse events (neutropenia was the most common cause of both dose delays in 13 (12%) and reductions in 17 (16%) of patients).

Efficacy of Lurbinectedin in SCLC Patients

At data cutoff, median follow-up was 17.1 months. According to the investigator assessment of all treated patients, 37 (35.2%) had an overall response as shown in

TABLE 17

| Parameter | Assessment by | Overall (n = 105) | Resistant Disease (CTFI <90 days) (n = 45) | Sensitive Disease (CTFI ≥90 days) (n = 60) |
|---|---|---|---|---|
| Overall response rate (CR + PR) (95% Cl) | Investigator | 35.2% (26.2-45.2) | 22.2% (11.2-37.1) | 45.0% (32.1-58.4) |
| | IRC | 30.5% (21.9-40.2) | 13.3% (5.1-26.8) | 43.3% (30.6-56.8) |
| Duration of response, median, months (95% Cl) | Investigator | 5.3 months (4.1-6.4) | 4.7 months (2.6-5.6) | 6.2 months (3.5-7.3) |
| | IRC | 5.1 months (4.9-6.4) | 4.8 months (2.4-5.3) | 5.3 months (4.9-7.0) |

In the pre-planned analysis of overall response by chemotherapy-free interval (>90 days vs<90 days) of 60 patients who had a chemotherapy-free interval of 90 days or longer (i.e., those with chemotherapy-sensitive disease), 27 (45.0%) had an overall response, with a median duration of response of 6.2 months, whereas in 45 patients who had a chemotherapy-free interval of less than 90 days (i.e., chemotherapy-resistant disease), ten (22.2%) had an overall response, with a median duration of response of 4.7 months.

Progression-Free Survival

Investigator-assessed median progression-free survival was 3.5 months (95% Cl 2.6-4.3) in the overall population: 4.6 months in patients with a chemotherapy-free interval of 90 days or longer and 2.6 months in patients with chemotherapy-free interval of less than 90 days. Eight (9%) of 94 patients who discontinued lurbinectedin treatment had disease progression with new lesions in the CNS. No increased incidence of CNS metastases was therefore observed.

Overall Survival

With a censoring of 37.1% (39 of 105 patients alive at data cutoff), median overall survival was 9.3 months (95% Cl 6.3-11.8) in the overall population, 11.9 months (9.7-16.2) in patients with a chemotherapy-free interval of 90 days or longer, and 5.0 months (4.1-6.3) in patients with chemotherapy-free interval of less than 90 days. Notably, 29 (48%) of 60 patients with a chemotherapy-free interval of 90 days or longer and seven (16%) of 45 patients with a chemotherapy-free interval of less than 90 days were alive at 1 year after the first dose administration.

In a post-hoc analysis, of the 37 patients who had an initial objective response, median overall survival exceeded 1 year in the overall population (12.6 months, 95% Cl 10.8-15.8) and in patients with sensitive disease (15.8 months, 10.2—not reached) and was 10.9 months in patients with resistant disease (10.9 months, 6.3-14.0).

Safety

All 105 treated patients were evaluable for safety (Table 18). The most common Grade 3-4 adverse events and laboratory abnormalities (in 2% of patients) were hematological disorders, including anemia (nine [9%] patients), leukopenia (30 [29%]), neutropenia (48 [46%]), thrombocytopenia (seven [7%]), and febrile neutropenia (five [5%]); of these, only febrile neutropenia was regarded as treatment related (Table 18). Notably, no cases of drug-induced liver injury were reported. 23 (22%) of 105 patients received G-CSF secondary prophylaxis or therapy for neutropenia. Serious treatment-related adverse events occurred in 11 (10%) of 105 patients; neutropenia and febrile neutropenia were the most common (five [5%] patients for each). Grade 3 pneumonia was reported in two (2%) patients; these episodes were associated with grade 3 febrile neutropenia and grade 4 neutropenia, lasted 3 days for one patient and 13 days for the other, and resolved with no clinical consequences. One patient had a grade 3 skin ulcer because of extravasation, with no clinical consequences. Only two (2%) patients discontinued lurbinectedin therapy because of treatment-related adverse events. No treatment-related deaths occurred, but 66 (63%) of 105 patients died from disease progression.

TABLE 18

| | Grade 1-2 | Grade 3 | Grade 4 |
|---|---|---|---|
| Haematological abnormalities (regardless of relation to study drug)* | | | |
| Anaemia | 91 (87%) | 9 (9%) | 0 |
| Leucopenia | 53 (50%) | 20 (19%) | 10 (10%) |
| Neutropenia | 27 (26%) | 22 (21%) | 26 (25%) |
| Thrombocytopenia | 39 (37%) | 3 (3%) | 4 (4%) |
| Biochemical abnormalities (regardless of relation to study drug)* | | | |
| Creatinine† | 86/104 (83%) | 0 | 0 |
| Alanine aminotransferase | 69/103 (67%) | 5/103 (5%) | 0 |
| γ-glutamyl transferase | 52/103 (50%) | 13/103 (13%) | 2/103 (2%) |
| Aspartate aminotransferase | 44/103 (43%) | 2/103 (2%) | 0 |
| Alkaline phosphatase | 31/103 (30%) | 3/103 (3%) | 0 |
| Treatment-related adverse events | | | |
| Fatigue | 54 (51%) | 7 (7%) | 0 |
| Nausea | 34 (32%) | 0 | 0 |
| Decreased appetite | 22 (21%) | 0 | 0 |
| Vomiting | 19 (18%) | 0 | 0 |
| Diarrhoea | 13 (14%) | 1 (1%) | 0 |
| Febrile neutropenia | 0 | 2 (2%) | 3 (3%) |
| Pneumonia | 0 | 2 (2%) | 0 |
| Skin ulcer | 0 | 1 (1%) | 0 |

Data are n (%) of patients.

NCI-CTCAE = National Cancer Institute Common Terminology Criteria for Adverse Events version 4.0.

*Based on all patients with laboratory data available.

†Version 4.0 of NCI-CTCAE grades any creatinine increases from baseline as abnormalities, even if creatinine values remain within the normal range.

Prior Immunotherapy

Post-hoc exploratory analysis was done on the response in patients who had previously received immunotherapy (n=8). Data from this group of patients showed a trend for a better response to single-agent lurbinectedin following first-line platinum-containing chemotherapy in combination with checkpoint inhibitors or second-line with nivolumab (Table 19). This is an important finding in light of the recent approval of atezolizumab in first-line SCLC in combination with carboplatin/etoposide; hence, lurbinectedin could provide a viable option for patients who progress on immunotherapy.

Summary and Conclusions

105 SCLC patients were enrolled and treated with lurbinectedin. Median follow-up was 17.1 months (IQR 6.5-25.3). Overall response by investigator assessment was seen in 37 patients (35.2%; 95% CI 26.2-45.2). The most common grade 3-4 adverse events (irrespective of causality) were hematological abnormalities-namely, anemia (in nine [9%] patients), leucopenia (30 [29%]), neutropenia (48 [46%]), and thrombocytopenia (seven [7%]). Serious treatment-related adverse events occurred in 11 (10%) patients, of which neutropenia and febrile neutropenia were the most common (five [5%] patients for each). No treatment-related deaths were reported.

Lurbinectedin was active as second-line therapy for SCLC in terms of overall response and had an acceptable and manageable safety profile. Lurbinectedin could represent a potential new treatment for patients with SCLC, who have few options especially in the event of a relapse.

Example 8: Clinical Study—Treatment of Solid Cancer Patients with Lurbinectedin and Irinotecan A clinical study of lurbinectedin in combination with irinotecan for patients afflicted with solid tumors was carried out. A Phase 1 trial to evaluate escalating doses of lurbinectedin on Day (D) 1 plus a fixed dose of irinotecan 75 mg/m$^2$ on D1 and D8 every 3 weeks (q3w) in patients with advanced solid tumors. Patients were enrolled following a standard 3+3 dose escalation design. Phase Ib/II expansion part at the recommended dose (RD) was performed to explore efficacy in indications where antitumor activity signal was observed.

Study Population

Details on inclusion and exclusion criteria can be found in Table 20.

TABLE 19

| Disease (resistant or sensitive)[a] | Last prior therapy: No. of prior regimens | Last prior therapy: Agent or regimen | Last prior therapy: Best response | Last prior therapy: TTP (months) | Lurbinectedin treatment: Best response | Lurbinectedin treatment: PFS (months) | Lurbinectedin treatment: DoR (months) | Lurbinectedin treatment: OS (months) |
|---|---|---|---|---|---|---|---|---|
| Resistant | 1 | C/E/Atezolizuma | PR | 3.9 | PR | 8.3 | 5.6 | 14.9 |
| Resistant | 2 | Nivolumab | PD | 2.5 | PR | 6.9 | 5.3 | 6.9+ |
| Resistant | 2 | CE/Atezolizumab | PR | 4.0 | PR | 6.3 | 5.1 | 12.6 |
| Resistant | 2 | Nivolumab | SD | 2.2 | SD | 6.0 | — | 12.0 |
| Resistant | 2 | Nivolumab | SD | 4.1 | PD | 1.3 | — | 4.9 |
| Sensitive | 1 | CE/Atezolizumab | PR | 7.6 | PR | 7.6 | 6.4 | 9.3 |
| Sensitive | 2 | Nivolumab | PD | 1.8 | PR | 4.7 | 2.8 | 10.8 |
| Sensitive | 2 | Nivolumab | PD | 1.4 | PD | 1.3 | — | 2.3 |

| Inclusion | Exclusion |
| --- | --- |
| Voluntarily signed and dated written informed consent prior to any specific-study procedure.<br>Age ≥18 years.<br>Eastern Cooperative Oncology Group (ECOG) performance status (PS) ≤1.<br>Life expectancy ≥3 months.<br>No more than two prior lines of cytotoxic-containing chemotherapy regimens for advanced disease. There is no limit for prior targeted therapy, hormonal therapy and immunotherapy (such as nivolumab).<br>Histologically or cytologically confirmed diagnosis of advanced disease of any of the following tumor types:<br>Glioblastoma; Soft-tissue sarcoma [excluding gastrointestinal stromal tumors (GIST)]; Endometrial carcinoma; Epithelial ovarian carcinoma (including primary peritoneal disease and/or fallopian tube carcinomas and/or endometrial adenocarcinomas) regardless of platinum sensitivity; Mesothelioma; Gastroenteropancreatic neuroendocrine tumors (GEP-NET); Small cell lung cancer (SCLC); Pancreatic adenocarcinoma; Gastric carcinoma; Colorectal carcinoma (CRC);<br>Expansion phase: Tumor-specific cohort(s) at the RD:<br>Measurable disease according to Response Evaluation Criteria in Solid Tumors (RECIST) v.1.1.<br>For patients with glioblastoma:<br>Measurable disease according to RECIST v.1.1 and RANO criteria.<br>Documented disease progression per RECIST v.1.1 during or immediately after last therapy according to any of the aforementioned criteria.<br>For patients with glioblastoma:<br>Documented disease progression per RECIST v.1.1 and RANO criteria.<br>At least three weeks since the last anticancer therapy (excluding immunotherapy that must be at least two weeks, provided that is not combined with chemotherapy), including investigational drugs and radiotherapy, and at least six weeks since nitrosoureas and mitomycin C (systemic).<br>For patients with glioblastoma: at least 12 weeks since the end of radiotherapy, except if:<br>The patient has a new lesion outside of the radiotherapy field, or<br>The patient has undergone brain surgery to remove the tumor before study entry, and progressive disease has been confirmed histologically.<br>Adequate bone marrow, renal, hepatic, and metabolic function (assessed ≤7 days before inclusion in the study):<br>Platelet count ≥100 × 10^9/L, hemoglobin ≥9.0 g/dL and absolute neutrophil count (ANC) ≥2.0 × 10^9/L.<br>Aspartate aminotransferase (AST) and alanine aminotransferase (ALT) ≤3.0 × the upper limit of normal (ULN), even in the presence of liver metastases.<br>Alkaline phosphatase (ALP) ≤2.5 × ULN (≤5 × ULN if disease-related/in the case of liver metastases).<br>Total bilirubin ≤1.5 × ULN or direct bilirubin ≤ ULN.<br>International Normalized Ratio (INR) <1.5 (except if patient is on oral anticoagulation therapy).<br>Calculated creatinine clearance (CrCL) ≥30 mL/minute (using Cockcroft-Gault formula).<br>Creatine phosphokinase (CPK) ≤2.5 × ULN.<br>Albumin ≥3.0 g/dL(*). | Concomitant diseases/conditions:<br>History or presence of unstable angina, myocardial infarction, congestive heart failure, or clinically significant valvular heart disease within the previous year.<br>Symptomatic arrhythmia or any uncontrolled arrhythmia requiring ongoing treatment.<br>Myopathy or any clinical situation that causes significant and persistent elevation of CPK (>2.5 × ULN in two different determinations performed one week apart).<br>Ongoing chronic alcohol consumption or cirrhosis with Child-Pugh score B or C.<br>Known Gilbert disease.<br>Active uncontrolled infection.<br>Known human immunodeficiency virus (HIV) infection. Known human immunodeficiency virus (HIV) or known hepatitis C virus (HCV) infection or active hepatitis B.<br>Any past or present chronic inflammatory colon and/or liver disease, past intestinal obstruction, pseudo or sub-occlusion or paralysis.<br>Evident symptomatic pulmonary fibrosis or interstitial pneumonitis, pleural or cardiac effusion rapidly increasing and/or necessitating prompt local treatment within seven days.<br>Any other major illness that, in the Investigator's judgment, will substantially increase the risk associated with the patient's participation in this study.<br>Prior treatment with PM01183, trabectedin (Yondelis ®) or topoisomerase I inhibitors (irinotecan, topotecan, etc.). Prior topoisomerase inhibitors (e.g., irinotecan) are only allowed in patients with colorectal carcinoma.<br>Prior bone marrow or stem cell transplantation, or radiation therapy in more than 35% of bone marrow.<br>Known brain metastases or leptomeningeal disease involvement.<br>Glioblastoma lesions (primary or locally advanced) are eligible. In SCLC, patients with brain metastases or leptomeningeal disease involvement are eligible provided they are radiologically stable, i.e. without evidence of progression for at least 4 weeks by repeat imaging (note that the repeat imaging should be performed during study screening), clinically stable and without requirement of steroid treatment (patients taking steroids in the process of already being tapered within two weeks prior to screening are allowed). Brain CT-scan or MRI results must be provided at baseline.<br>Women who are pregnant or breast feeding and fertile patients (men and women) who are not using an effective method of contraception. |

-continued

| Inclusion | Exclusion |
|---|---|
| Recovery to grade ≤1 or to baseline from any adverse event (AE) derived from previous treatment (excluding alopecia and/or cutaneous toxicity and/or peripheral neuropathy and/or fatigue grade ≤2). | |

(*)Limitation of the patient's ability to comply with the treatment or follow-up protocol.

Study Drug Formulation—Preparation and Administration

Lurbinectedin was presented as lyophilized powder for concentration for solution for infusion in 4 mg vials. Before use, the 4 mg vials were reconstituted with 8 mL of water for injection to give a solution containing 0.5 mg/mL of lurbinectedin. For administration to patients as an i.v. infusion, reconstituted vials were diluted with glucose 50 mg/mL (5%) solution for infusion or sodium chloride 9 mg/mL (0.9%) solution for infusion. The full composition and the reconstituted solution per mL was as shown in Table 12 supra.

Irinotecan was presented as lyophilized powder for concentration for solution for infusion in 40 mg, 100 mg, or 300 mg vials.

Dosage and Administration

Lurbinectedin was administered over a minimum total volume of 100 mL of solution for infusion (either on 5% glucose or 0.9% sodium chloride), through a central catheter, or over a minimum total volume of 250 mL if administered through a peripheral line, always over one hour at a fixed infusion rate.

Dose levels in patients at the escalation phase (n=39) were as shown in Table 21. Patients received lurbinectedin i.v. as a one-hour infusion on Day 1 and irinotecan, i.v. as a 90-minute infusion at days 1 and 8 every three weeks. Three weeks was defined as one treatment cycle.

TABLE 21

| Dose Level | Irinotecan (mg/m2), D1 & D8, q3w | Lurbinectedin (mg/m2), D1, q3w | Number of treated patients | DLTs/Evaluable patients | DLTs Description |
|---|---|---|---|---|---|
| 1 | 75 | 1.0 | 6 | 1/6 | Omission of D8 due to G3 neutropenia |
| 2 | 75 | 1.5 | 4 | 1/4 | Delay DLT (cycle 3); G3 FN |
| 3 (MTD without G-CSF) | 75 | 2.0 | 12 | 4/11 | Omission of D8 due to G3 neutropenia, omission of D8 due to G4 neutropenia, 2 episodes of G3 FN |
| 3* (RD with G-CSF) | 75 | 2.0 | 13 | 3/12 | Omission of D8 due to G2 thrombocytopenia, 2 episodes of omission D8 due to G3 neutropenia |
| 4* (MTD with G-CSF) | 75 | 2.4 | 4 | 2/3 | Omission of D8 due to G2 thrombocytopenia, omission of D8 due to G4 neutropenia |

Outcome Measures

Primary outcome measures were (1) maximum tolerated dose (MTD) and (2) recommended dose (RD). MTD was defined as lowest dose explored during dose escalation which one third or more of evaluable patients develop DLT in Cycle 1. RD was defined as highest dose level explored during dose escalation in which fewer than one third of evaluable patients develop DLT during Cycle 1.

Secondary outcome measures included safety evaluation, peak plasma concentration (Cmax), area-under-the plasma concentration versus time curve (AUC), volume of distribution based on the terminal half-life (Vz), volume of distribution at steady state (Vss), clearance (CL), half-life (t½), evaluation of antitumor response (RECIST v1.1, start of treatment until PD, other antitumor therapy, death or until 12 months after the inclusion of the last evaluable patient in the study (end of study), whichever occurs first), progression-free survival (from the date of first infusion of study treatment to the date of progression or death or until 12 months after end of study, whichever occurs first), and overall survival (from the date of first infusion to study treatment to the date or death or until 12 months after end of study, whichever occurs first).

Pharmacokinetic Evaluations

Patients underwent PK sampling for assessment of lurbinectedin, irinotecan, and SN38 (active metabolite of irinotecan), aimed at ruling out major drug-drug interactions.

Safety Evaluation

Patients were evaluated for safety if they had received any partial or complete infusion of lurbinectedin and irinotecan. All adverse events were graded according to the National Cancer Institute-Common Toxicity Criteria for Adverse Events (NCI-CTCAE, v4). The safety profile of patients was monitored throughout the treatment and up to 30 days after the last administration of study treatment (end of treatment), or until the patient started a new anti-tumor therapy or until the date of death, whichever occurred first. Treatment delays, dose reduction requirements, transfusions, and reason for treatment discontinuation was monitored throughout the study. Any treatment-related adverse events were followed until recovery to at least grade 1 or stabilization of symptoms or until the start of a new anti-tumor therapy, whichever occurred first.

Results 39 patients were initially treated at 5 dose levels (DL, see Table 21 supra); 13 at the recommended dose (RD). 56% were females, 69% had ECOG PS=1; median age was 58 years; median of 2 prior chemotherapy lines for advanced disease (range, 0-4) per pt. RD was defined as lurbinectedin 2.0 mg/m$^2$ on D1+irinotecan 75 mg/m$^2$ on D1 and D8 q3w+G-CSF. Dose limiting toxicities in Cycle 1 were observed in ⅔ evaluable patients at the maximum tolerated dose (MTD) and in 3/13 evaluable patients at the RD. At the MTD and the RD, DLTs were skipping irinotecan D8 doses due to grade (G) 3-4 neutropenia (n=3 patients) or G2-4 thrombocytopenia (n=2). At the RD common G1/2 toxicities were nausea, vomiting, fatigue, diarrhea, anorexia and neuropathy; G3/4 hematological abnormalities comprised neutropenia (33%), but no thrombocytopenia.

Pharmacokinetics Data

Concentration-time data of lurbinectedin, irinotecan, and SN-38 are available from 39 patients. Mean (±SD) of main PK parameters are provided in the Table below, along with those reported elsewhere for lurbinectedin single agent, and irinotecan and SN-38 (Camptosar Label).

Based on the comparability with reference PK data, these PK results of the three analytes evaluated do not suggest any type of major drug-drug interactions, thus indicating that the drug combination of lurbinectedin and irinotecan can be administered safely from a PK standpoint.

TABLE 22

| Compound | Dose Level (mg/m2) | n | Cmax (ug/L) | CL (L/h) | HL (h) | Vz (L) |
|---|---|---|---|---|---|---|
| Lurbinectedin | 1.0-2.4 | 39 | — | 9.9 (5.4) | 44.2 (22.4) | 580.9 (345.5) |
| | 3.2 (ref) | 329 | 127.5 (100.2) | 12.4 (7.6) | 42.6 (38.4) | 664.7 (460.3) |
| Irinotecan | 75 | 39 | 828.2 (174.7) | 30.2 (10.3) | 9.9 (4.3) | 233.2 (83.3) |
| | 125 (label) | 64 | 1660 (797) | 22.6 (10.2) | 11.7 (9) | 187 (82.5) |
| SN-38 | — | 39 | 18.1 (7.7) | 810.3 (574) | 18.6 (9.1) | 18232.3 (8208.4) |
| | — (label) | 64 | 26.3 (11.9) | NA | 21.0 (20) | NA |

Efficacy Data

Encouraging activity has been observed in patients with SCLC, including some cases as third line treatment. Signals of activity were also observed in endometrial carcinoma and soft tissue sarcoma (STS) and glioblastoma (GBM). Consequently, a Phase II expansion at the RD to further explore efficacy and safety in SCLC, GBM, STS, and endometrial carcinoma. A total of 59 patients were treated at the RD, including n=15 SCLC, n=11 endometrial cancer, n=10 STS, and n=20 GBM patients. Efficacy data per tumor type at all doses are shown in the table below.

TABLE 23

| Tumor Type (No of evaluable patients) | SCLC (n = 13) | Endometrial (n = 10) | STS (n = 10) | GBM (n = 16) |
|---|---|---|---|---|
| Median no. of cycles (range) | 8 (1-12) | 7 (2-37) | 4 (2-15) | 2 (1-7) |
| ORR* (PR) [n(%)] | 9 (69.2) | 3 (30) | 0 | 1 (6.3) |
| CBR (ORR + SD >4 mo) (%) | 76.9 | 60 | 40 | 18.8 |
| DCR (ORR + SD) (%) | 84.6 | 100 | 80 | 43.8 |
| Median PFS (mo) | 4.3 | 7.1 | 2.6 | 1.4 |
| Median DoR (mo) | 4.6 | 4.6 | — | — |
| PFS rate at 6 mo (%) | 36.3 | 50 | 33.8 | 7.1 |

Safety

Two patients (3.4%) discontinued treatment due to a treatment-related adverse event (Bilirubin G2, weakness G3). 17 patients (28.8%) had dose reductions (76% of reductions were due to day 8 irinotecan omissions related to adverse events). 19.8% of day 8 irinotecan infusions were omitted at the RD (mostly due to hematological toxicity). No treatment-related deaths occurred. A detailed description of adverse events and laboratory abnormalities observed in patients at RD is shown in Table 24.

TABLE 24

| | Adverse Events & Laboratory | Patients at RD LUR + IRI (n = 59) | |
|---|---|---|---|
| | Abnormalities | G1-2 (%) | G3-4 (%) |
| Treatment-related adverse events | Fatigue | 33 (55.9%) | 5 (8.5%) |
| | Nausea | 33 (55.9%) | 1 (1.7%) |
| | Vomiting | 15 (25.4%) | — |
| | Diarrhea | 25 (42.4%) | 5 (8.5%) |
| | Constipation | 7 (11.9%) | — |
| | Abdominal Pain | 6 (10.2%) | — |
| | Anorexia | 18 (30.5%) | — |
| | Febrile Neutropenia | — | 3 (5.1%) |
| Laboratory abnormalities | Anemia | 46 (78%) | 8 (13.6%) |
| | Neutropenia | 21 (35.6%) | 29 (49.1%) |
| | Thrombocytopenia | 30 (50.8%) | 6 (10.1%) |
| | ALT increase | 23 (39%) | 3 (5.1%) |
| | AST increases | 23 (39%) | 2 (3.4%) |

Summary and Conclusions

The RD is lurbinectedin 2.0 mg/$m^2$ on day 1 and irinotecan 75 mg/$m^2$ on day 1 and day 8 q3wk, with GCS-F, in solid tumors. DLTs are mostly day 8 irinotecan omissions in cycle 1 due to hematological toxicity. Main toxicities observed were myelosuppression, gastrointestinal and fatigue. Gastrointestinal and myelosuppression were predictable and manageable. Promising activity has been observed in SOLO. Notable activity has been observed in endometrial carcinoma, and hints of activity have been found in STS (especially Ewing and synovial sarcoma). Modest activity has been observed in glioblastoma patients. Expansion cohorts in SOLO, endometrial carcinoma and STS patients are still ongoing, to enroll a total of 20 patients in each indication.

Lurbinectedin Solid State Form Examples

Abbreviations

| | |
|---|---|
| DSC | Differential scanning calorimetry |
| DVS | Dynamic vapor sorption |
| XRPD | X-ray powder diffractograms |
| TG-FTIR | Thermogravimetry coupled with Fourier transformed infrared spectroscopy |
| r.h. | Relative humidity |

The X-ray powder diffractograms (XRPD) were obtained with a Stadi P diffractometer (Stoe & Cie GmbH) in transmission geometry, equipped with a curved Ge-crystal monochromator, a Cu-Kα1 radiation source and a Mythenl K Detector in step scan detector mode. The pattern was recorded at a tube voltage of 40 kV, tube current of 40 mA, applying a stepsize of 0.02° 2-theta with 12 seconds per step in the angular range of 1.5° to 50.5° 2-theta. The detector step was 1° 2-theta. A typical precision of the 2-theta values is in the range of about ±0.2° 2-theta. Thus a diffraction peak that appears at 5.0° 2-theta can appear between 4.8 and 5.2 2-theta on most X-ray diffractometers under standard conditions.

TG-FTIR experiments were conducted with a Thermo-Microbalance TG-209 (Netzsch) equipped with a FT-IR Spectrometer Vector 22 (Bruker) using Al crucible (open or with microhole) under N2 atmosphere with a heating range between 25 and 250° C. and a heating rate of 10° C./min.

DSC experiments were carried out with a Perkin Elmer DSC 7 using closed Au crucibles with a heating range between −50 to 250° C. and a heating rate of 10 or 20° C./min.

DVS experiments were carried out with a Projekt Messtechnik SPS 11-100n multi-sample water vapor sorption analyzer. The sample was allowed to equilibrate at 50% r.h. before starting a pre-defined humidity program. The program was:

2 h at 50% r.h.

50 to 0% r.h. (5%/h)

5 h at 0% r.h.

0 to 95% r.h (5%/h)

5 h at 95% r.h.

95 to 50% (5%/h)

2 h at 50% r.h.

Example 9. Manufacture of Amorphous Form A of Lurbinectedin

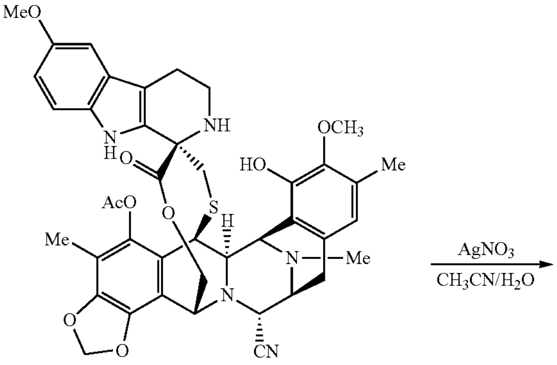

Comp 1

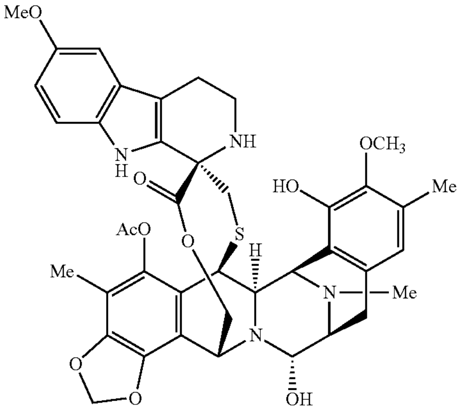

(I)

Figure 1:
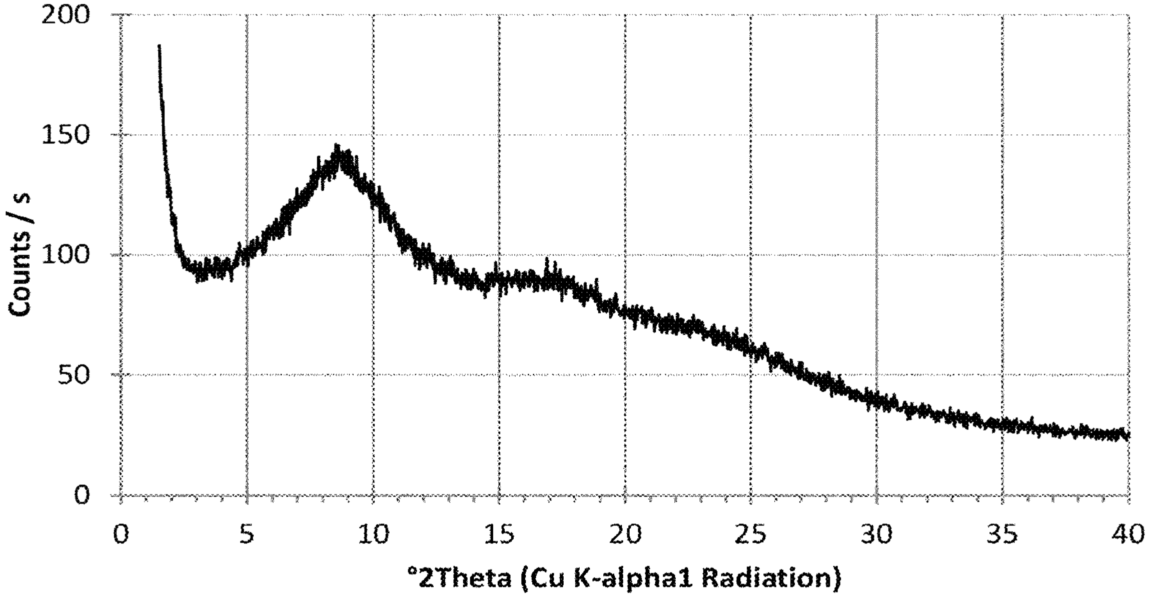
FIG. 1: X-ray powder diffractogram (XRPD) of Form A of lurbinectedin (Batch R05)

Form A of lurbinectedin was obtained following the procedure described in WO 03/014127. The XRPD pattern of Form A of lurbinectedin confirmed that this form is amorphous. See FIG. 1. Several batches of Form A of lurbinectedin were manufactured by this method. The analytical results of five of them are shown in Table 25.

TABLE 25

| | | Batch | | | | |
|---|---|---|---|---|---|---|
| | | P01 | P02 | P03 | P04 | R05 |
| Impurities (% Area) | Total | 0.3 | 0.4 | 0.3 | 0.2 | 0.4 |
| | Total | 1.4 | 1.9 | 1.9 | 2.1 | 2.5 |
| Residual Solvents (% w/w) | Acetonitrile | 0.01 | <LOQ | <LOQ | <LOQ | <LOQ |
| | Dichloro-methane | <LOQ | <LOQ | 0.01 | <LOQ | <LOQ |
| | Ethyl acetate | <LOQ | <LOQ | <LOQ | <LOQ | <LOQ |
| | Hexane | <LOQ | 0.01 | <LOQ | <LOQ | <LOQ |
| | Pentane | 0.2 | 0.2 | 0.3 | 0.5 | 0.3 |
| | Methanol | 1.1 | 1.7 | 1.6 | 1.6 | 2.2 |
| Water Content (% w/w) | | 0.9 | 1.2 | 1.6 | 1.6 | 1.1 |

ND: not detected
LOQ: limit of quantification

Table 26 shows the impurity profile of several batches of Form A lurbinectedin.

TABLE 26

| Impurity RRT approx. | Form A F02 | G01 | K02 | K03 | K04 | M01 | M02 | M03 | P01 | P02 | P03 | P04 | R05 |
|---|---|---|---|---|---|---|---|---|---|---|---|---|---|
| 0.66-0.69 | 0.19 | 0.06 | — | — | — | — | — | — | — | — | — | — | — |
| 0.72-0.76 | 0.06 | 0.11 | 0.09 | 0.07 | 0.10 | 0.10 | 0.08 | 0.12 | 0.10 | 0.09 | 0.09 | 0.09 | 0.10 |
| 0.90-0.92 | — | — | — | — | — | — | — | — | — | — | — | — | — |
| 1.10-1.11 | 0.17 | 0.50 | 0.13 | 0.17 | 0.20 | 0.08 | 0.10 | 0.11 | 0.15 | 0.09 | 0.08 | — | 0.09 |
| 1.12 | — | — | — | — | — | — | — | — | — | — | 0.07 | — | — |
| 1.27-1.34 | 0.12 | — | — | — | — | — | — | — | — | — | — | — | — |
| 1.29-1.30 | — | — | 0.07 | 0.37 | 0.11 | 0.10 | 0.17 | 0.10 | 0.09 | 0.06 | 0.09 | 0.10 | 0.05 |
| 1.30-1.32 | 0.09 | 0.13 | 0.19 | 0.08 | 0.08 | 0.18 | 0.08 | 0.11 | — | 0.13 | — | — | — |
| 1.28-1.37 | — | — | — | — | — | — | 0.08 | — | — | — | — | — | — |
| 2.37 | — | — | — | — | — | — | — | — | — | — | — | — | 0.13 |
| 2.41-2.52 | 0.07 | — | — | — | — | — | — | — | — | — | — | — | — |
| 2.85 | 0.07 | — | — | — | — | — | — | — | — | — | — | — | — |

RRT-Relative Retention Time

Example 10. Manufacture of Form B of Lurbinectedin

Crude lurbinectedin (10 g), which was obtained as described in Example 1, was dissolved in aqueous HCl (0.1 M, 390 mL). The aqueous solution was washed with $CH_2Cl_2$ (2×335 mL) and with n-pentane (1×335 mL) and treated with an aqueous solution of $NH_4Cl/NH_4OH$ (prepared by dissolving 17.5 g of $NH_4Cl$ and 20 mL of $NH_4OH$ in 250 mL of water, 68 mL) to precipitate Form B of lurbinectedin, that was filtered, washed with water and dried under vacuum to give 7.5 g, 9.45 mmol, yield 81% of Form B of lurbinectedin.

Several batches of Form B of lurbinectedin were manufactured by this method. The analytical results of ten of them are shown in Table 27

TABLE 27

| | | Batch 1711182-2 | 1711189-2 | 1799069 | 1924129-LT | 1924128-LT | R01 | R02 | R03 | R04 | P05 |
|---|---|---|---|---|---|---|---|---|---|---|---|
| Total Impurities (% Area) | | 0.3 | 0.3 | 0.4 | 0.4 | 0.4 | 0.3 | 0.3 | 0.3 | 0.4 | 0.3 |
| Residual Solvents (% w/w) | Total | 0.0 | 0.0 | 0.0 | 0.0 | 0.0 | 0.0 | 0.0 | 0.0 | 0.0 | 0.0 |
| | Acetonitrile | <LOQ | <LOQ | <LOQ | <LOQ | <LOQ | <LOQ | <LOQ | <LOQ | <LOQ | <LOQ |
| | $CH_2Cl_2$ | <LOQ | <LOQ | <LOQ | <LOQ | <LOQ | <LOQ | <LOQ | <LOQ | <LOQ | <LOQ |
| | AcOEt | NA | NA | NA | NA | NA | <LOQ | NA | NA | NA | <LOQ |
| | Hexane | NA | NA | NA | NA | NA | <LOQ | NA | NA | NA | <LOQ |
| | Pentane | <LOQ | <LOQ | <LOQ | <LOQ | <LOQ | <LOQ | <LOQ | <LOQ | <LOQ | <LOQ |
| | Methanol | <LOQ | <LOQ | <LOQ | <LOQ | <LOQ | <LOQ | NA | <LOQ | <LOQ | <LOQ |
| Water Content (% w/w) | | 2.4 | 2.5 | 2.0 | 4.1 | 3.0 | 1.9 | 2.0 | 1.7 | 2.6 | 2.1 |

LOQ: limit of quantification
NA: not analysed

An additional advantage of Form B of lurbinectedin over Form A of lurbinectedin is the absence of residual solvents.

Table 28 shows the impurity profile (% area) of several batches of Form B of lurbinectedin

TABLE 28

| Impurity RRT aprox | Form B R01 | R02 | R03 | R04 | 1711182-2 | 1711189-2 | 1799069 | 1924129-LT | 1924128-LT | P05 |
|---|---|---|---|---|---|---|---|---|---|---|
| 0.66-0.69 | — | — | 0.05 | 0.05 | — | 0.05 | — | 0.07 | 0.06 | — |
| 0.72-0.76 | 0.22 | 0.28 | 0.22 | 0.26 | 0.34 | 0.30 | 0.31 | 0.24 | 0.25 | 0.24 |
| 0.90-0.92 | — | — | — | — | — | — | — | 0.08 | 0.07 | — |
| 1.10-1.11 | 0.09 | — | — | 0.07 | — | — | 0.06 | — | — | 0.07 |
| 1.12 | — | — | — | — | — | — | — | — | — | — |

TABLE 28-continued

| Impurity RRT aprox | Form B R01 | R02 | R03 | R04 | 1711182-2 | 1711189-2 | 1799069 | 1924129-LT | 1924128-LT | P05 |
|---|---|---|---|---|---|---|---|---|---|---|
| 1.27-1.34 | — | — | — | — | — | — | — | — | — | — |
| 1.29-1.30 | — | — | — | — | — | — | — | — | — | — |
| 1.30-1.32 | — | — | — | — | — | — | — | — | — | — |
| 1.28-1.37 | — | — | — | — | — | — | — | — | — | — |
| 2.41-2.52 | — | — | — | — | — | — | — | — | — | — |
| 2.85 | — | — | — | — | — | — | — | — | — | — |

RRT-Relative Retention Time

A comparison between the impurity profiles of forms A and B of lurbinectedin clearly shows that Form B of lurbinectedin consistently presents fewer impurities than Form A of lurbinectedin.

Solid State Characterization—Form B of Lurbinectedin was Characterized by XRPD, IR, TG-FTIR, DSC and DVS.

The XRPD pattern of several batches of Form B of lurbinectedin confirmed that this form is partly crystalline (broad peaks, amorphous background) and that the process for its manufacture is reproducible. See FIGS. 2*a* and 2*b*. XRPD angles 2-theta and their relative intensities of two batches of Form B of lurbinectedin are shown in Table 29

TABLE 29

XRPD angles 2-theta, relative intensities of two batches of Form B of lurbinectedin

| Batch 1924128-LT Angle [2-theta] | Relative Intensity [%] | Batch 1924129-LT Angle [2-theta] | Relative intensity [%] |
|---|---|---|---|
| 6.2 | 84 | 6.2 | 73 |
| 7.6 | 100 | 7.7 | 100 |
| 9.0 | 62 | 9.0 | 64 |
| 9.8 | 31 | 9.6 | 30 |
| 10.9 | 98 | 10.9 | 100 |
| 12.4 | 41 | 12.4 | 40 |
| 14.9 | 75 | 14.8 | 77 |
| 15.3 | 74 | 15.3 | 76 |
| 18.4 | 29 | 18.3 | 29 |
| 19.2 | 34 | 19.2 | 35 |
| 20.7 | 31 | 20.7 | 32 |
| 24.9 | 26 | 24.9 | 27 |
| 26.5 | 32 | 26.5 | 33 |

TG-FTIR indicates degradation above 150° C. for Form B of lurbinectedin. A release of 2.6% of water was detected. See FIG. 3.

Estimation of the amorphous content by DSC was not possible. Degradation was observed to begin above 130° C., see FIG. 4. A glass transition temperature or melting point was not detected.

Figure 5:
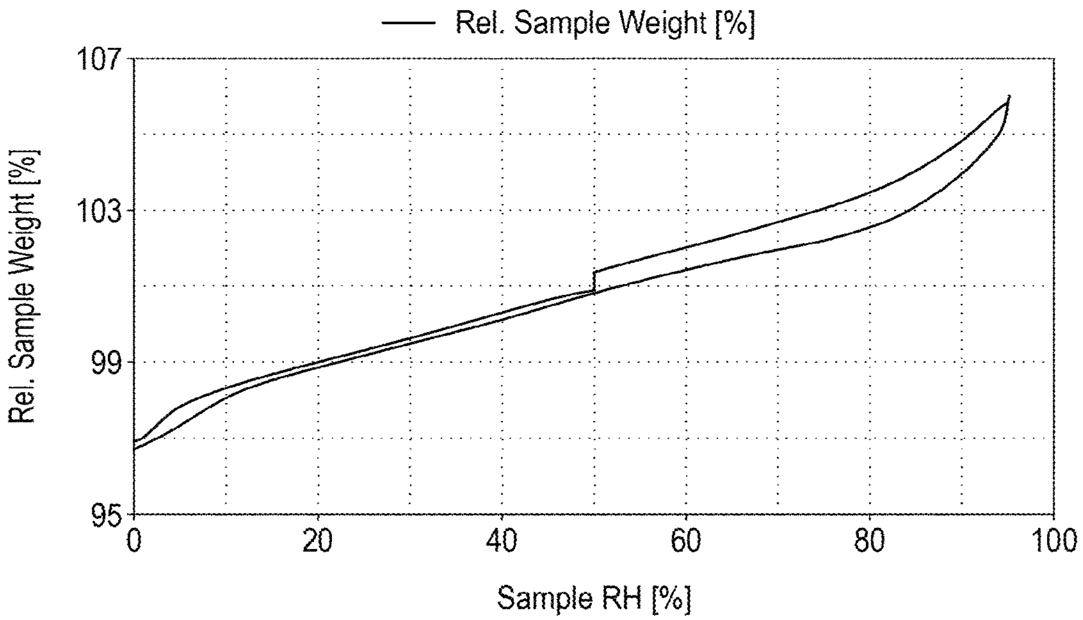
FIG. 5: DVS of Form B of lurbinectedin (Batch P05).

DVS indicates a continuous water uptake and release with no steps and almost no hysteresis. This is due to the partly amorphous character of Form B. The sample is not deliquescent. A mass change of Δm (50 to 96% r.h.)≈4% was observed, indicating that Form B of lurbinectedin is hygroscopic. Upon lowering the relative humidity again, the water content decreased and nearly returned to the original mass, see FIG. 5.

Figure 6:
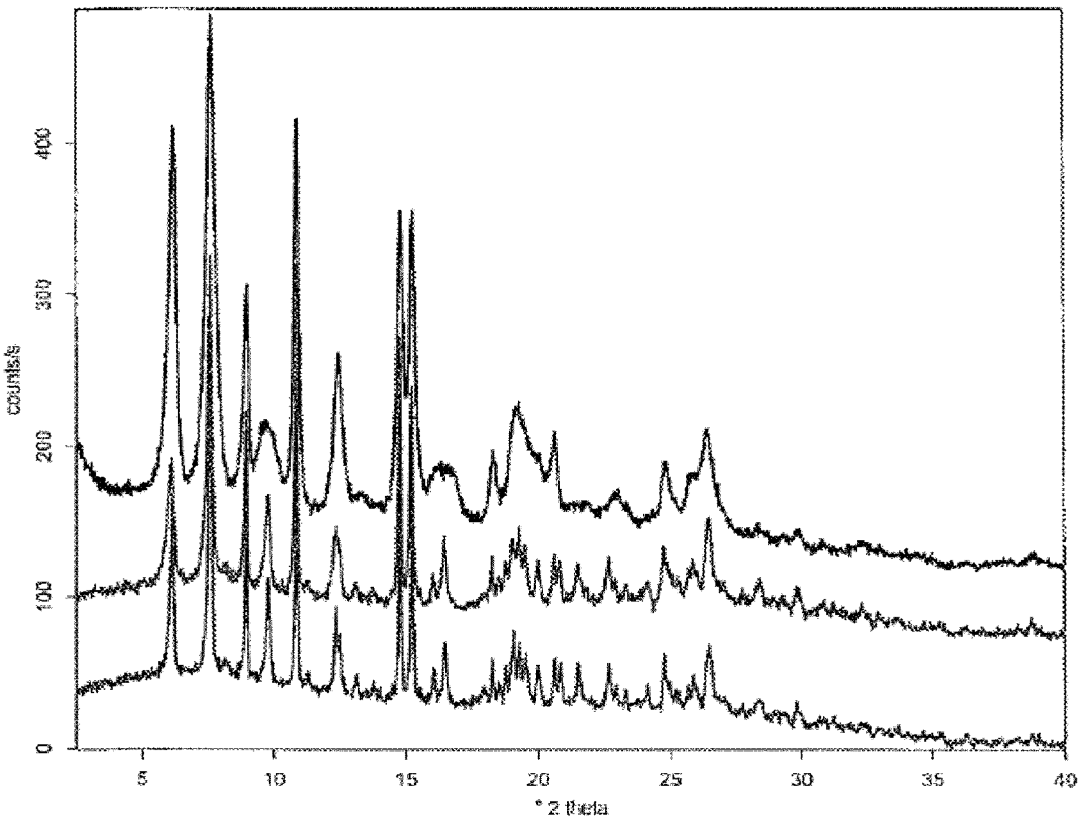
FIG. 6: Superimposed XRPD patterns of Form B of lurbinectedin in an initial 1:1 mixture of Forms A and B of lurbinectedin, after 6 h of phase equilibration in water and after 24 h of phase equilibration in water, from top to bottom. (Mixtures were prepared mixing Form A of lurbinectedin (batch P02) and Form B of lurbinectedin (batch 1711182-2)).

Relative Stability of Form B of lurbinectedin—three 1:1 mixtures of forms A and B of lurbinectedin (15 mg each) were prepared and suspended in water (1 mL). Samples were taken after 6 and 24 hours. The powder patterns after 6 and 24 hours agree with that of the Form B starting material. See FIG. 6. Both patterns after phase equilibration show sharper peaks and higher peak resolution. These are indications of improved crystallinity. A quantification of the amorphous content was not possible with the available data.

Figure 7A:
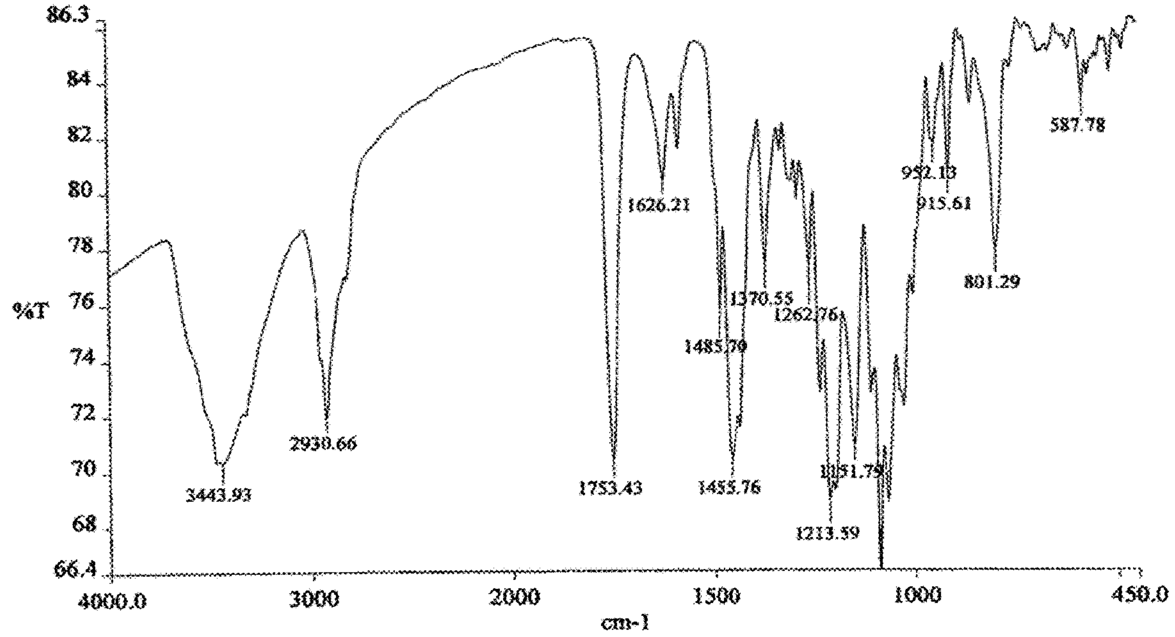
Figure 7B:
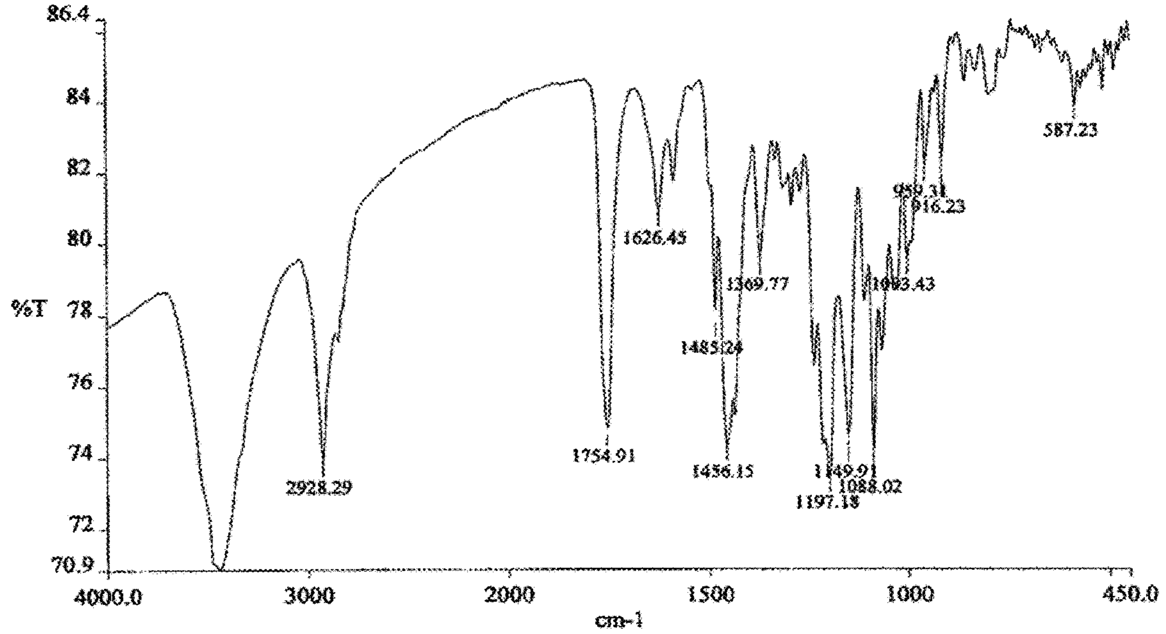

IR spectra were obtained for Form A of lurbinectedin, shown in FIG. 7*a*, and for Form B of lurbinectedin, shown in FIG. 7*b*. The correlation factor between the IR of three batches of Form B of lurbinectedin and the IR of Form A of lurbinectedin varies from 0.81 to 0.86. On the other hand, the correlation factor of several IR spectra of Form A of lurbinectedin varies from 0.97 to 0.99.

Example 11. Electrostatic Charge Measurements in Air

The electrostatic charges of two batches of Form A of lurbinectedin (Batches P04 and R05) and of Form B of lurbinectedin (Batch 1924129-LT and 1924128-LT) have been measured using a Faraday cage (See FIG. 8) constructed of stainless steel with concentric spheres with ratios 10, 15 and 20 cm. This technique consists in placing the sample to be measured (q) in the interior of the inner sphere (a) and measuring the difference of potential induced between sphere (a) and another conductor of reference, sphere (b). The external sphere (c) is grounded in order to shield the system. The measurements of the difference of potential were carried out with a precision electrometer (Keithley 617, resolution 10 fC).

Measurements were carried out under controlled atmosphere of dry nitrogen in order to avoid the effect of ambient humidity on the electrostatic charge of the samples. Samples were introduced in glass capsules using non-conductor instrumental to avoid loses of electrostatic charge. The capsules loaded with the samples were introduced in the Faraday cage through a grounded conductor tube to avoid parasitic static charges in the glass capsule. The entry and removal of the capsules was done with a computer-controlled servo engine, in order to ensure a constant rate of introduction and removal of the capsules in each measurement to minimize the creation of static charges due to friction of the insulator elements.

Figure 9A:
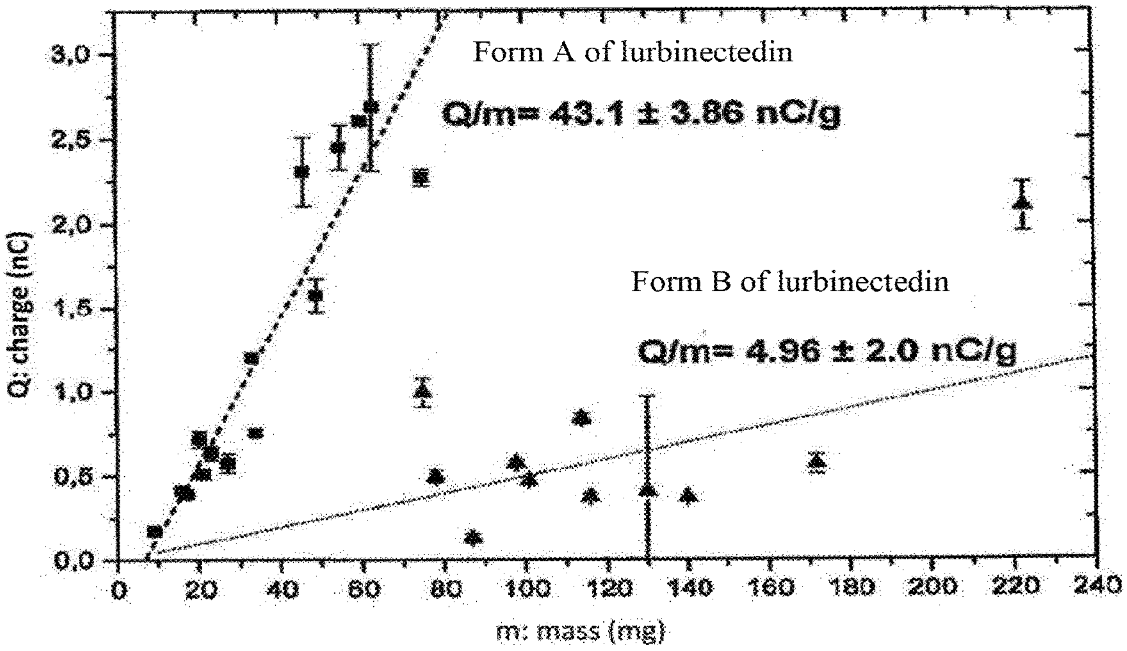
Figure 9B:
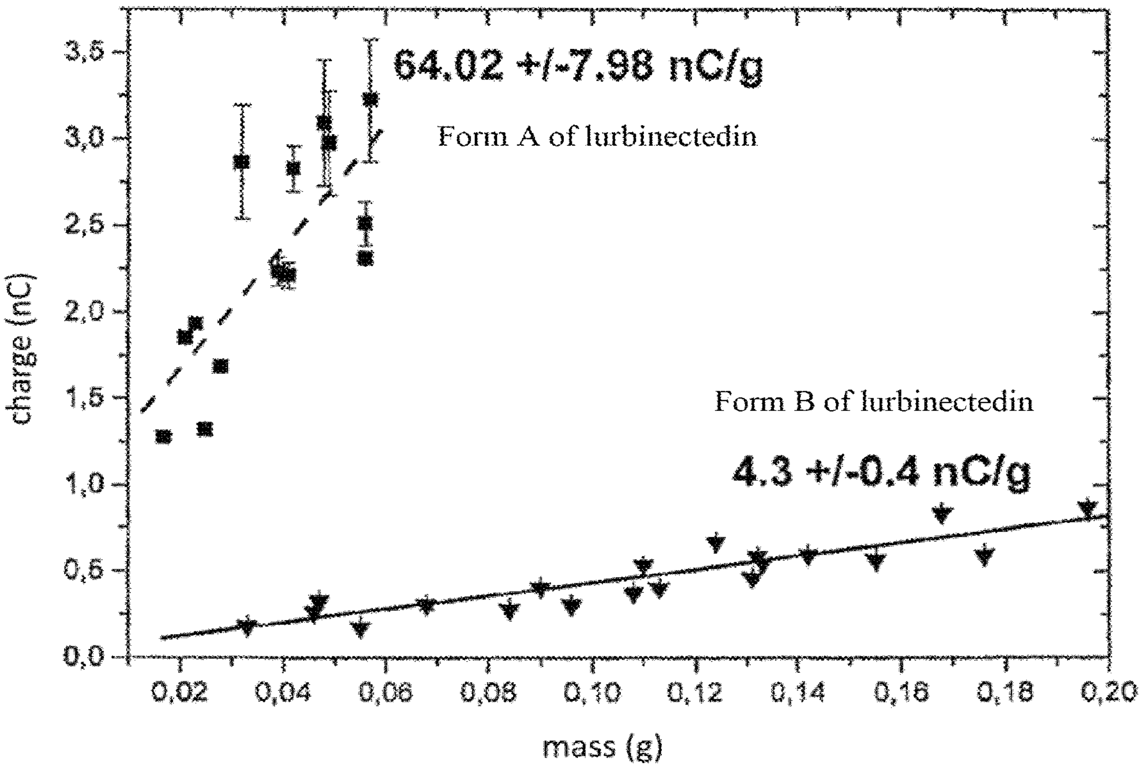

Results: Several measurements with different amounts of material were carried out for each batch of each form of lurbinectedin. Before loading the capsules, they were washed and their remaining static charge was measured in order to correct the levels. Each sample was introduced and removed five times and, after each introduction, several consecutive measurements were taken in order to average any possible drift effect. FIGS. 9*a* and 9*b* summarized the results of such measurement for each pair of batches of forms A and B of lurbinectedin.

The measured charge Q increases with the amount of analyzed material. Both forms of lurbinectedin have a positive electrostatic charge. Form A of lurbinectedin has a total static charge considerably higher than Form B of lurbinectedin. The data was fitted by lineal regression (dashed lines in FIGS. 9*a* and 9*b*) to obtain the charge density (Q/m) as the slope of the line. The extrapolation of the lineal regression to a mass of 0 mg represents the remnant electrostatic charge of the glass capsules, and does not affect the value of Q/m. The results of this regression and the dispersion of charge density are summarized in Table 30. All ranges are given with a 95% confidence.

TABLE 30

| Form | Batch | Average charge density (Q/m) (nC/g) | Dispersion of charge density (Q/m) (nC/g) |
|---|---|---|---|
| A | P04 | 43.1 ± 3.86 | 7.6 ± 2.8 |
| | R05 | 64.02 ± 7.98 | 15.23 ± 5.64 |
| B | 1924129-LT | 4.96 ± 2.0 | 3.4 ± 1.4 |
| | 1924128-LT | 4.3 ± 0.4 | 1.01 ± 0.3 |

Figure 10A:
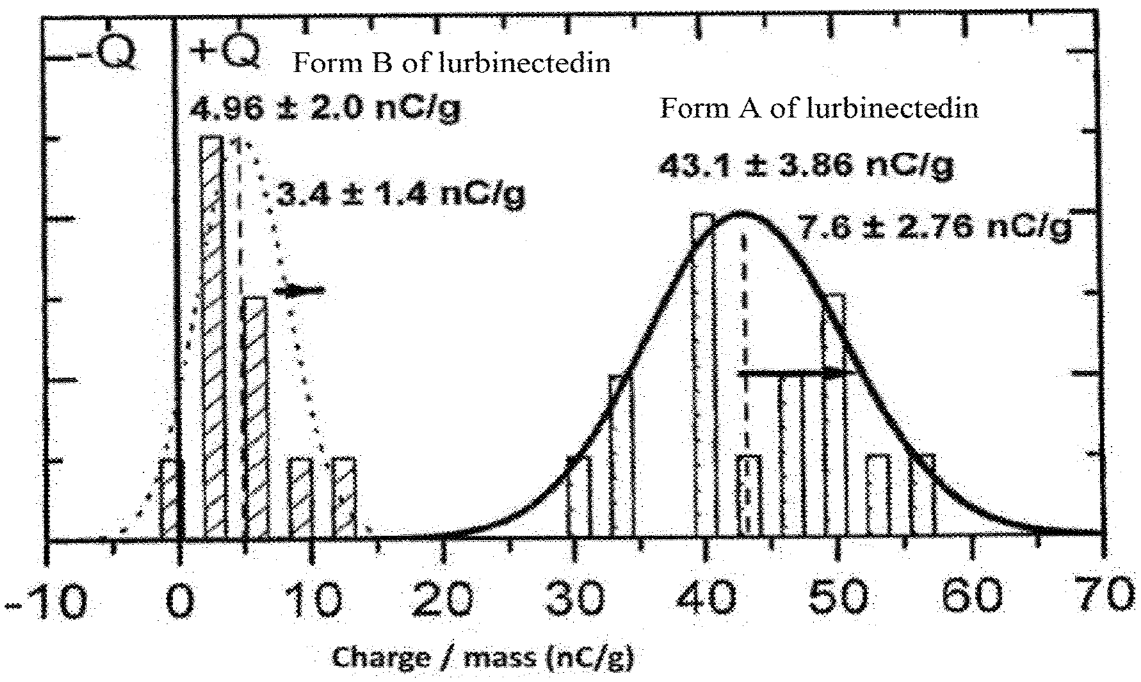
Figure 10B:
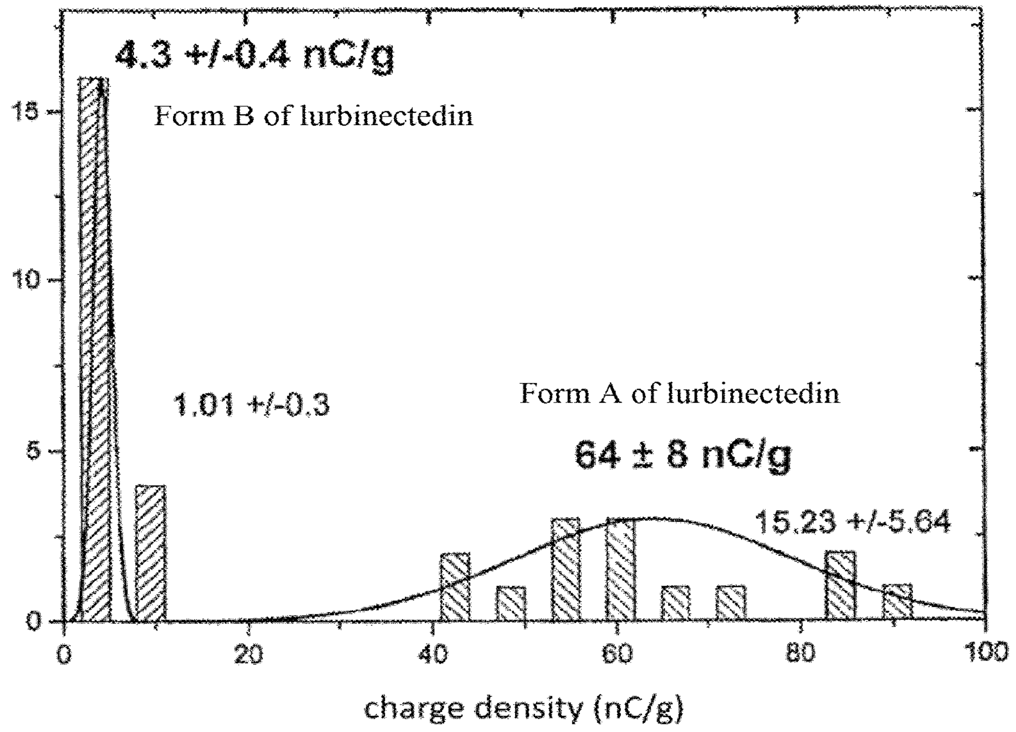

FIGS. 10*a* and 10*b* show the distribution of charge density for each pair of batches of forms A and B of lurbinectedin.

Form B of lurbinectedin is shown to have an average charge density one order of magnitude lower than Form A of lurbinectedin. This difference in triboelectrization has been demonstrated using two different batches of each form.

Example 12. Exemplary Process for the Manufacture of a Pharmaceutical Composition Using Form B as Starting Material Form B of lurbinectedin was dissolved in a concentrated lactic acid solution (0.31 M) at a concentration of 25 mg/ml. Then, this solution was diluted with water of injection (WFI) to a lactic acid solution (0.1 M) containing PM01183 at a concentration of 8.33 mg/ml.

This solution was then added under stirring into a sucrose/buffer solution (pH=4.2) previously prepared, composed of lactic acid (3.7 mg/ml), sodium hydroxide (1.1 mg/ml) and the bulking agent, sucrose (167.7 mg/ml). If required, the mixed solution will be adjusted to pH=4.0 with lactic acid solution or sodium hydroxide solution.

Then, the bulk solution was brought to final volume or weight (considering a density value of 1.04 g/cc), generating the final bulk solution (0.5 mg/ml lurbinectedin, 2.76 mg/ml lactic acid, 0.64 mg/ml NaOH, 100 mg/ml sucrose).

The bulk solution was then filtered through sterilizing PVDF filters (0.22 m) and filled into 30 ml glass vials at 8 ml/vial.

The vials were lyophilised according to a cycle detailed in Table 31. After lyophilization, vials were sealed with flip-off seals and stored at +5° C.

TABLE 31

| Step (conditions) | Time |
|---|---|
| Freezing, −5° C. | 1.5 h |
| Freezing, −40° C. | 5.5 h |
| Primary drying (−25° C., 0.1-0.2 mb) | 60 h |
| Secondary drying (+25° C., maximum vacuum) | 30 h |
| Stoppering | NA |

NA: not applicable

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims (and clauses). Those skilled in the art will recognize or be able to ascertain using no more than routine experimentation, many equivalents to the specific embodiments of the invention described herein. Such equivalents are intended to be encompassed by the following claims (and clauses).

All publications, patents and patent applications mentioned in this specification are herein incorporated by reference into the specification to the same extent as if each individual publication, patent or patent application was specifically and individually indicated to be incorporated herein by reference in their entireties.

The invention will now be described with reference to the following clauses:

1. A method of treating small cell lung cancer (SCLC) in a patient in need thereof, comprising:
   (1) administering a prophylactic dose of a corticosteroid and a serotonin antagonist effective to reduce nausea associated with administration of lurbinectedin to the patient on the day of and prior to administration of lurbinectedin to the patient; and
   (2) administering lurbinectedin at a dose of 2 to 3.2 $mg/m^2$ to the patient by intravenous infusion.
2. The method of clause 1, wherein the corticosteroid is dexamethasone intravenously administered at a dose of 8 mg of dexamethasone or a dose of a corticosteroid equivalent to 8 mg of dexamethasone administered intravenously.
3. The method of clause 1 or 2, wherein the serotonin antagonist is ondansetron intravenously administered at a dose of 8 mg of ondansetron or a dose of a serotonin antagonist equivalent to 8 mg of ondansetron administered intravenously.
4. The method of any one of clauses 1 to 3, further comprising administering one or more antiemetic agents within 2, 3, or 4 days after administration of lurbinectedin to the patient.
5. The method of clause 4, wherein the one or more antiemetic agents administered after lurbinectedin administration are selected from a corticosteroid, a serotonin antagonist, and metoclopramide.
6. The method of clause 5, wherein the one or more antiemetic agents are administered at a dose of 4 mg dexamethasone, 8 mg ondansetron, or 10 mg metoclopramide, or a combination thereof.
7. The method of any of clauses 1-6, wherein the patient is not treated with doxorubicin in combination with the lurbinectedin.
8. The method of any of clauses 1-7, wherein the patient has progressed after prior platinum-containing therapy or prior immunotherapy.
9. A method of treating small cell lung cancer (SCLC), including metastatic SCLC, in a patient in need thereof, comprising:
   (1) administering a first dose of 3.2 $mg/m^2$ of lurbinectedin to the patient by intravenous infusion if the patient has an absolute neutrophil count of at least 1500 $cells/mm^3$ and a platelet count of at least $100,000/mm^3$; and
   (2) identifying an adverse reaction in the patient after said administering, wherein the adverse reaction is Grade 2 hepatotoxicity or other adverse reaction, ≥Grade 3 (severe) hepatotoxicity or other adverse reaction, Grade 4 thrombocytopenia (Platelet count less than 25,000 cells/$mm^3$), Grade 3 thrombocytopenia (Platelet count less than 50,000 cells/$mm^3$) with bleeding, Grade 4 neutropenia (Neutrophil count less than 500 cells/$mm^3$), or any grade febrile neutropenia (Neutrophil count <LLN);

(3) after the adverse reaction is identified and at the later of 21 days of the first dose or after the patient's neutrophil count is greater than 1500 cells/$mm^3$; platelet count is greater than about 100,000 $mm^3$ and, optionally, hemoglobin levels are greater than about 9 g/dL and the hepatotoxicity or other adverse reaction is Grade 1 or less:

(i) if the identified adverse reaction consists of isolated Grade 4 neutropenia (Neutrophil count less than 500 cells/$mm^3$), administering to the patient a dose of lurbinectedin that is equal to the first dose every three weeks with G-CSF prophylaxis;

(ii) if the identified adverse reaction consists of Grade 2 hepatoxocity or other adverse reaction, administering to the patient a dose of lurbinectedin that is equal to the first dose every three weeks; or (ii) if the identified adverse reaction is ≥Grade 3 (severe) hepatotoxicity or other adverse reaction, Grade 4 thrombocytopenia (Platelet count less than 25,000 cells/$mm^3$), Grade 3 thrombocytopenia (Platelet count less than 50,000 cells/$mm^3$) with bleeding, or any grade febrile neutropenia is, administering to the patient a reduced dose of lurbinectedin compared to the first dose every 3 weeks.

10. The method of clause 9, wherein the first reduced dose is 2.6 mg/$m^2$.

11. The method of clause 10, wherein if the patient experiences after being administered a reduced dose of 2.6 mg/$m^2$, an adverse reaction of ≥Grade 3 (severe) hepatotoxicity or other adverse reaction, Grade 4 thrombocytopenia (Platelet count less than 25,000 cells/$mm^3$), Grade 3 thrombocytopenia (Platelet count less than 50,000 cells/$mm^3$) with bleeding, or any grade febrile neutropenia, then at the later of 21 days of the administration of the prior dose or after the patient's neutrophil count is greater than 1500 cells/$mm^3$; platelet count is greater than about 100,000 $mm^3$ and, optionally, hemoglobin levels are greater than about 9 g/dL and the hepatotoxicity or other adverse reaction is Grade 1 or less, administering to the patient a second reduced dose of 2.0 mg/$m^2$ lurbinectedin every three weeks.

12. The method of clause 11, further comprising discontinuing administration of lurbinectedin after identification of the adverse reaction after administration of the second reduced dose or if the patient does not recover to an absolute neutrophil count of at least 1500 cells/$mm^3$ and platelet count of at least 100,000/$mm^3$ within 2 weeks of the scheduled dose.

13. The method of any of the preceding clauses in which the lurbinectedin is administered as an infusion formulation prepared by diluting a reconstituted lyophilized formulation comprising 4 mg lurbinectedin, a buffer derived from an organic carboxylic acid (e.g. lactic acid), and a disaccharide (e.g. sucrose), which, when reconstituted has a pH of 3.5 to 4.5.

14. A method of treating small cell lung cancer (SCLC) in a patient in need thereof, comprising:

administering to the patient lurbinectedin at a dose of 3.2 mg/$m^2$ by intravenous infusion of a lurbinectedin infusion solution, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.

15. The method of clause 14, wherein the disaccharide is sucrose and optionally wherein the composition comprises lurbinectedin and sucrose at a ratio of 1 mol lurbinectedin:455 to 465 mol sucrose.

16. The method of clause 14 or 15 wherein the organic carboxylic acid is lactic acid and optionally wherein the composition comprises lurbinectedin and the lactic acid at a ratio of 1 mol lurbinectedin:44 to 54 mol lactic acid.

17. The method of any one of clauses 14 to 16 wherein the pH is 3.8 to 4.5

18. The method of any one of clauses 14 to 17, wherein the lyophilized composition is reconstituted in about 8 mL of an aqueous solution to obtain the reconstituted solution.

19. The method of clause 18, wherein the lurbinectedin infusion solution is prepared by diluting the reconstituted solution with an isotonic solution.

20. The method of any one of clauses 14 to 19, wherein the reconstituted solution is diluted with at least 100 mL or at least 250 mL of the isotonic solution to prepare the lurbinectedin infusion solution.

21. The method of clause 20, wherein the isotonic solution is a 0.9% sodium chloride solution or a 5% dextrose solution.

22. The method of any one of the preceding clauses, wherein the lyophilized composition comprises:

22.1 mg of lactic acid;

5.1 mg of sodium hydroxide; and 800 mg of sucrose or wherein the lyophilized composition comprises 800 mg of sucrose, 0.245 mmol of lactate and 0.128 mmol of sodium.

23. The method of any one of the preceding clauses, wherein the lyophilized composition is provided in a 30 mL vial.

24. The method of any one of the preceding clauses, wherein the lyophilized composition comprises Impurity D at a value no greater than 0.8%, 0.7%, 0.6%, 0.5%, or 0.4% wt/wt based on the total weight of lurbinectedin.

25. The method of any one of the preceding clauses, wherein the lyophilized composition does not comprise a phosphate buffer.

26. The method of any one of the preceding clauses wherein the reconstituted solution or the lurbinectedin infusion solution comprises Impurity D at a value no greater than 0.8%, 0.7%, 0.6%, 0.5%, or 0.4% wt/wt based on the total weight of lurbinectedin.

27. The method of any one of clauses 14 to 26, further comprising administering a prophylactic dose of a corticosteroid and a serotonin antagonist effective to reduce nausea associated with administration of lurbinectedin to the patient on the day of and prior to administration of lurbinectedin to the patient.

28. The method of clause 27, wherein the corticosteroid is dexamethasone intravenously administered at a dose of 8 mg of dexamethasone or a dose of a corticosteroid equivalent to 8 mg of dexamethasone administered intravenously.

29. The method of clause 27 or 28, wherein the serotonin antagonist is ondansetron intravenously administered at a dose of 8 mg of ondansetron or a dose of a serotonin antagonist equivalent to 8 mg of ondansetron administered intravenously.

30. The method of any one of clauses 27 to 29, further comprising administering one or more antiemetic agents within 2, 3, or 4 days after administration of lurbinectedin to the patient.

31. The method of clause 30, wherein the one or more antiemetic agents are selected from a corticosteroid, a serotonin antagonist, and metoclopramide.

32. The method of clause 31, wherein the one or more antiemetic agents are 4 mg dexamethasone, 8 mg ondansetron, or 10 mg metoclopramide, or a combination thereof.

33. The method of any preceding clause further comprising administering G-CSF to the patient identified as having a neutrophil countless than 500/mm$^3$ or any value below a normal range and associated with infection/sepsis.

34. The method of any preceding clause, wherein one dose of lurbinectedin is administered per treatment cycle and the patient undergoes at least 1, 2, 3, 4, 5, 6, 7, 8, 9 10, 11, 12, 13, 14, 15, 16, 17, 18, 19, 21, 22, 23, or 24 treatment cycles.

35. The method of any preceding clause, wherein the overall response rate is at least 11% or at least 20% for patients with a CTFI interval <90 days or wherein the overall response rate is at least 30% or at least 40% for patients with a CTFI interval >90 days.

36. The method of any preceding clause, wherein the duration of response is at least 2.5 months or at least 4.5 months for the patient with a CTFI interval <90 days or wherein the duration of response is at least 3.5 months, 5 months or 6 months for the patient with a CTFI interval >90 days.

37. The method of any preceding clause, wherein the patient had not received a platinum-containing therapy in at least 30 or at least 60 or at least 90 days prior to administration of lurbinectedin.

38. The method of any preceding clause, wherein the patient ceased responding to a platinum-containing therapy prior to administration of lurbinectedin.

39. The method of any preceding clause, wherein the patient has previously been administered an immunotherapy.

40. The method of clause 39, wherein the immunotherapy is an anti-CTLA-4 antibody, an anti-PD-1 antibody or an anti-PD-L1 antibody 41. The method of clause 40, wherein the immunotherapy is atezolizumab, optionally in combination with carboplatin and etoposide, or nivolumab.

42. The method of any of clauses 39 to 41, wherein the patient has progressed after being administered the immunotherapy.

43. The method of any preceding clause, wherein the patient has a calculated creatinine clearance greater than 30 mL/min and an AST or ALT less than 3×ULN or bilirubin less than 1.5×ULN.

44. The method of any preceding clause, wherein lurbinectedin is administered to a patient as a 1 hour intravenous infusion, to achieve total plasma $C_{max}$ within 80% to 125% of about 107 μg/L and AUC∞ within 80% to 125% of about 551 μg*h/L.

45. A method of storing a lyophilized lurbinectedin composition comprising
storing a lyophilized composition comprising 4 mg lurbinectedin; a buffer derived from an organic carboxylic acid; and a disaccharide at a temperature of 5° C.±3° C. for at least 48 months,
wherein the lyophilized composition is formulated such that reconstitution with 8 mL of water will yield a solution having a pH of 3.5 to 4.5 and
wherein after the at least 24 months storage, the amount of Impurity D present in the composition is not more than 0.8% wt./wt. of the total lurbinectedin weight.

46. The method of clause 45, wherein after at least 48 months of storage, the amount of Impurity D present in the composition is not more than 0.8% wt./wt. of the total lurbinectedin weight.

47. The method of clause 45 or 46, wherein the lyophilized composition comprises 4 mg lurbinectedin; 22.1 mg lactic acid; 5.1 mg sodium hydroxide; and 800 mg sucrose or wherein the lyophilized composition comprises 800 mg of sucrose, 0.245 mmol of lactate and 0.128 mmol of sodium.

48. The method of any one of clauses 45 to 47, wherein the lyophilized composition is stored in a 30 mL vial.

49. A pharmaceutical product comprising
a vial containing a lyophilized composition consisting of 4 mg lurbinectedin; 22.1 mg lactic acid; 5.1 mg sodium hydroxide; and 800 mg sucrose or a lyophilized composition consisting of 800 mg of sucrose, 0.245 mmol of lactate and 0.128 mmol of sodium;
a label affixed to the vial comprising an expiration date that is at least 24 months from the date of manufacture.

50. The pharmaceutical product of clause 49, wherein the label affixed to the vial comprises an expiration date that is at least 48 months from the date of manufacture.

51. The pharmaceutical product of clause 49 or 50, wherein the vial is a 30 mL vial.

52. The pharmaceutical product of any one of clauses 49 to 51, wherein the lyophilized composition comprises Impurity D at a value no greater than 0.8%, 0.7%, 0.6%, 0.5%, or 0.4% wt/wt of the total lurbinectedin weight.

53. The pharmaceutical product of any one of clauses 49 to 52, wherein the lyophilized composition does not comprise a phosphate buffer.

54. A method of treating solid tumor, endometrial cancer, SCLC, soft tissue sarcoma, glioblastoma, pancreatic adenocarcinoma, mesothelioma, colorectal carcinoma, or epithelial ovarian cancer in a patient in need thereof, the method comprising:
administering to the patient lurbinectedin and a topoisomerase inhibitor selected from SN-38 and irinotecan on day one of a treatment cycle;
wherein the lurbinectedin is administered at a dose of 1 to 2.5 mg/m$^2$ and
wherein the topoisomerase inhibitor is administered at a dose equivalent to 50 to 75 mg of irinotecan/m$^2$.

55. The method of clause 54, wherein a dose of the topoisomerase inhibitor equivalent to 50 mg to 75 mg of irinotecan/m$^2$ is administered on day 8 of the treatment cycle.

56. The method of clause 54 or 55, wherein the treatment cycle is an 18, 19, 20, 21, 22, 23, 24, or 25 day cycle.

57. The method of any of clauses 54 to 56 wherein the lurbinectedin is administered at a dose of 2 $mg/m^2$.
58. The method of any of clauses 54 to 57 wherein the topoisomerase inhibitor is irinotecan and is administered at a dose of 75 $mg/m^2$.
59. The method of any of clauses 54 to 58 wherein the treatment cycle is 21 days.
60. The method of any of clauses 54 to 59 wherein the solid tumor is SCLC, endometrial carcinoma, soft tissue sarcoma or glioblastoma.
61. The method of any of clauses 54 to 60 wherein the patient is administered G-CSF to manage the myelosuppressive effects of said treatment.
62. The method of any of clauses 54 to 61 wherein if after the administration on day 1 the patient exhibits hematological toxicity, then omitting the administration of the dose of irinotecan on day 8 of the treatment cycle.
63. The method of any one of clauses 54 to 62, further comprising administering one or more antiemetics on day one of a treatment cycle.
64. The method of any of clauses 55 to 64 in which the lurbinectedin is administered as an infusion formulation prepared by diluting a reconstituted lyophilized formulation of 4 mg lurbinectedin, 22.1 mg lactic acid or 0.245 mmol lactate, 5.1 mg sodium hydroxide or 0.128 mmol sodium, and 800 mg sucrose, which, when reconstituted has a pH of 3.5 to 4.5.
65. The method of clause 64 wherein the pH is 3.8 to 4.5
66. The method of clause 64 or 65, wherein the lyophilized composition is reconstituted in about 8 mL of an aqueous solution to obtain the reconstituted solution.
67. The method of clause 66, wherein the lurbinectedin infusion solution is prepared by diluting the reconstituted solution with an isotonic solution.
68. The method of any one of clauses 64 to 67, wherein the reconstituted solution is diluted with at least 100 mL or at least 250 mL of the isotonic solution to prepare the lurbinectedin infusion solution.
69. The method of clause 68, wherein the isotonic solution is a 0.9% sodium chloride solution or a 5% dextrose solution.
70. The method of any one of clauses 64 to 69, wherein the lyophilized composition is provided in a 30 mL vial.
71. The method of any one of clauses 64 to 70, wherein the lyophilized composition comprises Impurity D at a value no greater than 0.8%, 0.7%, 0.6%, 0.5%, or 0.4% wt/wt.
72. The method of any one of clauses 64 to 71 wherein the reconstituted solution or the lurbinectedin infusion solution comprises Impurity D at a value no greater than 0.8%, 0.7%, 0.6%, 0.5%, or 0.4% wt/wt.
73. A pharmaceutical composition prepared by
    lyophilizing an aqueous stock solution comprising lurbinectedin, an organic carboxylic acid, sodium hydroxide, and sucrose to produce a lyophilized powder,
    wherein the concentration of lurbinectedin in the aqueous stock solution is 0.5 mg/mL, wherein the ratio lurbinectedin to sucrose is 1 mol of lurbinectedin to 455 to 465 mol sucrose and wherein the lyophilized powder is formulated such that reconstitution with 8 mL of water will yield a solution having a pH of 3.5 to 4.1; and
    storing the lyophilized powder at 5° C.±3° C. for 30 months to 60 months to produce the pharmaceutical composition,
    wherein after storage the amount of Impurity D present in the composition is not more than 0.8% wt./wt. of the total lurbinectedin weight.
74. A method of administering a pharmaceutical composition comprising
    reconstituting a lyophilized pharmaceutical composition in a vial after the composition has been stored for 30 to 60 months,
    wherein the lyophilized pharmaceutical composition was prepared by lyophilizing a stock solution comprising 4 mg of lurbinectedin, a buffer derived from an organic carboxylic acid, and sucrose,
    wherein the composition comprises lurbinectedin and disaccharide at a ratio of 1 mol lurbinectedin:455 to 465 mol sucrose,
    wherein the lyophilized composition is formulated such that reconstitution with 8 mL of water will yield a solution having a pH of 3.5 to 4.5; and
    administering the reconstituted solution to a patient.
75. The method of clause 74, wherein the pharmaceutical composition comprises a lurbinectedin amount that is at least 95% of the amount of lurbinectedin on day one of storage.
76. The method of clause 74 or 75, wherein the vial is a 30 mL vial.
77. A method of treating SCLC in a patient in need thereof comprising
    administering lurbinectedin at a dose of 2 to 3.2 $mg/m^2$ to the patient by intravenous infusion;
    wherein the patient was administered an immunotherapeutic antibody for treating SCLC prior to beginning the treatment cycle and
    wherein the duration of response is at least 2 months, 3 months, 4 months, 5 months or 6 months or wherein the overall response rate is at least 40%.
78. The method of clause 77, wherein the immunotherapeutic antibody is an anti-CTLA-4 antibody, an anti-PD-1 antibody or an anti-PD-L1 antibody.
79. The method of clause 78, wherein the immunotherapeutic antibody is atezolizumab or nivolumab.
80. The method of clause 79, wherein the immunotherapeutic antibody was administered to the patient concurrently with a chemotherapeutic.
81. The method of clause 80, wherein the chemotherapeutic is carboplatin or etoposide.
82. The method of clause 81, wherein the immuno-oncogenic therapeutic antibody is atezolizumab and the chemotherapeutic is carboplatin or etoposide.
83. The method of any one of clause 69 to 74, wherein one dose of lurbinectedin is administered per treatment cycle and the treatment cycle is an 18, 19, 20, 21, 22, 23, 24, or 25 day cycle.
84. The method of any one of clause 77 to 83, wherein one dose of lurbinectedin is administered per treatment cycle and the patient undergoes at least 2, 3, 4, 5, 6, 7, 8, 9 10, 11, 12, 13, 14, 15, 16, 17, 18, 19, 21, 22, 23, or 24 treatment cycles.
85. The method of any one of clause 77 to 84, wherein the overall response rate is at least 40% or at least 50% or at least 60%.
86. The method of any one of clause 77 to 85, wherein the duration of response is at least 2 months, 3 months, 4 months, 5 months or 6 months.
87. The method of any one of clause 77 to 86, wherein the patient had not received the immuno-oncogenic therapeutic antibody in at least 30 or at least 60 or at least 90 days prior to administration of lurbinectedin.

88. The method of any one of clause 77 to 87, wherein the patient ceased responding to the immuno-oncogenic therapeutic antibody prior to administration of lurbinectedin.
89. The method of any one of clause 77 to 87, wherein an immune-oncogenic therapeutic antibody is not administered concurrently with lurbinectedin.
90. A pharmaceutical composition comprising
   a lyophilized composition comprising 4 mg lurbinectedin, a buffer derived from an organic acid, and a disaccharide,
   wherein the lurbinectedin and disaccharide are present at a ratio of 1 mol lurbinectedin to 455 to 465 mol disaccharide,
   wherein the lyophilized composition is formulated such that reconstitution with 8 mL of water will yield a solution having a pH of 3.5 to 4.5, and
   wherein the lyophilized composition further comprises a degradation product resulting from deacetylation of lurbinectedin at a value no greater than 0.8%, 0.7%, 0.6%, 0.5%, or 0.4%. wt./wt based upon the total weight of lurbinectedin.
91. The pharmaceutical composition of clause 90, wherein the lurbinectedin and the organic acid are present at a ratio of 1 mol lurbinectedin to 44 to 54 mol organic acid.
92. The pharmaceutical composition of clause 90 or 91, wherein the vial is a 30 mL vial.
93. The pharmaceutical composition of any one of clauses 90 to 92, wherein the lyophilized composition does not comprise a phosphate buffer.
94. The pharmaceutical composition of any one of clauses 90 to 93, wherein the buffer derived from an organic acid is selected from a lactic acid buffer, a butyric acid buffer, a propionic acid buffer, a acetic acid buffer, a succinic acid buffer, a citric acid buffer, a ascorbic acid buffer, a tartaric acid buffer, a malic acid buffer, a maleic acid buffer, a fumaric acid buffer, a glutamic acid buffer, an aspartic acid buffer, a gluconic acid buffer, and a $\alpha$-ketoglutaric buffer.
95. The pharmaceutical composition of any one of clauses 90 to 94, wherein the buffer derived from an organic acid is lactic acid.
96. The pharmaceutical composition of any one of clauses 90 to 95, wherein the composition comprises 22.1 mg lactic acid; 5.1 mg sodium hydroxide; and 800 mg sucrose or wherein the composition comprises 800 mg of sucrose, 0.245 mmol of lactate and 0.128 mmol of sodium.
97. A method of reducing lurbinectedin degradation in a lyophilized formulation comprising lurbinectedin, the method comprising adding lactate buffer to a stock solution from which the lyophilized formulation is prepared, wherein the resulting ratio of lurbinectedin to lactate buffer is between 1 mol:44 mol and 1 mol:54 mol; wherein the lurbinectedin degradation product from deacetylation does not exceed 0.8% wt./wt. of the total lurbinectedin weight when stored at 5 degree C.±3 degree C. for at least 24 months or at least 36 months or at least 48 months or at least 60 months.
98. The method of clause 97, comprising adding sucrose to a stock solution from which the lyophilized formulation is prepared, wherein the resulting ratio of lurbinectedin to lactate buffer is between 1 mol:455 mol and 1 mol:465 mol;
99. The method of clause 97, wherein the lyophilized formulation does not contain a phosphate buffer.
100. A method of treating small cell lung cancer (SCLC) in a patient in need thereof, comprising administering lurbinectedin at a dose of 2 to 3.2 $mg/m^2$ to a patient by intravenous infusion every 3 weeks, wherein the lurbinectedin is provided in a lyophilized formulation comprising lurbinectedin, lactic acid, and sucrose, wherein the ratio of lurbinectedin:lactic acid:sucrose is between 1 mol:46 mol:455 mol and 1 mol:50 mol:465 mol, wherein the formulation is stable at 5 degree C.±3 degree C. for at least 24 months or at least 36 months or at least 48 months or at least 60 months such that the lurbinectedin degradation product from deacetylation does not exceed 0.8% wt./wt. of the total lurbinectedin weight.
101. The method of clause 100, wherein the topoisomerase inhibitor is administered at a dose equivalent to 75 mg of irinotecan/$m^2$ and lurbinectedin is administered at a dose of 2.0 $mg/m^2$.
102. A packaged, lyophilized composition, comprising
   4 mg lurbinectedin, a buffer derived from an organic acid and a disaccharide packaged in a vial,
   wherein the dissolution of the lyophilized composition in about 8 mL of water provides a lurbinectedin solution having a pH of about 3.5 to about 4.1, and
   wherein the lyophilized composition comprises less than about 0.3% of Impurity D (w/w based on lurbinectedin) when the composition is packaged, and wherein upon storage at about 5 degrees C. for about 24 months or about 36 months or about 48 months the composition comprises not more than about 0.8% of Impurity D (w/w based on lurbinectedin).
103. The composition of clause 102, wherein the composition comprises substantially the same amount of Impurity D (w/w based on lurbinectedin) when the composition is packaged and after storage of the composition at about 5 degrees C. for about 24 months or about 36 months or about 48 months.
104. The composition of any one of clauses 102-103, wherein the buffer is a salt of an organic anion selected from the group consisting of acetate, succinate, citrate and lactate.
105. The composition of clause 104, wherein the salt is lactate.
106. The composition of any one of clauses 102-105, wherein the disaccharide is selected from the group consisting of sucrose, trehalose, lactose and a combination of two or all three disaccharides thereof.
107. The composition of clause 106, wherein the disaccharide is sucrose.
108. The composition of clause 107, wherein the w/w ratio of lurbinectedin to sucrose is about 1:200.
109. The composition of any one of clauses 102-108, wherein the composition comprises: 4 mg lurbinectedin, 22.1 mg lactic acid, 5.1 mg sodium hydroxide, and 800 mg sucrose or wherein the lyophilized composition comprises 800 mg of sucrose, 0.245 mmol of lactate and 0.128 mmol of sodium.
110. The composition of any one of clauses 102-109, wherein the dissolution in about 8 mL of water provides a lurbinectedin solution having a pH of about 4.0.
111. A packaged, lyophilized composition, comprising
   4 mg lurbinectedin, a buffer derived from an organic acid and a disaccharide packaged in a vial,
   wherein the dissolution of the lyophilized composition in about 8 mL of water provides a lurbinectedin solution having a pH of about 3.8 to about 4.1, and wherein the lyophilized composition comprises less than about 0.3% of Impurity D (w/w based on lurbinectedin) when the composition is packaged, and wherein the composition comprises substantially the same amount Impurity D (w/w based on lurbinectedin) after the packaged composition has been stored at about 25 degrees C. and about 60% relative humidity for up to about 1, 2, 3, 6, 9, or 12 months.

112. The composition of clause 111 wherein the composition comprises: 4 mg lurbinectedin, 22.1 mg lactic acid, 5.1 mg sodium hydroxide, and 800 mg sucrose or wherein the lyophilized composition comprises 800 mg of sucrose, 0.245 mmol of lactate and 0.128 mmol of sodium.

113. The composition of clause 111 or clause 112, wherein dissolution in about 8 mL of water provides a lurbinectedin solution having a pH of about 4.0.

114. The composition of any one of clauses 102-113, wherein the composition is prepared by a process comprising:
(a) providing a solution of lurbinectedin and an organic acid;
(b) providing a solution of a base, an organic acid and a disaccharide;
(c) combining the solutions of Step (a) and Step (b);
(d) adjusting the pH of the solution of Step (c) to about 3.8 to about 4.1; and
(e) lyophilizing the solution of Step (d) to provide the lyophilized composition.

115. The composition of clause 114, wherein the organic acid is selected from the group consisting of citric acid, succinic acid, lactic acid and acetic acid.

116. The composition of clause 114, wherein the organic acid is lactic acid.

117. The composition of any one of clauses 114-116, wherein the base is sodium hydroxide.

118. The composition of any one of clauses 114-117, wherein the disaccharide is selected from the group consisting of sucrose, trehalose, lactose and a combination of two or all three disaccharides thereof.

119. The composition of any one of clauses 14-117, wherein the organic acid is lactic acid, the base is sodium hydroxide, and the disaccharide is sucrose.

120. A method of treating small cell lung cancer (SCLC) in a patient in need thereof, comprising:
1) dissolving a packaged, lyophilized composition comprising 4 mg lurbinectedin, a buffer derived from an organic acid and disaccharide in about 8 mL of water to provide a lurbinectedin solution having a pH of about 3.5 to about 4.1, and
2) administering about 2 to 3.2 $mg/m^2$ of lurbinectedin to a patient whose SCLC has progressed after prior platinum-containing therapy by intravenous infusion every 3 weeks and
wherein the lyophilized composition comprises less than about 0.3% of Impurity D (w/w based on lurbinectedin) at packaging, and wherein upon storage at about 5 degrees C. for about 24 months the composition comprises less than about 0.8% of Impurity D (w/w based on lurbinectedin).

121. The method of clause 120, wherein the administration comprises:
1) dissolving a packaged, lyophilized composition comprising 4 mg lurbinectedin, a buffer derived from an organic acid and disaccharide in about 8 mL of water to provide a lurbinectedin solution having a pH of about 3.8 to about 4.1, and
2) administering the lurbinectedin to the patient in need thereof,
wherein the lyophilized composition comprises less than about 0.3% of Impurity D (w/w based on lurbinectedin) when the composition is packaged, and wherein upon storage at about 5 degrees C. for about 24 months the composition comprises less than about 0.8% of Impurity D (w/w based on lurbinectedin).

122. The method of clause 120 or 121, wherein, prior to administration, the lyophilized composition is reconstituted in about 8 mL of an aqueous solution to obtain a reconstituted lurbinectedin solution.

123. The method of clause 122, wherein, prior to administration said reconstituted lurbinectedin solution is stored for up to 24 hours following reconstitution at room temperature or at 5° C.±3° C., wherein after storage the reconstituted lurbinectin solution comprises Impurity D not more than 0.8%, 0.7%, 0.6%, 0.5%, or 0.4% wt/wt lurbinectedin.

124. The method of clause 122 or 123, wherein a lurbinectedin infusion solution is prepared by diluting the reconstituted solution with an isotonic solution.

125. The method of clause 124, wherein the reconstituted solution is diluted with at least 100 mL or at least 250 mL of the isotonic solution to prepare the lurbinectedin infusion solution.

126. The method of clause 124 or 125, wherein the isotonic solution is a 0.9% sodium chloride solution or a 5% dextrose solution.

127. The method of any of clauses 120 to 126 wherein the infusion lurbinectedin solution is stored for up to 24 hours following reconstitution of the lyophilized lurbinectedin formulation at room temperature or at 5° C.±3° C., wherein after storage the reconstituted lurbinectin solution comprises Impurity D not more than 0.8%, 0.7%, 0.6%, 0.5%, or 0.4% wt/wt based on the total weight of lurbinectedin.

128. Use of lurbinectedin in the manufacture of a medicament for use in therapy for treating small cell lung cancer (SCLC) in a patient in need thereof wherein said medicament is to be administered at a dose of 2 to 3.2 $mg/m^2$ to the patient by intravenous infusion in combination with a prophylactic dose of a corticosteroid and a serotonin antagonist effective to reduce nausea associated with administration of lurbinectedin to the patient, wherein the prophylactic dose is administered on the day of and prior to administration of lurbinectedin to the patient.

129. The use of clause 128, wherein the corticosteroid is dexamethasone formulated for intravenous administration at a dose of 8 mg of dexamethasone or a dose of a corticosteroid equivalent to 8 mg of dexamethasone administered intravenously.

130. The use of clause 128 or 129, wherein the serotonin antagonist is ondansetron formulated for intravenous administration at a dose of 8 mg of ondansetron or a dose of a serotonin antagonist equivalent to 8 mg of ondansetron administered intravenously.

131. The use of any one of clauses 128 to 130, wherein said medicament is administered in combination with one or more antiemetic agents, which are administered within 2, 3, or 4 days after administration of lurbinectedin to the patient.

132. The use of clause 131, wherein the one or more antiemetic agents administered after lurbinectedin administration are selected from a corticosteroid, a serotonin antagonist, and metoclopramide.

133. The use of clause 132, wherein the one or more antiemetic agents are 4 mg dexamethasone, 8 mg ondansetron, or 10 mg metoclopramide, or a combination thereof.

134. The use of any of clauses 121-126, wherein the patient is not treated with doxorubicin in combination with the lurbinectedin.

135. The use of any of clauses 128-134, wherein the patient has progressed after prior platinum-containing therapy or prior immunotherapy.

136. Use of lurbinectedin in the manufacture of a medicament for use in therapy for treating small cell lung cancer (SCLC) in a patient in need thereof wherein said medicament is to be administered at a first dose of 3.2 $mg/m^2$ to the patient by intravenous infusion in a first treatment cycle and the same dose is administered in a subsequent treatment unless an adverse reaction is identified in the patient, wherein the adverse reaction is selected from the group consisting of: ≥Grade 3 (severe) non hematological toxicity, Grade 4 thrombocytopenia (Platelet count less than 25,000 cells/$mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;

after the adverse reaction is identified and after the patient's neutrophil count is greater than 1500 cells/$mm^3$; platelet count is greater than about 100,000 $mm^3$; and hemoglobin levels are greater than about 9 g/dL: the (i) if the identified adverse reaction consists of Grade 4 neutropenia (Neutrophil count less than 500 cells/$mm^3$), a dose of G-CSF is administered in combination with a dose of lurbinectedin that is equal to the first dose in the subsequent treatment cycle; or (ii) if the identified adverse reaction is not isolated Grade 4 neutropenia, a reduced dose of lurbinectedin compared to the first dose is administered to the patient, wherein administration of two doses of lurbinectedin are spaced apart by at least 21 days.

137. The use of clause 136, wherein a first reduced dose is 80 to 85% of the first dose after a first occurrence of the adverse reaction that is not isolated Grade 4 neutropenia or wherein a first reduced dose is to 2.6 $mg/m^2$ after a first occurrence of the adverse reaction that is not isolated Grade 4 neutropenia.

138. The use of clause 137, wherein a second reduced dose is 60-65% of the first dose after a second occurrence of the adverse reaction that is not isolated Grade 4 neutropenia or wherein a second reduced dose is to 2.0 $mg/m^2$ after a second occurrence of the adverse reaction that is not isolated Grade 4 neutropenia, wherein the second reduced is administered to the patient.

139. The use of clause 138, wherein the administration of lurbinectedin is discontinued after identification of the adverse reaction after administration of the second reduced dose.

140. The use of any of the preceding clauses in which the medicament is administered as an infusion formulation prepared by diluting a reconstituted lyophilized formulation of 4 mg lurbinectedin, 22.1 mg lactic acid or 0.245 mmol lactate, 5.1 mg sodium hydroxide or 0.128 mmol sodium, and 800 mg sucrose, which, when reconstituted has a pH of 3.5 to 4.5.

141. Use of lurbinectedin in the manufacture of a medicament for use in therapy for treating small cell lung cancer (SCLC) in a patient in need thereof wherein said medicament is to be administered at a dose of 3.2 $mg/m^2$ to the patient by intravenous infusion of a lurbinectedin infusion solution, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.

142. The use of clause 141, wherein the disaccharide is sucrose and optionally wherein the composition comprises lurbinectedin and sucrose at a ratio of 1 mol lurbinectedin:455 to 465 mol sucrose.

143. The use of clause 141 or 142 wherein the organic carboxylic acid is lactic acid and optionally wherein the composition comprises lurbinectedin and the lactic acid at a ratio of 1 mol lurbinectedin:44 to 54 mol lactic acid.

144. The use of any one of clauses 141 to 143 wherein the pH is 3.8 to 4.5

145. The use of any one of clauses 141 to 144, wherein the lyophilized composition is reconstituted in about 8 mL of an aqueous solution to obtain the reconstituted solution.

146. The use of clause 145, wherein the lurbinectedin infusion solution is prepared by diluting the reconstituted solution with an isotonic solution.

147. The use of any one of clauses 141 to 146, wherein the reconstituted solution is diluted with at least 100 mL or at least 250 mL of the isotonic solution to prepare the lurbinectedin infusion solution.

148. The use of clause 146, wherein the isotonic solution is a 0.9% sodium chloride solution or a 5% dextrose solution.

149. The use of any one of clauses 141 to 148, wherein the lyophilized composition comprises:

22.1 mg of lactic acid;

5.1 mg of sodium hydroxide; and 800 mg of sucrose or wherein the lyophilized composition comprises 800 mg of sucrose, 0.245 mmol of lactate and 0.128 mmol of sodium.

150. The use of any one of clauses 141 to 149, wherein the lyophilized composition is provided in a 30 mL vial.

151. The use of any one of clauses 141 to 150, wherein the lyophilized composition comprises Impurity D at a value no greater than 0.8%, 0.7%, 0.6%, 0.5%, or 0.4% wt/wt based upon the total weight of lurbinectedin.

152. The use of any one of clauses 141 to 151, wherein the lyophilized composition does not comprise a phosphate buffer.

153. The use of any one of clauses 141 to 152 wherein the reconstituted solution or the lurbinectedin infusion solution comprises Impurity D at a value no greater than 0.8%, 0.7%, 0.6%, 0.5%, or 0.4% wt/wt based upon the total weight of lurbinectedin.

154. The use of any one of clauses 141 to 153, administered in combination with a prophylactic dose of a corticosteroid and a serotonin antagonist effective to reduce nausea associated with administration of lurbinectedin to the patient, wherein the prophylactic dose is administered on the day of and prior to administration of lurbinectedin to the patient.

155. The use of clause 154, wherein the corticosteroid is dexamethasone formulated for intravenous administration at a dose of 8 mg of dexamethasone or a dose of a corticosteroid equivalent to 8 mg of dexamethasone administered intravenously.

156. The use of clause 154 or 155, wherein the serotonin antagonist is ondansetron formulated for intravenous administration at a dose of 8 mg of ondansetron or a dose of a serotonin antagonist equivalent to 8 mg of ondansetron administered intravenously.

157. The use of any one of clauses 154 to 156, wherein said medicament is administered in combination with one or more antiemetic agents, which are administered within 2, 3, or 4 days after administration of lurbinectedin to the patient.

158. The use of clause 157, wherein the one or more antiemetic agents are selected from a corticosteroid, a serotonin antagonist, and metoclopramide.

159. The use of clause 158, wherein the one or more antiemetic agents are 4 mg dexamethasone, 8 mg ondansetron, or 10 mg metoclopramide, or a combination thereof.

160. The use of any preceding clause wherein said medicament is administered in combination with G-CSF to the patient identified as having a neutrophil countless than $500/mm^3$ or any value below a normal range and associated with infection/sepsis.

161. The use of any preceding clause, wherein one dose of lurbinectedin is administered per treatment cycle and the patient undergoes at least 1, 2, 3, 4, 5, 6, 7, 8, 9 10, 11, 12, 13, 14, 15, 16, 17, 18, 19, 21, 22, 23, or 24 treatment cycles.

162. The use of any preceding clause, wherein the overall response rate is at least 11% or at least 20% for patients with a CTFI interval <90 days or wherein the overall response rate is at least 30% or at least 40% for patients with a CTFI interval >90 days.

163. The use of any preceding clause, wherein the duration of response is at least 2.5 months or at least 4.5 months for the patient with a CTFI interval <90 days or wherein the duration of response is at least 3.5 months, 5 months or 6 months for the patient with a CTFI interval >90 days.

164. The use of any preceding clause, wherein the patient had not received a platinum-containing therapy in at least 30 or at least 60 or at least 90 days prior to administration of lurbinectedin.

165. The use of any preceding clause, wherein the patient ceased responding to a platinum-containing therapy prior to administration of lurbinectedin.

166. The use of any preceding clause, wherein the patient has previously been administered an immunotherapy.

167. The use of clause 166, wherein the immunotherapy is an anti-CTLA-4 antibody, an anti-PD-1 antibody or an anti-PD-L1 antibody 168. The use of clause 167, wherein the immunotherapy is atezolizumab or nivolumab.

169. The use of any of clauses 166 to 168, wherein the patient has progressed after being administered the immunotherapy.

170. The use of any preceding clause, wherein the patient has a calculated creatinine clearance greater than 30 mL/min and an AST or ALT less than 3×ULN or bilirubin less than 1.5×ULN.

171. The use of any preceding clause, wherein lurbinectedin is administered to a patient as a 1 hour intravenous infusion, to achieve total plasma $C_{max}$ within 80% to 125% of about 107 μg/L and AUC∞ within 80% to 125% of about 551 μg*h/L.

172. Use of lurbinectedin in the manufacture of a medicament for use in therapy for treating endometrial cancer, SCLC, soft tissue sarcoma, glioblastoma, pancreatic adenocarcinoma, mesothelioma, colorectal carcinoma, or epithelial ovarian cancer in a patient in need thereof wherein said medicament is to be administered at a dose of 1 to 2.5 $mg/m^2$ to the patient by intravenous infusion in combination with a topoisomerase inhibitor selected from SN-38 and irinotecan on day one of a treatment cycle, wherein the topoisomerase inhibitor is administered at a dose equivalent to 50 to 75 mg of $irinotecan/m^2$.

173. The use of clause 172 wherein the lurbinectedin is administered at a dose of 2.0 $mg/m^2$ to and the irinotecan is administered at a dose of 75 $mg/m^2$ by intravenous administration on day 1 of the treatment cycle.

174. The use of clause 172 or 173, wherein a subsequent dose of irinotecan at 75 $mg/m^2$ is administered on day 8 of the treatment cycle.

175. The use of any of clauses 172 to 174 wherein said treatment cycle is 21 days.

176. The use of any of clauses 172 to 175, wherein the medicament is administered in combination with G-CSF during the treatment cycle.

177. The use of any of clauses 172 to 176, wherein if the patient exhibits hematologic toxicity after the dose on day 1, not administering a subsequent dose of irinotecan to said patient during the treatment cycle.

178. The use of any one of clauses 172 to 177, further comprising administering one or more antiemetics on day one of a treatment cycle.

179. The use of any one of clauses 172 to 178, wherein the patients is treated for endometrial cancer, SCLC, soft tissue sarcoma, or glioblastoma.

180. A use of a lyophilized pharmaceutical composition to administer a pharmaceutical composition to a patient in need thereof, wherein the lyophilized pharmaceutical composition is reconstituted in a vial after the composition has been stored for 30 to 60 months and administered to the patient, wherein the lyophilized pharmaceutical composition was prepared by lyophilizing a stock solution comprising 4 mg of lurbinectedin, a buffer derived from an organic carboxylic acid, and sucrose, wherein the composition comprises lurbinectedin and disaccharide at a ratio of 1 mol lurbinectedin:455 to 465 mol sucrose, wherein the lyophilized composition is formulated such that reconstitution with 8 mL of water will yield a solution having a pH of 3.5 to 4.5.

181. The use of clause 180, wherein the pharmaceutical composition comprises a lurbinectedin amount that is at least 95% of the amount of lurbinectedin on day one of storage.

182. The use of clause 180 or 181, wherein the vial is a 30 mL vial.

183. A use of lurbinectedin in the manufacture of a medicament for treating SCLC in a patient in need thereof wherein lurbinectedin is administered at a dose of 2 to 3.2 $mg/m^2$ to the patient by intravenous infusion;

wherein the patient was administered an immunotherapeutic antibody for treating SCLC prior to beginning the treatment cycle and wherein the duration of response is at least 2 months, 3 months, 4 months, 5 months or 6 months or wherein the overall response rate is at least 40%.

184. The use of clause 183, wherein the immunotherapeutic antibody is an anti-CTLA-4 antibody, an anti-PD-1 antibody or an anti-PD-L1 antibody.

185. The use of clause 184, wherein the immunotherapeutic antibody is atezolizumab or nivolumab.

186. The use of clause 185, wherein the immunotherapeutic antibody was administered to the patient concurrently with a chemotherapeutic.

187. The use of clause 186, wherein the chemotherapeutic is carboplatin or etoposide.

188. The use of clause 187, wherein the immuno-oncogenic therapeutic antibody is atezolizumab and the chemotherapeutic is carboplatin or etoposide.

189. The use of any one of clause 183 to 188, wherein one dose of lurbinectedin is administered per treatment cycle and the treatment cycle is an 18, 19, 20, 21, 22, 23, 24, or 25 day cycle.

190. The use of any one of clause 183 to 189, wherein one dose of lurbinectedin is administered per treatment cycle and the patient undergoes at least 2, 3, 4, 5, 6, 7, 8, 9 10, 11, 12, 13, 14, 15, 16, 17, 18, 19, 21, 22, 23, or 24 treatment cycles.

191. The use of any one of clause 183 to 190, wherein the patent is administered 5 lurbinectedin doses over a 17-week period or at least 6 lurbinectedin doses over a 20-week period or at least 7 lurbinectedin doses over a 22 week period.

192. The use of any one of clause 183 to 191, wherein the overall response rate is at least 40% or at least 50% or at least 60%.

193. The use of any one of clause 183 to 192, wherein the duration of response is at least 2 months, 3 months, 4 months, 5 months or 6 months.

194. The use of any one of clause 183 to 193, wherein the patient had not received the immuno-oncogenic therapeutic antibody in at least 30 or at least 60 or at least 90 days prior to administration of lurbinectedin.

195. The use of any one of clause 183 to 194, wherein the patient ceased responding to the immuno-oncogenic therapeutic antibody prior to administration of lurbinectedin.

196. The use of any one of clause 183 to 195, wherein an immune-oncogenic therapeutic antibody is not administered concurrently with lurbinectedin.

197. A use of lurbinectedin in the manufacture of a medicament for use in treating small cell lung cancer (SCLC) in a patient in need thereof, wherein the lurbinectedin is administered at a dose of 2 to 3.2 $mg/m^2$ to a patient by intravenous infusion every 3 weeks, wherein the medicament is provided in a lyophilized formulation comprising lurbinectedin, lactic acid, and sucrose, wherein the ratio of lurbinectedin: lactic acid:sucrose is between 1 mol:46 mol:455 mol and 1 mol:50 mol:465 mol, wherein the formulation is stable at 5 degree C.±3 degree C. for at least 24 months or at least 36 months or at least 48 months or at least 60 months such that the lurbinectedin degradation product from deacetylation does not exceed 0.8% wt./wt. of the total lurbinectedin weight.

198. The use of clause 197, wherein the medicament is used in combination with a topoisomerase inhibitor administered at a dose equivalent to 75 mg of irinotecan/$m^2$ and lurbinectedin administered at a dose of 2.0 $mg/m^2$.

199. A use of lurbinectedin for manufacture of a medicament for use in treating small cell lung cancer (SCLC) in a patient in need thereof, wherein the medicament is a packaged lyophilized composition that comprises 4 mg lurbinectedin, a buffer derived from an organic acid and disaccharide and is dissolved in about 8 mL of water to provide a lurbinectedin solution having a pH of about 3.5 to about 4.1, for administration of about 2 to 3.2 $mg/m^2$ of lurbinectedin to a patient whose SCLC has progressed after prior platinum-containing therapy by intravenous infusion every 3 weeks and wherein the lyophilized composition comprises less than about 0.3% of Impurity D (w/w based on lurbinectedin) when the composition is packaged, and wherein upon storage at about 5 degrees C. for about 24 months or about 36 months the composition comprises less than about 0.8% of Impurity D (w/w based on lurbinectedin).

200. The use of any one of clauses 128-199, wherein the medicament is a packaged, lyophilized composition comprising 4 mg lurbinectedin, a buffer derived from an organic acid and disaccharide and is dissolved in about 8 mL of water to provide a lurbinectedin solution having a pH of about 3.8 to about 4.1 for administration to the patient in need thereof, wherein the lyophilized composition comprises less than about 0.3% of Impurity D (w/w based on lurbinectedin) when the composition is packaged, and wherein upon storage at about 5 degrees C. for about 24 months or about 36 months the composition comprises less than about 0.8% of Impurity D (w/w based on lurbinectedin).

201. The use of any of the proceeding clauses, wherein, prior to administration, the lyophilized composition is reconstituted in about 8 mL of an aqueous solution to obtain a reconstituted lurbinectedin solution.

202. The use of clause 201, wherein, prior to administration said reconstituted lurbinectedin solution is stored for up to 24 hours following reconstitution at room temperature or at 5° C.±3° C., wherein after storage the reconstituted lurbinectin solution comprises Impurity D not more than 0.8%, 0.7%, 0.6%, 0.5%, or 0.4% wt/wt based upon the total weight of lurbinectedin.

203. The use of clause 201 or 202, wherein a lurbinectedin infusion solution is prepared by diluting the reconstituted solution with an isotonic solution.

204. The use of clause 203, wherein the reconstituted solution is diluted with at least 100 mL or at least 250 mL of the isotonic solution to prepare the lurbinectedin infusion solution.

205. The use of clause 203 or 204, wherein the isotonic solution is a 0.9% sodium chloride solution or a 5% dextrose solution.

206. The use of any of clauses 203 to 205 wherein the infusion lurbinectedin solution is stored for up to 24 hours following reconstitution of the lyophilized lurbinectedin formulation at room temperature or at 5° C.±3° C., wherein after storage the reconstituted lurbinectedin solution comprises Impurity D not more than 0.8%, 0.7%, 0.6%, 0.5%, or 0.4% wt/wt based upon the total weigh of lurbinectedin.

207. A composition for treatment of small cell lung cancer (SCLC) in a patient in need thereof, comprising:
   (1) administering a prophylactic dose of a corticosteroid and a serotonin antagonist effective to reduce nausea associated with administration of lurbinectedin to the patient on the day of and prior to administration of lurbinectedin to the patient; and
   (2) administering lurbinectedin at a dose of 2 to 3.2 $mg/m^2$ to the patient by intravenous infusion.
208. The composition of clause 207, wherein the corticosteroid is dexamethasone intravenously administered at a dose of 8 mg of dexamethasone or a dose of a corticosteroid equivalent to 8 mg of dexamethasone administered intravenously.
209. The composition of clause 207 or 208, wherein the serotonin antagonist is ondansetron intravenously administered at a dose of 8 mg of ondansetron or a dose of a serotonin antagonist equivalent to 8 mg of ondansetron administered intravenously.
210. The composition of any one of clauses 207 to 209, further comprising administering one or more antiemetic agents within 2, 3, or 4 days after administration of lurbinectedin to the patient.
211. The composition of clause 210, wherein the one or more antiemetic agents administered after lurbinectedin administration are selected from a corticosteroid, a serotonin antagonist, and metoclopramide.
212. The composition of clause 211, wherein the one or more antiemetic agents are 4 mg dexamethasone, 8 mg ondansetron, or 10 mg metoclopramide, or a combination thereof.
213. The composition of any of clauses 207-212, wherein the patient has progressed after prior platinum-containing therapy or prior immunotherapy.
214. A composition for treatment of small cell lung cancer (SCLC) in a patient in need thereof, comprising:
   (1) administering a first dose of 3.2 $mg/m^2$ of lurbinectedin to the patient by intravenous infusion; and
   (2) identifying an adverse reaction in the patient, wherein the adverse reaction is selected from the group consisting of: ≥Grade 3 (severe) non hematological toxicity, Grade 4 thrombocytopenia (Platelet count less than 25,000 $cells/mm^3$), Grade 3 thrombocytopenia (Platelet count less than 50,000 cells/$mm^3$) with bleeding that requires transfusion, Grade 4 neutropenia (Neutrophil count less than 500 cells/$mm^3$), or any grade neutropenia (Neutrophil count <LLN) that is associated with infection/sepsis or any other of the adverse reactions;
   (3) after the adverse reaction is identified and after the patient's neutrophil count is greater than 1500 cells/$mm^3$; platelet count is greater than about 100,000 $mm^3$; and hemoglobin levels are greater than about 9 g/dL:
      (i) if the identified adverse reaction consists of Grade 4 neutropenia (Neutrophil count less than 500 $cells/mm^3$), administering to the patient a dose of G-CSF and a dose of lurbinectedin that is equal to the first dose; or
      (ii) if the identified adverse reaction is not solely Grade 4 neutropenia, administering to the patient a reduced dose of lurbinectedin compared to the first dose,
   wherein administration of two doses of lurbinectedin are spaced apart by at least 21 days.
215. The composition of clause 214, wherein a first reduced dose is 80 to 85% of the first dose after a first occurrence of the adverse reaction that is not solely Grade 4 neutropenia or wherein a first reduced dose is to 2.6 $mg/m^2$ after a first occurrence of the adverse reaction that is not solely Grade 4 neutropenia.
216. The composition of clause 215, wherein a second reduced dose is 60-65% of the first dose after a second occurrence of the adverse reaction that is not solely Grade 4 neutropenia or wherein a second reduced dose is to 2.0 $mg/m^2$ after a second occurrence of the adverse reaction that is not solely Grade 4 neutropenia, wherein the second reduced is administered to the patient.
217. The composition of clause 216, further comprising discontinuing administration of lurbinectedin after identification of the adverse reaction after administration of the second reduced dose.
218. The composition of any of the preceding clauses in which the lurbinectedin is administered as an infusion formulation prepared by diluting a reconstituted lyophilized formulation of 4 mg lurbinectedin, 22.1 mg lactic acid, 5.1 mg sodium hydroxide and 800 mg sucrose, which, when reconstituted has a pH of 3.5 to 4.5.
219. A composition for treatment of small cell lung cancer (SCLC) in a patient in need thereof, comprising:
   administering to the patient lurbinectedin at a dose of 3.2 $mg/m^2$ by intravenous infusion of a lurbinectedin infusion solution, wherein the lurbinectedin infusion solution administered to the patient is prepared from a lyophilized composition comprising 4 mg lurbinectedin, a buffer derived from an organic carboxylic acid, and a disaccharide reconstituted to form a reconstituted solution at a pH of 3.5 to 4.5.
220. The composition of clause 219, wherein the disaccharide is sucrose and optionally wherein the composition comprises lurbinectedin and sucrose at a ratio of 1 mol lurbinectedin:455 to 465 mol sucrose.
221. The composition of clause 219 or 220 wherein the organic carboxylic acid is lactic acid and optionally wherein the composition comprises lurbinectedin and the lactic acid at a ratio of 1 mol lurbinectedin:44 to 54 mol lactic acid.
222. The composition of any one of clauses 219 to 221 wherein the pH is 3.8 to 4.5
223. The composition of any one of clauses 219 to 222, wherein the lyophilized composition is reconstituted in about 8 mL of an aqueous solution to obtain the reconstituted solution.
224. The composition of clause 223, wherein the lurbinectedin infusion solution is prepared by diluting the reconstituted solution with an isotonic solution.
225. The composition of any one of clauses 219 to 224, wherein the reconstituted solution is diluted with at least 100 mL or at least 250 mL of the isotonic solution to prepare the lurbinectedin infusion solution.
226. The composition of clause 225, wherein the isotonic solution is a 0.9% sodium chloride solution or a 5% dextrose solution.
227. The composition of any one of clauses 219 to 226, wherein the lyophilized composition comprises:
   22.1 mg of lactic acid;
   5.1 mg of sodium hydroxide; and
   800 mg of sucrose.
228. The composition of any one of clauses 219 to 227, wherein the lyophilized composition is provided in a 30 mL vial.
229. The composition of any one of clauses 219 to 228, wherein the lyophilized composition comprises Impurity D at a value no greater than 0.8%, 0.7%, 0.6%, 0.5%, or 0.4% wt/wt based on the total weight of lurbinectedin.

230. The composition of any one of clauses 219 to 229, wherein the lyophilized composition does not comprise a phosphate buffer.

231. The composition of any one of clauses 219 to 231 wherein the reconstituted solution or the lurbinectedin infusion solution comprises Impurity D at a value no greater than 0.8%, 0.7%, 0.6%, 0.5%, or 0.4% wt/wt based on the total weight of lurbinectedin.

232. The composition of any one of clauses 219 to 231, further comprising administering a prophylactic dose of a corticosteroid and a serotonin antagonist effective to reduce nausea associated with administration of lurbinectedin to the patient on the day of and prior to administration of lurbinectedin to the patient.

233. The composition of clause 232, wherein the corticosteroid is dexamethasone intravenously administered at a dose of 8 mg of dexamethasone or a dose of a corticosteroid equivalent to 8 mg of dexamethasone administered intravenously.

234. The composition of clause 232 or 233, wherein the serotonin antagonist is ondansetron intravenously administered at a dose of 8 mg of ondansetron or a dose of a serotonin antagonist equivalent to 8 mg of ondansetron administered intravenously.

235. The composition of any one of clauses 232 to 234, further comprising administering one or more antiemetic agents within 2, 3, or 4 days after administration of lurbinectedin to the patient.

236. The composition of clause 235, wherein the one or more antiemetic agents are selected from a corticosteroid, a serotonin antagonist, and metoclopramide.

237. The composition of clause 236, wherein the one or more antiemetic agents are 4 mg dexamethasone, 8 mg ondansetron, or 10 mg metoclopramide, or a combination thereof.

238. The composition of any preceding clause further comprising administering G-CSF to the patient identified as having a neutrophil countless than $500/mm^3$ or any value below a normal range and associated with infection/sepsis.

239. The composition of any preceding clause, wherein one dose of lurbinectedin is administered per treatment cycle and the patient undergoes at least 1, 2, 3, 4, 5, 6, 7, 8, 9 10, 11, 12, 13, 14, 15, 16, 17, 18, 19, 21, 22, 23, or 24 treatment cycles.

240. The composition of any preceding clause, wherein the overall response rate is at least 11% or at least 20% for patients with a CTFI interval <90 days or wherein the overall response rate is at least 30% or at least 40% for patients with a CTFI interval >90 days.

241. The composition of any preceding clause, wherein the duration of response is at least 2.5 months or at least 4.5 months for the patient with a CTFI interval <90 days or wherein the duration of response is at least 3.5 months, 5 months or 6 months for the patient with a CTFI interval >90 days.

242. The composition of any preceding clause, wherein the patient had not received a platinum-containing therapy in at least 30 or at least 60 or at least 90 days prior to administration of lurbinectedin.

243. The composition of any preceding clause, wherein the patient ceased responding to a platinum-containing therapy prior to administration of lurbinectedin.

244. The composition of any preceding clause, wherein the patient has previously been administered an immunotherapy.

245. The composition of clause 244, wherein the immunotherapy is an anti-CTLA-4 antibody, an anti-PD-1 antibody or an anti-PD-L1 antibody 246. The composition of clause 245, wherein the immunotherapy is atezolizumab or nivolumab.

247. The composition of any of clauses 244 to 246, wherein the patient has progressed after being administered the immunotherapy.

248. The composition of any preceding clause, wherein the patient has a calculated creatinine clearance greater than 30 mL/min and an AST or ALT less than 3×ULN or bilirubin less than 1.5×ULN.

249. The composition of any preceding clause, wherein lurbinectedin is administered to a patient as a 1 hour intravenous infusion, to achieve total plasma $C_{max}$ within 80% to 125% of about 107 μg/L and AUC∞ within 80% to 125% of about 551 μg*h/L.

250. A composition for treatment of endometrial cancer, SCLC, soft tissue sarcoma, glioblastoma, pancreatic adenocarcinoma, mesothelioma, colorectal carcinoma, or epithelial ovarian cancer in a patient in need thereof, the treatment comprising administering to the patient lurbinectedin and a topoisomerase inhibitor selected from SN-38 and irinotecan on day one of a treatment cycle;

wherein the lurbinectedin is administered at a dose of 1 to 2.5 $mg/m^2$ and wherein the topoisomerase inhibitor is administered at a dose equivalent to 50 to 75 mg of irinotecan/$m^2$.

251. The composition of clause 250 wherein the lurbinectedin is administered at a dose of 2.0 $mg/m^2$ to and the irinotecan is administered at a dose of 75 $mg/m^2$ by intravenous administration on day 1 of the treatment cycle.

252. The composition of clause 250 or 251, wherein a subsequent dose of irinotecan at 75 $mg/m^2$ is administered on day 8 of the treatment cycle.

253. The composition of any of clauses 250 to 252 wherein said treatment cycle is 21 days.

254. The composition of any of clauses 250 to 254, wherein the medicament is administered in combination with G-CSF during the treatment cycle.

255. The composition of any of clauses 250 to 254, wherein if the patient exhibits hematologic toxicity after the dose on day 1, not administering a subsequent dose of irinotecan to said patient during the treatment cycle.

256. The composition of any one of clauses 250 to 255, further comprising administering one or more antiemetics on day one of a treatment cycle.

257. The composition of any one of clauses 250 to 256, wherein the patients is treated for endometrial cancer, SCLC, soft tissue sarcoma, or glioblastoma.

258. A composition for treatment of SCLC in a patient in need thereof comprising administering lurbinectedin at a dose of 2 to 3.2 $mg/m^2$ to the patient by intravenous infusion;

wherein the patient was administered an immunotherapeutic antibody for treating SCLC prior to beginning the treatment cycle and wherein the duration of response is at least 2 months, 3 months, 4 months, 5 months or 6 months or wherein the overall response rate is at least 40%.

259. The composition of clause 258, wherein the immunotherapeutic antibody is an anti-CTLA-4 antibody, an anti-PD-1 antibody or an anti-PD-L1 antibody.
260. The composition of clause 259, wherein the immunotherapeutic antibody is atezolizumab or nivolumab.
261. The composition of clause 260, wherein the immunotherapeutic antibody was administered to the patient concurrently with a chemotherapeutic.
262. The composition of clause 261, wherein the chemotherapeutic is carboplatin or etoposide.
263. The composition of clause 262, wherein the immuno-oncogenic therapeutic antibody is atezolizumab and the chemotherapeutic is carboplatin or etoposide.
264. The composition of any one of clauses 258 to 263, wherein one dose of lurbinectedin is administered per treatment cycle and the treatment cycle is an 18, 19, 20, 21, 22, 23, 24, or 25 day cycle.
265. The composition of any one of clauses 258 to 264, wherein one dose of lurbinectedin is administered per treatment cycle and the patient undergoes at least 2, 3, 4, 5, 6, 7, 8, 9 10, 11, 12, 13, 14, 15, 16, 17, 18, 19, 21, 22, 23, or 24 treatment cycles.
266. The composition of any one of clauses 258 to 264, wherein the overall response rate is at least 40% or at least 50% or at least 60%.
267. The composition of any one of clauses 258 to 264, wherein the duration of response is at least 2 months, 3 months, 4 months, 5 months or 6 months.
268. The composition of any one of clauses 258 to 264, wherein the patient had not received the immuno-oncogenic therapeutic antibody in at least 30 or at least 60 or at least 90 days prior to administration of lurbinectedin.
269. The composition of any one of clauses 258 to 264, wherein the patient ceased responding to the immuno-oncogenic therapeutic antibody prior to administration of lurbinectedin.
270. The composition of any one of clauses 258 to 269, wherein an immune-oncogenic therapeutic antibody is not administered concurrently with lurbinectedin.
271. A composition for the treatment of small cell lung cancer (SCLC) in a patient in need thereof, comprising administering lurbinectedin at a dose of 2 to 3.2 $mg/m^2$ to a patient by intravenous infusion every 3 weeks, wherein the lurbinectedin is provided in a lyophilized formulation comprising lurbinectedin, a buffer derived from lactic acid, and sucrose, wherein the ratio of lurbinectedin:lactic acid:sucrose is between 1 mol:46 mol:455 mol and 1 mol:50 mol:465 mol, wherein the formulation is stable at 5 degree C.±3 degree C. for at least 24 months or at least 36 months or at least 48 months or at least 60 months such that the lurbinectedin degradation product from deacetylation does not exceed 0.8% wt./wt. of the total lurbinectedin weight.
272. A composition for the treatment of small cell lung cancer (SCLC) in a patient in need thereof, comprising:
1) dissolving a packaged, lyophilized composition comprising 4 mg lurbinectedin, a buffer derived from an organic acid and disaccharide in about 8 mL of water to provide a lurbinectedin solution having a pH of about 3.5 to about 4.1,
and
2) administering about 2 to 3.2 $mg/m^2$ of lurbinectedin to a patient whose SCLC has progressed after prior platinum-containing therapy by intravenous infusion every 3 weeks and
wherein the lyophilized composition comprises less than about 0.3% of Impurity D (w/w based on lurbinectedin) when the composition is packaged, and wherein upon storage at about 5 degrees C. for about 24 months the composition comprises less than about 0.8% of Impurity D (w/w based on lurbinectedin).
273. The method, composition or use of any one of clauses 1-45, 54-72, 74-89, 100-101, and 120-272, 93-94 and 113-120, wherein the patient is an adult patient.
274. The method, composition or use of any one of clauses 1-45, 54-72, 74-89, 100-101, and 120-273, wherein the cancer is metastatic SCLC.
275. The method, composition or use of any one of clauses 1-45, 54-72, 74-89, 100-101, and 120-274, wherein the cancer is metastatic SCLC with disease progression after platinum based chemotherapy.
276. A method of reducing adverse events associated with the administration of lurbinectedin for the treatment of cancer in a patient in need thereof, the method comprising:
administering lurbinectedin at a dose of 3.2 $mg/m^2$ to the patient by intravenous infusion;
determining if the patient experiences an adverse event selected from the group consisting of neutropenia, thrombocytopenia and hepatotoxicity; and
modifying the dose if the patient experiences neutropenia, thrombocytopenia or hepatotoxicity,
wherein the 3.2 $mg/m^2$ dose of lurbinectedin is administered every 21 days when there is no dose modification (i.e., normal administration schedule).
277. The method of clause 276, wherein prior to the administration, the patient's absolute neutrophil count (ANC) is at least 1,500 $cells/mm^3$ and platelet count is at least $100,000/mm^3$.
278. The method of any one of clauses 276-277, wherein the dose is modified by delaying the administration of lurbinectedin compared to the normal administration schedule.
279. The method of any one of clauses 276-278, wherein the dose is modified by reducing the amount of administered lurbinectedin compared to the normal administration schedule.
280. The method of clause 279, wherein the dose modification comprises administering lurbinectedin at a dose of 2.6 $mg/m^2$ every 21 days.
281. The method of clause 279, wherein the dose modification comprises administering lurbinectedin at a dose of 2.0 $mg/m^2$ every 21 days.
282. The method of any one of clauses 276-277, wherein when the patient experiences a Grade 4 neutropenia or any grade febrile neutropenia; the dose is modified by withholding lurbinectedin treatment until the patient's neutropenia is Grade ≤1 and when the patient's neutropenia is Grade ≤1 administering lurbinectedin at a dose of 2.6 $mg/m^2$ every 21 days.
283. The method of any one of clauses 276-277, wherein when the patient experiences an isolated Grade 4 neutropenia neutropenia (neutrophil count less than 500 $cells/mm^3$); the dose is modified by withholding lurbinectedin treatment until the patient's neutropenia is Grade ≤1 and when the patient's neutropenia is Grade ≤1 administering lurbinectedin at a dose of 3.2 $mg/m^2$ every 21 days in conjunction with G-CSF prophylaxis.

284. The method of any one of clauses 276-277, wherein when the patient experiences a Grade 3 thrombocytopenia with bleeding or Grade 4 thrombocytopenia;

the dose is modified by withholding lurbinectedin treatment until the patient's platelet count is at least $100,000/mm^3$ and when the patient's platelet count is at least $100,000/mm^3$ administering lurbinectedin at a dose of 2.6 $mg/m^2$ every 21 days.

285. The method of any one of clauses 276-277, wherein when the patient experiences Grade 2 hepatotoxicity, the dose is modified by withholding lurbinectedin treatment until the patient's hepatotoxicity is Grade ≤1 and when the hepatotoxicity is Grade ≤1 administering lurbinectedin at a dose of 3.2 $mg/m^2$ every 21 days.

286. The method of any one of clauses 276-277, wherein when the patient experiences Grade 3 hepatotoxicity, the dose is modified by withholding lurbinectedin treatment until the patient's hepatotoxicity is Grade ≤1 and when the hepatotoxicity is Grade ≤1 administering lurbinectedin at a dose of 2.6 $mg/m^2$ every 21 days.

287. The method of any one of clauses 282-286, further comprising:

determining if the patient experiences an adverse event selected from the group consisting of neutropenia, thrombocytopenia and hepatotoxicity at the modified dose; and further modifying the dose if the patient experiences neutropenia, thrombocytopenia or hepatotoxicity.

288. The method of clause 287, wherein when the patient experiences a Grade 4 neutropenia or any grade febrile neutropenia at the modified dose; the dose is further modified by withholding lurbinectedin treatment until the patient's neutropenia is Grade ≤1 and when the patient's neutropenia is Grade ≤1 administering lurbinectedin at a dose of 2.0 $mg/m^2$ every 21 days.

289. The method of clause 287, wherein when the patient experiences a Grade 3 thrombocytopenia with bleeding or Grade 4 thrombocytopenia at the modified dose;

the dose is further modified by withholding lurbinectedin treatment until the patient's platelet count is at least $100,000/mm^3$ and when the patient's platelet count is at least $100,000/mm^3$ administering lurbinectedin at a dose of 2.0 $mg/m^2$ every 21 days.

290. The method of clause 287, wherein when the patient experiences Grade 2 hepatotoxicity at the modified dose, the dose is further modified by withholding lurbinectedin treatment until the patient's hepatotoxicity is Grade ≤1 and when the hepatotoxicity is Grade ≤1 administering lurbinectedin at a dose of 3.2 $mg/m^2$ every 21 days.

291. The method of clause 287, wherein when the patient experiences Grade ≥3 hepatotoxicity at the modified dose, the dose is further modified by withholding lurbinectedin treatment until the patient's hepatotoxicity is Grade ≤1 and when the hepatotoxicity is Grade ≤1 administering lurbinectedin at a dose of 2.0 $mg/m^2$ every 21 days.

292. The method of any one of clauses 277-291, wherein the administration is permanently discontinued when the withholding of lurbinectedin treatment is greater than two weeks.

292a. The method of any one of clauses 282, 283 and 288, wherein when the withholding of lurbinectedin treatment to achieve Grade ≤1 neutropenia exceeds two weeks the administration is permanently discontinued.

292b. The method of any one of clauses 284 and 289, wherein when the withholding of lurbinectedin treatment to achieve a platelet count of at least $100,000/mm^3$ exceeds two weeks the administration is permanently discontinued.

292c. The method of any one of clauses 285, 286, 290 and 291, wherein when the withholding of lurbinectedin treatment to achieve Grade ≤1 hepatotoxicity exceeds two weeks the administration is permanently discontinued.

293. The method of any one of clauses 277-291, wherein the administration is permanently discontinued if patient is unable to tolerate a dose of 2 $mg/m^2$.

294. The method of any one of clauses 277-293, wherein the cancer is metastatic SCLC with disease progression after platinum based chemotherapy.

295. A method of safely administering lurbinectedin for the treatment of cancer in a patient in need thereof, the method comprising:

determining if the patient is being administered a CYP3A inhibitor; and when the patient is administered a moderate or strong CYP3A inhibitor warning of a potential drug/drug interaction due to the combination of the CYP3A inhibitor and lurbinectedin; and when the coadministration of a moderate CYP3A inhibitor and lurbinectedin is cannot be avoided, administering lurbinectedin at a modified dose compared to the normal administration schedule.

296. The method of clause 295, wherein the warning is to avoid the coadministration of the strong or moderate CYP3A inhibitor and lurbinectedin.

297. The method of clause 295, wherein the patient is coadministered a moderate CYP3A inhibitor and lurbinectedin at lurbinectedin at a dose of 2.6 $mg/m^2$ every 21 days.

298. The method of clause 295, wherein the patient is coadministered a moderate CYP3A inhibitor and lurbinectedin at a dose of 2.0 $mg/m^2$ every 21 days.

299. A lyophilized composition, comprising 4 mg lurbinectedin, a buffer derived from an organic acid and a disaccharide, and wherein the lyophilized composition comprises less than about 0.8% of Impurity D (w/w based on lurbinectedin) when the composition is stored at about 25 degrees C. and about 60% relative humidity for up to about 1, 2, 3, 6, 9, or 12 months.

300. The lyophilized composition of clause 299, wherein the lyophilized composition comprises less than about 0.5% of Impurity D (w/w based on lurbinectedin) when the composition is stored at about 25 degrees C. and about 60% relative humidity for up to about 1, 2, 3, 6, 9, or 12 months.

301. The lyophilized composition of clause 299, wherein the lyophilized composition comprises less than about 0.3% of Impurity D (w/w based on lurbinectedin) when the composition is stored at about 25 degrees C. and about 60% relative humidity for up to about 1, 2, 3, 6, 9, or 12 months.

302. The lyophilized composition of clause 299, wherein the lyophilized composition comprises less than about 0.1% of Impurity D (w/w based on lurbinectedin) when the composition is stored at about 25 degrees C. and about 60% relative humidity for up to about 1, 2, 3, 6, 9, or 12 months.

303. The lyophilized composition of any one of clauses 299-302, wherein the organic acid is selected from the group consisting of citric acid, succinic acid, lactic acid and acetic acid.

304. The lyophilized composition of clause 303, wherein the organic acid is lactic acid.
305. The lyophilized composition of any one of clauses 299-304, wherein the disaccharide is selected from the group consisting of sucrose, trehalose, lactose and a combination of two or all three disaccharides thereof.
306. The lyophilized composition of any one of clauses 299-305, wherein the organic acid is lactic acid, and the disaccharide is sucrose.
307. The lyophilized composition of any one of clauses 299-306, wherein the composition comprises: 4 mg lurbinectedin, 22.1 mg lactic acid, 5.1 mg sodium hydroxide, and 800 mg sucrose or wherein the lyophilized composition comprises 800 mg of sucrose, 0.245 mmol of lactate and 0.128 mmol of sodium.
308. The lyophilized composition of any one of clauses 299-307, wherein the dissolution of the lyophilized composition in about 8 mL of water provides a lurbinectedin solution having a pH of about 3.8 to about 4.1
309. The lyophilized composition of any one of clauses 299-307, wherein dissolution in about 8 mL of water provides a lurbinectedin solution having a pH of about 4.0.
310. The lyophilized composition of any one of clauses 299-307, wherein dissolution in about 8 mL of water provides a lurbinectedin solution comprising 0.47-0.5 mg/mL of lurbinectedin and having a pH of about 3.5-4.5 and comprising.
311. The lyophilized composition of any one of clauses 299-310, wherein the lyophilized composition is packaged in a vial.
311a. The lyophilized composition of any one of clauses 299-311, wherein the lyophilized composition is packaged in a 30 mL vial.
312. Lurbinectedin Form B of the formula (1):

(I)

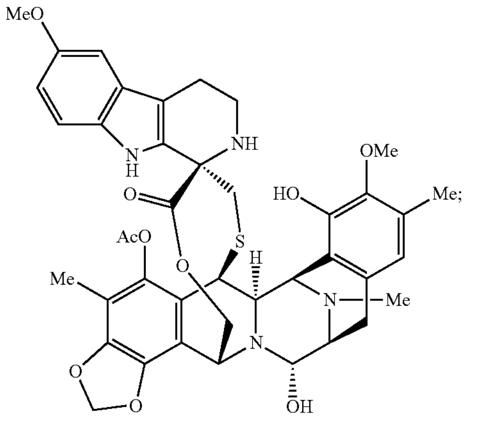

that exhibits a X-ray powder diffraction pattern comprising four or more peaks at 2-theta angles selected from the group consisting of 6.2±0.2, 7.6 0.2°, 9.0±0.2°, 10.9±0.2°, 14.9±0.2° and 15.3±0.2°.
313. Lurbinectedin according to clause 312, wherein the X-ray powder diffraction pattern comprises five or more peaks at 2-theta angles selected from the group consisting of 6.2±0.2°, 7.6±0.2°, 9.0±0.2°, 10.9±0.2°, 14.9±0.2° and 15.3±0.2°.
314. Lurbinectedin according to clause 312, wherein the X-ray powder diffraction pattern comprises peaks at 2-theta angles of 6.2±0.2°, 7.6±0.2°, 9.0±0.2°, 10.9±0.2°, 14.9±0.2° and 15.3±0.2°.

315. Lurbinectedin according to any one of clauses 312 to 314, further comprising peaks at 2-theta angles of 12.4±0.2°, 19.2±0.2° and 26.5±0.2°.
316. Lurbinectedin according to any one of clauses 312 to 315, further comprising peaks at 2-theta angles of 18.4±0.2°, 20.7±0.2 and 24.9±0.2°.
317. Lurbinectedin according to clause 312 further comprising peaks and relative intensities of:

| Angle [2-theta] | Relative intensity [%] |
|---|---|
| 6.2 ± 0.2° | 79 ± 6 |
| 7.6 ± 0.2° | 100 ± 3 |
| 9.0 ± 0.2° | 63 ± 3 |
| 10.9 ± 0.2° | 100 ± 3 |
| 14.9 ± 0.2° | 76 ± 3 |
| 15.3 ± 0.2° | 75 ± 3 |

318. Lurbinectedin according to clause 312, further comprising peaks and relative intensities of:

| Angle [2-theta] | Relative intensity [%] | Angle [2-theta] | Relative intensity [%] |
|---|---|---|---|
| 6.2 ± 0.2° | 79 ± 6 | 14.9 ± 0.2° | 76 ± 3 |
| 7.6 ± 0.2° | 100 ± 3 | 15.3 ± 0.2° | 75 ± 3 |
| 9.0 ± 0.2° | 63 ± 3 | 19.2 ± 0.2° | 34 ± 3 |
| 10.9 ± 0.2° | 100 ± 3 | 26.5 ± 0.2° | 33 ± 3 |
| 12.4 ± 0.2° | 40 ± 3 | | |

319. Lurbinectedin according to clause 312, further comprising peaks and relative intensities of:

| Angle [2-theta] | Relative intensity [%] | Angle [2-theta] | Relative intensity [%] |
|---|---|---|---|
| 6.2 ± 0.2° | 79 ± 6 | 15.3 ± 0.2° | 75 ± 3 |
| 7.6 ± 0.2° | 100 ± 3 | 18.4 ± 0.2° | 29 ± 3 |
| 9.0 ± 0.2° | 63 ± 3 | 19.2 ± 0.2° | 34 ± 3 |
| 10.9 ± 0.2° | 100 ± 3 | 20.7 ± 0.2° | 32 ± 3 |
| 12.4 ± 0.2° | 40 ± 3 | 24.9 ± 0.2° | 26 ± 3 |
| 14.9 ± 0.2° | 76 ± 3 | 26.5 ± 0.2° | 33 ± 3 |

320. Lurbinectedin according to any one of clauses 312 to 319, that exhibits an X-ray powder diffraction patter substantially the same as any one of the X-ray powder diffraction patterns shown in FIG. 2*a* or 2*b*.
321. Lurbinectedin according to any one of clauses 312 to 320, further characterized by an IR spectrum comprising peaks at wavelengths ($cm^1$) of 2928, 1755, 1626, 1485, 1456, 1370, 1197, 1150, 1088, 1003, 959, 916, and 587.
322. Lurbinectedin according to any one of clauses 312 to 321, further characterized by a TG-FTIR degradation above 150° C.; and/or characterized by a TG-FTIR mass change to 150° C. being due to loss of water; and/or characterized by a TG-FTIR mass change to 150° C. being due to loss of less than about 5%, less than about 4%, or less than about 3% water; and/or characterized by TG-FTIR indicating a loss of water, preferably around 2-3% water, more preferably 2.6% water.
323. Lurbinectedin according to any one of clauses 312 to 322, further characterized by DSC wherein degradation begins above 130° C.

324. Lurbinectedin according to any one of clauses 312 to 323, further characterized by an average charge density of not more than about 30 nC/g, not more than about 20 nC/g, not more than about 10 nC/g, not more than about 6 nC/g, not more than about 5 nC/g, about 5±2 nC/g, about 4±2 nC/g, about 4-5 nC/g, about 5 nC/g, or about 4 nC/g.
325. Lurbinectedin according to any one of clauses 312 to 324, further characterized by a dispersion of charge density of less than 4.8 nC/g, of between about 0.7 nC/g to less than 4.8 nC/g, or 2.4±2 nC/g.
326. Lurbinectedin according to any one of clauses 312 to 325, characterized by a water content of above 1.6% w/w, or of 1.7-5% w/w.
327. Lurbinectedin according to any one of clauses 312 to 326, further characterized by residual solvents of not more than 1%, 0.5%, 0.1% or substantially not detected.
328. Partially crystalline lurbinectedin.
329. Partially crystalline lurbinectedin according to clause 328, wherein the partially crystalline lurbinectedin comprises lurbinectedin Form B as defined in any one of clauses 312 to 327.
330. Partially crystalline lurbinectedin, according to clause 328 or 329, comprising at least a detectible amount of crystalline lurbinectedin, up to 1% crystalline lurbinectedin, up to 5% crystalline lurbinectedin, up to 10% crystalline lurbinectedin, up to 20% crystalline lurbinectedin, up to 30% crystalline lurbinectedin, up to 40% crystalline lurbinectedin, up to 50% crystalline lurbinectedin, up to 60% crystalline lurbinectedin, up to 70% crystalline lurbinectedin, up to 80% crystalline lurbinectedin, up to 90% crystalline lurbinectedin, up to 95% crystalline lurbinectedin, up to 98% crystalline lurbinectedin, or substantially pure crystalline lurbinectedin.
331. Partially crystalline lurbinectedin, according to any one of clauses 328 to 330, comprising at least a detectible amount of Form B, up to 1% w/w Form B, up to 5% w/w Form B, up to 10% w/w Form B, up to 20% w/w Form B, up to 30% w/w Form B, up to 40% w/w Form B, up to 50% w/w Form B, up to 60% w/w Form B, up to 70% w/w Form B, up to 80% w/w Form B, up to 90% w/w Form B, up to 95% w/w Form B, up to 98% w/w Form B, or substantially pure Form B.
332. Partially crystalline lurbinectedin, according to any one of clauses 328 to 331, comprising at least a detectible amount of amorphous lurbinectedin, up to 1% w/w amorphous lurbinectedin, up to 5% w/w amorphous lurbinectedin, up to 10% w/w amorphous lurbinectedin, up to 20% w/w amorphous lurbinectedin, up to 30% w/w amorphous lurbinectedin, up to 40% w/w amorphous lurbinectedin, up to 50% w/w amorphous lurbinectedin, up to 60% w/w amorphous lurbinectedin, up to 70% w/w amorphous lurbinectedin, up to 80% w/w amorphous lurbinectedin, up to 90% w/w amorphous lurbinectedin, up to 95% w/w amorphous lurbinectedin, or up to 98% w/w amorphous lurbinectedin.
333. A pharmaceutical composition or a pharmaceutical intermediate comprising partially crystalline lurbinectedin according to any one of clauses 328 to 332.
334. Pharmaceutical compositions made from a process including partially crystalline lurbinectedin according to any one of clauses 328 to 332.
335. The composition of clause 333 or clause 334, wherein the composition has a total water content of not more than 3%; and/or residual solvents of not more than 1%, 0.5%, 0.1% or substantially not detected; and/or total impurities of not more than 1.9%, 1.8%, 1.7%, 1.6%, 1.5%, 1.4%, or 1.3%; and/or not more than 0.8% of impurity D; and/or not more than 0.3% of any unspecified impurity; and/or total related substances of not more than 2.0% and any unspecified substances (highest) not more than 0.7%.
336. The pharmaceutical composition of any one of clauses 333 to 335, wherein the pharmaceutical composition is a lyophilized composition.
337. A process for the preparation of Form B of lurbinectedin as defined in any one of clauses 312 to 327, comprising the steps of:
a) preparing an acidic aqueous solution comprising lurbinectedin or a protonated form thereof; and
b) basifying the resulting acid aqueous solution with a base or a buffer to precipitate Form B of lurbinectedin.
338. The process according to clause 337 wherein the acidic aqueous solution comprising lurbinectedin is prepared by dissolving any form of lurbinectedin in acid water.
339. The process according to clause 337 wherein the acid water is an aqueous solution of HCl, preferably 0.1 M.
340. The process according to any one of clauses 337 to 339, wherein the resulting acid aqueous solution is basified with a buffer.
341. The process according to clause 340 wherein the buffer is $NH_4Cl/NH_4OH$.
342. The process according to any one of clauses 337 to 341, further comprising a washing step between steps a) and b), wherein the aqueous acid solution is washed one or more times with a pharmaceutically-acceptable, water immiscible, polar solvent and one or more times with a pharmaceutically-acceptable, water immiscible, non-polar solvent, preferably C5-C7 alkane.
343. The processes according to clause 342, wherein the aqueous acid solution is washed one or more times with dichloromethane and one or more times with n-pentane.
344. The process according to any one of clauses 337 to 343 wherein Form B of lurbinectedin is collected by filtration.
345. The process according to any one of clauses 337 to 344 wherein Form B of lurbinectedin is dried under vacuum.
346. The process according to any one of clauses 337 to 345 wherein Form B of lurbinectedin is converted into a different physical form.
347. The process according to clause 346 wherein the different physical form is amorphous.
348. A pharmaceutical composition comprising lurbinectedin as defined in any one of clauses 312 to 327, and a pharmaceutically acceptable carrier.
349. A pharmaceutical composition comprising lurbinectedin and a pharmaceutically acceptable carrier, wherein said pharmaceutical composition is manufactured via lurbinectedin as defined in any one of clauses 312 to 327.
350. The pharmaceutical composition to clause 348 or 349, wherein the pharmaceutical composition comprises lurbinectedin and a disaccharide.
351. A process for the manufacture of a lurbinectedin composition, said process employing lurbinectedin as defined in any one of clauses 312 to 327, or partially crystalline lurbinectedin as defined in any one of clauses 328 to 332; preferably as a starting material.

352. The process according to clause 351, wherein the process comprises pre-dissolving the lurbinectedin in an organic acid.

353. The process according to clause 352, wherein the organic acid has a pH less than 4, preferably less than 3.5, more preferably less than 3, or around 3.

354. The process according to clause 352 or 353, wherein the organic acid has a molarity of around 0.1M to 0.5M, preferably around 0.2M to 0.4M, more preferably around 0.3M, or 0.31M.

355. The process according to any one of clauses 352 to 354, wherein the organic acid has a molarity of around 0.1M to 0.5M, preferably around 0.2M to 0.4M, more preferably around 0.3M, or 0.31M.

356. The process according to any one of clauses 352 to 354, wherein the pre-dissolution step is at least 30 minutes, at least 60 minutes or at least 90 minutes, between 30-90 minutes, between 60-90 minutes, between 60-70 minutes or around 60 minutes.

357. The process according to any one of clauses 352 to clause 356, wherein the solution is diluted with water for injection (WFI) to form a target concentration; wherein the target concentration is optionally 8.3 mg/mL in 0.1M organic acid.

358. The process according to any one of clauses 352 to 357, wherein the organic acid is a carboxylic acid such as succinic acid, citric acid, acetic acid or lactic acid, preferably lactic acid.

359. The process according to any one of clauses 351 to 358, wherein a solution comprising an organic buffer and bulking agent (e.g. disaccharide) is prepared to form a buffer solution.

360. The process according to clause 359, wherein the buffer solution has a pH of about 5.6 or less, preferably about 4 to about 5.6, or about 4.2 to about 5.6.

361. The process according to clause 359 or 360, wherein the buffer is derived from an organic acid, preferably an organic carboxylic acid, such as organic carboxylic acid buffer, such as, a lactic acid buffer, a butyric acid buffer, a propionic acid buffer, a acetic acid buffer, a succinic acid buffer, a citric acid buffer, a ascorbic acid buffer, a tartaric acid buffer, a malic acid buffer, a maleic acid buffer, a fumaric acid buffer, a glutamic acid buffer, an aspartic acid buffer, a gluconic acid buffer, and a α-ketoglutaric buffer.

362. The process according to any one of clauses 359 to 361, wherein the bulking agent is a disaccharide, preferably sucrose.

363. The process according to any one of clauses 352 to 362, wherein the dissolved lurbinectedin solution as defined in any one of clauses 352 to 358 is mixed with the buffer solution according to any one of clauses 359 to 362 to form the final bulk solution.

364. The process according to clause 363, wherein the final bulk solution is adjusted with WFI to achieve the final target weight.

365. The process according to any one of clauses 352 to 364, wherein the final target composition comprises 0.5 mg/mL lurbinectedin in 0.03M sodium lactate buffer pH=4+10% (w/v) sucrose.

366. The process according to any one of clauses 352 to 365, wherein the bulk solution according to any one of clauses 363 to 365 undergoes sterilization filtration before filling into vials.

367. The process according to any one of clauses 351 to 366, wherein the composition undergoes freeze-drying to form a lyophilized formulation.

368. The process according to clause 367, wherein the lyophilized composition is labelled for use.

369. The process according to clause 367 or 368, wherein the lyophilized composition is reconstituted for use.

370. The process according to clause 369, wherein the composition is reconstitution with 8 mL of water to yield a solution having a pH of 3.5 to 4.5 and a lurbinectedin concentration of 0.5 mg/ml.

371. The process according to clause 369 or 370, wherein the reconstituted solution is diluted to form an infusion solution; optionally with 0.9% sodium chloride solution or a 5% dextrose solution; further optionally wherein the reconstituted solution is diluted with at least 100 mL or at least 250 mL to prepare a lurbinectedin infusion solution.

372. A lurbinectedin infusion solution made according to the process of any one of clauses 351 to 371.

373. A reconstituted solution made according to the process of any one of clauses 351 to 370.

374. A lyophilized composition made according to the process of any one of clauses 351 to 368.

375. A bulk composition made according to the process of any one of clauses 351 to 366.

376. Lurbinectedin as defined in any one of clauses 312 to 327, or partially crystalline lurbinectedin as defined in any one of clauses 328 to 332, for use as a medicament.

377. Lurbinectedin as defined in any one of clauses 312 to 327, or partially crystalline lurbinectedin as defined in any one of clauses 328 to 332, for use in the manufacture of a medicament.

378. Lurbinectedin as defined in any one of clauses 312 to 327, or partially crystalline lurbinectedin as defined in any one of clauses 328 to 332, for use in the manufacture of a medicament for the treatment of cancer.

379. A method of treating an individual affected by cancer comprising administering to said affected individual a therapeutically effective amount of lurbinectedin as defined in any one of clauses 312 to 327, or partially crystalline lurbinectedin as defined in any one of clauses 328 to 332.

380. A method of treating an individual affected by cancer comprising administering to said affected individual a therapeutically effective amount of a lurbinectedin composition manufactured using lurbinectedin as defined in any one of clauses 312 to 327, or partially crystalline lurbinectedin as defined in any one of clauses 328 to 332.

381. A composition, method, use or process as defined in any one of clauses 1 to 380, wherein reference to reconstitution of 4 mg lurbinectedin in 8 mL with a concentration of 0.5 mg/mL is reference to a calculated concentration of 0.47 mg/mL in 8.55 mL.

382. Lurbinectedin substantially as hereinbefore described with reference to the examples, excluding comparative examples.

383. Lurbinectedin compositions, substantially as hereinbefore described with reference to the examples, excluding comparative examples.

We claim:

1. A method of treating metastatic small cell lung cancer (SCLC) in a patient after platinum-based chemotherapy, said method comprising administering, within 35 days of receiving a treatment cycle comprising a dose of 3.2 $mg/m^2$ of lurbinectedin by intravenous infusion as sole chemotherapy agent, a subsequent treatment cycle comprising a dose of 2.6 $mg/m^2$ lurbinectedin by intravenous infusion as sole chemotherapy agent to the patient having at the time of the administration of the dose of 2.6 $mg/m^2$ of lurbinectedin:

a) metastatic SCLC, b) a platelet count of at least 100,000/$mm^3$, and c) an absolute neutrophil count of at least 1,500 cells/$mm^3$;

wherein the patient previously experienced Grade 4 neutropenia or any grade febrile neutropenia subsequent to receiving the dose of 3.2 $mg/m^2$ of lurbinectedin; and wherein one dose of lurbinectedin is administered per treatment cycle, and wherein each treatment cycle is 21 to 35 days.

2. The method according to claim 1, wherein each treatment cycle is 21 days.

3. The method according to claim 1 further comprising: administering, within 35 days of receiving a treatment cycle comprising a dose of 2.6 $mg/m^2$ of lurbinectedin by intravenous infusion as sole chemotherapy agent, a treatment cycle comprising a dose of 2.0 $mg/m^2$ lurbinectedin by intravenous infusion as sole chemotherapy agent to the patient having at the time of the administration of the dose of 2.0 $mg/m^2$ of lurbinectedin:

(a) a platelet count of at least 100,000/$mm^3$, and (b) an absolute neutrophil count of at least 1,500 cells/$mm^3$, wherein the patient previously experienced Grade 4 neutropenia or any grade febrile neutropenia subsequent to receiving the dose of 2.6 $mg/m^2$ of lurbinectedin.

4. The method according to claim 3, wherein each treatment cycle is 21 days.

5. The method according to claim 1, wherein the platinum-based chemotherapy is carboplatin or is cisplatin and etoposide; and the platinum-based chemotherapy is given in combination with immunotherapy.

6. The method according to claim 2, wherein the platinum-based chemotherapy is carboplatin or is cisplatin and etoposide; and the platinum-based chemotherapy is given in combination with immunotherapy.

7. The method according to claim 1, wherein the platinum-based chemotherapy is carboplatin and etoposide; and the platinum-based chemotherapy is given in combination with immunotherapy.

8. The method according to claim 2, wherein the platinum-based chemotherapy is carboplatin and etoposide; and the platinum-based chemotherapy is given in combination with immunotherapy.

9. The method according to claim 7, wherein the immunotherapy is atezolizumab.

10. The method according to claim 8, wherein the immunotherapy is atezolizumab.

11. The method according to claim 1, wherein the metastatic SCLC is extensive stage SCLC (ES-SCLC).

12. The method according to claim 2, wherein the metastatic SCLC is extensive stage SCLC (ES-SCLC).

13. The method according to claim 5, wherein the metastatic SCLC is extensive stage SCLC (ES-SCLC).

14. The method according to claim 9, wherein the metastatic SCLC is extensive stage SCLC (ES-SCLC).

15. The method according to claim 10, wherein the metastatic SCLC is extensive stage SCLC (ES-SCLC).

16. A method of treating metastatic small cell lung cancer (SCLC) in a patient after platinum-based chemotherapy, said method comprising:

(a) administering a treatment cycle comprising a dose of 3.2 $mg/m^2$ of lurbinectedin by intravenous infusion as sole chemotherapy agent to the patient having, at the time of the administration of the dose of 3.2 $mg/m^2$ of lurbinectedin:

(i) metastatic SCLC, (ii) an absolute neutrophil count of at least 1,500 cells/$mm^3$, and (iii) a platelet count of at least 100,000/$mm^3$;

wherein the patient experienced Grade 4 neutropenia or any grade febrile neutropenia subsequent to the administration of the dose of 3.2 $mg/m^2$ of lurbinectedin and returns within 35 days of the administration of the dose of 3.2 $mg/m^2$ of lurbinectedin to an absolute neutrophil count of at least 1,500 cells/$mm^3$ after experiencing the Grade 4 neutropenia or any grade febrile neutropenia; and (b) administering by intravenous infusion as sole chemotherapy agent a treatment cycle comprising a dose of 2.6 $mg/m^2$ of lurbinectedin to the patient after the absolute neutrophil count returns to at least 1,500 cells/$mm^3$ and provided the patient has a platelet count of at least 100,000/$mm^3$; and wherein one dose of lurbinectedin is administered per treatment cycle, and wherein each treatment cycle is 21 to 35 days.

17. The method according to claim 16, wherein each treatment cycle is 21 days.

18. The method according to claim 16 further comprising: administering, within 35 days of receiving a dose of 2.6 $mg/m^2$ of lurbinectedin by intravenous infusion as sole chemotherapy agent, a treatment cycle comprising a dose of 2.0 $mg/m^2$ lurbinectedin by intravenous infusion as sole chemotherapy agent to the patient having at the time of the administration of the dose of 2.0 $mg/m^2$ of lurbinectedin:

(a) a platelet count of at least 100,000/$mm^3$ and (b) an absolute neutrophil count of at least 1,500 cells/$mm^3$, wherein the patient previously experienced Grade 4 neutropenia or any grade febrile neutropenia subsequent to receiving the dose of 2.6 $mg/m^2$ of lurbinectedin.

19. The method according to claim 18, wherein each treatment cycle is 21 days.

20. The method according to claim 16, wherein the platinum-based chemotherapy is carboplatin or is cisplatin and etoposide; and the platinum-based chemotherapy is given in combination with immunotherapy.

21. The method according to claim 17, wherein the platinum-based chemotherapy is carboplatin or is cisplatin and etoposide; and the platinum-based chemotherapy is given in combination with immunotherapy.

22. The method according to claim 16, wherein the platinum-based chemotherapy is carboplatin and etoposide; and the platinum-based chemotherapy is given in combination with immunotherapy.

23. The method according to claim 17, wherein the platinum-based chemotherapy is carboplatin and etoposide; and the platinum-based chemotherapy is given in combination with immunotherapy.

24. The method according to claim 22, wherein the immunotherapy is atezolizumab.

25. The method according to claim 23, wherein the immunotherapy is atezolizumab.

26. The method according to claim 16, wherein the metastatic SCLC is extensive stage SCLC (ES-SCLC).

27. The method according to claim 17, wherein the metastatic SCLC is extensive stage SCLC (ES-SCLC).

28. The method according to claim 20, wherein the metastatic SCLC is extensive stage SCLC (ES-SCLC).

29. The method according to claim 24, wherein the metastatic SCLC is extensive stage SCLC (ES-SCLC).

30. The method according to claim 25, wherein the metastatic SCLC is extensive stage SCLC (ES-SCLC).

* * * * *